(12) United States Patent
Blume et al.

(10) Patent No.: US 9,689,874 B2
(45) Date of Patent: *Jun. 27, 2017

(54) PROTEIN BIOMARKER PANELS FOR DETECTING COLORECTAL CANCER AND ADVANCED ADENOMA

(71) Applicant: Applied Proteomics, Inc., San Diego, CA (US)

(72) Inventors: John Blume, Bellingham, WA (US); Jeffrey Jones, Glendale, CA (US); Ryan Benz, Huntington Beach, CA (US); Athit Kao, San Marcos, CA (US); Lisa Croner, San Diego, CA (US); Roslyn Dillon, Cardiff, CA (US); Jia You, San Diego, CA (US); Bruce Wilcox, Harrisonburg, VA (US)

(73) Assignee: APPLIED PROTEOMICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/094,767

(22) Filed: Apr. 8, 2016

(65) Prior Publication Data

US 2016/0299144 A1    Oct. 13, 2016

Related U.S. Application Data

(60) Provisional application No. 62/146,158, filed on Apr. 10, 2015, provisional application No. 62/160,560, filed on May 12, 2015, provisional application No. 62/165,846, filed on May 22, 2015, provisional application No. 62/196,889, filed on Jul. 24, 2015, provisional application No. 62/239,771, filed on Oct. 9, 2015.

(51) Int. Cl.
*G01N 33/574*    (2006.01)

(52) U.S. Cl.
CPC ... *G01N 33/57419* (2013.01); *G01N 2333/47* (2013.01); *G01N 2333/70564* (2013.01); *G01N 2333/70596* (2013.01); *G01N 2333/99* (2013.01)

(58) Field of Classification Search
None
See application file for complete search history.

(56) References Cited

U.S. PATENT DOCUMENTS

| | | |
|---|---|---|
| 4,444,879 A | 4/1984 | Foster et al. |
| 4,517,289 A | 5/1985 | Milford et al. |
| 4,816,567 A | 3/1989 | Cabilly et al. |
| 4,921,789 A | 5/1990 | Salem et al. |
| 5,674,753 A | 10/1997 | Harvey et al. |
| 5,736,343 A | 4/1998 | Landry |
| 5,786,158 A | 7/1998 | Artavanis-Tsakonas et al. |
| 5,790,761 A | 8/1998 | Heseltine et al. |
| 5,800,347 A | 9/1998 | Skates et al. |
| 5,983,211 A | 11/1999 | Heseltine et al. |
| 6,210,887 B1 | 4/2001 | Schweinfest et al. |
| 6,316,208 B1 | 11/2001 | Roberts et al. |
| 6,322,986 B1 | 11/2001 | Ross |
| 6,440,661 B1 | 8/2002 | Oogreid et al. |
| 6,531,283 B1 | 3/2003 | Kingsmore et al. |
| 6,589,745 B2 | 7/2003 | Kaufmann |
| 6,706,506 B2 | 3/2004 | Gudas et al. |
| 7,153,700 B1 | 12/2006 | Pardee et al. |
| 7,229,770 B1 | 6/2007 | Price et al. |
| 7,312,086 B2 | 12/2007 | Feder et al. |
| 7,402,403 B1 | 7/2008 | Robertson et al. |
| 7,526,387 B2 | 4/2009 | Baker et al. |
| 7,577,683 B2 | 8/2009 | Cho et al. |
| 7,736,861 B1 | 6/2010 | Lin et al. |
| 7,807,379 B2 | 10/2010 | Holten-Andersen et al. |
| 7,811,778 B2 | 10/2010 | Goldenring |
| 7,833,736 B2 | 11/2010 | Haack et al. |
| 7,883,842 B2 | 2/2011 | Juhl et al. |
| 7,892,758 B2 | 2/2011 | Sharma et al. |
| 7,939,261 B2 | 5/2011 | Baker et al. |
| 7,951,528 B2 | 5/2011 | Juhl et al. |
| 7,991,560 B2 | 8/2011 | Kaushikkar et al. |
| 8,029,764 B2 | 10/2011 | Buckhaults et al. |
| 8,114,604 B2 | 2/2012 | Robertson et al. |
| 8,143,302 B2 | 3/2012 | Marnett et al. |
| 2001/0041365 A1 | 11/2001 | Laposata |

(Continued)

FOREIGN PATENT DOCUMENTS

| | | |
|---|---|---|
| EP | 1171771 B1 | 6/2005 |
| EP | 1078264 B1 | 12/2005 |

(Continued)

OTHER PUBLICATIONS

Thorsen et al (Journal of Translational Medicine, 2013, 11(253): 1-13).*
Kopetz et al (Journal of Clinical Oncology, 2010, 28(2): 453-459).*
Ahlquist, et al. Colorectal cancer screening by detection of altered human DNA in stool: feasibility of a multitarget assay panel. Gastroenterology. Nov. 2000;119(5):1219-27.
Altman, et al. Diagnostic tests. 1: Sensitivity and specificity. BMJ. Jun. 11, 1994;308(6943):1552.
Alvarez-Chaver, et al. Proteomics for discovery of candidate colorectal cancer biomarkers. World J Gastroenterol. Apr. 14, 2014;20(14):3804-24. doi: 10.3748/wjg.v20.i14.3804.
Anderson, et al. A comparison of selected mRNA and protein abundances in human liver. Electrophoresis. Mar.-Apr. 1997;18(3-4):533-7.
AU Application No. 11201504241Q Search Report and Written Opinion Issued Apr. 25, 2016.
Brock, et al. A multiplex serum protein assay for determining the probability of colorectal cancer. Am J Cancer Res. 2012;2(5):598-605. Epub Aug. 20, 2012.

(Continued)

*Primary Examiner* — Sean Aeder
(74) *Attorney, Agent, or Firm* — Wilson Sonsini Goodrich & Rosati

(57) ABSTRACT

Disclosed herein are panels related to the diagnosis or recognition of colon and colorectal cancer in a subject. The disclosed panels and related methods are used to predict or assess colon tumor status in a patient. They can be used to determine nature of tumor, recurrence, or patient response to treatments. Some embodiments of the methods include generating a report for clinical management.

21 Claims, 31 Drawing Sheets
(7 of 31 Drawing Sheet(s) Filed in Color)

(56) References Cited

U.S. PATENT DOCUMENTS

| | | |
|---|---|---|
| 2003/0064385 A1 | 4/2003 | Dressman et al. |
| 2003/0096755 A1 | 5/2003 | Brunner et al. |
| 2003/0186248 A1 | 10/2003 | Erlander et al. |
| 2005/0153382 A1 | 7/2005 | Zou et al. |
| 2005/0226884 A1 | 10/2005 | Price et al. |
| 2006/0040306 A1 | 2/2006 | Leiby et al. |
| 2006/0105419 A1 | 5/2006 | Blankenberg et al. |
| 2006/0141497 A1 | 6/2006 | Finkelstein et al. |
| 2007/0111244 A1 | 5/2007 | Georges et al. |
| 2007/0231304 A1 | 10/2007 | Sobol et al. |
| 2008/0108084 A1 | 5/2008 | Robertson et al. |
| 2008/0145852 A1 | 6/2008 | Shuber |
| 2008/0153113 A1 | 6/2008 | Robertson et al. |
| 2008/0160515 A1 | 7/2008 | Juhl et al. |
| 2008/0161420 A1 | 7/2008 | Shuber |
| 2008/0255764 A1 | 10/2008 | Ritchie et al. |
| 2008/0286801 A1 | 11/2008 | Arjol et al. |
| 2008/0311567 A1 | 12/2008 | Bruckl et al. |
| 2009/0035801 A1 | 2/2009 | Goldknopf et al. |
| 2009/0142332 A1 | 6/2009 | Ried et al. |
| 2009/0150315 A1 | 6/2009 | Wirtz et al. |
| 2009/0155842 A1 | 6/2009 | Baak et al. |
| 2009/0291434 A1 | 11/2009 | Cowens et al. |
| 2010/0055724 A1 | 3/2010 | Taylor et al. |
| 2010/0099086 A1 | 4/2010 | Liew et al. |
| 2010/0204299 A1 | 8/2010 | Regnier et al. |
| 2010/0240068 A1 | 9/2010 | Karl et al. |
| 2010/0240081 A1 | 9/2010 | Rollinger et al. |
| 2010/0248244 A1 | 9/2010 | Song et al. |
| 2010/0261221 A1 | 10/2010 | Lee |
| 2010/0304410 A1 | 12/2010 | Kijanka et al. |
| 2010/0330079 A1 | 12/2010 | Ruegg et al. |
| 2011/0014204 A1 | 1/2011 | Feinberg et al. |
| 2011/0059858 A1 | 3/2011 | Kas et al. |
| 2011/0065605 A1 | 3/2011 | Krek et al. |
| 2011/0076700 A1 | 3/2011 | Kohno et al. |
| 2011/0104256 A1 | 5/2011 | Wang et al. |
| 2011/0129860 A1 | 6/2011 | Karl et al. |
| 2011/0182879 A1 | 7/2011 | Meyers et al. |
| 2011/0236396 A1 | 9/2011 | Pinto Morais De Carvalho et al. |
| 2011/0236916 A1 | 9/2011 | Zou et al. |
| 2011/0245087 A1 | 10/2011 | Weiss |
| 2011/0269158 A1 | 11/2011 | Zitzler et al. |
| 2011/0294134 A1 | 12/2011 | Livneh et al. |
| 2011/0315552 A1 | 12/2011 | Stults et al. |
| 2012/0021414 A1 | 1/2012 | Shen-Orr et al. |
| 2012/0064078 A1 | 3/2012 | Luo et al. |
| 2012/0149022 A1 | 6/2012 | Aw |
| 2014/0141986 A1 | 5/2014 | Spetzler et al. |
| 2014/0170242 A1 | 6/2014 | Wagner et al. |
| 2014/0234854 A1 | 8/2014 | Blume et al. |
| 2014/0364326 A1 | 12/2014 | Guergova-Kuras et al. |
| 2015/0111220 A1 | 4/2015 | Blume et al. |
| 2015/0111221 A1 | 4/2015 | Blume et al. |
| 2015/0111223 A1 | 4/2015 | Blume et al. |
| 2015/0111230 A1 | 4/2015 | Blume et al. |

FOREIGN PATENT DOCUMENTS

| | | |
|---|---|---|
| EP | 0892809 B1 | 5/2006 |
| EP | 1499896 B1 | 8/2006 |
| EP | 2111550 B1 | 11/2011 |
| EP | 2171465 B1 | 12/2011 |
| WO | WO-9502413 A1 | 1/1995 |
| WO | WO-9958978 A2 | 11/1999 |
| WO | WO-0070096 A2 | 11/2000 |
| WO | WO-0206330 A2 | 1/2002 |
| WO | WO-02076280 A2 | 10/2002 |
| WO | WO-02077233 A2 | 10/2002 |
| WO | WO-03065003 A2 | 8/2003 |
| WO | WO-03083141 A1 | 10/2003 |
| WO | WO-03097872 A2 | 11/2003 |
| WO | WO-2005008213 A2 | 1/2005 |
| WO | WO-2006047787 A2 | 5/2006 |
| WO | WO-2006053592 A1 | 5/2006 |
| WO | WO-2006102526 A2 | 9/2006 |
| WO | WO-2007016367 A2 | 2/2007 |
| WO | WO-2007030928 A2 | 3/2007 |
| WO | WO-2007060420 A1 | 5/2007 |
| WO | WO-2008073858 A2 | 6/2008 |
| WO | WO-2008116178 A2 | 9/2008 |
| WO | WO-2009015299 A1 | 1/2009 |
| WO | WO-2009040782 A2 | 4/2009 |
| WO | WO-2009099651 A1 | 8/2009 |
| WO | WO-2009101620 A1 | 8/2009 |
| WO | WO-2010009368 A2 | 1/2010 |
| WO | WO-2010096154 A2 | 8/2010 |
| WO | WO-2011047358 A1 | 4/2011 |
| WO | WO-2011119934 A2 | 9/2011 |
| WO | WO-2012013931 A1 | 2/2012 |
| WO | WO-2012115885 A1 | 8/2012 |
| WO | WO-2013152989 A2 | 10/2013 |
| WO | WO-2013162368 A1 | 10/2013 |
| WO | WO-2014085826 A2 | 6/2014 |

OTHER PUBLICATIONS

Clackson, et al. Making antibody fragments using phage display libraries. Nature. Aug. 15, 1991;352(6336):624-8.

Clinical Chemistry, Principles Procedures Correlations, Second Edition, An Introduction to Clinical Chemistry, 1992, pp. 76-77.

Colucci, et al., Outpatient Practice Management Tips, Coloretal Polyps, Clinical Medine & Research, vol. 1, No. 3; 2003, pp. 261-262.

Eisenberg, et al. Human housekeeping genes are compact. Trends Genet. Jul. 2003;19(7):362-5.

Ewald, et al. [Pyruvate kinase M2 (tumor M2-PK) as a screening tool for colorectal cancer (CRC). A review of current published data]. Z Gastroenterol. Dec. 2005;43(12):1313-7.

Gygi, et al. Correlation between protein and mRNA abundance in yeast. Mol Cell Biol. Mar. 1999;19(3):1720-30.

Heid, et al. Real time quantitative PCR. Genome Res. Oct. 1996;6(10):986-94.

Henry L. R. et al., Clinical implications of fibroblast activation protein in patients with colon cancer. Clinical Cancer Research, 13(6); 1736-1741 (Mar. 15, 2007).

International search report and written opinion dated Aug. 12, 2014 for PCT Application No. PCT/US2013/072691.

International search report and written opinion dated Sep. 4, 2015 for PCT Application No. PCT/US2015/023187.

Jimenez, et al. Proteomics of colorectal cancer: overview of discovery studies and identification of commonly identified cancer-associated proteins and candidate CRC serum markers. J Proteomics. Sep. 10, 2010;73(10):1873-95. doi: 10.1016/j.jprot.2010.06.004. Epub Jun. 23, 2010.

Kirana C. et al., Cathepsin D expression in colorectal cancer: from proteomic discovery through validation using western blotting, immunohistochemistry, and tissue microarrays. International Journal of Proteomics, 2012(245819); 1-10: (Jun. 24, 2012).

Kohler, et al. Continuous cultures of fused cells secreting antibody of predefined specificity. Nature. Aug. 7, 1975;256(5517):495-7.

Lange, et al. Selected reaction monitoring for quantitative proteomics: a tutorial. Molecular Systems Biology 4; Article No. 222; doi:10.1038/msb.2008.61.

Loong. Understanding sensitivity and specificity with the right side of the brain. BMJ. Sep. 27, 2003;327(7417):716-9.

Marin Gastroenterology, Patient Education, Colon Polyps 2011, pp. 1-2.

Marks, et al. By-passing immunization. Human antibodies from V-gene libraries displayed on phage. J Mol Biol. Dec. 5, 1991;222(3):581-97.

Metodieva, et al. A peptide-centric approach to breast cancer biomarker discovery utilizing label-free multiple reaction monitoring mass spectrometry. Proteomics Clin Appl. Jan. 2009;3(1):78-82. doi: 10.1002/prca.200800072. Epub Nov. 20, 2008.

Murakoshi, et al. Plasma biomarker discovery and validation for colorectal cancer by quantitative shotgun mass spectrometry and protein microarray. Cancer Sci. Mar. 2011;102(3):630-8. doi: 10.1111/j.1349-7006.2010.01818.x. Epub Dec. 28, 2010.

Office action dated Apr. 20, 2015 for U.S. Appl. No. 14/526,265.

(56) References Cited

OTHER PUBLICATIONS

Office action dated May 18, 2015 for U.S. Appl. No. 14/526,181.
Office action dated May 19, 2015 for U.S. Appl. No. 14/526,282.
Office action dated May 27, 2015 for U.S. Appl. No. 14/526,221.
Office action dated Jun. 9, 2015 for U.S. Appl. No. 14/094,594.
Office action dated Nov. 5, 2015 for U.S. Appl. No. 14/526,265.
Office action dated Nov. 27, 2015 for U.S. Appl. No. 14/526,181.
Office action dated Nov. 30, 2015 for U.S. Appl. No. 14/526,282.
Office action dated Dec. 7, 2015 for U.S. Appl. No. 14/526,221.
Patton, et al. Components of the protein synthesis and folding machinery are induced in vascular smooth muscle cells by hypertrophic and hyperplastic agents. Identification by comparative protein phenotyping and microsequencing. J Biol Chem. Sep. 8, 1995;270(36):21404-10.
Patton. Proteome analysis. II. Protein subcellular redistribution: linking physiology to genomics via the proteome and separation technologies involved. J Chromatogr B Biomed Sci Appl. Feb. 5, 1999;722(1-2):203-23.
Pawa, et al. Screening for colorectal cancer: established and emerging modalities. Nat Rev Gastroenterol Hepatol. Nov. 1, 2011;8(12):711-22. doi: 10.1038/nrgastro.2011.205.
Strongin, W. Sensitivity, Specificity, and Predictive Value of Diagnostic Tests: Definitions and Clinical applications. Laboratory Diagnosis of Viral Infections. Lennette, ed. Marcel Dekker, Inc. New York, pp. 211-219, 1992.
Final Office Action Mailed Apr. 13, 2016 for U.S. Appl. No. 14/094,594.
Advisory Office Action Mailed Mar. 18, 2016 for U.S. Appl. No. 14/526,221.
Advisory Office Action Mailed May 12, 2016 for U.S. Appl. No. 14/526,282.
Wang, et al. Metabolomics and detection of colorectal cancer in humans: a systematic review. Future Oncol. Sep. 2010;6(9):1395-406. doi: 10.2217/fon.10.107.
Wild, et al. A combination of serum markers for the early detection of colorectal cancer. Clin. Cancer Res. 2010; 16:6111-6121.
Xie L. et al., Novel proteomic strategy reveal combined alpha1 antitrypsin and cathepsin D as biomarkers for colorectal cancer early screening. Journal of Proteome Research, 9(9); Jul. 14, 2010.
Database Medline [Online] US National Library of Medicine (NLM), Bethesda, MD, US; Aug. 1990 (Aug. 1990), Yuan M: "[Value of fecal detection of cancer-associated antigens using monoclonal antibodies in the diagnosis of colorectal cancer].", XP002690733, Database accession No. NLM2086118 & Zhonghua Wai Ke Za Zhi [Chinese Journal of Surgery] Aug. 1990, vol. 28, No. 8, Aug. 1990 (Aug. 1990), pp. 497-500, 511, ISSN: 0529-5815.
Deug-Chan Lee et al. Protein Profiling underscores immunological functions of uterine cervical mucus plug in human pregnancy, Journal of Proteomics, 74(6); 817-828 (2011).
Di Marzio, L. Detection of Alkaline Sphingomyelinase Activity in Human Stool; Proposed Role as a New Diagnostic and Prognostic Marker of Colorectal Cancer. Cancer Epidemiology, Biomarkers & Prevention, 14(4); 856-862 (2005).
European Application No. 13 858410.7 Extended European Search Report Mailed Aug. 11, 2016.
He, Z. et al. The Potential of carcinoembryonic antigen, p53, Ki-67 and glutathion Stransferase-π as clinico-histopathological markers for colorectal cancer. Journal of Biomedical Research 2010 24(1):51-57.
International Application No. PCT/US2016/026773 International Search Report and Written Opinion Mailed Jul. 19, 2016.
U.S. Appl. No. 14/526,181 Non-Final Office Action Mailed Jun. 22, 2016.
U.S. Appl. No. 14/526,221 Non-final Office Action Mailed Jun. 23, 2016.
U.S. Appl. No. 14/526,265 Office Action Mailed Aug. 16, 2016.
U.S. Appl. No. 14/526,282 Non-Final Office Action Mailed Jun. 28, 2016.
Volmer, Martin W. et al. Differential proteome analysis of conditioned media to detect Smad4 regulated secreted biomarkers in colon cancer, PROTEOMICS, 5(10); 2587-2601 (2005).
Xiaoyang, L. et al. A High-quality secretome of A549 cells aided the discovery of C4b-binding protein as a novel serum biomarker for non-small cell lung cancer. Journal of Proteomics, 74(4);528-538 (2011).
Zimmermann-Nielsen, E. et al. Complement activation mediated by mannan-binding lectin in plasma from healthy individuals and from patients with SLE, Crohn's disease and colorectal cancer. Suppressed activation by SLE plasma. Scandinavian Journal of Immunology, 55;105-110 (2002).
Denkert et al. Metabolite profiling of human colon carcinoma-deregulation of TCA cycle and amino acid turnover, Molecular Cancer 7(72); 1-15 (2008).
International Application No. PCT/US2015/023187 International Preliminary Report on Patentability Issued on Oct. 4, 2016.
SG Application No. 11201504241Q Search Report and Written Opinion Issued Apr. 25, 2016.
Talieri, Maroulio et al. Cathepsin B and cathepsin D expression in the progression of colorectal adenoma to carcinoma, Cancer Letters 205:97-106 (2004).
U.S. Appl. No. 14/526,181 Final Office Action Mailed Dec. 12, 2016.
U.S. Appl. No. 14/526,282 Final Office Action Mailed Dec. 2, 2016.
U.S. Appl. No. 14/526,221 Final Office Action Mailed Dec. 15, 2016.
Young, et al Fecal Tests: From Blood to Molecular Markers, Curr Colorectal Cancer Rep, 7:62-70 (2011).

* cited by examiner

FIG. 1 CRC Biomarker Development

FIG. 2 CRC Panel AUC (Validated 0.83)

FIG. 3 Advanced Adenoma Panel AUC Plot

Protein levels for CRC vs healthy control

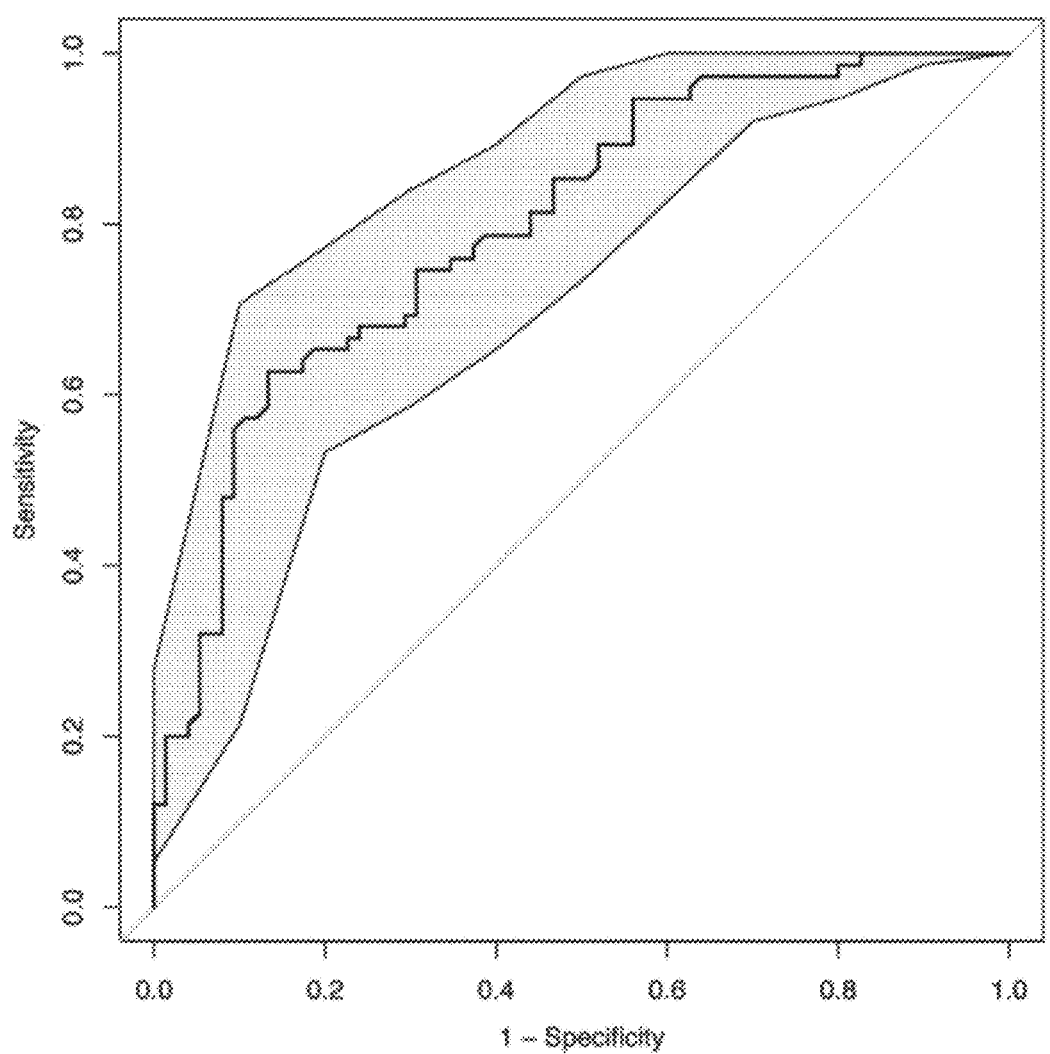
FIG. 7B Model 1 Validation ROC AUC =0.80

FIG. 8A Model 2 Discovery ROC AUC =0.84
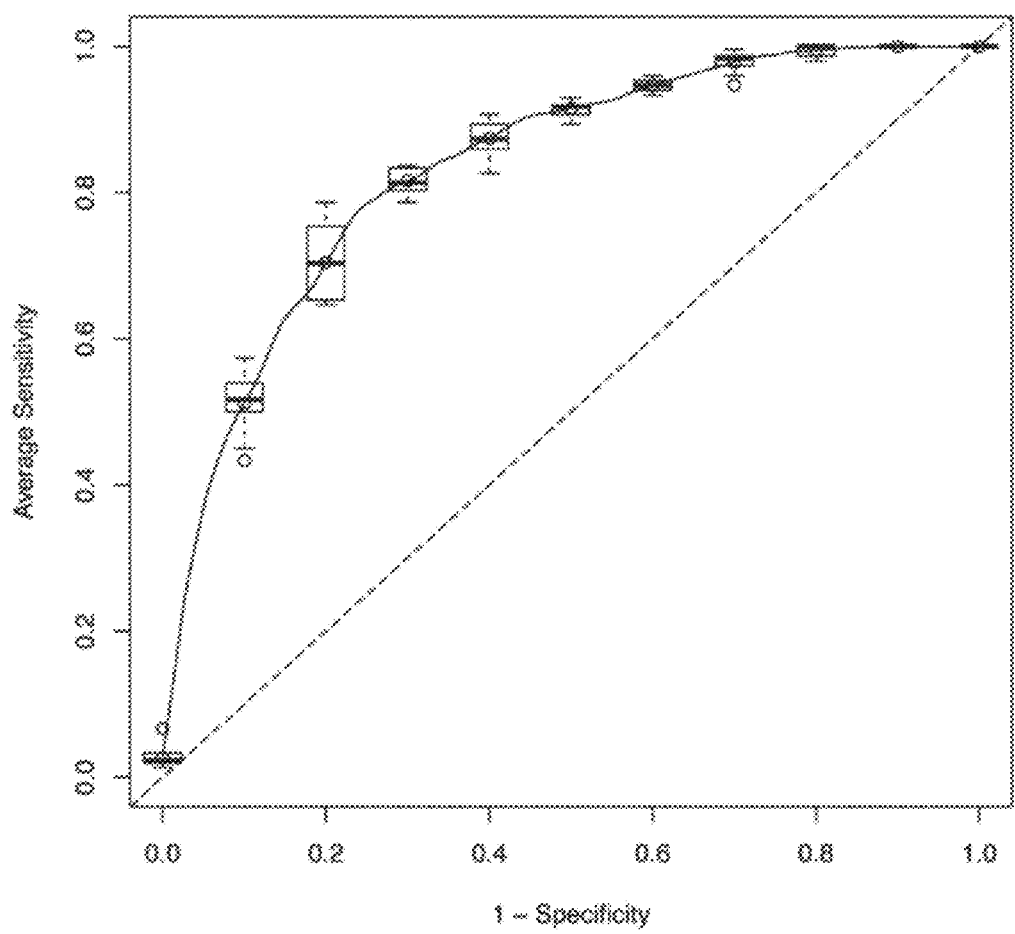

FIG. 8B Model 2 Validation ROC AUC =0.81
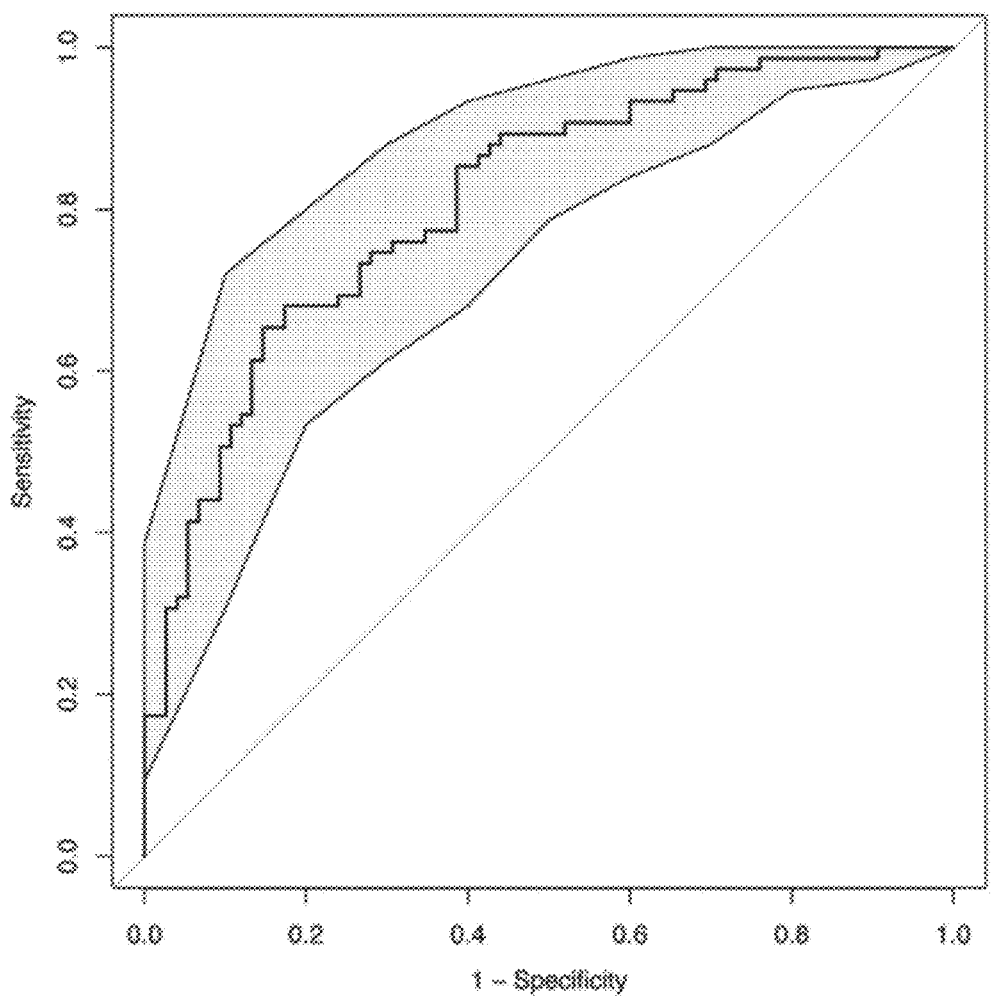

FIG. 9A Model 3 Discovery ROC AUC =0.82
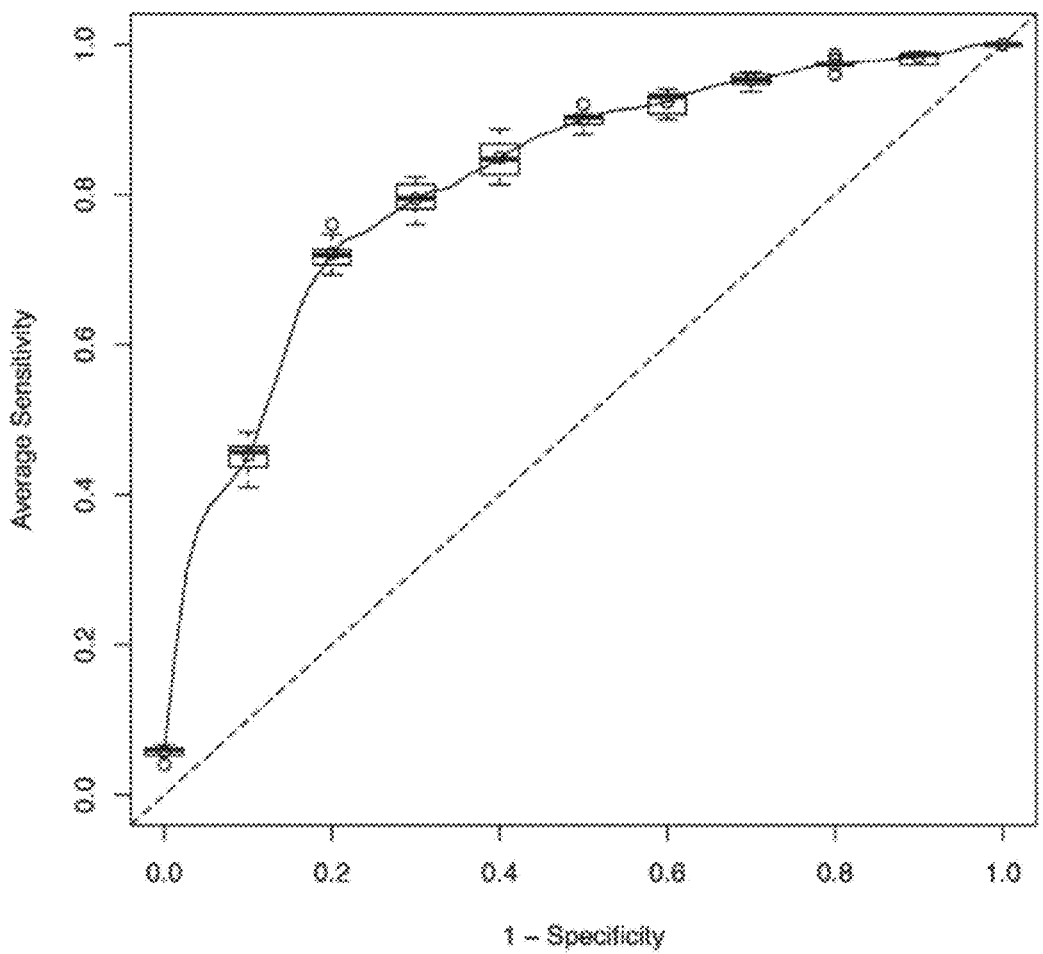

FIG. 9B Model 3 Validation ROC AUC =0.82
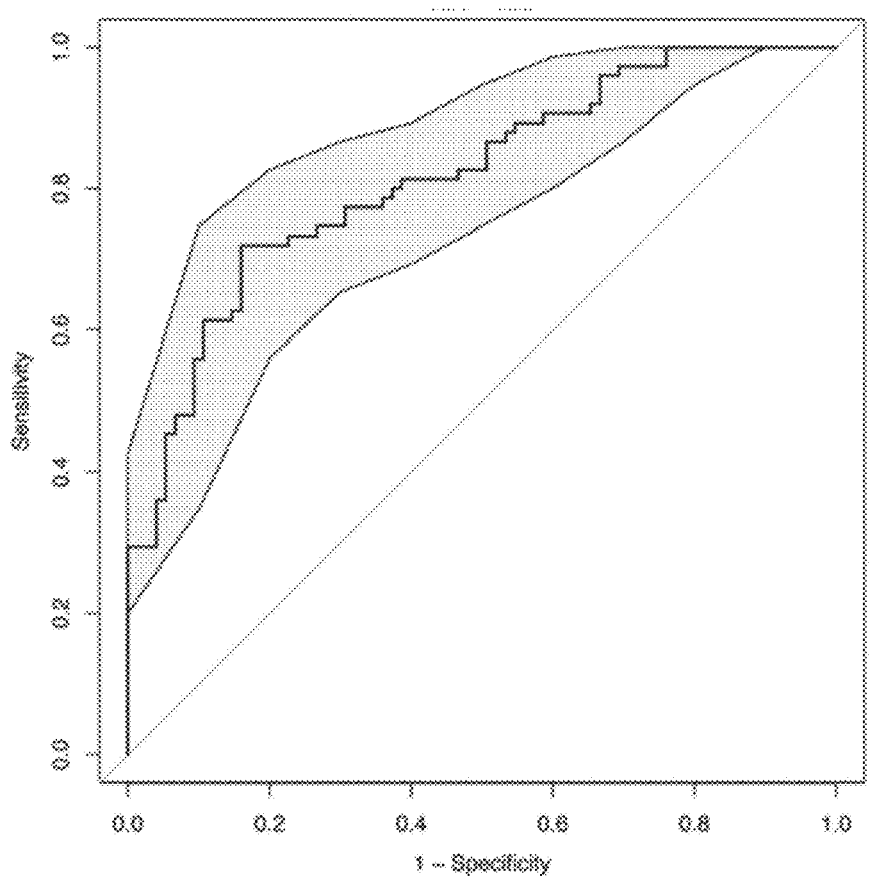

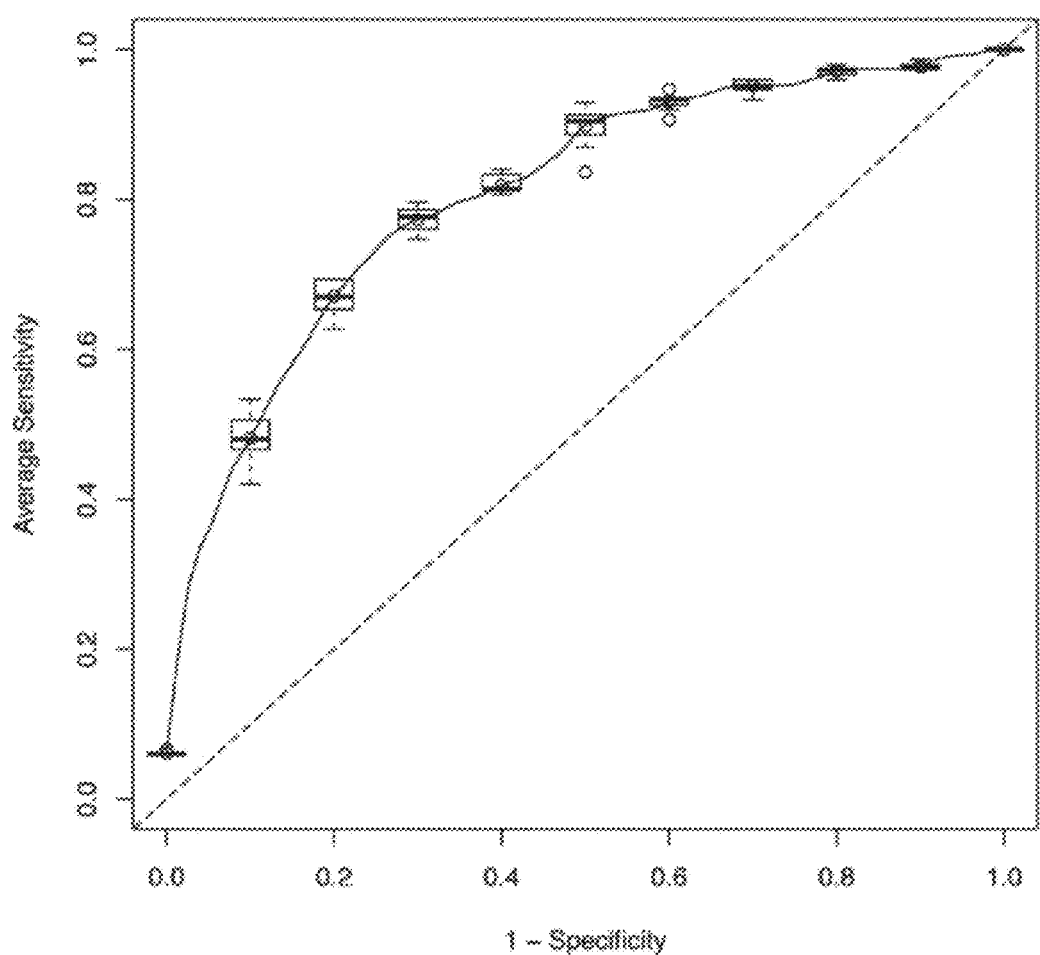
FIG. 10A Model 4 Discovery ROC AUC =0.81

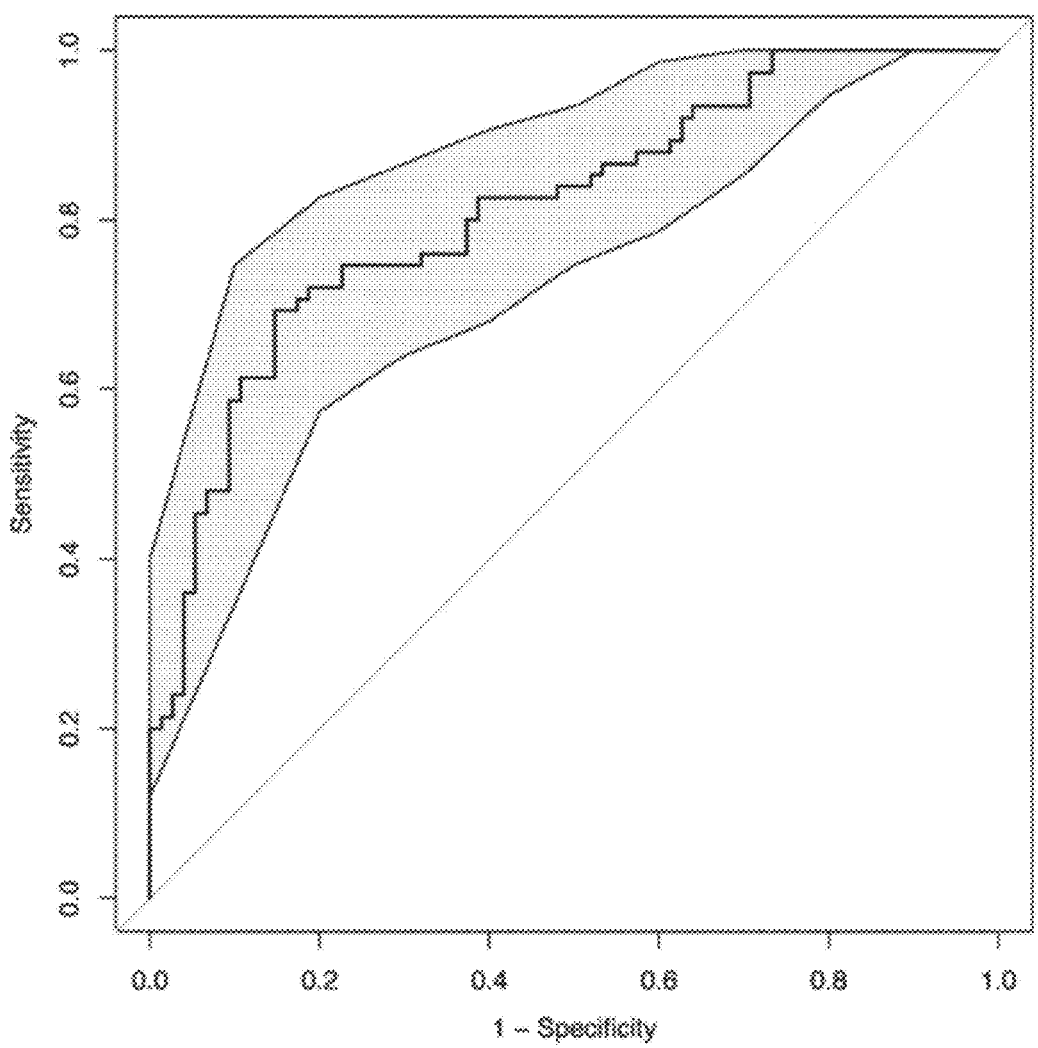
FIG. 10B Model 4 Validation ROC AUC =0.81

FIG. 11A Model 5 Discovery ROC AUC =0.86
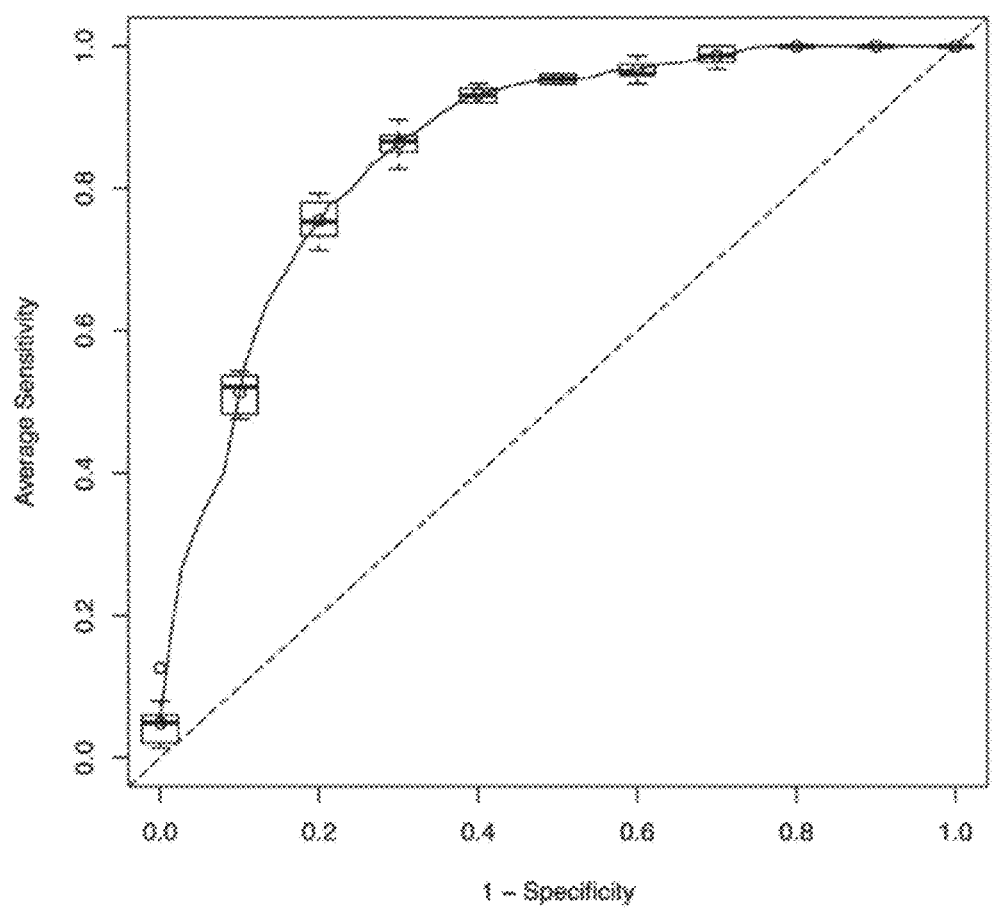

FIG. 11B Model 5 Validation ROC AUC =0.82
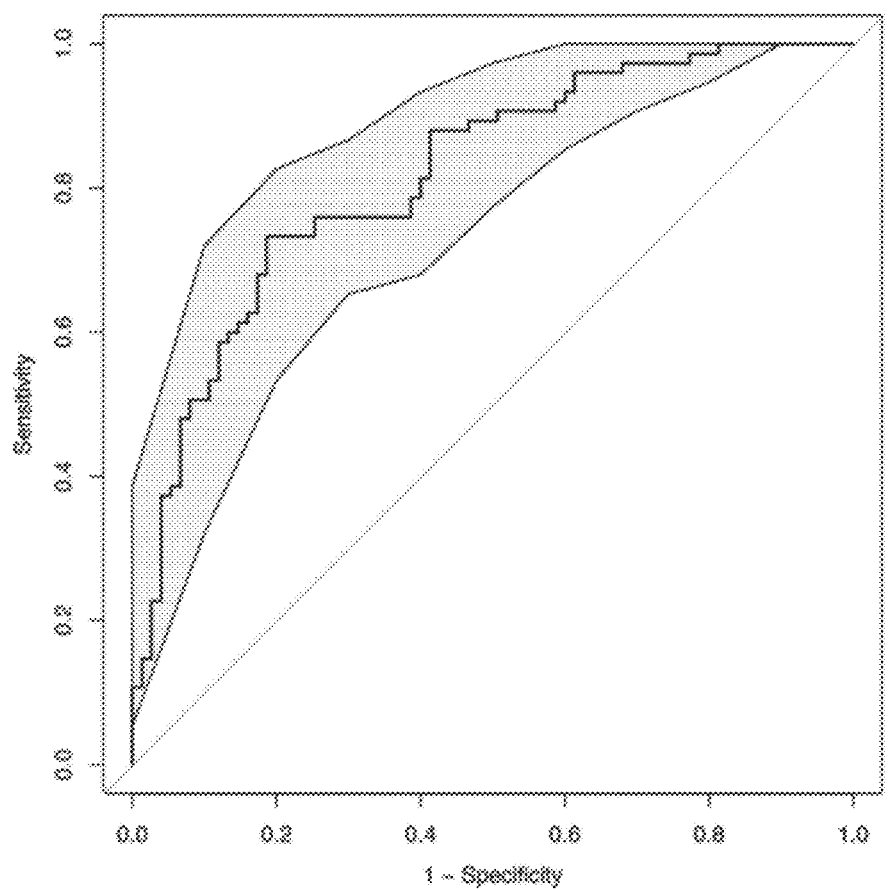

FIG. 12A Model 6 Discovery ROC AUC =0.86
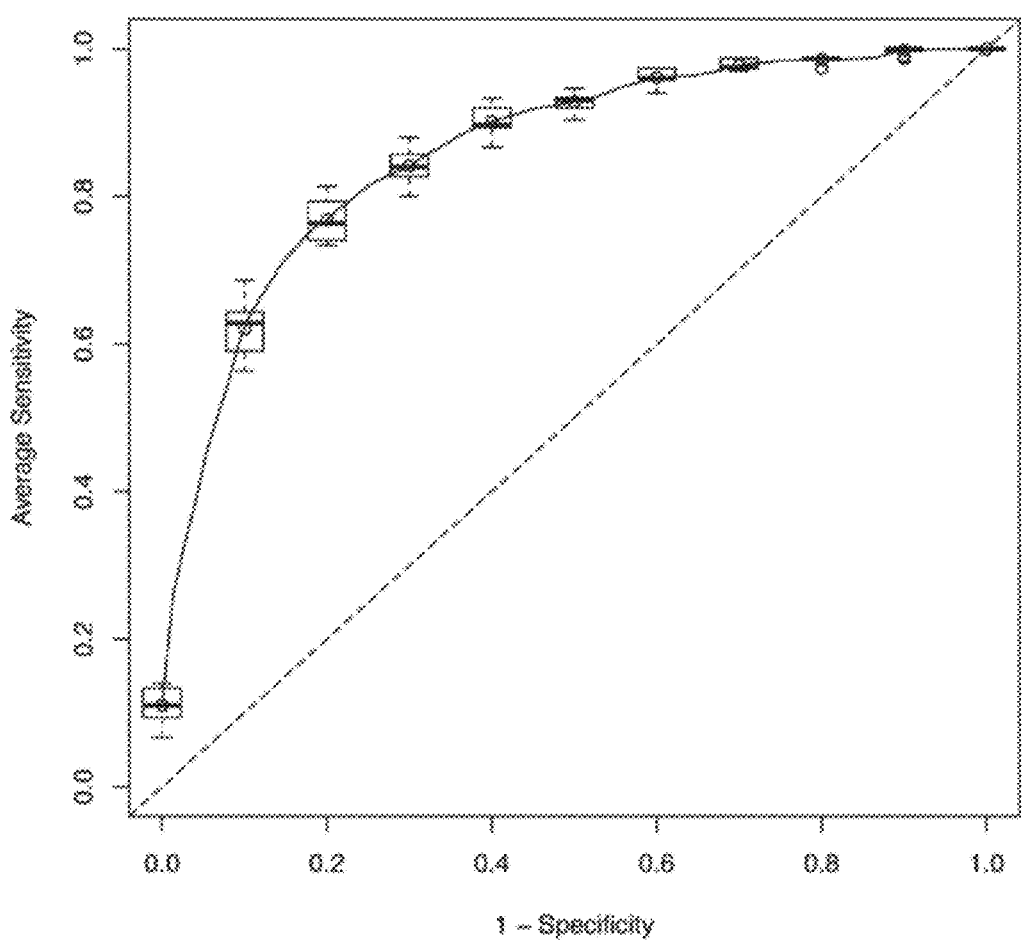

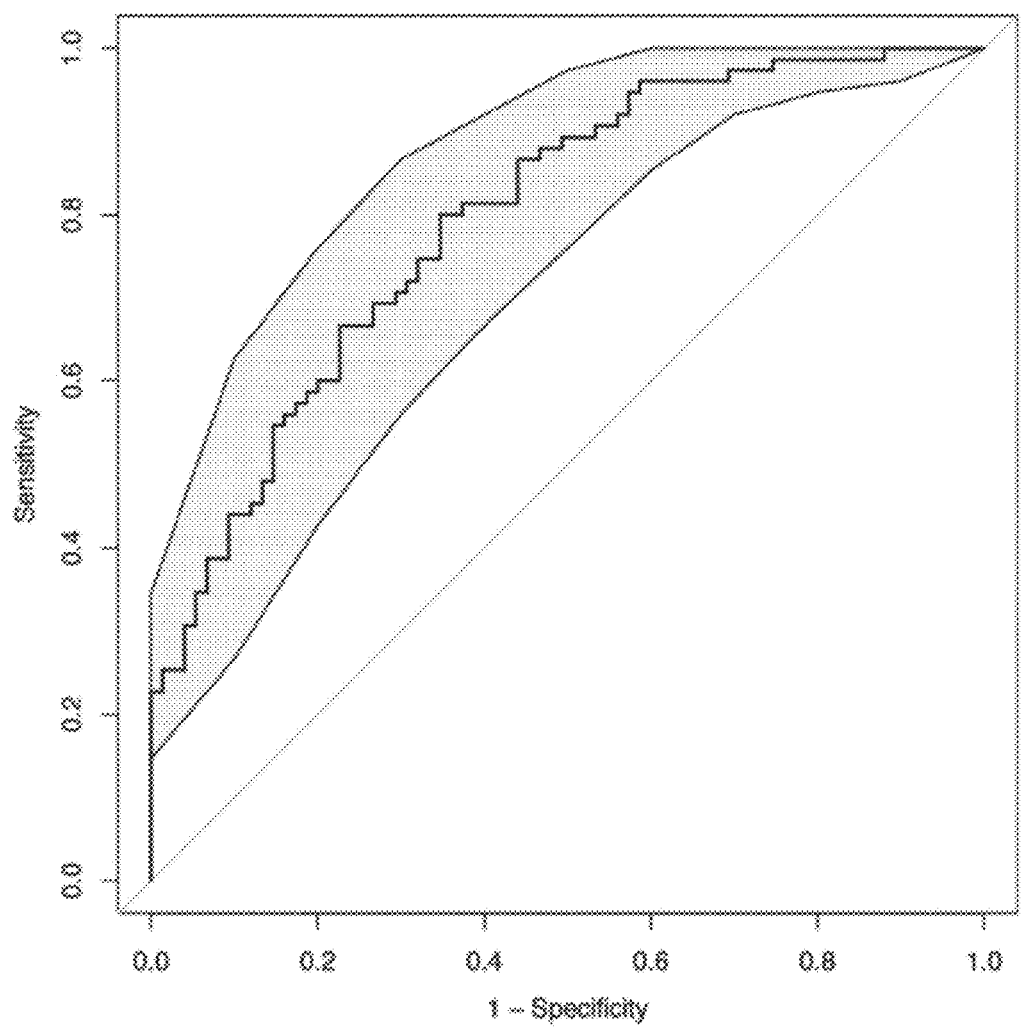
FIG. 12B Model 6 Validation ROC AUC =0.80

FIG. 13A Model 7 Discovery ROC AUC =0.83
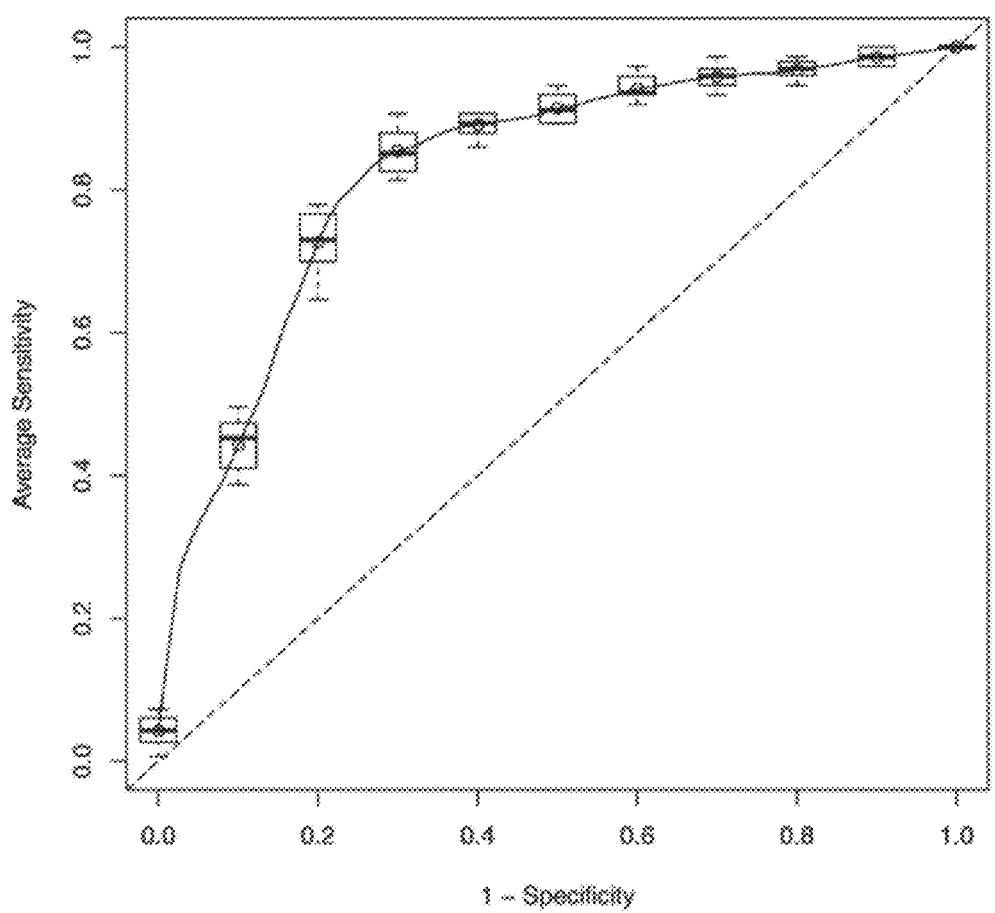

FIG. 13B Model 7 Validation ROC AUC =0.81
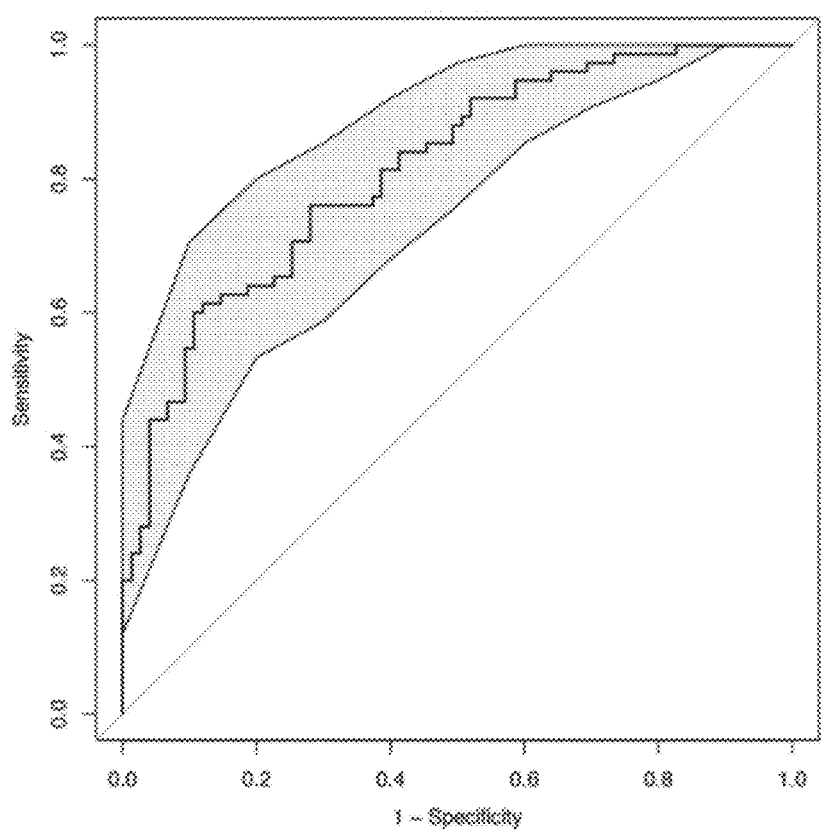

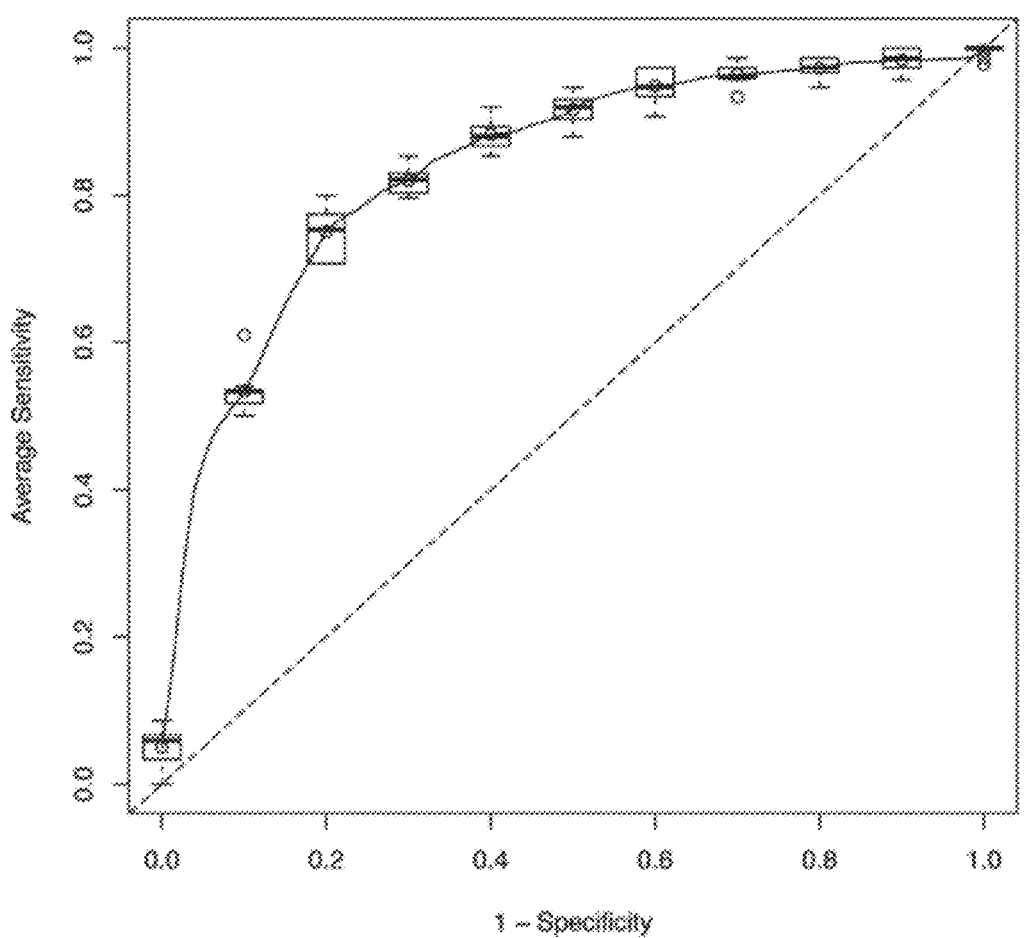
FIG. 14A Model 8 Discovery ROC AUC =0.84

FIG. 14B Model 8 Validation ROC AUC =0.78
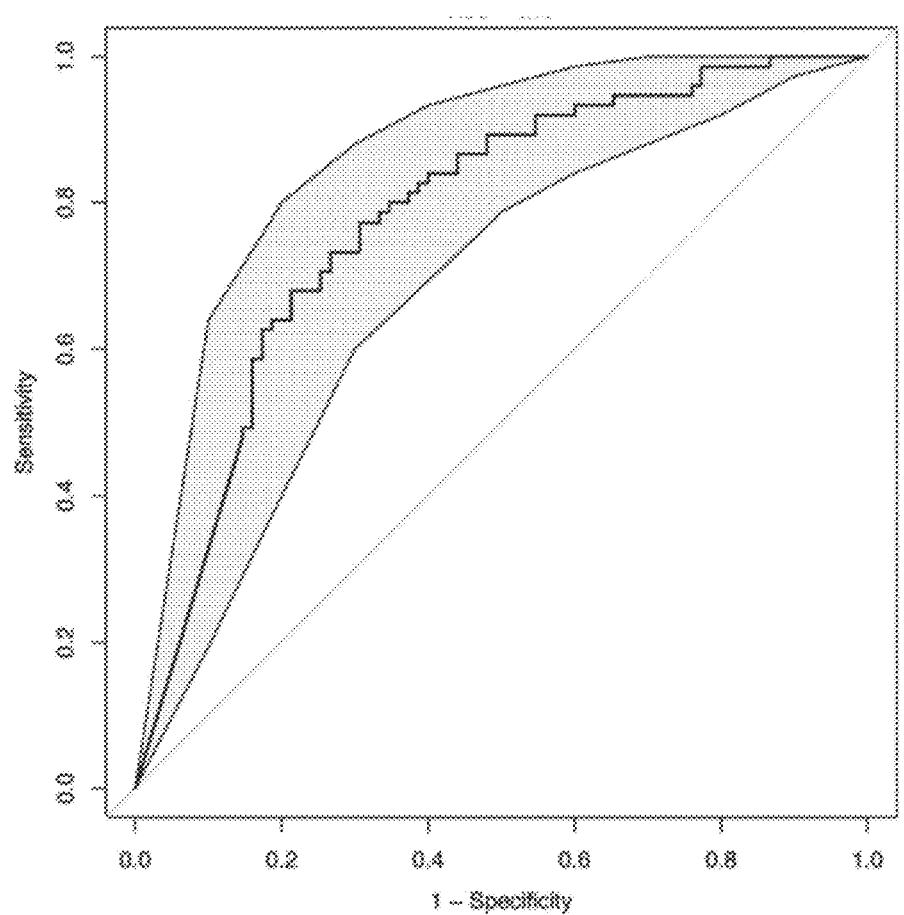

FIG. 15A Model 9 Discovery ROC AUC =0.85
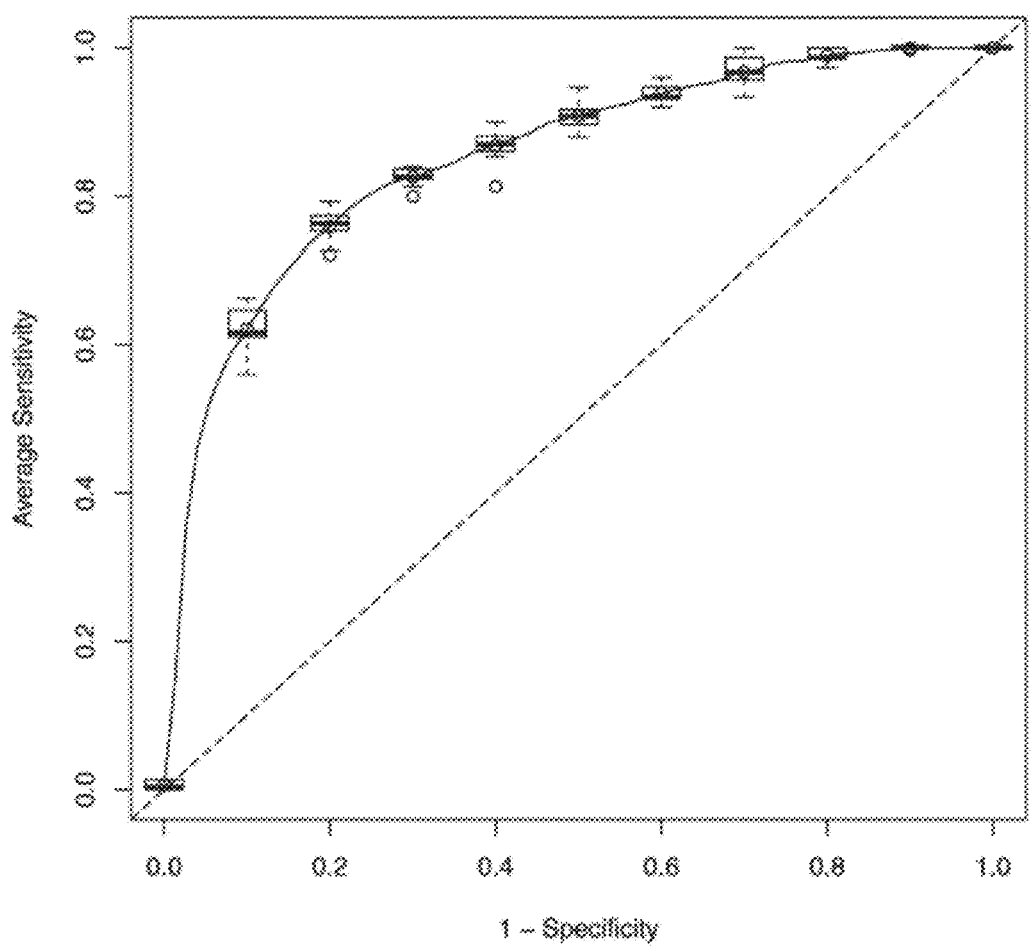

FIG. 15B Model 9 Validation ROC AUC =0.80
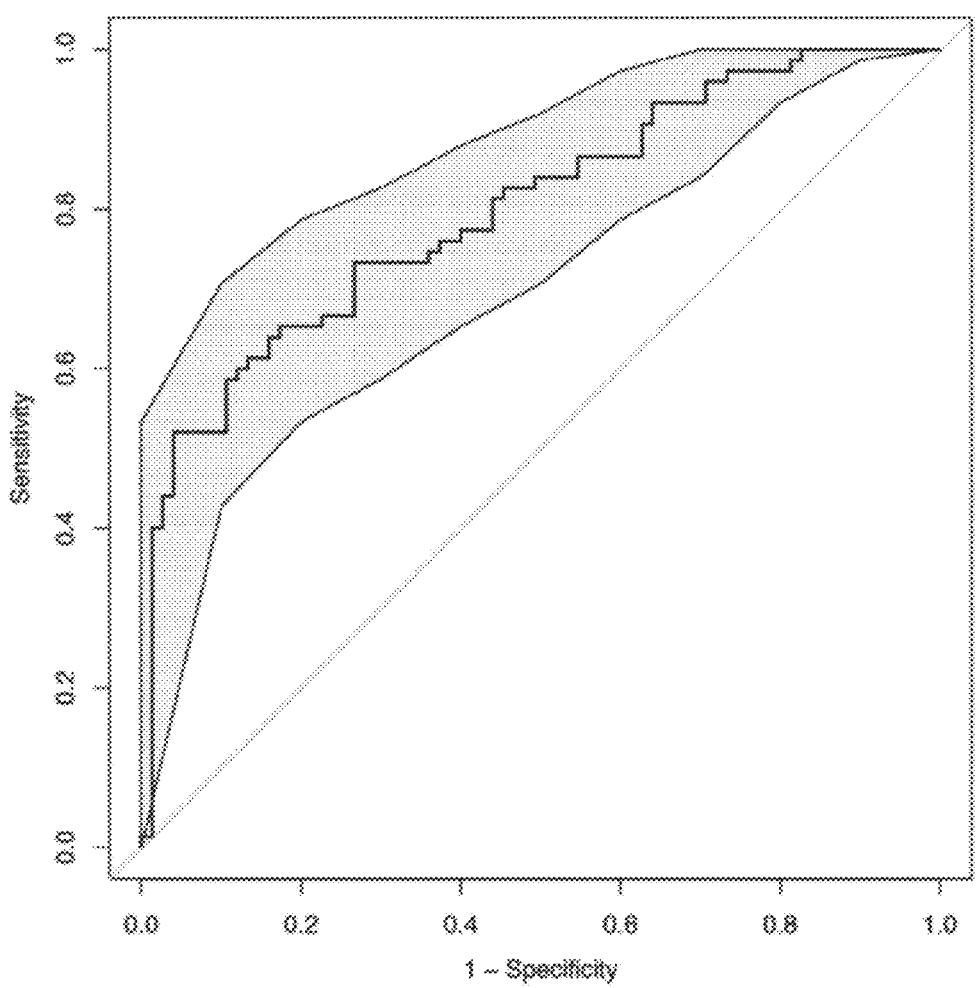

FIG. 16A Model 10 Discovery ROC AUC =0.85
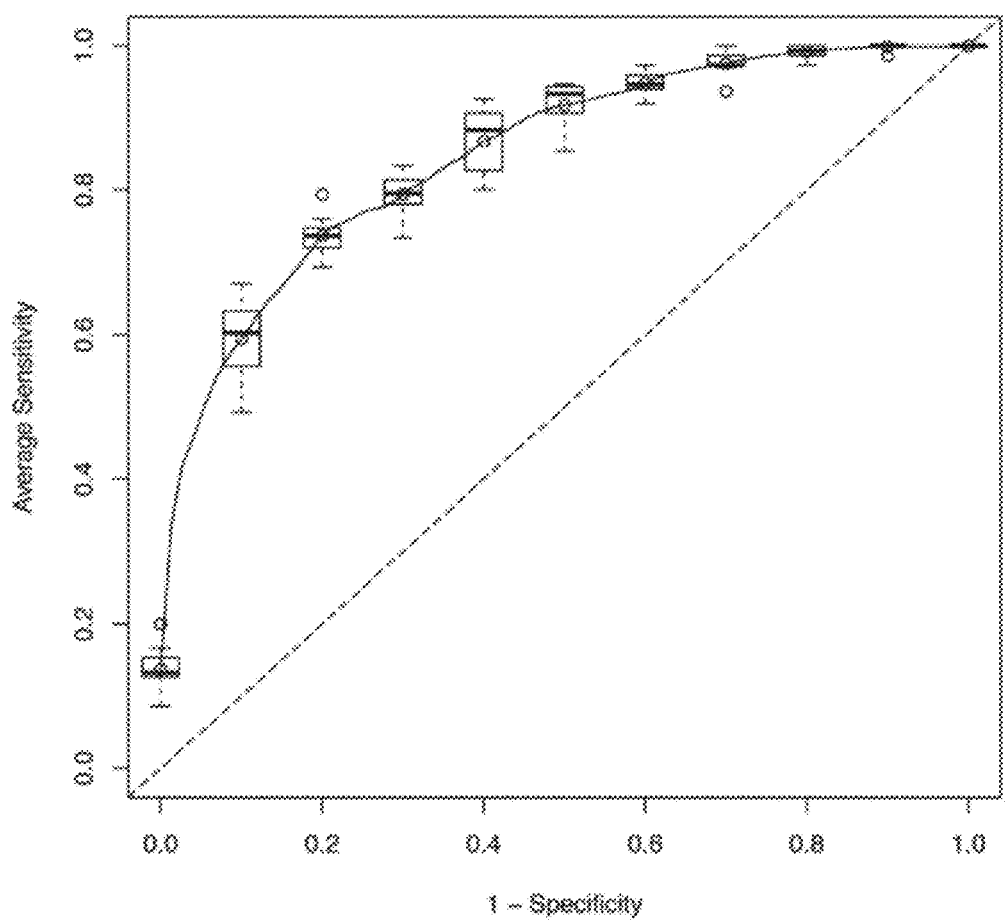

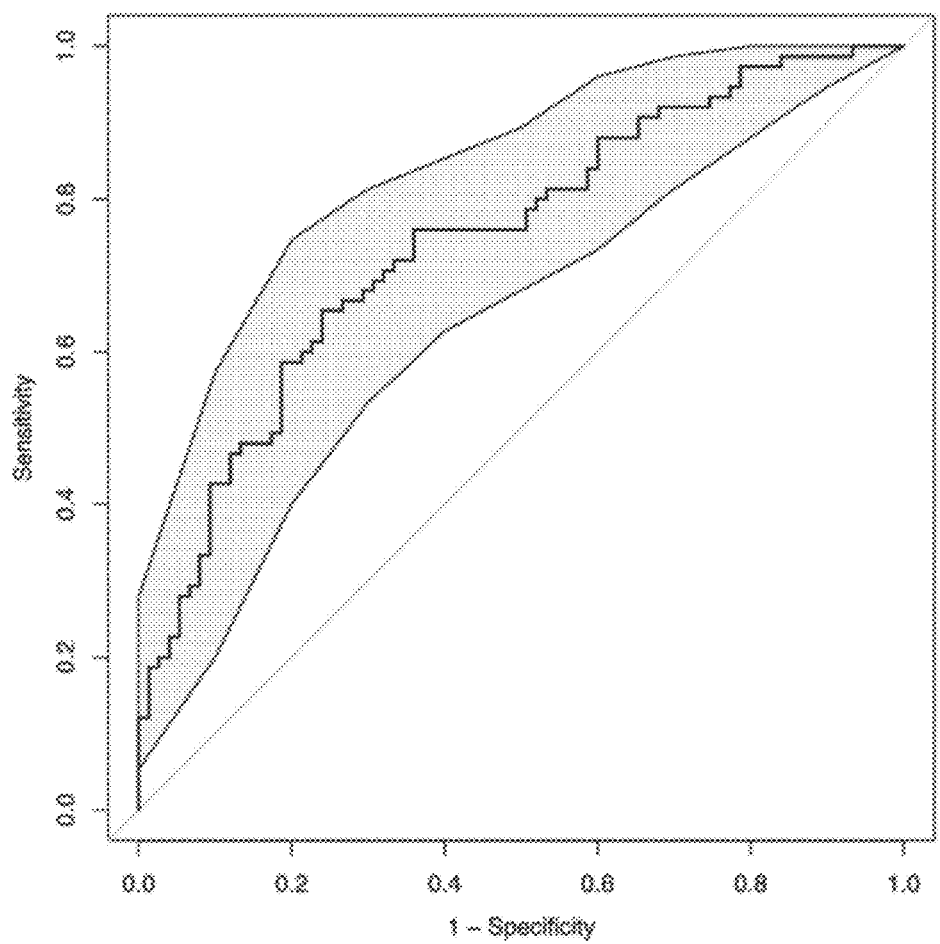
FIG. 16B Model 10 Validation ROC AUC =0.75

FIG. 17A Model 5 with NOC/Discovery ROC AUC =0.87
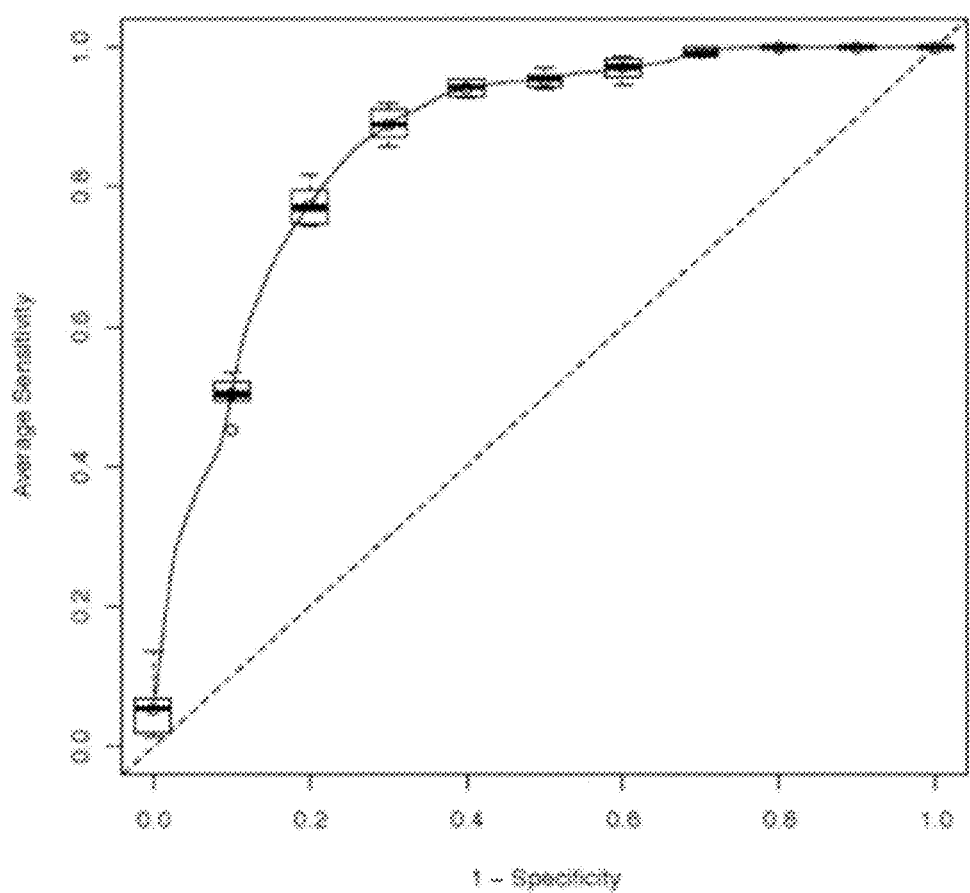

FIG. 17B Model 5 with NOC Validation ROC AUC =0.85
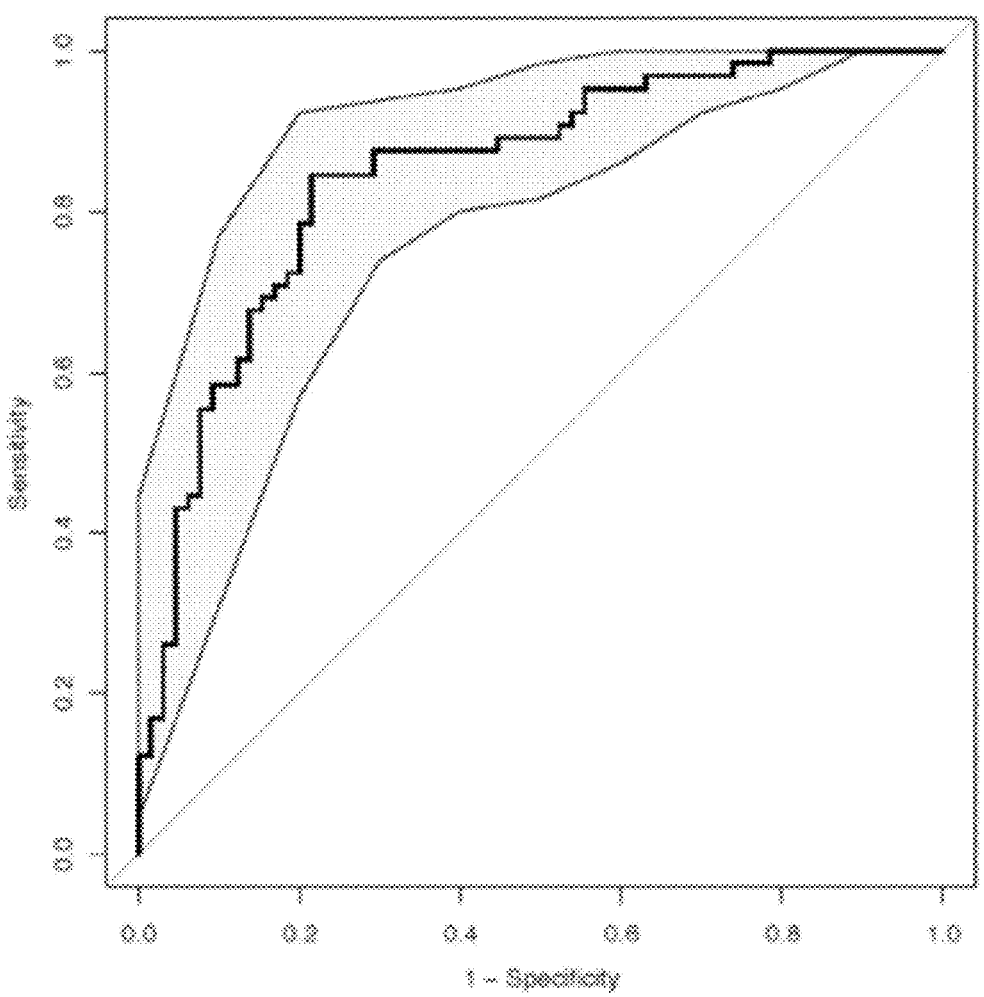

FIG. 18 Max Accuracy plot for Models 1-10
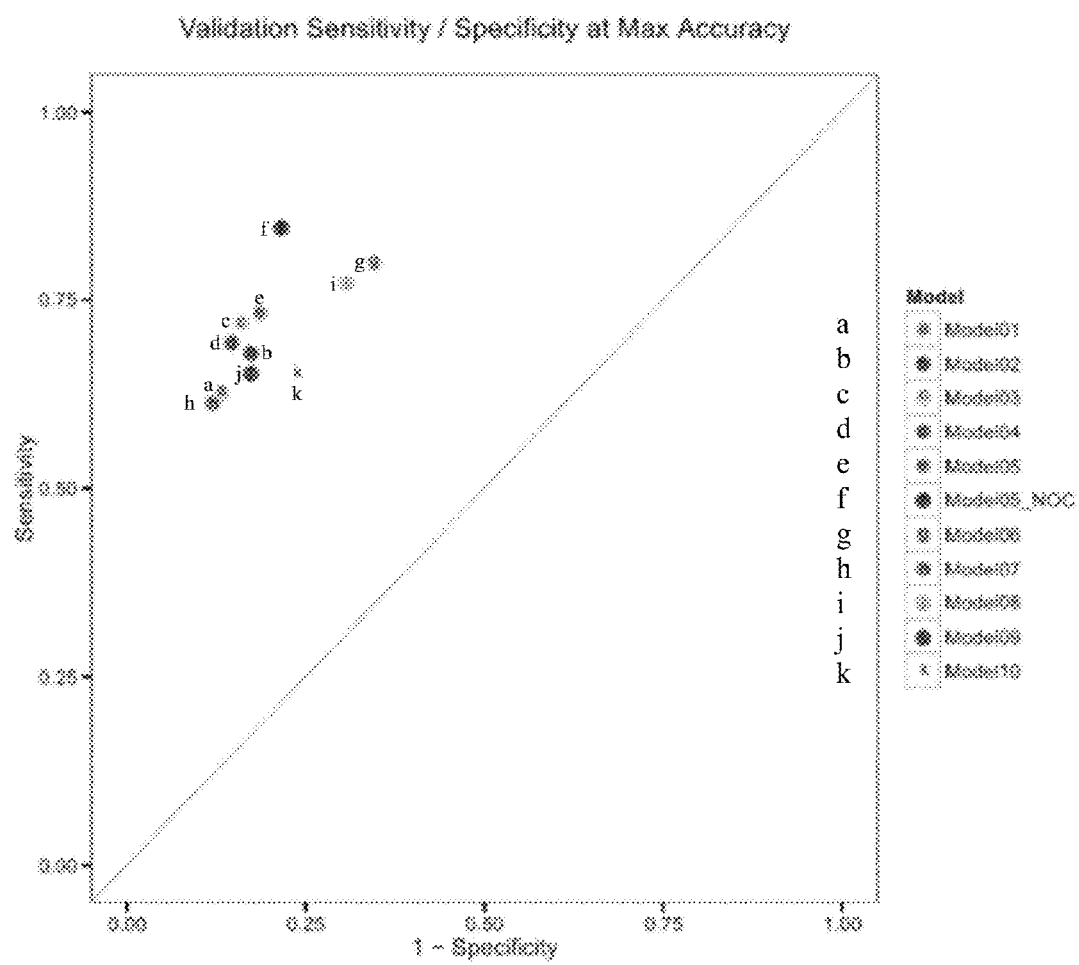

FIG. 19 – Computer System
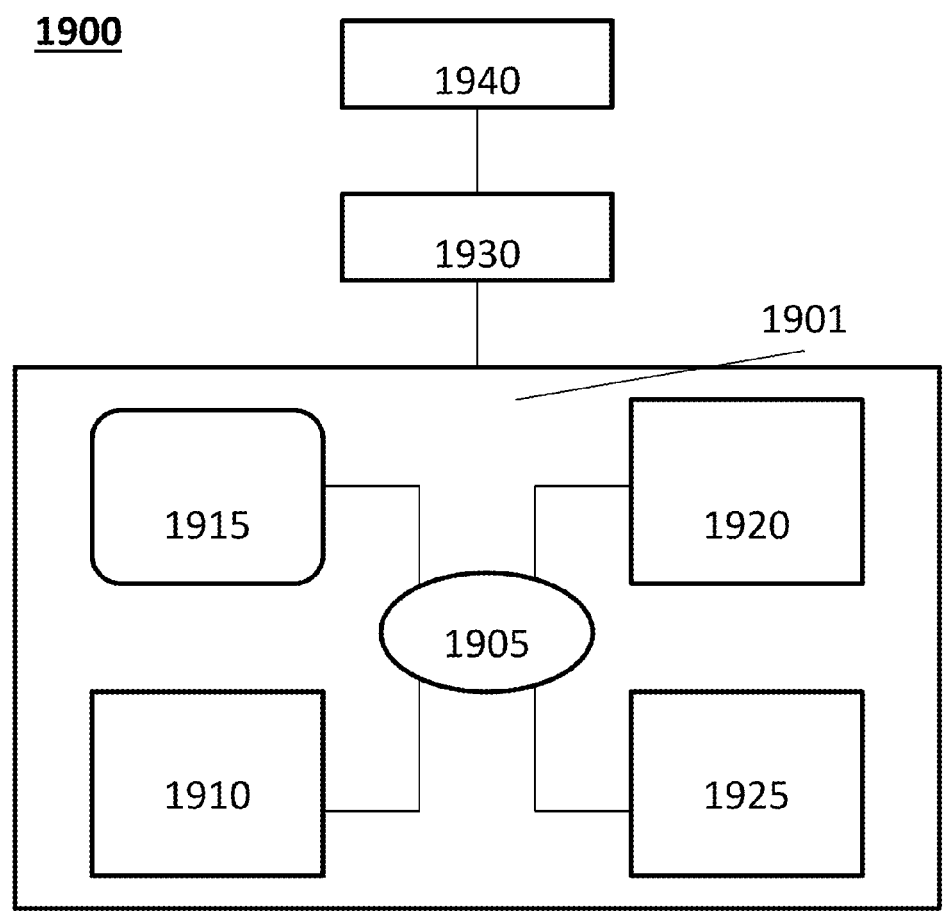

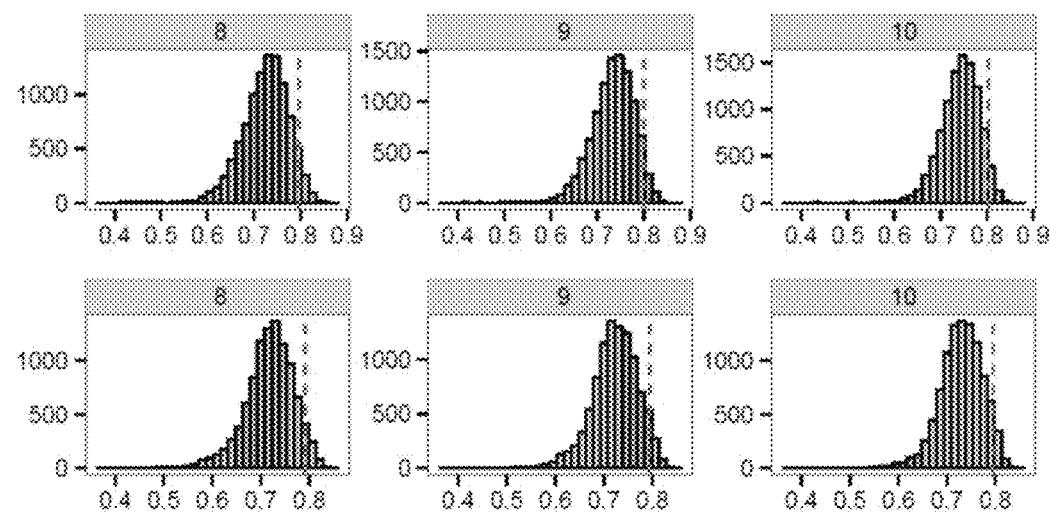
FIG. 20 Random panel AUC Distribution curves generated through SVM (top) and Random Forest (bottom)

SEQUENCE LISTING

```
<160> NUMBER OF SEQ ID NOS: 60

<210> SEQ ID NO 1
<211> LENGTH: 201
<212> TYPE: PRT
<213> ORGANISM: Homo sapiens

<400> SEQUENCE: 1

Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
            20                  25                  30

Asn Ala Thr Leu Asp Gln Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asp Gln Cys Ile Tyr Asn Thr Thr Tyr
                85                  90                  95

Leu Asn Val Gln Arg Glu Asn Gly Thr Ile Ser Arg Tyr Val Gly Gly
            100                 105                 110

Gln Glu His Phe Ala His Leu Leu Ile Leu Arg Asp Thr Lys Thr Tyr
        115                 120                 125
```

```
Met Leu Ala Phe Asp Val Asn Asp Glu Lys Asn Trp Gly Leu Ser Val
            130                 135                 140

Tyr Ala Asp Lys Pro Glu Thr Thr Lys Glu Gln Leu Gly Glu Phe Tyr
145                 150                 155                 160

Glu Ala Leu Asp Cys Leu Arg Ile Pro Lys Ser Asp Val Val Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
            195                 200

<210> SEQ ID NO 2
<211> LENGTH: 418
<212> TYPE: PRT
<213> ORGANISM: Homo sapiens

<400> SEQUENCE: 2

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
```

```
            290                 295                 300
Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Ala Pro Leu Lys
                340                 345                 350

Leu Ser Lys Ala Val His Lys Ala Val Leu Thr Ile Asp Glu Lys Gly
                355                 360                 365

Thr Glu Ala Ala Gly Ala Met Phe Leu Glu Ala Ile Pro Met Ser Ile
        370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 3
<211> LENGTH: 423
<212> TYPE: PRT
<213> ORGANISM: Homo sapiens

<400> SEQUENCE: 3

Met Glu Arg Met Leu Pro Leu Leu Ala Leu Gly Leu Leu Ala Ala Gly
1               5                   10                  15

Phe Cys Pro Ala Val Leu Cys His Pro Asn Ser Pro Leu Asp Glu Glu
                20                  25                  30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
        50                  55                  60

Val Leu Lys Ala Pro Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
                85                  90                  95

Thr Glu Ile Leu Lys Gly Leu Lys Phe Asn Leu Thr Glu Thr Ser Glu
                100                 105                 110

Ala Glu Ile His Gln Ser Phe Gln His Leu Leu Arg Thr Leu Asn Gln
            115                 120                 125

Ser Ser Asp Glu Leu Gln Leu Ser Met Gly Asn Ala Met Phe Val Lys
        130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
            180                 185                 190

Thr Asp Leu Ile Lys Asp Leu Asp Ser Gln Thr Met Met Val Leu Val
        195                 200                 205

Asn Tyr Ile Phe Phe Lys Ala Lys Trp Glu Met Pro Phe Asp Pro Gln
            210                 215                 220

Asp Thr His Gln Ser Arg Phe Tyr Leu Ser Lys Lys Lys Trp Val Met
225                 230                 235                 240

Val Pro Met Met Ser Leu His His Leu Thr Ile Pro Tyr Phe Arg Asp
```

```
                    245                 250                 255
Glu Glu Leu Ser Cys Thr Val Val Glu Leu Lys Tyr Thr Gly Asn Ala
                260                 265                 270

Ser Ala Leu Phe Ile Leu Pro Asp Gln Asp Lys Met Glu Glu Val Glu
            275                 280                 285

Ala Met Leu Leu Pro Glu Thr Leu Lys Arg Trp Arg Asp Ser Leu Glu
        290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Ala
                325                 330                 335

Phe Thr Ser Lys Ala Asp Leu Ser Gly Ile Thr Gly Ala Arg Asn Leu
                340                 345                 350

Ala Val Ser Gln Val Val His Lys Ala Val Leu Asp Val Phe Glu Glu
            355                 360                 365

Gly Thr Glu Ala Ser Ala Ala Thr Ala Val Lys Ile Thr Leu Leu Ser
        370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Lys Gln Ala
                420

<210> SEQ ID NO 4
<211> LENGTH: 267
<212> TYPE: PRT
<213> ORGANISM: Homo sapiens

<400> SEQUENCE: 4

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190
```

```
Glu Leu Arg Gln Arg Leu Ala Ala Arg Leu Gly Ala Leu Lys Glu Asn
            195                 200                 205

Gly Gly Ala Arg Leu Ala Glu Tyr His Ala Lys Ala Thr Glu His Leu
        210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

<210> SEQ ID NO 5
<211> LENGTH: 412
<212> TYPE: PRT
<213> ORGANISM: Homo sapiens

<400> SEQUENCE: 5

```
Met Gln Pro Ser Ser Leu Leu Pro Leu Ala Leu Cys Leu Leu Ala Ala
1               5                   10                  15

Pro Ala Ser Ala Leu Val Arg Ile Pro Leu His Lys Phe Thr Ser Ile
                20                  25                  30

Arg Arg Thr Met Ser Glu Val Gly Gly Ser Val Glu Asp Leu Ile Ala
            35                  40                  45

Lys Gly Pro Val Ser Lys Tyr Ser Gln Ala Val Pro Ala Val Thr Glu
50                  55                  60

Gly Pro Ile Pro Glu Val Leu Lys Asn Tyr Met Asp Ala Gln Tyr Tyr
65                  70                  75                  80

Gly Glu Ile Gly Ile Gly Thr Pro Pro Gln Cys Phe Thr Val Val Phe
            85                  90                  95

Asp Thr Gly Ser Ser Asn Leu Trp Val Pro Ser Ile His Cys Lys Leu
                100                 105                 110

Leu Asp Ile Ala Cys Trp Ile His His Lys Tyr Asn Ser Asp Lys Ser
            115                 120                 125

Ser Thr Tyr Val Lys Asn Gly Thr Ser Phe Asp Ile His Tyr Gly Ser
            130                 135                 140

Gly Ser Leu Ser Gly Tyr Leu Ser Gln Asp Thr Val Ser Val Pro Cys
145                 150                 155                 160

Gln Ser Ala Ser Ala Ser Ala Leu Gly Gly Val Lys Val Glu Arg
                165                 170                 175

Gln Val Phe Gly Glu Ala Thr Lys Gln Pro Gly Ile Thr Phe Ile Ala
            180                 185                 190

Ala Lys Phe Asp Gly Ile Leu Gly Met Ala Tyr Pro Arg Ile Ser Val
            195                 200                 205

Asn Asn Val Leu Pro Val Phe Asp Asn Leu Met Gln Gln Lys Leu Val
            210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
                245                 250                 255

Gly Ser Leu Ser Tyr Leu Asn Val Thr Arg Lys Ala Tyr Trp Gln Val
            260                 265                 270

His Leu Asp Gln Val Glu Val Ala Ser Gly Leu Thr Leu Cys Lys Glu
            275                 280                 285

Gly Cys Glu Ala Ile Val Asp Thr Gly Thr Ser Leu Met Val Gly Pro
            290                 295                 300
```

```
Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
                325                 330                 335

Ala Ile Thr Leu Lys Leu Gly Lys Gly Tyr Lys Leu Ser Pro Glu
            340                 345                 350

Asp Tyr Thr Leu Lys Val Ser Gln Ala Gly Lys Thr Leu Cys Leu Ser
            355                 360                 365

Gly Phe Met Gly Met Asp Ile Pro Pro Ser Gly Pro Leu Trp Ile
370                 375                 380

Leu Gly Asp Val Phe Ile Gly Arg Tyr Tyr Thr Val Phe Asp Arg Asp
385                 390                 395                 400

Asn Asn Arg Val Gly Phe Ala Glu Ala Ala Arg Leu
                405                 410

<210> SEQ ID NO 6
<211> LENGTH: 252
<212> TYPE: PRT
<213> ORGANISM: Homo sapiens

<400> SEQUENCE: 6

Met Gly Pro Pro Ser Ala Ser Pro His Arg Glu Cys Ile Pro Trp Gln
1               5                   10                  15

Gly Leu Leu Leu Thr Ala Ser Leu Leu Asn Phe Trp Asn Pro Pro Thr
            20                  25                  30

Thr Ala Lys Leu Thr Ile Glu Ser Met Pro Leu Ser Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Ala Ala Tyr Ser
                85                  90                  95

Gly Arg Glu Thr Ile Tyr Thr Asn Ala Ser Leu Leu Ile Gln Asn Val
            100                 105                 110

Thr Gln Asn Asp Ile Gly Phe Tyr Thr Leu Gln Val Ile Lys Ser Asp
        115                 120                 125

Leu Val Asn Glu Glu Ala Thr Gly Gln Phe His Val Tyr Gln Glu Asn
    130                 135                 140

Ala Pro Gly Leu Pro Val Gly Ala Val Ala Gly Ile Val Thr Gly Val
145                 150                 155                 160

Leu Val Gly Val Ala Leu Val Ala Ala Leu Val Cys Phe Leu Leu Leu
                165                 170                 175

Ala Lys Thr Gly Arg Thr Ser Ile Gln Arg Asp Leu Lys Glu Gln Gln
            180                 185                 190

Pro Gln Ala Leu Ala Pro Gly Arg Gly Pro Ser His Ser Ser Ala Phe
        195                 200                 205

Ser Met Ser Pro Leu Ser Thr Ala Gln Ala Pro Leu Pro Asn Pro Arg
    210                 215                 220

Thr Ala Ala Ser Ile Tyr Glu Glu Leu Leu Lys His Asp Thr Asn Ile
225                 230                 235                 240

Tyr Cys Arg Met Asp His Lys Ala Glu Val Ala Ser
                245                 250
```

```
<210> SEQ ID NO 7
<211> LENGTH: 449
<212> TYPE: PRT
<213> ORGANISM: Homo sapiens

<400> SEQUENCE: 7

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Pro Lys Ser Arg
    210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu
    370                 375                 380
```

```
Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
            405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
            435                 440                 445

Glu

<210> SEQ ID NO 8
<211> LENGTH: 1663
<212> TYPE: PRT
<213> ORGANISM: Homo sapiens

<400> SEQUENCE: 8

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
                20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
        50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
290                 295                 300
```

-continued

```
Lys Val Leu Leu Asp Gly Val Gln Asn Pro Arg Ala Glu Asp Leu Val
305                 310                 315                 320
Gly Lys Ser Leu Tyr Val Ser Ala Thr Val Ile Leu His Ser Gly Ser
                325                 330                 335
Asp Met Val Gln Ala Glu Arg Ser Gly Ile Pro Ile Val Thr Ser Pro
            340                 345                 350
Tyr Gln Ile His Phe Thr Lys Thr Pro Lys Tyr Phe Lys Pro Gly Met
        355                 360                 365
Pro Phe Asp Leu Met Val Phe Val Thr Asn Pro Asp Gly Ser Pro Ala
    370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
            420                 425                 430
Glu Ala Glu Gln Ala Thr Arg Thr Met Gln Ala Leu Pro Tyr Ser Thr
        435                 440                 445
Val Gly Asn Ser Asn Asn Tyr Leu His Leu Ser Val Leu Arg Thr Glu
    450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                485                 490                 495
Lys Gly Arg Leu Leu Lys Ala Gly Arg Gln Val Arg Glu Pro Gly Gln
            500                 505                 510
Asp Leu Val Val Leu Pro Leu Ser Ile Thr Thr Asp Phe Ile Pro Ser
        515                 520                 525
Phe Arg Leu Val Ala Tyr Tyr Thr Leu Ile Gly Ala Ser Gly Gln Arg
    530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
                565                 570                 575
Pro Gly Gln Gln Met Thr Leu Lys Ile Glu Gly Asp His Gly Ala Arg
            580                 585                 590
Val Val Leu Val Ala Val Asp Lys Gly Val Phe Val Leu Asn Lys Lys
    595                 600                 605
Asn Lys Leu Thr Gln Ser Lys Ile Trp Asp Val Val Glu Lys Ala Asp
610                 615                 620
Ile Gly Cys Thr Pro Gly Ser Gly Lys Asp Tyr Ala Gly Val Phe Ser
625                 630                 635                 640
Asp Ala Gly Leu Thr Phe Thr Ser Ser Ser Gly Gln Gln Thr Ala Gln
                645                 650                 655
Arg Ala Glu Leu Gln Cys Pro Gln Pro Ala Ala Arg Arg Arg Arg Ser
            660                 665                 670
Val Gln Leu Thr Glu Lys Arg Met Asp Lys Val Gly Lys Tyr Pro Lys
        675                 680                 685
Glu Leu Arg Lys Cys Cys Glu Asp Gly Met Arg Glu Asn Pro Met Arg
    690                 695                 700
Phe Ser Cys Gln Arg Arg Thr Arg Phe Ile Ser Leu Gly Glu Ala Cys
705                 710                 715                 720
Lys Lys Val Phe Leu Asp Cys Cys Asn Tyr Ile Thr Glu Leu Arg Arg
```

-continued

```
                725                 730                 735
Gln His Ala Arg Ala Ser His Leu Gly Leu Ala Arg Ser Asn Leu Asp
            740                 745                 750
Glu Asp Ile Ile Ala Glu Asn Ile Val Ser Arg Ser Glu Phe Pro
            755                 760                 765
Glu Ser Trp Leu Trp Asn Val Glu Asp Leu Lys Glu Pro Pro Lys Asn
770                 775                 780
Gly Ile Ser Thr Lys Leu Met Asn Ile Phe Leu Lys Asp Ser Ile Thr
785                 790                 795                 800
Thr Trp Glu Ile Leu Ala Val Ser Met Ser Asp Lys Lys Gly Ile Cys
                805                 810                 815
Val Ala Asp Pro Phe Glu Val Thr Val Met Gln Asp Phe Phe Ile Asp
            820                 825                 830
Leu Arg Leu Pro Tyr Ser Val Val Arg Asn Glu Gln Val Glu Ile Arg
            835                 840                 845
Ala Val Leu Tyr Asn Tyr Arg Gln Asn Gln Glu Leu Lys Val Arg Val
850                 855                 860
Glu Leu Leu His Asn Pro Ala Phe Cys Ser Leu Ala Thr Thr Lys Arg
865                 870                 875                 880
Arg His Gln Gln Thr Val Thr Ile Pro Pro Lys Ser Ser Leu Ser Val
                885                 890                 895
Pro Tyr Val Ile Val Pro Leu Lys Thr Gly Leu Gln Glu Val Glu Val
            900                 905                 910
Lys Ala Ala Val Tyr His His Phe Ile Ser Asp Gly Val Arg Lys Ser
            915                 920                 925
Leu Lys Val Val Pro Glu Gly Ile Arg Met Asn Lys Thr Val Ala Val
930                 935                 940
Arg Thr Leu Asp Pro Glu Arg Leu Gly Arg Glu Gly Val Gln Lys Glu
945                 950                 955                 960
Asp Ile Pro Pro Ala Asp Leu Ser Asp Gln Val Pro Asp Thr Glu Ser
                965                 970                 975
Glu Thr Arg Ile Leu Leu Gln Gly Thr Pro Val Ala Gln Met Thr Glu
            980                 985                 990
Asp Ala Val Asp Ala Glu Arg Leu Lys His Leu Ile Val Thr Pro Ser
            995                 1000                1005
Gly Cys Gly Glu Gln Asn Met Ile Gly Met Thr Pro Thr Val Ile
            1010                1015                1020
Ala Val His Tyr Leu Asp Glu Thr Glu Gln Trp Glu Lys Phe Gly
            1025                1030                1035
Leu Glu Lys Arg Gln Gly Ala Leu Glu Leu Ile Lys Lys Gly Tyr
            1040                1045                1050
Thr Gln Gln Leu Ala Phe Arg Gln Pro Ser Ser Ala Phe Ala Ala
            1055                1060                1065
Phe Val Lys Arg Ala Pro Ser Thr Trp Leu Thr Ala Tyr Val Val
            1070                1075                1080
Lys Val Phe Ser Leu Ala Val Asn Leu Ile Ala Ile Asp Ser Gln
            1085                1090                1095
Val Leu Cys Gly Ala Val Lys Trp Leu Ile Leu Glu Lys Gln Lys
            1100                1105                1110
Pro Asp Gly Val Phe Gln Glu Asp Ala Pro Val Ile His Gln Glu
            1115                1120                1125
Met Ile Gly Gly Leu Arg Asn Asn Asn Glu Lys Asp Met Ala Leu
            1130                1135                1140
```

-continued

Thr Ala Phe Val Leu Ile Ser Leu Gln Glu Ala Lys Asp Ile Cys
1145                1150                1155

Glu Glu Gln Val Asn Ser Leu Pro Gly Ser Ile Thr Lys Ala Gly
1160                1165                1170

Asp Phe Leu Glu Ala Asn Tyr Met Asn Leu Gln Arg Ser Tyr Thr
1175                1180                1185

Val Ala Ile Ala Gly Tyr Ala Leu Ala Gln Met Gly Arg Leu Lys
1190                1195                1200

Gly Pro Leu Leu Asn Lys Phe Leu Thr Thr Ala Lys Asp Lys Asn
1205                1210                1215

Arg Trp Glu Asp Pro Gly Lys Gln Leu Tyr Asn Val Glu Ala Thr
1220                1225                1230

Ser Tyr Ala Leu Leu Ala Leu Leu Gln Leu Lys Asp Phe Asp Phe
1235                1240                1245

Val Pro Pro Val Val Arg Trp Leu Asn Glu Gln Arg Tyr Tyr Gly
1250                1255                1260

Gly Gly Tyr Gly Ser Thr Gln Ala Thr Phe Met Val Phe Gln Ala
1265                1270                1275

Leu Ala Gln Tyr Gln Lys Asp Ala Pro Asp His Gln Glu Leu Asn
1280                1285                1290

Leu Asp Val Ser Leu Gln Leu Pro Ser Arg Ser Ser Lys Ile Thr
1295                1300                1305

His Arg Ile His Trp Glu Ser Ala Ser Leu Leu Arg Ser Glu Glu
1310                1315                1320

Thr Lys Glu Asn Glu Gly Phe Thr Val Thr Ala Glu Gly Lys Gly
1325                1330                1335

Gln Gly Thr Leu Ser Val Val Thr Met Tyr His Ala Lys Ala Lys
1340                1345                1350

Asp Gln Leu Thr Cys Asn Lys Phe Asp Leu Lys Val Thr Ile Lys
1355                1360                1365

Pro Ala Pro Glu Thr Glu Lys Arg Pro Gln Asp Ala Lys Asn Thr
1370                1375                1380

Met Ile Leu Glu Ile Cys Thr Arg Tyr Arg Gly Asp Gln Asp Ala
1385                1390                1395

Thr Met Ser Ile Leu Asp Ile Ser Met Met Thr Gly Phe Ala Pro
1400                1405                1410

Asp Thr Asp Asp Leu Lys Gln Leu Ala Asn Gly Val Asp Arg Tyr
1415                1420                1425

Ile Ser Lys Tyr Glu Leu Asp Lys Ala Phe Ser Asp Arg Asn Thr
1430                1435                1440

Leu Ile Ile Tyr Leu Asp Lys Val Ser His Ser Glu Asp Asp Cys
1445                1450                1455

Leu Ala Phe Lys Val His Gln Tyr Phe Asn Val Glu Leu Ile Gln
1460                1465                1470

Pro Gly Ala Val Lys Val Tyr Ala Tyr Tyr Asn Leu Glu Glu Ser
1475                1480                1485

Cys Thr Arg Phe Tyr His Pro Glu Lys Glu Asp Gly Lys Leu Asn
1490                1495                1500

Lys Leu Cys Arg Asp Glu Leu Cys Arg Cys Ala Glu Glu Asn Cys
1505                1510                1515

Phe Ile Gln Lys Ser Asp Asp Lys Val Thr Leu Glu Glu Arg Leu
1520                1525                1530

-continued

Asp Lys Ala Cys Glu Pro Gly Val Asp Tyr Val Tyr Lys Thr Arg
1535                1540                1545

Leu Val Lys Val Gln Leu Ser Asn Asp Phe Asp Glu Tyr Ile Met
    1550                1555                1560

Ala Ile Glu Gln Thr Ile Lys Ser Gly Ser Asp Glu Val Gln Val
    1565                1570                1575

Gly Gln Gln Arg Thr Phe Ile Ser Pro Ile Lys Cys Arg Glu Ala
    1580                1585                1590

Leu Lys Leu Glu Glu Lys Lys His Tyr Leu Met Trp Gly Leu Ser
    1595                1600                1605

Ser Asp Phe Trp Gly Glu Lys Pro Asn Leu Ser Tyr Ile Ile Gly
    1610                1615                1620

Lys Asp Thr Trp Val Glu His Trp Pro Glu Glu Asp Glu Cys Gln
    1625                1630                1635

Asp Glu Glu Asn Gln Lys Gln Cys Gln Asp Leu Gly Ala Phe Thr
    1640                1645                1650

Glu Ser Met Val Val Phe Gly Cys Pro Asn
    1655                1660

<210> SEQ ID NO 9
<211> LENGTH: 559
<212> TYPE: PRT
<213> ORGANISM: Homo sapiens

<400> SEQUENCE: 9

Met Ser Ala Cys Arg Ser Phe Ala Val Ala Ile Cys Ile Leu Glu Ile
1               5                   10                  15

Ser Ile Leu Thr Ala Gln Tyr Thr Thr Ser Tyr Asp Pro Glu Leu Thr
                20                  25                  30

Glu Ser Ser Gly Ser Ala Ser His Ile Asp Cys Arg Met Ser Pro Trp
            35                  40                  45

Ser Glu Trp Ser Gln Cys Asp Pro Cys Leu Arg Gln Met Phe Arg Ser
        50                  55                  60

Arg Ser Ile Glu Val Phe Gly Gln Phe Asn Gly Lys Arg Cys Thr Asp
65                  70                  75                  80

Ala Val Gly Asp Arg Arg Gln Cys Val Pro Thr Glu Pro Cys Glu Asp
                85                  90                  95

Ala Glu Asp Asp Cys Gly Asn Asp Phe Gln Cys Ser Thr Gly Arg Cys
            100                 105                 110

Ile Lys Met Arg Leu Arg Cys Asn Gly Asp Asn Asp Cys Gly Asp Phe
        115                 120                 125

Ser Asp Glu Asp Asp Cys Glu Ser Glu Pro Arg Pro Pro Cys Arg Asp
    130                 135                 140

Arg Val Val Glu Glu Ser Glu Leu Ala Arg Thr Ala Gly Tyr Gly Ile
145                 150                 155                 160

Asn Ile Leu Gly Met Asp Pro Leu Ser Thr Pro Phe Asp Asn Glu Phe
                165                 170                 175

Tyr Asn Gly Leu Cys Asn Arg Asp Arg Asp Gly Asn Thr Leu Thr Tyr
            180                 185                 190

Tyr Arg Arg Pro Trp Asn Val Ala Ser Leu Ile Tyr Glu Thr Lys Gly
        195                 200                 205

Glu Lys Asn Phe Arg Thr Glu His Tyr Glu Glu Gln Ile Glu Ala Phe
    210                 215                 220

Lys Ser Ile Ile Gln Glu Lys Thr Ser Asn Phe Asn Ala Ala Ile Ser
225                 230                 235                 240

-continued

Leu Lys Phe Thr Pro Thr Glu Thr Asn Lys Ala Glu Gln Cys Cys Glu
            245                 250                 255

Glu Thr Ala Ser Ser Ile Ser Leu His Gly Lys Gly Ser Phe Arg Phe
            260                 265                 270

Ser Tyr Ser Lys Asn Glu Thr Tyr Gln Leu Phe Leu Ser Tyr Ser Ser
        275                 280                 285

Lys Lys Glu Lys Met Phe Leu His Val Lys Gly Glu Ile His Leu Gly
    290                 295                 300

Arg Phe Val Met Arg Asn Arg Asp Val Val Leu Thr Thr Thr Phe Val
305                 310                 315                 320

Asp Asp Ile Lys Ala Leu Pro Thr Thr Tyr Glu Lys Gly Glu Tyr Phe
                325                 330                 335

Ala Phe Leu Glu Thr Tyr Gly Thr His Tyr Ser Ser Ser Gly Ser Leu
            340                 345                 350

Gly Gly Leu Tyr Glu Leu Ile Tyr Val Leu Asp Lys Ala Ser Met Lys
        355                 360                 365

Arg Lys Gly Val Glu Leu Lys Asp Ile Lys Arg Cys Leu Gly Tyr His
    370                 375                 380

Leu Asp Val Ser Leu Ala Phe Ser Glu Ile Ser Val Gly Ala Glu Phe
385                 390                 395                 400

Asn Lys Asp Asp Cys Val Lys Arg Gly Glu Gly Arg Ala Val Asn Ile
                405                 410                 415

Thr Ser Glu Asn Leu Ile Asp Asp Val Val Ser Leu Ile Arg Gly Gly
            420                 425                 430

Thr Arg Lys Tyr Ala Phe Glu Leu Lys Glu Lys Leu Leu Arg Gly Thr
        435                 440                 445

Val Ile Asp Val Thr Asp Phe Val Asn Trp Ala Ser Ser Ile Asn Asp
    450                 455                 460

Ala Pro Val Leu Ile Ser Gln Lys Leu Ser Pro Ile Tyr Asn Leu Val
465                 470                 475                 480

Pro Val Lys Met Lys Asn Ala His Leu Lys Lys Gln Asn Leu Glu Arg
                485                 490                 495

Ala Ile Glu Asp Tyr Ile Asn Glu Phe Ser Val Arg Lys Cys His Thr
            500                 505                 510

Cys Gln Asn Gly Gly Thr Val Ile Leu Met Asp Gly Lys Cys Leu Cys
        515                 520                 525

Ala Cys Pro Phe Lys Phe Glu Gly Ile Ala Cys Glu Ile Ser Lys Gln
    530                 535                 540

Lys Ile Ser Glu Gly Leu Pro Ala Leu Glu Phe Pro Asn Glu Lys
545                 550                 555

<210> SEQ ID NO 10
<211> LENGTH: 224
<212> TYPE: PRT
<213> ORGANISM: Homo sapiens

<400> SEQUENCE: 10

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
210                 215                 220

<210> SEQ ID NO 11
<211> LENGTH: 491
<212> TYPE: PRT
<213> ORGANISM: Homo sapiens

<400> SEQUENCE: 11

Met Lys Arg Met Val Ser Trp Ser Phe His Lys Leu Lys Thr Met Lys
1               5                   10                  15

His Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro
    50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
    130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

```
Ile Gln Lys Leu Glu Ser Asp Val Ser Ala Gln Met Glu Tyr Cys Arg
    210                 215                 220
Thr Pro Cys Thr Val Ser Cys Asn Ile Pro Val Val Ser Gly Lys Glu
225                 230                 235                 240
Cys Glu Glu Ile Ile Arg Lys Gly Gly Glu Thr Ser Glu Met Tyr Leu
                245                 250                 255
Ile Gln Pro Asp Ser Ser Val Lys Pro Tyr Arg Val Tyr Cys Asp Met
            260                 265                 270
Asn Thr Glu Asn Gly Gly Trp Thr Val Ile Gln Asn Arg Gln Asp Gly
        275                 280                 285
Ser Val Asp Phe Gly Arg Lys Trp Asp Pro Tyr Lys Gln Gly Phe Gly
290                 295                 300
Asn Val Ala Thr Asn Thr Asp Gly Lys Asn Tyr Cys Gly Leu Pro Gly
305                 310                 315                 320
Glu Tyr Trp Leu Gly Asn Asp Lys Ile Ser Gln Leu Thr Arg Met Gly
                325                 330                 335
Pro Thr Glu Leu Leu Ile Glu Met Glu Asp Trp Lys Gly Asp Lys Val
            340                 345                 350
Lys Ala His Tyr Gly Gly Phe Thr Val Gln Asn Glu Ala Asn Lys Tyr
        355                 360                 365
Gln Ile Ser Val Asn Lys Tyr Arg Gly Thr Ala Gly Asn Ala Leu Met
370                 375                 380
Asp Gly Ala Ser Gln Leu Met Gly Glu Asn Arg Thr Met Thr Ile His
385                 390                 395                 400
Asn Gly Met Phe Phe Ser Thr Tyr Asp Arg Asp Asn Asp Gly Trp Leu
                405                 410                 415
Thr Ser Asp Pro Arg Lys Gln Cys Ser Lys Glu Asp Gly Gly Gly Trp
            420                 425                 430
Trp Tyr Asn Arg Cys His Ala Ala Asn Pro Asn Gly Arg Tyr Tyr Trp
        435                 440                 445
Gly Gly Gln Tyr Thr Trp Asp Met Ala Lys His Gly Thr Asp Asp Gly
450                 455                 460
Val Val Trp Met Asn Trp Lys Gly Ser Trp Tyr Ser Met Arg Lys Met
465                 470                 475                 480
Ser Met Lys Ile Arg Pro Phe Phe Pro Gln Gln
                485                 490

<210> SEQ ID NO 12
<211> LENGTH: 453
<212> TYPE: PRT
<213> ORGANISM: Homo sapiens

<400> SEQUENCE: 12

Met Ser Trp Ser Leu His Pro Arg Asn Leu Ile Leu Tyr Phe Tyr Ala
1               5                   10                  15
Leu Leu Phe Leu Ser Ser Thr Cys Val Ala Tyr Val Ala Thr Arg Asp
            20                  25                  30
Asn Cys Cys Ile Leu Asp Glu Arg Phe Gly Ser Tyr Cys Pro Thr Thr
        35                  40                  45
Cys Gly Ile Ala Asp Phe Leu Ser Thr Tyr Gln Thr Lys Val Asp Lys
    50                  55                  60
Asp Leu Gln Ser Leu Glu Asp Ile Leu His Gln Val Glu Asn Lys Thr
65                  70                  75                  80
Ser Glu Val Lys Gln Leu Ile Lys Ala Ile Gln Leu Thr Tyr Asn Pro
                85                  90                  95
```

Asp Glu Ser Ser Lys Pro Asn Met Ile Asp Ala Ala Thr Leu Lys Ser
                100                 105                 110

Arg Lys Met Leu Glu Glu Ile Met Lys Tyr Glu Ala Ser Ile Leu Thr
            115                 120                 125

His Asp Ser Ser Ile Arg Tyr Leu Gln Glu Ile Tyr Asn Ser Asn Asn
        130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
    290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
    370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln His His Leu Gly Gly Ala Lys
            420                 425                 430

Gln Val Arg Pro Glu His Pro Ala Glu Thr Glu Tyr Asp Ser Leu Tyr
        435                 440                 445

Pro Glu Asp Asp Leu
        450

<210> SEQ ID NO 13
<211> LENGTH: 739
<212> TYPE: PRT
<213> ORGANISM: Homo sapiens

<400> SEQUENCE: 13

Met Pro Ser Pro Arg Pro Val Leu Leu Arg Gly Ala Arg Ala Ala Leu

-continued

```
1               5                   10                  15
Leu Leu Leu Leu Pro Pro Arg Leu Leu Ala Arg Pro Ser Leu Leu
            20                  25                  30

Arg Arg Ser Leu Ser Ala Ala Ser Cys Pro Pro Ile Ser Leu Pro Ala
            35                  40                  45

Ala Ala Ser Arg Ser Ser Met Asp Gly Ala Gly Glu Glu Val Leu
    50                  55                  60

Ala Pro Leu Arg Leu Ala Val Arg Gln Gln Gly Asp Leu Val Arg Lys
65                  70                  75                  80

Leu Lys Glu Asp Lys Ala Pro Gln Val Asp Val Asp Lys Ala Val Ala
                85                  90                  95

Glu Leu Lys Ala Arg Lys Arg Val Leu Glu Ala Lys Glu Leu Ala Leu
            100                 105                 110

Gln Pro Lys Asp Asp Ile Val Asp Arg Ala Lys Met Glu Asp Thr Leu
            115                 120                 125

Lys Arg Arg Phe Phe Tyr Asp Gln Ala Phe Ala Ile Tyr Gly Gly Val
        130                 135                 140

Ser Gly Leu Tyr Asp Phe Gly Pro Val Gly Cys Ala Leu Lys Asn Asn
145                 150                 155                 160

Ile Ile Gln Thr Trp Arg Gln His Phe Ile Gln Glu Gln Ile Leu
                165                 170                 175

Glu Ile Asp Cys Thr Met Leu Thr Pro Glu Pro Val Leu Lys Thr Ser
            180                 185                 190

Gly His Val Asp Lys Phe Ala Asp Phe Met Val Lys Asp Val Lys Asn
        195                 200                 205

Gly Glu Cys Phe Arg Ala Asp His Leu Leu Lys Ala His Leu Gln Lys
    210                 215                 220

Leu Met Ser Asp Lys Lys Cys Ser Val Glu Lys Lys Ser Glu Met Glu
225                 230                 235                 240

Ser Val Leu Ala Gln Leu Asp Asn Tyr Gly Gln Gln Glu Leu Ala Asp
                245                 250                 255

Leu Phe Val Asn Tyr Asn Val Lys Ser Pro Ile Thr Gly Asn Asp Leu
            260                 265                 270

Ser Pro Pro Val Ser Phe Asn Leu Met Phe Lys Thr Phe Ile Gly Pro
            275                 280                 285

Gly Gly Asn Met Pro Gly Tyr Leu Arg Pro Glu Thr Ala Gln Gly Ile
        290                 295                 300

Phe Leu Asn Phe Lys Arg Leu Leu Glu Phe Asn Gln Gly Lys Leu Pro
305                 310                 315                 320

Phe Ala Ala Ala Gln Ile Gly Asn Ser Phe Arg Asn Glu Ile Ser Pro
                325                 330                 335

Arg Ser Gly Leu Ile Arg Val Arg Glu Phe Thr Met Ala Glu Ile Glu
            340                 345                 350

His Phe Val Asp Pro Ser Glu Lys Asp His Pro Lys Phe Gln Asn Val
            355                 360                 365

Ala Asp Leu His Leu Tyr Leu Tyr Ser Ala Lys Ala Gln Val Ser Gly
        370                 375                 380

Gln Ser Ala Arg Lys Met Arg Leu Gly Asp Ala Val Glu Gln Gly Val
385                 390                 395                 400

Ile Asn Asn Thr Val Leu Gly Tyr Phe Ile Gly Arg Ile Tyr Leu Tyr
                405                 410                 415

Leu Thr Lys Val Gly Ile Ser Pro Asp Lys Leu Arg Phe Arg Gln His
            420                 425                 430
```

Met Glu Asn Glu Met Ala His Tyr Ala Cys Asp Cys Trp Asp Ala Glu
            435                 440                 445

Ser Lys Thr Ser Tyr Gly Trp Ile Glu Ile Val Gly Cys Ala Asp Arg
        450                 455                 460

Ser Cys Tyr Asp Leu Ser Cys His Ala Arg Ala Thr Lys Val Pro Leu
465                 470                 475                 480

Val Ala Glu Lys Pro Leu Lys Glu Pro Lys Thr Val Asn Val Val Gln
                485                 490                 495

Phe Glu Pro Ser Lys Gly Ala Ile Gly Lys Ala Tyr Lys Lys Asp Ala
            500                 505                 510

Lys Leu Val Met Glu Tyr Leu Ala Ile Cys Asp Glu Cys Tyr Ile Thr
        515                 520                 525

Glu Met Glu Met Leu Leu Asn Glu Lys Gly Glu Phe Thr Ile Glu Thr
    530                 535                 540

Glu Gly Lys Thr Phe Gln Leu Thr Lys Asp Met Ile Asn Val Lys Arg
545                 550                 555                 560

Phe Gln Lys Thr Leu Tyr Val Glu Val Val Pro Asn Val Ile Glu
                565                 570                 575

Pro Ser Phe Gly Leu Gly Arg Ile Met Tyr Thr Val Phe Glu His Thr
            580                 585                 590

Phe His Val Arg Glu Gly Asp Glu Gln Arg Thr Phe Phe Ser Phe Pro
        595                 600                 605

Ala Val Val Ala Pro Phe Lys Cys Ser Val Leu Pro Leu Ser Gln Asn
    610                 615                 620

Gln Glu Phe Met Pro Phe Val Lys Glu Leu Ser Glu Ala Leu Thr Arg
625                 630                 635                 640

His Gly Val Ser His Lys Val Asp Asp Ser Ser Gly Ser Ile Gly Arg
                645                 650                 655

Arg Tyr Ala Arg Thr Asp Glu Ile Gly Val Ala Phe Gly Val Thr Ile
            660                 665                 670

Asp Phe Asp Thr Val Asn Lys Thr Pro His Thr Ala Thr Leu Arg Asp
        675                 680                 685

Arg Asp Ser Met Arg Gln Ile Arg Ala Glu Ile Ser Glu Leu Pro Ser
    690                 695                 700

Ile Val Gln Asp Leu Ala Asn Gly Asn Ile Thr Trp Ala Asp Val Glu
705                 710                 715                 720

Ala Arg Tyr Pro Leu Phe Glu Gly Gln Glu Thr Gly Lys Lys Glu Thr
                725                 730                 735

Ile Glu Glu

<210> SEQ ID NO 14
<211> LENGTH: 782
<212> TYPE: PRT
<213> ORGANISM: Homo sapiens

<400> SEQUENCE: 14

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

```
Glu Pro Gly Leu Gln Ile Trp Arg Val Glu Lys Phe Asp Leu Val Pro
 65                  70                  75                  80

Val Pro Thr Asn Leu Tyr Gly Asp Phe Phe Thr Gly Asp Ala Tyr Val
                 85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
        115                 120                 125

Ala Ile Phe Thr Val Gln Leu Asp Asp Tyr Leu Asn Gly Arg Ala Val
130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
                165                 170                 175

Lys His Val Val Pro Asn Glu Val Val Val Gln Arg Leu Phe Gln Val
            180                 185                 190

Lys Gly Arg Arg Val Val Arg Ala Thr Glu Val Pro Val Ser Trp Glu
        195                 200                 205

Ser Phe Asn Asn Gly Asp Cys Phe Ile Leu Asp Leu Gly Asn Asn Ile
210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270

Val Leu Gly Pro Lys Pro Ala Leu Pro Ala Gly Thr Glu Asp Thr Ala
        275                 280                 285

Lys Glu Asp Ala Ala Asn Arg Lys Leu Ala Lys Leu Tyr Lys Val Ser
290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350

Glu Glu Arg Lys Ala Ala Leu Lys Thr Ala Ser Asp Phe Ile Thr Lys
        355                 360                 365

Met Asp Tyr Pro Lys Gln Thr Gln Val Ser Val Leu Pro Glu Gly Gly
370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
            420                 425                 430

Met Ala Ala Gln His Gly Met Asp Asp Asp Gly Thr Gly Gln Lys Gln
        435                 440                 445

Ile Trp Arg Ile Glu Gly Ser Asn Lys Val Pro Val Asp Pro Ala Thr
450                 455                 460

Tyr Gly Gln Phe Tyr Gly Gly Asp Ser Tyr Ile Ile Leu Tyr Asn Tyr
465                 470                 475                 480
```

-continued

Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
            515                 520                 525

Gly Lys Glu Pro Ala His Leu Met Ser Leu Phe Gly Gly Lys Pro Met
            530                 535                 540

Ile Ile Tyr Lys Gly Gly Thr Ser Arg Glu Gly Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
            595                 600                 605

Gly Ala Ser Glu Ala Glu Lys Thr Gly Ala Gln Glu Leu Leu Arg Val
            610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                645                 650                 655

Leu Lys Asp Lys Lys Met Asp Ala His Pro Pro Arg Leu Phe Ala Cys
            660                 665                 670

Ser Asn Lys Ile Gly Arg Phe Val Ile Glu Glu Val Pro Gly Glu Leu
            675                 680                 685

Met Gln Glu Asp Leu Ala Thr Asp Asp Val Met Leu Leu Asp Thr Trp
            690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
                725                 730                 735

Asn Arg Asp Arg Arg Thr Pro Ile Thr Val Val Lys Gln Gly Phe Glu
            740                 745                 750

Pro Pro Ser Phe Val Gly Trp Phe Leu Gly Trp Asp Asp Asp Tyr Trp
            755                 760                 765

Ser Val Asp Pro Leu Asp Arg Ala Met Ala Glu Leu Ala Ala
            770                 775                 780

<210> SEQ ID NO 15
<211> LENGTH: 406
<212> TYPE: PRT
<213> ORGANISM: Homo sapiens

<400> SEQUENCE: 15

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
                20                  25                  30

Cys Pro Lys Pro Pro Glu Ile Ala His Gly Tyr Val Glu His Ser Val
            35                  40                  45

Arg Tyr Gln Cys Lys Asn Tyr Tyr Lys Leu Arg Thr Glu Gly Asp Gly
        50                  55                  60

Val Tyr Thr Leu Asn Asp Lys Lys Gln Trp Ile Asn Lys Ala Val Gly
65              70                  75                  80

```
Asp Lys Leu Pro Glu Cys Glu Ala Asp Gly Cys Pro Lys Pro Pro
                85                  90                  95

Glu Ile Ala His Gly Tyr Val Glu His Ser Val Arg Tyr Gln Cys Lys
                100                 105                 110

Asn Tyr Tyr Lys Leu Arg Thr Glu Gly Asp Gly Val Tyr Thr Leu Asn
            115                 120                 125

Asn Glu Lys Gln Trp Ile Asn Lys Ala Val Gly Asp Lys Leu Pro Glu
        130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
                180                 185                 190

Asn Glu Gln Trp Leu Leu Thr Thr Ala Lys Asn Leu Phe Leu Asn His
            195                 200                 205

Ser Glu Asn Ala Thr Ala Lys Asp Ile Ala Pro Thr Leu Thr Leu Tyr
        210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
                245                 250                 255

Ser Val Asn Glu Arg Val Met Pro Ile Cys Leu Pro Ser Lys Asp Tyr
                260                 265                 270

Ala Glu Val Gly Arg Val Gly Tyr Val Ser Gly Trp Gly Arg Asn Ala
            275                 280                 285

Asn Phe Lys Phe Thr Asp His Leu Lys Tyr Val Met Leu Pro Val Ala
        290                 295                 300

Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
                325                 330                 335

His Thr Phe Cys Ala Gly Met Ser Lys Tyr Gln Glu Asp Thr Cys Tyr
            340                 345                 350

Gly Asp Ala Gly Ser Ala Phe Ala Val His Asp Leu Glu Glu Asp Thr
        355                 360                 365

Trp Tyr Ala Thr Gly Ile Leu Ser Phe Asp Lys Ser Cys Ala Val Ala
370                 375                 380

Glu Tyr Gly Val Tyr Val Lys Val Thr Ser Ile Gln Asp Trp Val Gln
385                 390                 395                 400

Lys Thr Ile Ala Glu Asn
                405
```

<210> SEQ ID NO 16
<211> LENGTH: 115
<212> TYPE: PRT
<213> ORGANISM: Homo sapiens

<400> SEQUENCE: 16

```
Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
```

```
            35                  40                  45
Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala
        115

<210> SEQ ID NO 17
<211> LENGTH: 314
<212> TYPE: PRT
<213> ORGANISM: Homo sapiens

<400> SEQUENCE: 17

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Phe Arg Arg
            165                 170                 175

Pro Asp Ile Gln Tyr Pro Asp Ala Thr Asp Glu Asp Ile Thr Ser His
        180                 185                 190

Met Glu Ser Glu Glu Leu Asn Gly Ala Tyr Lys Ala Ile Pro Val Ala
    195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
            245                 250                 255

His Ser Asp Val Ile Asp Ser Gln Glu Leu Ser Lys Val Ser Arg Glu
        260                 265                 270

Phe His Ser His Glu Phe His Ser His Glu Asp Met Leu Val Val Asp
    275                 280                 285
```

```
Pro Lys Ser Lys Glu Glu Asp Lys His Leu Lys Phe Arg Ile Ser His
    290                 295                 300

Glu Leu Asp Ser Ala Ser Ser Glu Val Asn
305                 310
```

<210> SEQ ID NO 18
<211> LENGTH: 199
<212> TYPE: PRT
<213> ORGANISM: Homo sapiens

<400> SEQUENCE: 18

```
Met Ser Ser Gly Asn Ala Lys Ile Gly His Pro Ala Pro Asn Phe Lys
1               5                   10                  15

Ala Thr Ala Val Met Pro Asp Gly Gln Phe Lys Asp Ile Ser Leu Ser
                20                  25                  30

Asp Tyr Lys Gly Lys Tyr Val Val Phe Phe Tyr Pro Leu Asp Phe
            35                  40                  45

Thr Phe Val Cys Pro Thr Glu Ile Ile Ala Phe Ser Asp Arg Ala Glu
    50                  55                  60

Glu Phe Lys Lys Leu Asn Cys Gln Val Ile Gly Ala Ser Val Asp Ser
65                  70                  75                  80

His Phe Cys His Leu Ala Trp Val Asn Thr Pro Lys Lys Gln Gly Gly
                85                  90                  95

Leu Gly Pro Met Asn Ile Pro Leu Val Ser Asp Pro Lys Arg Thr Ile
            100                 105                 110

Ala Gln Asp Tyr Gly Val Leu Lys Ala Asp Glu Gly Ile Ser Phe Arg
        115                 120                 125

Gly Leu Phe Ile Ile Asp Asp Lys Gly Ile Leu Arg Gln Ile Thr Val
130                 135                 140

Asn Asp Leu Pro Val Gly Arg Ser Val Asp Glu Thr Leu Arg Leu Val
145                 150                 155                 160

Gln Ala Phe Gln Phe Thr Asp Lys His Gly Glu Val Cys Pro Ala Gly
                165                 170                 175

Trp Lys Pro Gly Ser Asp Thr Ile Lys Pro Asp Val Gln Lys Ser Lys
            180                 185                 190

Glu Tyr Phe Ser Lys Gln Lys
        195
```

<210> SEQ ID NO 19
<211> LENGTH: 412
<212> TYPE: PRT
<213> ORGANISM: Homo sapiens

<400> SEQUENCE: 19

```
Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
                20                  25                  30

Gly Pro Leu Leu Ala Arg Asp Arg Gln Ala Thr Glu Tyr Glu Tyr
            35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95
```

```
Gly Ala Val Thr Glu Leu Thr Thr Glu Leu Ala Asn Met Gly Asn Leu
                100                 105                 110

Ser Thr Asp Ser Ala Ala Met Glu Ile Gln Thr Thr Gln Pro Ala Ala
        115                 120                 125

Thr Glu Ala Gln Thr Thr Gln Pro Val Pro Thr Glu Ala Gln Thr Thr
    130                 135                 140

Pro Leu Ala Ala Thr Glu Ala Gln Thr Thr Arg Leu Thr Ala Thr Glu
145                 150                 155                 160

Ala Gln Thr Thr Pro Leu Ala Ala Thr Glu Ala Gln Thr Thr Pro Pro
                165                 170                 175

Ala Ala Thr Glu Ala Gln Thr Thr Gln Pro Thr Gly Leu Glu Ala Gln
            180                 185                 190

Thr Thr Ala Pro Ala Ala Met Glu Ala Gln Thr Thr Ala Pro Ala Ala
        195                 200                 205

Met Glu Ala Gln Thr Thr Pro Pro Ala Ala Met Glu Ala Gln Thr Thr
    210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
                245                 250                 255

Ala Ala Met Glu Ala Leu Ser Thr Glu Pro Ser Ala Thr Glu Ala Leu
            260                 265                 270

Ser Met Glu Pro Thr Thr Lys Arg Gly Leu Phe Ile Pro Phe Ser Val
        275                 280                 285

Ser Ser Val Thr His Lys Gly Ile Pro Met Ala Ala Ser Asn Leu Ser
    290                 295                 300

Val Asn Tyr Pro Val Gly Ala Pro Asp His Ile Ser Val Lys Gln Cys
305                 310                 315                 320

Leu Leu Ala Ile Leu Ile Leu Ala Leu Val Ala Thr Ile Phe Phe Val
                325                 330                 335

Cys Thr Val Val Leu Ala Val Arg Leu Ser Arg Lys Gly His Met Tyr
            340                 345                 350

Pro Val Arg Asn Tyr Ser Pro Thr Glu Met Val Cys Ile Ser Ser Leu
        355                 360                 365

Leu Pro Asp Gly Gly Glu Gly Pro Ser Ala Thr Ala Asn Gly Gly Leu
    370                 375                 380

Ser Lys Ala Lys Ser Pro Gly Leu Thr Pro Glu Pro Arg Glu Asp Arg
385                 390                 395                 400

Glu Gly Asp Asp Leu Thr Leu His Ser Phe Leu Pro
                405                 410

<210> SEQ ID NO 20
<211> LENGTH: 93
<212> TYPE: PRT
<213> ORGANISM: Homo sapiens

<400> SEQUENCE: 20

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
                20                  25                  30

Asp Leu Lys Lys Leu Leu Glu Thr Glu Cys Pro Gln Tyr Ile Arg Lys
            35                  40                  45

Lys Gly Ala Asp Val Trp Phe Lys Glu Leu Asp Ile Asn Thr Asp Gly
        50                  55                  60
```

```
Ala Val Asn Phe Gln Glu Phe Leu Ile Leu Val Ile Lys Met Gly Val
 65                  70                  75                  80

Ala Ala His Lys Lys Ser His Glu Glu Ser His Lys Glu
                 85                  90
```

<210> SEQ ID NO 21
<211> LENGTH: 114
<212> TYPE: PRT
<213> ORGANISM: Homo sapiens

<400> SEQUENCE: 21

```
Met Thr Cys Lys Met Ser Gln Leu Glu Arg Asn Ile Glu Thr Ile Ile
  1               5                  10                  15

Asn Thr Phe His Gln Tyr Ser Val Lys Leu Gly His Pro Asp Thr Leu
                 20                  25                  30

Asn Gln Gly Glu Phe Lys Glu Leu Val Arg Lys Asp Leu Gln Asn Phe
             35                  40                  45

Leu Lys Lys Glu Asn Lys Asn Glu Lys Val Ile Glu His Ile Met Glu
         50                  55                  60

Asp Leu Asp Thr Asn Ala Asp Lys Gln Leu Ser Phe Glu Glu Phe Ile
 65                  70                  75                  80

Met Leu Met Ala Arg Leu Thr Trp Ala Ser His Glu Lys Met His Glu
                 85                  90                  95

Gly Asp Glu Gly Pro Gly His His His Lys Pro Gly Leu Gly Glu Gly
            100                 105                 110

Thr Pro
```

<210> SEQ ID NO 22
<211> LENGTH: 122
<212> TYPE: PRT
<213> ORGANISM: Homo sapiens

<400> SEQUENCE: 22

```
Met Lys Leu Leu Thr Gly Leu Val Phe Cys Ser Leu Val Leu Gly Val
  1               5                  10                  15

Ser Ser Arg Ser Phe Phe Ser Phe Leu Gly Glu Ala Phe Asp Gly Ala
                 20                  25                  30

Arg Asp Met Trp Arg Ala Tyr Ser Asp Met Arg Glu Ala Asn Tyr Ile
             35                  40                  45

Gly Ser Asp Lys Tyr Phe His Ala Arg Gly Asn Tyr Asp Ala Ala Lys
         50                  55                  60

Arg Gly Pro Gly Gly Val Trp Ala Ala Glu Ala Ile Ser Asp Ala Arg
 65                  70                  75                  80

Glu Asn Ile Gln Arg Phe Phe Gly His Gly Ala Glu Asp Ser Leu Ala
                 85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
            115                 120
```

<210> SEQ ID NO 23
<211> LENGTH: 472
<212> TYPE: PRT
<213> ORGANISM: Homo sapiens

<400> SEQUENCE: 23

```
Met Ala Thr Lys Cys Gly Asn Cys Gly Pro Gly Tyr Ser Thr Pro Leu
```

-continued

```
1               5               10              15
Glu Ala Met Lys Gly Pro Arg Glu Glu Ile Val Tyr Leu Pro Cys Ile
                20              25              30
Tyr Arg Asn Thr Gly Thr Glu Ala Pro Asp Tyr Leu Ala Thr Val Asp
                35              40              45
Val Asp Pro Lys Ser Pro Gln Tyr Cys Gln Val Ile His Arg Leu Pro
    50              55              60
Met Pro Asn Leu Lys Asp Glu Leu His His Ser Gly Trp Asn Thr Cys
65              70              75              80
Ser Ser Cys Phe Gly Asp Ser Thr Lys Ser Arg Thr Lys Leu Val Leu
                85              90              95
Pro Ser Leu Ile Ser Ser Arg Ile Tyr Val Val Asp Val Gly Ser Glu
                100             105             110
Pro Arg Ala Pro Lys Leu His Lys Val Ile Glu Pro Lys Asp Ile His
                115             120             125
Ala Lys Cys Glu Leu Ala Phe Leu His Thr Ser His Cys Leu Ala Ser
    130             135             140
Gly Glu Val Met Ile Ser Ser Leu Gly Asp Val Lys Gly Asn Gly Lys
145             150             155             160
Gly Gly Phe Val Leu Leu Asp Gly Glu Thr Phe Glu Val Lys Gly Thr
                165             170             175
Trp Glu Arg Pro Gly Gly Ala Ala Pro Leu Gly Tyr Asp Phe Trp Tyr
                180             185             190
Gln Pro Arg His Asn Val Met Ile Ser Thr Glu Trp Ala Ala Pro Asn
                195             200             205
Val Leu Arg Asp Gly Phe Asn Pro Ala Asp Val Glu Ala Gly Leu Tyr
    210             215             220
Gly Ser His Leu Tyr Val Trp Asp Trp Gln Arg His Glu Ile Val Gln
225             230             235             240
Thr Leu Ser Leu Lys Asp Gly Leu Ile Pro Leu Glu Ile Arg Phe Leu
                245             250             255
His Asn Pro Asp Ala Ala Gln Gly Phe Val Gly Cys Ala Leu Ser Ser
                260             265             270
Thr Ile Gln Arg Phe Tyr Lys Asn Glu Gly Gly Thr Trp Ser Val Glu
                275             280             285
Lys Val Ile Gln Val Pro Pro Lys Lys Val Lys Gly Trp Leu Leu Pro
    290             295             300
Glu Met Pro Gly Leu Ile Thr Asp Ile Leu Leu Ser Leu Asp Asp Arg
305             310             315             320
Phe Leu Tyr Phe Ser Asn Trp Leu His Gly Asp Leu Arg Gln Tyr Asp
                325             330             335
Ile Ser Asp Pro Gln Arg Pro Arg Leu Thr Gly Gln Leu Phe Leu Gly
                340             345             350
Gly Ser Ile Val Lys Gly Gly Pro Val Gln Val Leu Glu Asp Glu Glu
                355             360             365
Leu Lys Ser Gln Pro Glu Pro Leu Val Val Lys Gly Lys Arg Val Ala
    370             375             380
Gly Gly Pro Gln Met Ile Gln Leu Ser Leu Asp Gly Lys Arg Leu Tyr
385             390             395             400
Ile Thr Thr Ser Leu Tyr Ser Ala Trp Asp Lys Gln Phe Tyr Pro Asp
                405             410             415
Leu Ile Arg Glu Gly Ser Val Met Leu Gln Val Asp Val Asp Thr Val
                420             425             430
```

```
Lys Gly Gly Leu Lys Leu Asn Pro Asn Phe Leu Val Asp Phe Gly Lys
        435                 440                 445

Glu Pro Leu Gly Pro Ala Leu Ala His Glu Leu Arg Tyr Pro Gly Gly
    450                 455                 460

Asp Cys Ser Ser Asp Ile Trp Ile
465                 470

<210> SEQ ID NO 24
<211> LENGTH: 760
<212> TYPE: PRT
<213> ORGANISM: Homo sapiens

<400> SEQUENCE: 24

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
            20                  25                  30

Asn Ser Glu Glu Asn Thr Met Arg Ala Leu Thr Leu Lys Asp Ile Leu
        35                  40                  45

Asn Gly Thr Phe Ser Tyr Lys Thr Phe Phe Pro Asn Trp Ile Ser Gly
50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Glu Met Leu Ala Thr
        195                 200                 205

Lys Tyr Ala Leu Trp Trp Ser Pro Asn Gly Lys Phe Leu Ala Tyr Ala
210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
        275                 280                 285

Ser Asp Tyr Tyr Phe Ser Trp Leu Thr Trp Val Thr Asp Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
```

-continued

```
                325                 330                 335
Glu His Ile Glu Glu Ser Arg Thr Gly Trp Ala Gly Gly Phe Phe Val
                340                 345                 350
Ser Thr Pro Val Phe Ser Tyr Asp Ala Ile Ser Tyr Lys Ile Phe
                355                 360                 365
Ser Asp Lys Asp Gly Tyr Lys His Ile His Tyr Ile Lys Asp Thr Val
                370                 375                 380
Glu Asn Ala Ile Gln Ile Thr Ser Gly Lys Trp Glu Ala Ile Asn Ile
385                 390                 395                 400
Phe Arg Val Thr Gln Asp Ser Leu Phe Tyr Ser Ser Asn Glu Phe Glu
                405                 410                 415
Glu Tyr Pro Gly Arg Arg Asn Ile Tyr Arg Ile Ser Ile Gly Ser Tyr
                420                 425                 430
Pro Pro Ser Lys Lys Cys Val Thr Cys His Leu Arg Lys Glu Arg Cys
                435                 440                 445
Gln Tyr Tyr Thr Ala Ser Phe Ser Asp Tyr Ala Lys Tyr Tyr Ala Leu
                450                 455                 460
Val Cys Tyr Gly Pro Gly Ile Pro Ile Ser Thr Leu His Asp Gly Arg
465                 470                 475                 480
Thr Asp Gln Glu Ile Lys Ile Leu Glu Glu Asn Lys Glu Leu Glu Asn
                485                 490                 495
Ala Leu Lys Asn Ile Gln Leu Pro Lys Glu Glu Ile Lys Lys Leu Glu
                500                 505                 510
Val Asp Glu Ile Thr Leu Trp Tyr Lys Met Ile Leu Pro Pro Gln Phe
                515                 520                 525
Asp Arg Ser Lys Lys Tyr Pro Leu Leu Ile Gln Val Tyr Gly Gly Pro
                530                 535                 540
Cys Ser Gln Ser Val Arg Ser Val Phe Ala Val Asn Trp Ile Ser Tyr
545                 550                 555                 560
Leu Ala Ser Lys Glu Gly Met Val Ile Ala Leu Val Asp Gly Arg Gly
                565                 570                 575
Thr Ala Phe Gln Gly Asp Lys Leu Leu Tyr Ala Val Tyr Arg Lys Leu
                580                 585                 590
Gly Val Tyr Glu Val Glu Asp Gln Ile Thr Ala Val Arg Lys Phe Ile
                595                 600                 605
Glu Met Gly Phe Ile Asp Glu Lys Arg Ile Ala Ile Trp Gly Trp Ser
                610                 615                 620
Tyr Gly Gly Tyr Val Ser Ser Leu Ala Leu Ala Ser Gly Thr Gly Leu
625                 630                 635                 640
Phe Lys Cys Gly Ile Ala Val Ala Pro Val Ser Ser Trp Glu Tyr Tyr
                645                 650                 655
Ala Ser Val Tyr Thr Glu Arg Phe Met Gly Leu Pro Thr Lys Asp Asp
                660                 665                 670
Asn Leu Glu His Tyr Lys Asn Ser Thr Val Met Ala Arg Ala Glu Tyr
                675                 680                 685
Phe Arg Asn Val Asp Tyr Leu Leu Ile His Gly Thr Ala Asp Asp Asn
                690                 695                 700
Val His Phe Gln Asn Ser Ala Gln Ile Ala Lys Ala Leu Val Asn Ala
705                 710                 715                 720
Gln Val Asp Phe Gln Ala Met Trp Tyr Ser Asp Gln Asn His Gly Leu
                725                 730                 735
Ser Gly Leu Ser Thr Asn His Leu Tyr Thr His Met Thr His Phe Leu
                740                 745                 750
```

-continued

```
Lys Gln Cys Phe Ser Leu Ser Asp
        755                 760

<210> SEQ ID NO 25
<211> LENGTH: 760
<212> TYPE: PRT
<213> ORGANISM: Homo sapiens

<400> SEQUENCE: 25

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
```

```
                    355                 360                 365
Glu Ser Lys Asn Val Lys Leu Thr Val Ser Asn Val Leu Lys Glu Ile
370                 375                 380

Lys Ile Leu Asn Ile Phe Gly Val Ile Lys Gly Phe Val Glu Pro Asp
385                 390                 395                 400

His Tyr Val Val Gly Ala Gln Arg Asp Ala Trp Gly Pro Gly Ala
                405                 410                 415

Ala Lys Ser Gly Val Gly Thr Ala Leu Leu Lys Leu Ala Gln Met
                420                 425                 430

Phe Ser Asp Met Val Leu Lys Asp Gly Phe Gln Pro Ser Arg Ser Ile
435                 440                 445

Ile Phe Ala Ser Trp Ser Ala Gly Asp Phe Gly Ser Val Gly Ala Thr
450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
                500                 505                 510

Val Lys His Pro Val Thr Gly Gln Phe Leu Tyr Gln Asp Ser Asn Trp
                515                 520                 525

Ala Ser Lys Val Glu Lys Leu Thr Leu Asp Asn Ala Ala Phe Pro Phe
530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
                580                 585                 590

Val Ala Gly Gln Phe Val Ile Lys Leu Thr His Asp Val Glu Leu Asn
                595                 600                 605

Leu Asp Tyr Glu Arg Tyr Asn Ser Gln Leu Leu Ser Phe Val Arg Asp
610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
                660                 665                 670

Lys Leu Asn Asp Arg Val Met Arg Val Glu Tyr His Phe Leu Ser Pro
                675                 680                 685

Tyr Val Ser Pro Lys Glu Ser Pro Phe Arg His Val Phe Trp Gly Ser
                690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
                740                 745                 750

Val Trp Asp Ile Asp Asn Glu Phe
        755                 760

<210> SEQ ID NO 26
```

-continued

```
<211> LENGTH: 308
<212> TYPE: PRT
<213> ORGANISM: Homo sapiens

<400> SEQUENCE: 26

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Ala Glu Leu Leu Ser Pro Gly Ser Val Asp Pro Leu Thr Arg
1               5                   10                  15
```

```
<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Ala Glu Leu
1

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Ala Glu Leu Leu
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Ala Glu Leu Leu Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ile Ala Glu Leu Leu Ser Pro
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Ala Glu Leu Leu Ser Pro Gly
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 33

Ile Ala Glu Leu Leu Ser Pro Gly Ser
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Ala Glu Leu Leu Ser Pro Gly Ser Val
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Ala Glu Leu Leu Ser Pro Gly Ser Val Asp
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Ala Glu Leu Leu Ser Pro Gly Ser Val Asp Pro
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Ala Glu Leu Leu Ser Pro Gly Ser Val Asp Pro Leu
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Ala Glu Leu Leu Ser Pro Gly Ser Val Asp Pro Leu Thr
1               5                   10

<210> SEQ ID NO 39
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Glu Leu Leu Ser Pro Gly Ser Val Asp Pro Leu Thr Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Leu Leu Ser Pro Gly Ser Val Asp Pro Leu Thr Arg
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Leu Ser Pro Gly Ser Val Asp Pro Leu Thr Arg
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Ser Pro Gly Ser Val Asp Pro Leu Thr Arg
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Pro Gly Ser Val Asp Pro Leu Thr Arg
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Gly Ser Val Asp Pro Leu Thr Arg
```

```
<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Ser Val Asp Pro Leu Thr Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Val Asp Pro Leu Thr Arg
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val Asp Pro Leu Thr Arg
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Pro Leu Thr Arg
1               5

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Leu Thr Arg
1

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 50

Ala Asp Leu Ser Gly Ile Thr Gly Ala Arg
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Glu His Tyr Glu Glu Gln Ile Glu Ala Phe Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Ser Asp Thr Ser Tyr Val Ser Leu Lys
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Tyr Ser Ile Phe Ser Tyr Ala Thr Lys
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Ala Phe Val Phe Pro Lys
1               5

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Gly Ala Leu Asn Ser Asn Asp Ala Phe Val Leu Lys
1               5                   10

<210> SEQ ID NO 56

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Leu Asn Ser Ile Ile Asp Val Tyr His Lys
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Ala Asp Val Trp Phe Lys
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Leu Gln Asn Phe Leu Lys
1               5

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Gly His Pro Asp Thr Leu Asn Gln Gly Glu Phe Lys
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Lys Ile Thr Asp Leu Ile Lys
1               5
```

PROTEIN BIOMARKER PANELS FOR DETECTING COLORECTAL CANCER AND ADVANCED ADENOMA

RELATED APPLICATIONS

The present application claims the benefit of U.S. Provisional Application Ser. No. 62/146,158, filed Apr. 10, 2015, which is hereby incorporated by reference in its entirety; the present application claims the benefit of U.S. Provisional Application Ser. No. 62/160,560, filed May 12, 2015, which is hereby incorporated by reference in its entirety; the present application claims the benefit of U.S. Provisional Application Ser. No. 62/165,846, filed May 22, 2015, which is hereby incorporated by reference in its entirety; the present application claims the benefit of U.S. Provisional Application Ser. No. 62/196,889, filed Jul. 24, 2015, which is hereby incorporated by reference in its entirety; and the present application claims the benefit of U.S. Provisional Application Ser. No. 62/239,771, filed Oct. 9, 2015, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 11 2016, is named 36765-738.201 SL.txt and is 107,300 bytes in size.

BACKGROUND OF THE INVENTION

Colorectal cancer (CRC) can result from uncontrolled cell growth in the colon or rectum (parts of the large intestine), or in the appendix. CRC can develop from a colon polyp. A colon polyp typically comprises a benign clump of cells that forms on the lining of the large intestine or rectum. While many colon polyps are non-malignant, a polyp can develop into an adenoma. Colorectal adenomas can then grow into advanced colorectal adenomas, which can then develop into CRC.

Colorectal cancer is a leading cause of cancer-related deaths in the United States with over 142, 820 diagnosed cases and over 50,000 deaths in 2013. According to a 2011 study, there are an estimated 1.2 million diagnoses per year and 600,000 deaths worldwide. CRC is one of the most preventable cancers given its typically slow progression from early stages to metastatic disease and available tools for its diagnosis, but it is one of the least prevented cancers. This is at least partly due to the poor compliance with available screening by patients due to the invasive or unpleasant nature of the current screening tests.

The risk of developing CRC increases with age. Ninety percent of new cases and 93% of deaths occur in people age 50 and older. During their 60s, men have a 10-fold increased risk of developing CRC compared to their 40s. Regular screening allows for the removal of advanced colorectal adenomas or precancerous polyps and detection of early stage cancer, which is the key factor in the effective treatment of the disease.

The survival rate for patients diagnosed with CRC is highly dependent on when it is caught. CRC usually progresses through four stages, defined as Stage I through Stage IV. Stages I and II are local stages, during which aberrant cell growth is confined to the colon or rectum. Stage III is a regional stage, meaning the cancer has spread to the surrounding tissue but remains local. Stage IV is distal and indicates that the cancer has spread throughout the other organs of the body, most commonly the liver or lungs. It is estimated that the five-year survival rate is over 90% for those patients who were diagnosed with Stage I CRC, compared to 13% for a Stage IV diagnosis. If caught early, CRC is typically treated by surgical removal of the cancer. After the cancer spreads, surgical removal of the cancer is typically followed by chemotherapy Colonoscopy and sigmoidoscopy remain the gold standard for detecting colon cancer. However, the highly invasive nature and the expense of these exams contribute to low acceptance from the population. Furthermore, such highly invasive procedures expose subjects to risk of complications such as infection.

The most common non-invasive test for colorectal cancer is the fecal occult blood test ("FOBT"). Unfortunately, in addition to its high false-positive rate, the sensitivity of the FOBT remains around 50% and may have less sensitivity for detection of early stage CRC. Numerous serum markers, such as carcinoembryonic antigen ("CEA"), carbohydrate antigen 19-9, and lipid-associated sialic acid, have been investigated in colorectal cancer. However, their low sensitivity has induced the American Society of Clinical Oncology to state that none can be recommended for screening and diagnosis, and that their use should be limited to post-surgery surveillance.

Because of the significantly increased chance of survival if CRC is detected early in the disease progression, CRC is one of three cancers for which the American Cancer Society, or ACS, recommends routine screening (breast and cervical cancer are the others). In the United States, screening for CRC is currently recommended by the ACS and the U.S. Preventative Services Task Force, or USPSTF, for all men and women aged 50-75 using fecal occult blood testing, or FOBT, which is a fecal test, or one of two procedures: colonoscopy or sigmoidoscopy. Despite the benefits of routine screening on improving five-year survival rates if CRC is diagnosed early, the rate of screening compliance is low due in part to the limitations of existing solutions.

SUMMARY OF THE INVENTION

Provided herein are methods of assessing a colorectal cancer status in an individual. Also provided herein are methods of assessing a colorectal cancer risk status in a blood sample of an individual. Some such methods comprise the steps of obtaining a circulating blood sample from the individual; obtaining a biomarker panel level for a biomarker panel comprising a list of proteins in the sample comprising AACT, CO3, CO9, MIF, and PSGL to comprise panel information from said individual; comparing said panel information from said individual to a reference panel information set corresponding to a known colorectal cancer status; and categorizing said individual as having said colorectal cancer status if said individual's reference panel information does not differ significantly from said reference panel information set. Various aspects of these methods are recited below, contemplated as distinct or in combination. Methods are also contemplated to include methods wherein obtaining a circulating blood sample comprises drawing blood from a vein or artery of the individual. Methods are also contemplated to include methods wherein the panel information comprises age information for the individual. Optionally, the list of proteins comprises AACT, CO3, CO9, MIF, PSGL, CATD, CEA and SEPR. Optionally, the list of proteins comprises no more than 15 proteins. In some cases the list comprises more than 8 proteins, where in a CRC signal is derived from the list of proteins comprising AACT, CO3, CO9, MIF, PSGL, CATD, CEA and SEPR. Optionally, the list of proteins comprises no more than 8 proteins. In some cases, the list of proteins comprises AACT, CO3, CO9, MIF, PSGL, CATD, CEA and SEPR. Optionally, the categorizing has a sensitivity of at least 81% and a specificity of at least 78%. Methods are also contemplated to comprise transmitting a report of results of said categorizing a health practitioner. Optionally, the report indicates a sensitivity of at least 81%. Optionally, the report indicates a specificity of at least 78%. Optionally, the report recommends that a colonoscopy be performed. Optionally, the individual undergoes a colonoscopy. Optionally, the report recommends an independent surgical intervention. Optionally, the individual undergoes an independent surgical intervention. Optionally, the report recommends undergoing an independent cancer assay. Optionally, the individual undergoes an independent cancer assay. Optionally, the report recommends undergoing a stool cancer assay. Optionally, the individual undergoes a stool cancer assay. Optionally, the report recommends administering an anticancer composition. Optionally, an anticancer composition is administered to the individual. Optionally, the report recommends continued monitoring. Optionally, at least one biomarker level of said individual's panel information differs significantly from a corresponding value from said reference panel, and wherein said individual's panel level as a whole does not differ significantly from said reference panel level. Also contemplated herein are methods wherein no parameter of said individual's reference panel information in isolation is indicative of said colorectal cancer status in said individual at a sensitivity of greater than 65% or a specificity of greater than 65%. Optionally, the obtaining protein levels comprises contacting a fraction of the circulating blood sample to a set of antibodies, wherein the set of antibodies comprises antibodies specific to AACT, CO3, CO9, MIF, and PSGL. Optionally, the obtaining protein levels comprises subjecting a fraction of the circulating blood sample to a mass spectrometric analysis. Optionally, at least one of said comparing and said categorizing is performed on a computer configured to analyze reference panel information. Optionally, said reference panel information set corresponding to a known colorectal cancer status comprises a product of a machine learning model. Optionally, the machine learning model is trained using at least 100 biomarker panels corresponding to known colorectal health status. Panels disclosed herein distinguish samples having a CRC signal not only from samples from healthy individuals but also from samples from individuals having other types cancer or other cell cycle or cell proliferation aliments, as indicated in FIG. 4.

Also provided herein are methods of monitoring efficacy of a colorectal cancer treatment regimen in an individual. Some such methods comprise the steps of obtaining a first sample comprising circulating blood from the individual at a first time point; administering the treatment regimen to the individual; obtaining a second sample comprising circulating blood from the individual at a second time point; obtaining a first panel level comprising protein levels for a list of proteins in the first sample and a second panel level comprising protein levels for a list of proteins in the second sample, said list comprising AACT, CO3, CO9, MIF, and PSGL to comprise panel information for said first sample and said second sample; wherein a change in protein levels indicates efficacy of the colorectal cancer treatment. Also provided herein are ex vivo methods of monitoring efficacy of a colorectal cancer treatment in an individual. Some such methods comprise the steps of obtaining a first sample comprising circulating blood from the individual at a first time point; obtaining a second sample comprising circulating blood from the same individual receiving a colorectal cancer treatment at a second time point; obtaining a first panel level comprising protein levels for a list of proteins in the first sample and a second panel level comprising protein levels for a list of proteins in the second sample, said list comprising AACT, CO3, CO9, MIF, and PSGL to comprise panel information for said first sample and said second sample; wherein a change in protein levels indicates efficacy of the colorectal cancer treatment. Various aspects of these methods are recited below, contemplated as distinct or in combination. Methods are contemplated to include obtaining the first sample comprises drawing blood from a vein or artery of the individual. Optionally, the colorectal cancer treatment or treatment regimen comprises administration of a pharmaceutical composition. Optionally, the colorectal cancer treatment or treatment regimen comprises administration of a chemotherapeutic agent. Optionally, the colorectal cancer treatment or treatment regimen comprises a colonoscopy. Optionally, the colorectal cancer treatment or treatment regimen comprises a polypectomy. Optionally, the colorectal cancer treatment or treatment regimen comprises radiotherapy. Methods are also contemplated to include methods comprising comparing said first sample panel level and said second panel level to at least one panel level of a healthy reference, wherein the second sample panel level being more similar to the panel level of the healthy reference indicates efficacy of the colorectal cancer treatment. Optionally, methods comprise said first sample panel level and said second panel level to at least one panel level of a healthy reference, wherein the first sample panel level being more similar to the panel level of the colorectal cancer reference indicates efficacy of the colorectal cancer treatment. Optionally, the list of proteins comprises AACT, CO3, CO9, MIF, PSGL, CATD, CEA and SEPR. Optionally, the list of proteins comprises no more than 15 proteins. Optionally, the list of proteins comprises no more than 8 proteins. Optionally, the list of proteins comprises AACT, CO3, CO9, MIF, PSGL, CATD, CEA and SEPR. Optionally, methods comprise changing the colorectal cancer treatment or treatment regimen if no efficacy is indicated. Optionally, methods comprise repeating colorectal cancer treatment or the treatment regimen if no efficacy is indicated. Optionally, methods comprise continuing the colorectal cancer treatment or treatment regimen if no efficacy is indicated. Optionally, methods comprise discontinuing the colorectal cancer treatment or treatment regimen if efficacy is indicated.

Also provided herein are panels of proteins indicative of an individual's colorectal cancer status. Some such panels comprise at least 5 proteins selected from the list consisting of AACT, CO3, CO9, MIF, PSGL, CATD, CEA and SEPR, wherein measurement of the panel at a level that does not differ significantly from a reference panel from circulating blood of an individual is indicative of the individual's colorectal cancer status corresponding to a reference panel colorectal cancer status at a sensitivity of at least 81% and a specificity of at least 78%; and wherein no constituent protein level of said panel is indicative of the individual's colorectal cancer status at a sensitivity of greater than 65% and a specificity of greater than 65%. Various aspects of these panels are recited below, contemplated as distinct and in combination. Panels are contemplated to comprise at least 6 proteins selected from the list consisting of AACT, CO3, CO9, MIF, PSGL, CATD, CEA and SEPR. Optionally, panels comprise no more than 12 proteins, of which at least 4 proteins selected from the list consisting of AACT, CO3, CO9, MIF, PSGL, CATD, CEA and SEPR. Optionally, panels comprise no more than 12 proteins, wherein the panel of proteins comprises AACT, CO3, CO9, MIF, PSGL, CATD, CEA and SEPR. Optionally, panels consist of AACT, CO3, CO9, MIF, PSGL, CATD, CEA and SEPR. Also contemplated herein are any of the abovementioned panels of proteins for use in assessing a colorectal cancer status according to any of the above methods or monitoring efficacy of a colorectal cancer treatment according to any of the above methods.

Also provided herein are kits comprising an antibody panel, said antibody panel comprising antibodies that identify at least 5 proteins selected from the list consisting of AACT, CO3, CO9, MIF, PSGL, CATD, CEA and SEPR. Various aspects of these kits are recited below, contemplated as distinct or in combination. Kits are contemplated to comprise an antibody that binds to a control protein. Optionally, kits comprise no more than 15 antibodies. Optionally, kits comprise no more than 12 antibodies. Optionally, said antibody panel comprises antibodies that identify all of AACT, CO3, CO9, MIF, PSGL, CATD, CEA and SEPR. Optionally kits comprise instructions functionally related to use of the kit to assess a patient colorectal cancer status. Also contemplated herein are any of the abovementioned kits for use in assessing a colorectal cancer status according to any of the above methods or monitoring efficacy of a colorectal cancer treatment according to any of the above methods.

Also contemplated herein are computer systems configured to assess a colorectal cancer risk in an individual. Some such computer systems comprise a memory unit for receiving data comprising measurement of a panel of proteins comprising at least 5 proteins selected from the list consisting of AACT, CO3, CO9, MIF, PSGL, CATD, CEA and SEPR from a biological sample comprising circulating blood, computer-executable instructions for assessing a colorectal cancer risk associated with said measurement of said panel of proteins, an output unit for delivering a report assessing said colorectal cancer risk associated with said measurement of said panel of proteins. Optionally, said panel comprises at least 6 proteins selected from the list consisting of AACT, CO3, CO9, MIF, PSGL, CATD, CEA and SEPR. Optionally, said panel comprises no more than 12 proteins, of which at least 5 proteins selected from the list consisting of AACT, CO3, CO9, MIF, PSGL, CATD, CEA and SEPR. Optionally, said panel comprises no more than 12 proteins, wherein the panel of proteins comprises AACT, CO3, CO9, MIF, PSGL, CATD, CEA and SEPR. Optionally, said panel consists of AACT, CO3, CO9, MIF, PSGL, CATD, CEA and SEPR. Optionally, the memory unit is configured for receiving data comprising measurement of a second panel of proteins. Optionally, said data comprising measurement of a panel of proteins comprises ELISA data. Optionally, said data comprising measurement of a panel of proteins comprises mass spectrometry data. Optionally, assessing a colorectal cancer risk comprises comparing said data to a reference panel associated with a known colorectal cancer status. Optionally, said individual is assigned said known colorectal cancer status when said data does not differ significantly from said reference panel. Optionally, said reference panel indicates presence of colorectal cancer. Optionally, said reference panel indicates absence of colorectal cancer. Optionally, assessing a colorectal cancer risk is performed on a computer configured to analyze reference panel information. Optionally, said memory unit comprises at least one reference panel information set corresponding to a known colorectal cancer status. Optionally, the at least one reference panel information set comprises a machine learning model. Computer systems are also contemplated wherein the machine learning model is trained using at least 100 biomarker panels corresponding to known colorectal health status. Optionally, said report indicates a sensitivity of at least 81% and a specificity of at least 78%. Optionally, said report indicates a sensitivity of at least 81%. Optionally, said report indicates a specificity of at least 78%. Optionally, said report recommends that a colonoscopy be performed. Optionally, said report recommends an independent surgical intervention. Optionally, said report recommends undergoing an independent cancer assay. Optionally, said report recommends undergoing a stool cancer assay. Optionally, said report recommends administering an anticancer composition. Optionally, said report recommends continued monitoring. Computer systems herein are also contemplated wherein at least one parameter of said individual's reference panel information differs significantly from a corresponding value from said reference panel information set, and wherein said individual's reference panel information does not differ significantly from said reference panel information set. Optionally, no single protein of said panel indicates the individual's colorectal cancer status at a specificity of greater than 65% or a sensitivity of greater than 65%. Optionally, the memory unit is configured to receive age information from said individual. Optionally, the computer-executable instructions factor in age of the individual when assessing said colorectal cancer risk associated with said measurement of said panel of proteins.

Also provided herein are methods of assessing an advanced adenoma risk status in an individual. Also provided herein are methods of assessing an advanced adenoma risk status in a blood sample of an individual. Some such methods include comprising the steps of obtaining a circulating blood sample from the individual; obtaining protein levels for a list of proteins relevant to advanced adenoma in the sample comprising at least three of CATD, CLUS, GDF15 and SAA1 to comprise biomarker panel information from said individual; comparing said panel information from said individual to a reference panel information set corresponding to a known advanced adenoma status; and categorizing said individual as having said advanced adenoma risk status if said individual's reference panel information does not differ significantly from said reference panel information set. Various aspects of these methods are recited below, contemplated as distinct or in combination. Methods herein are contemplated to include obtaining a circulating blood sample comprises drawing blood from a vein or artery of the individual. Optionally, the panel information comprises age information for the individual. Optionally, the list of proteins comprises no more than 15 proteins. Optionally, the list of proteins comprises no more than 5 proteins. Optionally, list of proteins comprises CATD, CLUS, GDF15 and SAA1. Optionally, the categorizing has a sensitivity of at least 50% and a specificity of at least 80%. Optionally, the categorizing has a sensitivity of at least 47% and a specificity of at least 83%. Optionally, the categorizing has a sensitivity of at least 47% and a specificity of at least 80%. Optionally, methods herein comprise transmitting a report of results of said categorizing to a healthcare professional. Optionally, the report indicates a sensitivity of at least 47%. Optionally, the report indicates a sensitivity of at least 50%. Optionally, the report indicates a specificity of at least 80%. Optionally, the report recommends that a colonoscopy be performed. Optionally, the individual undergoes a colonoscopy. Optionally, the report recommends an independent surgical intervention. Optionally, the individual undergoes an independent surgical intervention. Optionally, the report recommends undergoing an independent cancer assay. Optionally, the individual undergoes an independent cancer assay. Optionally, the report recommends undergoing a stool cancer assay. Optionally, the individual undergoes a stool cancer assay. Optionally, the report recommends administering an anticancer composition. Optionally, an anticancer composition is administered to the individual. Optionally, the report recommends continued monitoring. Methods are also contemplated herein wherein at least one parameter of said individual's reference panel differs significantly from a corresponding value from said reference panel set, and wherein said individual's reference panel information as a whole does not differ significantly from said reference panel information set. Optionally, methods are contemplated wherein no parameter of said individual's reference panel information in isolation is indicative of said advanced adenoma status in said individual at a sensitivity of greater than 65% or a specificity of greater than 65%. Optionally, the obtaining protein levels comprises contacting a fraction of the circulating blood sample to a set of antibodies, wherein the set of antibodies comprises antibodies specific to CATD, CLUS, GDF15 and SAA1. Optionally, the obtaining protein levels comprises subjecting a fraction of the circulating blood sample to a mass spectrometric analysis. Optionally, the obtaining protein levels comprises contacting the sample to protein binding DNA aptamers. Optionally, the obtaining protein levels comprises contacting the sample to an antibody array. Optionally, at least one of said comparing and said categorizing is performed on a computer configured to analyze reference panel information. Optionally, said reference panel information set corresponding to a known advanced adenoma status comprises is a product of a machine learning model. Optionally, the machine learning model is trained using at least 100 biomarker panels corresponding to known colorectal health status.

Also provided herein are methods of monitoring efficacy of an advanced adenoma treatment regimen in an individual. Some such methods comprise the steps of obtaining a first sample comprising circulating blood from the individual at a first time point; administering the treatment regimen to the individual; obtaining a second sample comprising circulating blood from the individual at a second time point; obtaining a first panel level protein levels for a list of proteins relevant to advanced adenoma assessment in the first sample and a second panel level protein levels for a list of proteins relevant to advanced adenoma assessment in the second sample, said list comprising CATD, CLUS, GDF15 and SAA1 to comprise panel information for said first sample and said second sample; wherein a change in protein levels indicates efficacy of the advanced adenoma treatment. Also provided herein are ex vivo methods of monitoring efficacy of an advanced adenoma treatment in an individual. Some such methods comprise the steps of obtaining a first sample comprising circulating blood from the individual at a first time point; obtaining a second sample comprising circulating blood from the same individual receiving an advanced adenoma treatment at a second time point; obtaining a first panel level comprising protein levels for a list of proteins in the first sample and a second panel level comprising protein levels for a list of proteins in the second sample, said list comprising CATD, CLUS, GDF15 and SAA1 to comprise panel information for said first sample and said second sample; wherein a change in protein levels indicates efficacy of the colorectal cancer treatment. Various aspects of these methods are recited below, contemplated as distinct or in combination. Methods are also included wherein obtaining the first sample comprises drawing blood from a vein or artery of the individual. Optionally, the advanced adenoma treatment or treatment regimen comprises administration of a pharmaceutical composition. Optionally, the advanced adenoma treatment or treatment regimen comprises administration of a chemotherapeutic agent. Optionally, the advanced adenoma treatment or treatment regimen comprises a colonoscopy. Optionally, the advanced adenoma treatment or treatment regimen comprises a polypectomy. Optionally, the advanced adenoma treatment or treatment regimen comprises radiotherapy. Methods are also contemplated comprising comparing said first sample protein levels and said second panel protein levels to protein levels of a healthy reference, wherein the second sample levels being more similar to the protein levels of the healthy reference indicates efficacy of the advanced adenoma treatment. Optionally, comparing said first sample protein levels and said second panel protein levels to protein levels of an advanced adenoma reference, wherein the first sample levels being more similar to the protein levels of the advanced adenoma reference indicates efficacy of the advanced adenoma treatment. Optionally, the list of proteins relevant to advanced adenoma assessment comprises CATD, CLUS, GDF15 and SAA1. Optionally, the list of proteins relevant to advanced adenoma assessment comprises no more than 12 proteins. Optionally, the list of proteins relevant to advanced adenoma assessment comprises no more than 8 proteins. Optionally, the list of proteins relevant to advanced adenoma assessment consists of CATD, CLUS, GDF15 and SAA1. Optionally, methods herein comprise changing the advanced adenoma treatment or treatment regimen if no efficacy is indicated. Also contemplated herein are methods comprising repeating the advanced adenoma treatment or treatment regimen if no efficacy is indicated. Optionally, methods are contemplated to comprise continuing the advanced adenoma treatment or treatment regimen if no efficacy is indicated. Optionally, methods are contemplated to comprise discontinuing the advanced adenoma treatment or treatment regimen if efficacy is indicated.

Also provided herein are panels of proteins indicative of an individual's advanced adenoma status. Some such panels are contemplated to comprise at least 3 proteins relevant to advanced adenoma assessment selected from the list consisting of CATD, CLUS, GDF15 and SAA1, wherein measurement of the panel at a level that does not differ significantly from a reference panel from circulating blood of an individual is indicative of the individual's advanced adenoma status corresponding to a reference panel advanced adenoma status at a sensitivity of at least 50% and a specificity of at least 80%; and wherein no constituent protein level of said panel is indicative of the individual's advanced adenoma status at a sensitivity of greater than 65% and a specificity of greater than 65%. Panels are contemplated to comprise proteins relevant to advanced adenoma assessment CATD, CLUS, GDF15 and SAA1.

Also provided herein are kits comprising an antibody panel, said antibody panel comprising antibodies that identify at least 3 proteins advanced adenoma assessment selected from the list consisting of CATD, CLUS, GDF15 and SAA1. Various aspects of these kits are recited below, contemplated as distinct or in combination. Kits are contemplated to comprise an antibody that binds to a control protein. Optionally, kits comprise no more than 15 antibodies. Optionally, kits comprise no more than 12 antibodies. Optionally, said antibody panel comprises antibodies that identify all of CATD, CLUS, GDF15 and SAA1. Optionally kits comprise instructions functionally related to use of the kit to assess a patient advanced adenoma status. Also contemplated herein are any of the abovementioned panels of proteins for use in assessing a colorectal cancer status according to any of the above methods or monitoring efficacy of a colorectal cancer treatment according to any of the above methods. Also contemplated herein are any of the abovementioned kits for use in assessing a colorectal cancer status according to any of the above methods or monitoring efficacy of a colorectal cancer treatment according to any of the above methods.

Also contemplated herein are computer systems configured to assess advanced adenoma risk in an individual. Some such computer systems comprise a memory unit for receiving data comprising measurement of a panel of proteins comprising at least 3 proteins selected from the list consisting of CATD, CLUS, GDF15 and SAA1 from a biological sample comprising circulating blood, computer-executable instructions for assessing advanced adenoma risk associated with said measurement of said panel of proteins, an output unit for delivering a report assessing said advanced adenoma risk associated with said measurement of said panel of proteins. Optionally, said panel comprises CATD, CLUS, GDF15 and SAA1. Optionally, said panel comprises no more than 12 proteins, of which at least 5 proteins selected from the list consisting of AACT, CO3, CO9, MIF, PSGL, CATD, CEA and SEPR. Optionally, said panel comprises no more than 12 proteins, wherein the panel of proteins comprises CATD, CLUS, GDF15 and SAA1. Optionally, said panel consists of CATD, CLUS, GDF15 and SAA1. Optionally, the memory unit is configured for receiving data comprising measurement of a second panel of proteins. Optionally, said data comprising measurement of a panel of proteins comprises ELISA data. Optionally, said data comprising measurement of a panel of proteins comprises mass spectrometry data. Optionally, assessing a advanced adenoma risk comprises comparing said data to a reference panel associated with a known advanced adenoma status. Optionally, said individual is assigned said known advanced adenoma status when said data does not differ significantly from said reference panel. Optionally, said reference panel indicates presence of advanced adenoma. Optionally, said reference panel indicates absence of advanced adenoma. Optionally, assessing a advanced adenoma risk is performed on a computer configured to analyze reference panel information. Optionally, said memory unit comprises at least one reference panel information set corresponding to a known advanced adenoma status. Optionally, the at least one reference panel information set comprises a machine learning model. Computer systems are also contemplated wherein the machine learning model is trained using at least 100 biomarker panels corresponding to known colorectal health status. Optionally, said report indicates a sensitivity of at least 50% and a specificity of at least 80%. Optionally, said report indicates a sensitivity of at least 50%. Optionally, said report indicates a specificity of at least 80%. Optionally, said report recommends that a colonoscopy be performed. Optionally, said report recommends an independent surgical intervention. Optionally, said report recommends undergoing an independent cancer assay. Optionally, said report recommends undergoing a stool cancer assay. Optionally, said report recommends administering an anticancer composition. Optionally, said report recommends continued monitoring. Computer systems herein are also contemplated wherein at least one parameter of said individual's reference panel information differs significantly from a corresponding value from said reference panel information set, and wherein said individual's reference panel information does not differ significantly from said reference panel information set.

Optionally, no single protein of said panel indicates the individual's advanced adenoma status at a specificity of greater than 65% or a sensitivity of greater than 65%. Optionally, the memory unit is configured to receive age information from said individual. Optionally, the computer-executable instructions factor in age of the individual when assessing said advanced adenoma risk associated with said measurement of said panel of proteins.

Also provided herein are methods of assessing a colorectal health risk status in an individual. Also provided herein are ex vivo methods of assessing a colorectal health risk status in a blood sample of an individual. Some such methods comprise the steps of obtaining a circulating blood sample from the individual; obtaining a biomarker panel level for a biomarker panel comprising a list of proteins in the sample comprising AACT, CO3, CO9, MIF, PSGL, SEPR, CEA, CATD, CLUS, GDF15 and SAA1, and obtaining an age for the individual, wherein AACT, CO3, CO9, MIF, PSGL, SEPR, CEA, CATD, and age comprise colorectal cancer panel information from said individual; and wherein CATD, CLUS, GDF15 and SAA1 comprise advanced adenoma panel information from said individual; comparing said colorectal cancer panel information from said individual to a reference colorectal cancer panel information set corresponding to a known colorectal cancer status; comparing said advanced adenoma panel information from said individual to a reference advanced adenoma panel information set corresponding to a known advanced adenoma status; and categorizing said individual as having a colorectal health risk if either of said colorectal cancer panel or said advanced adenoma panel does not differ significantly from a reference panel positive for a colorectal health risk. Various aspects of these methods are recited below, contemplated as distinct or in combination. Methods herein are contemplated to include obtaining a circulating blood sample comprises drawing blood from a vein or artery of the individual. Optionally, the panel information comprises age information for the individual. Optionally, the list of proteins comprises no more than 20 proteins. Optionally, the list of proteins comprises no more than 11 proteins. Optionally, the categorizing has a sensitivity of at least 80% and a specificity of at least 50%. Optionally, the categorizing has a sensitivity of at least 80% and a specificity of at least 47%. Optionally, the categorizing has a sensitivity of at least 83% and a specificity of at least 47%. Optionally, methods herein comprise transmitting a report of results of said categorizing to a healthcare professional. Optionally, the report indicates a sensitivity of at least 8%. Optionally, the report indicates a specificity of at least 50%. Optionally, the report recommends that a colonoscopy be performed. Optionally, the individual undergoes a colonoscopy. Optionally, the report recommends an independent surgical intervention. Optionally, the individual undergoes an independent surgical intervention. Optionally, the report recommends undergoing an independent cancer assay. Optionally, the individual undergoes an independent cancer assay. Optionally, the report recommends undergoing a stool cancer assay. Optionally, the individual undergoes a stool cancer assay. Optionally, the report recommends administering an anticancer composition. Optionally, an anticancer composition is administered to the individual. Optionally, the report recommends continued monitoring. Methods are also contemplated herein wherein at least one parameter of said individual's reference panel differs significantly from a corresponding value from said reference panel set, and wherein said individual's reference panel information as a whole does not differ significantly from said reference panel information set. Optionally, methods are contemplated wherein no parameter of said individual's reference panel information in isolation is indicative of said advanced adenoma status in said individual at a sensitivity of greater than 65% or a specificity of greater than 65%. Optionally, the obtaining protein levels comprises contacting a fraction of the circulating blood sample to a set of antibodies, wherein the set of antibodies comprises antibodies specific to AACT, CO3, CO9, MIF, PSGL, SEPR, CEA, CATD, CLUS, GDF15 and SAA1. Optionally, the obtaining protein levels comprises subjecting a fraction of the circulating blood sample to a mass spectrometric analysis. Optionally, the obtaining protein levels comprises contacting the sample to protein binding DNA aptamers. Optionally, the obtaining protein levels comprises contacting the sample to an antibody array. Optionally, at least one of said comparing and said categorizing is performed on a computer configured to analyze reference panel information. Optionally, said reference panel information set corresponding to a known advanced adenoma status comprises is a product of a machine learning model. Optionally, the machine learning model is trained using at least 100 biomarker panels corresponding to known colorectal health status.

Provided herein are methods, compositions, kits, computer readable media, and systems for the diagnosis and/or treatment of at least one of advanced colorectal adenoma and colorectal cancer. Through the methods and compositions provided herein, a sample is taken from an individual such as an individual at risk of advanced colorectal adenoma or colorectal cancer. The sample is assayed to determine the accumulation levels of a panel of markers such as proteins, for example a panel of markers comprising or consisting of the markers in panels disclosed herein. In many cases the panels comprise proteins that individually are known to play a role in indicating the presence of advanced colorectal adenoma or colorectal cancer, while in other cases the panels comprise a protein or proteins not know to correlate with advanced colorectal adenoma or colorectal cancer. However, in all cases the identification and accumulation of markers into a panel results in a level of specificity, sensitivity or specificity and sensitivity that substantially surpasses that of individual markers or smaller or less accurate sets of markers.

Additionally, methods, panels and other tests disclosed herein substantially surpass the sensitivity, specificity, or sensitivity and specificity of currently available tests such as currently available blood-based tests. Panel accumulation levels are measured in a number of ways in various embodiments, for example through an ELISA assay, through mass spectroscopy analysis or through alternate approaches to protein accumulation level quantification.

Panel accumulation levels are compared to a positive control or negative control standard, or to a model of advanced colorectal adenoma or colorectal cancer accumulation levels or of healthy accumulation levels, such that a prediction is made regarding an assayed individual's health status. In some cases, a panel assay result is accompanied by a recommendation regarding an intervention or an alternate verification of the panel assay results.

Provided herein are biomarker panels and assays useful for the diagnosis and/or treatment of at least one of advanced colorectal adenoma and colorectal cancer.

Also provided herein are kits, comprising a computer readable medium described herein, and instructions for use of the computer readable medium.

A number of treatment regimens are contemplated herein and known to one of skill in the art, such as chemotherapy, administration of a biologic therapeutic agent, and surgical intervention such as low anterior resection or abdominoperineal resection, or ostomy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7B illustrates a Validation ROC AUC plot for CRC Model 1.
FIG. 8A illustrates a Discovery ROC AUC plot for CRC Model 2.
FIG. 8B illustrates a Validation ROC AUC plot for CRC Model 2.
FIG. 9A illustrates a Discovery ROC AUC plot for CRC Model 3.
FIG. 9B illustrates a Validation ROC AUC plot for CRC Model 3.
FIG. 10A illustrates a Discovery ROC AUC plot for CRC Model 4.
FIG. 10B illustrates a Validation ROC AUC plot for CRC Model 4.
FIG. 11A illustrates a Discovery ROC AUC plot for CRC Model 5.
FIG. 11B illustrates a Validation ROC AUC plot for CRC Model 5.
FIG. 12A illustrates a Discovery ROC AUC plot for CRC Model 6.
FIG. 12B illustrates a Validation ROC AUC plot for CRC Model 6.
FIG. 13A illustrates a Discovery ROC AUC plot for CRC Model 7.
FIG. 13B illustrates a Validation ROC AUC plot for CRC Model 7.
FIG. 14A illustrates a Discovery ROC AUC plot for CRC Model 8.
FIG. 14B illustrates a Validation ROC AUC plot for CRC Model 8.
FIG. 15A illustrates a Discovery ROC AUC plot for CRC Model 9.
FIG. 15B illustrates a Validation ROC AUC plot for CRC Model 9.
FIG. 16A illustrates a Discovery ROC AUC plot for CRC Model 10.
FIG. 16B illustrates a Validation ROC AUC plot for CRC Model 10.
FIG. 17A illustrates a Discovery ROC AUC plot for CRC Model 5 with NOC.
FIG. 17B illustrates a Validation ROC AUC plot for CRC Model 5 with NOC.
FIG. 18 illustrates a Max Accuracy plot for CRC Models 1-10.
FIG. 19 depicts a Computer System architecture consistent with the Methods, Compositions, Kits and Systems disclosed herein.

FIG. 20 presents AUC values for randomly generated CRC panels from a targeted-MS enriched biomarker population.

DETAILED DESCRIPTION

Figure 1:
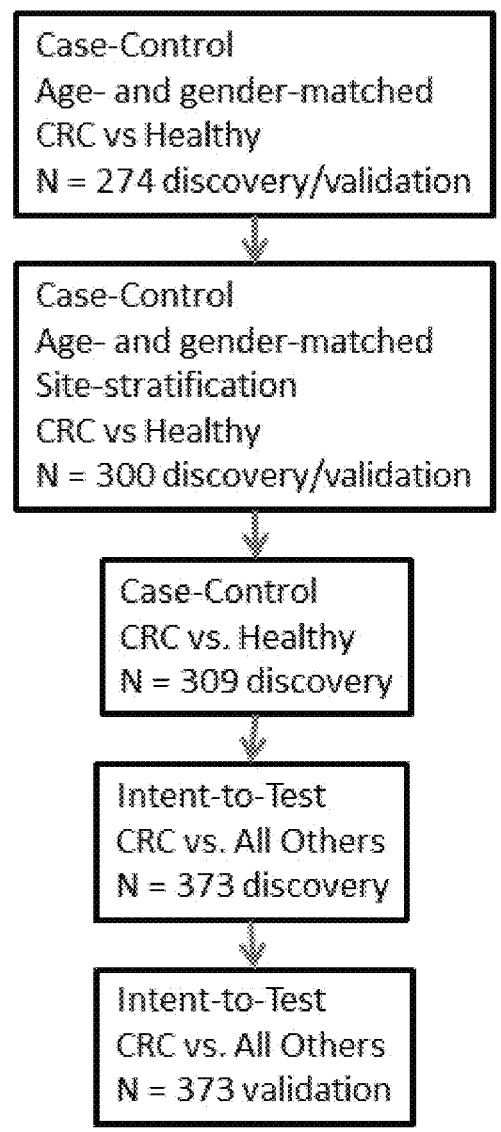
FIG. 1 depicts a Biomarker Panel development pipeline.

Provided herein are biomarker panels, methods, compositions, kits, and systems for the non-invasive assessment of colorectal health, for example through the detection of at least one of advanced colorectal adenoma ("AA") and colorectal cancer ("CRC"). Biomarker panels, methods, compositions, kits, and systems described herein are used to determine a likelihood that a subject has a colorectal condition such as at least one of an advanced colorectal adenoma and CRC through the noninvasive assay of a sample taken from circulating blood circulating blood. Some such biomarker panels are used noninvasively to detect a colorectal health issue such as colorectal cancer with a sensitivity of as much as 81% or greater, and a specificity of as much as 78% or greater. An exemplary CRC biomarker panel comprises the markers AACT, CATD, CEA, CO3, CO9, MIF, PSGL, and SEPR, and the non-protein biomarker of age of the individual providing the sample. Some such biomarker panels are used noninvasively to detect a colorectal health issue such as an advanced adenoma with a sensitivity of as much as 50% or greater, and a specificity of as much as 80% or greater. An exemplary biomarker panel relevant to advanced adenoma assessment comprises the markers CATD, CLUS, GDF15 and SAA1.

Biomarker panels as disclosed herein share a property that sensitive, specific conclusions regarding an individual's colorectal health are made using protein level information derived from circulating blood, alone or in combination with other information such as an individual's age, gender, health history or other characteristics. A benefit of the present protein panels is that they provide a sensitive, specific colorectal health assessment using conveniently, noninvasively obtained samples. There is no need to rely upon data obtained from an intrusive abdominal assay such as a colonoscopy or a sigmoidoscopy, or from stool sample material. As a result compliance rates are substantially higher, and colorectal health issues are more easily recognized early in their progression, so that they may be more efficiently treated. Ultimately, the effect of this benefit is measured in lives saved, and is substantial.

Biomarker panels as disclosed herein are selected such that their predictive value as panels is substantially greater than the predictive value of their individual members. Panel members generally do not co-vary with one another, such that panel members provide independent contributions to the panel's overall health signal. Accordingly, a panel is able to substantially outperform the performance of any individual constituent indicative of an individual's colorectal health status, such that a commercially and medicinally relevant degree of confidence (such as sensitivity, specificity or sensitivity and specificity) is obtained. Thus, in the panels as disclosed herein, multiple panel members indicative of a health issue provide a much stronger signal than is found, for example in a panel wherein two or more members rise or fall in strict concert such that the signal derived therefrom is effectively a single signal, repeated twice. Accordingly, panels as disclosed herein are robust to variation in single constituent measurements. For example because panel members vary independently of one another, panels herein often indicate a health risk despite the fact that one or more than one individual members of the panel would not indicate that the health risk is present if measured alone. In some cases, panels herein indicate a health risk at a significant level of confidence despite the fact that no individual panel member indicates the health risk at a significant level of confidence on its own. In some cases, panels herein indicate a health risk at a significant level of confidence despite the fact that at least one individual member indicates at a significant level of confidence that the health risk is not present.

Biomarkers consistent with the panels herein comprise biological molecules that circulate in the bloodstream of an individual, such as proteins. Readily available information such as individual's age, gender, weight, height, body mass index or other easily measured or obtained information is also eligible as a marker in some cases. In particular, some panels herein rely upon age, gender, or age and gender as biomarkers.

Common to many biomarkers herein is the ease with which they are assayed in an individual. Biomarkers herein are readily obtained by a blood draw from an artery or vein of an individual, or are obtained via interview or by simple biometric analysis. A benefit of the ease with which biomarkers herein are obtained is that invasive assays such as colonoscopy or sigmoidoscopy are not required for biomarker measurement. Similarly, stool samples are not required for biomarker determination. As a result, panel information as disclosed herein is often readily obtained through a blood draw in combination with a visit to a doctor's office. Compliance rates are accordingly substantially higher than are compliance rates for colorectal health assays involving stool samples or invasive procedures.

Exemplary panels disclosed herein comprise circulating proteins or fragments thereof that are recognizably or uniquely mapped to their parent protein, and in some cases comprise a readily obtained biomarker such as an individual's age.

Characteristics of Panels Disclosed Herein Relative to Other Biomarker Panels

Panels disclosed herein substantially outperform individual markers or randomly generated panels. Although at least some members of the panels herein are implicated in cancer, the panels herein far outperform panels derived randomly from any art teachings. This is illustrated by examination of panel performance as compared to individual members, randomly generated panels, and in light of the unpredictability of individual markers for any individual health assessment.

Panels were constructed from an original candidate pool of 187 potential biomarkers selected from the literature. See FIG. 1. Using a 274 member age and gender matched discovery sample set, targeted mass spectroscopy was used to identify 28 biomarkers from the original set that co-vary with health status of the 274 members of the discovery sample set. This 28 member set is not a random selection of the 187 member original candidate pool, and the 28 member set was not selected from the original 187 member candidate pool based upon any teaching in the art.

The 28 member set was tested against a separate age and gender matched 300 member sample set to come to CRC panels as disclosed herein, such as the 8 member panel comprising AACT, CO3, CO9, MIF, PSGL, CATD, CEA and SEPR. This and similar panels were selected from an original 187 member candidate pool but are not taught to be particularly effective in combination to the exclusion of other candidate pool constituents. Rather, the panel is come to through repeated analysis of independently derived samples in combination with the inventor's own insights into panel construction and health status prediction.

Figure 2:
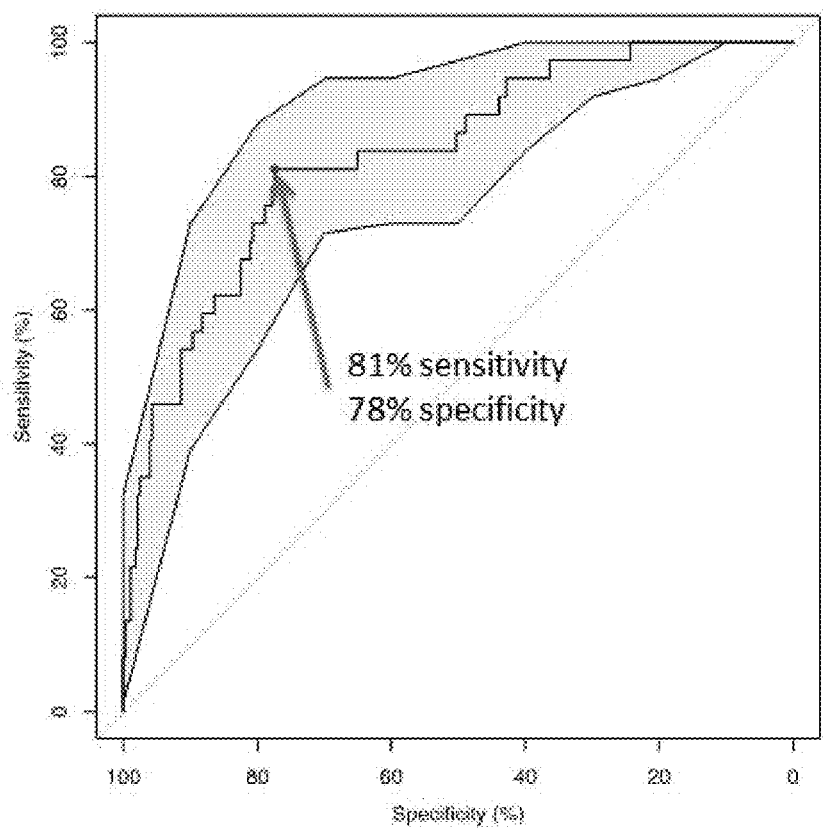
FIG. 2 illustrates an AUC curve for a lead CRC panel.
Figure 3:
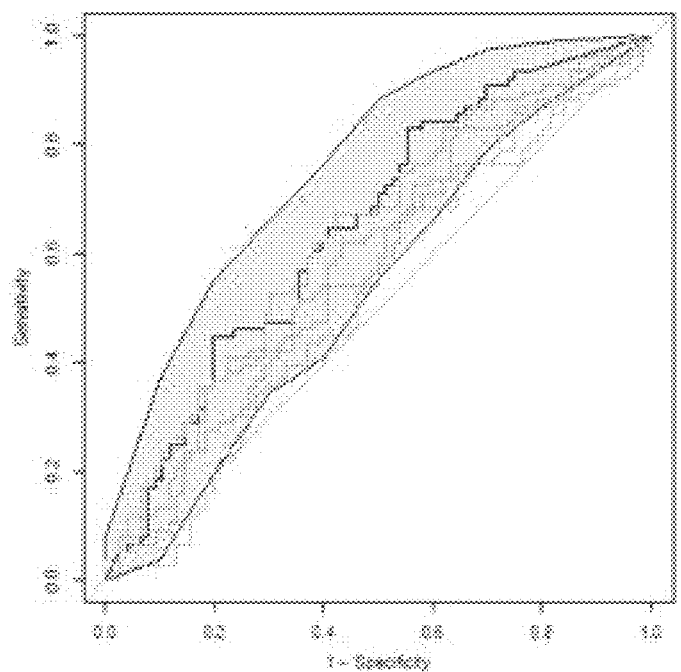
FIG. 3 illustrates an AUC curve for a lead AA panel.

FIG. 2 depicts an AUC plot for a lead CRC panel derived herein. The AUC plot clearly illustrates that the CRC panel performs substantially better than random chance, as depicted by the diagonal on this figure. FIG. 3 depicts an AUC plot for a lead AA panel derived herein. The AUC plot clearly illustrates that the AA panel performs substantially better than random chance, as depicted by the diagonal on this figure.

Biomarker panels herein perform substantially better than any random selection of biomarkers individually implicated in cancer generally, such as those of the 187 member candidate pool. That is, if one of skill in the art were to start with a list of biomarkers available in the literature and randomly assemble, or even assemble in light of teachings available to one of skill in the art, a biomarker panel to use to assay for a colorectal health issue such as colorectal cancer or advanced adenoma in an individual, one does not come to a biomarker as disclosed herein. Biomarker panels disclosed herein substantially outperform randomly selected panels and panels selected in light of the art.

Biomarker panels herein perform substantially better than any individual constituent marker individually implicated in cancer generally, such as those of the 187 member candidate pool. Some individual biomarkers indicate CRC or advanced adenoma, but with a sensitivity and a specificity that is far below that of the biomarker panels as disclosed herein. Use of individual biomarkers, or combinations of biomarkers not recited or readily apparent to one of skill in the art from the disclosure herein, is not contemplated pursuant to this disclosure.

Figure 5:
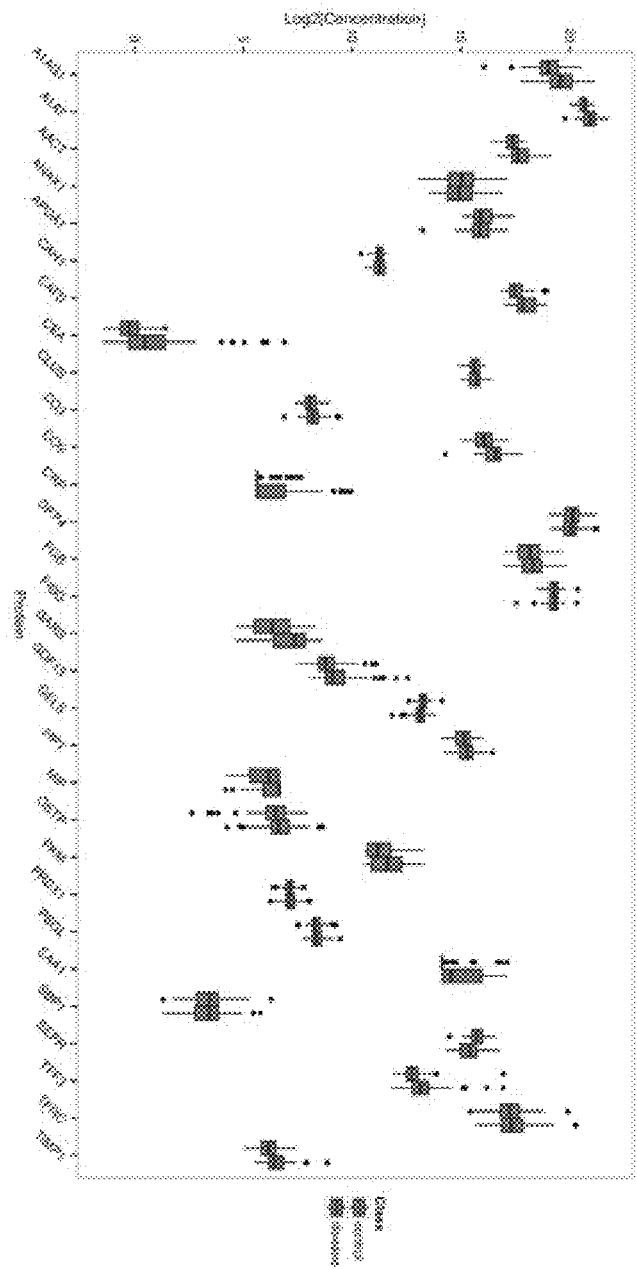
FIG. 5 presents protein levels from biomarker proteins in CRC and healthy control samples.
Figure 6:
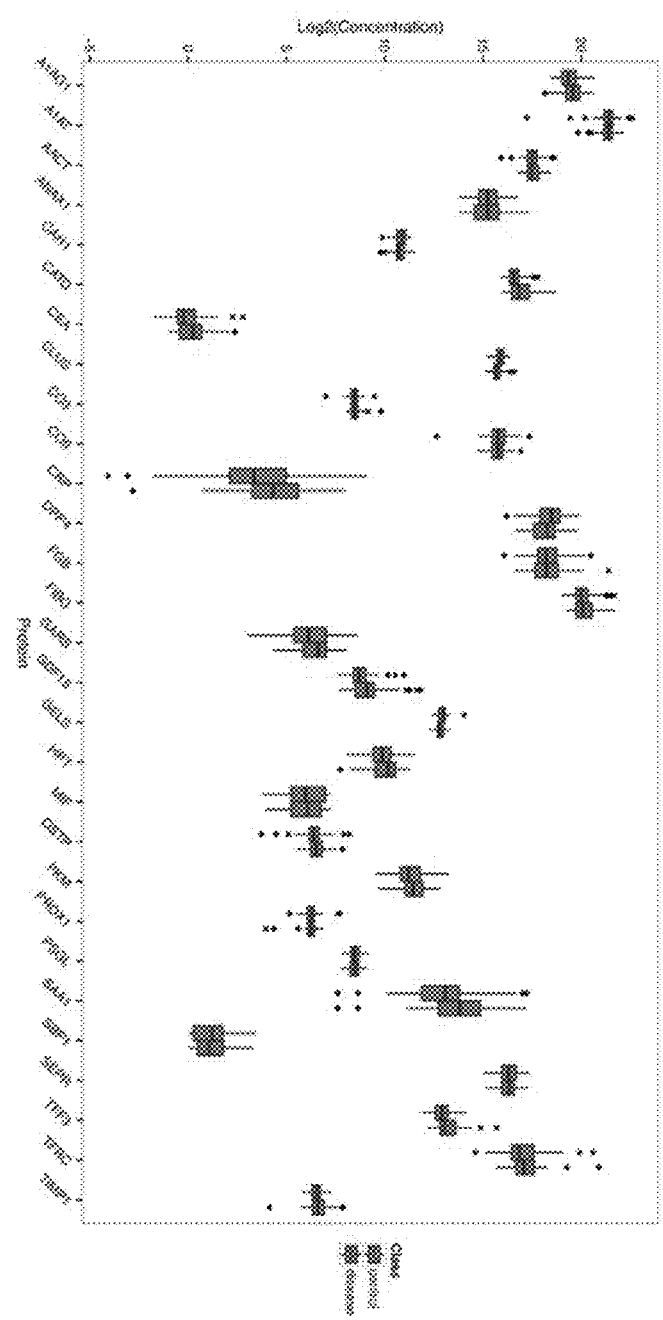
FIG. 6 presents protein levels from biomarker proteins in AA and healthy control samples.

Reference is made to FIGS. 5 and 6. In these figures, individual protein levels are compared between samples that are positive or negative for CRC (FIG. 5) or AA (FIG. 6). Proteins presented in these figures are not randomly selected, rather they are chosen from the MS-enriched set of 28 proteins identified from among the 187 protein list identified in the art as being potentially of relevance to cancer health assessment. For each paired boxplot, the healthy sample levels are at left or top, while the CRC or AA positive protein levels are depicted at right or bottom. For the vast majority of individual protein markers, there is little difference between the condition positive and condition negative protein levels. Levels are not identical, but the difference in most cases does not look to one of skill in the art to be significant, particularly at a level at which one would base a colorectal health assessment. With a few exceptions, such as FIG. 5 CEA, CRP, or GARS levels, the listed protein levels are quite similar between condition and no-condition samples. See, as representative examples FIG. 5 A1AG1, A1AT, AACT, ANAX1, APOA1, CAH1, CO9, GELS, HTP, OSTP or PSGL, among others. The situation for FIG. 6 is quite similar, with individual protein levels rarely differing very conspicuously between condition positive and condition negative individuals.

It is clear from FIG. 5 and FIG. 6 that no individual marker, even from this targeted-MS enriched set, is expected to perform as well as the panels presented herein. Furthermore, there is little suggestion from the protein levels presented in FIG. 5 or FIG. 6 that combinations of protein levels may have a synergistic effect so as to attain the performance of the panels as disclosed herein.

Aggregation of protein markers alone does not accomplish the level of performance of the panels disclosed herein. Reference is made to Example 21, below. Random panels are generated from the targeted MS-enriched set of 28 markers, and their performance is compared to that of the panels herein. The enriched 28 member set is already expected to yield panels that perform much better than those generated from the unenriched parent 187 marker set. It is observed that the panels herein, particularly the panels of 8-10 members, as shown, substantially outperform panels generated at random from an already enriched set of protein markers. These random panels do not represent panels that one would come to from the art, as they are already enriched from the 187 member list as mentioned in the art as being relevant to cancer detection. Thus, even performance comparable to levels seen in the randomly generated panels from the 28 marker set represents a substantial improvement over more generally apparent panels. Panels herein, however generally match (AA lead panel) or more often substantially outperform (CRC panels) up to almost 100% of the randomly generated panels from the enriched set of 28 markers. See again Example 21.

Biomarker panels herein yield results that are more reliable, more sensitive and more specific than simply the collection of their individual constituents. That is, in some cases individual biomarkers are detected at levels that are individually not informative with a degree of sensitivity and specificity to be medically relevant, but the level of the biomarker panel nonetheless provides a colorectal health assessment with a degree of confidence that is medically actionable. In some cases no individual biomarker of the panel is present at a level that is individually indicative of a health issue warranting follow-up, but the biomarker panel as a whole, assessed as indicated herein, provides an assessment that is indicative of a health issue warranting follow-up.

Biomarkers herein yield results that are in some cases qualitatively different from those of their constituent biomarkers. That is, in some cases one or more individual biomarkers of the panel are present at a level that is individually indicative of a colorectal health status that is contradictory to the health status indicated by the level of the panel as a whole, including the contradictory biomarker. In such cases, it is often found that independent health assessment, for example by colonoscopy or by stool sample analysis, supports the panel assessment rather than the health status assessment provided by the contradictory individual marker.

Reference is made to Example 22 below. In that example the CRC biomarker panels provide predictions that are inconsistent with the predictions that result from looking at constituent biomarker levels in isolation. The protein CO3, in particular, is measured at a level in the CRC-positive individual, patient 1, that is intermediate between the CO3 levels observed for two CRC-negative individuals. If one were scoring these biomarkers individually rather than as parts of a panel, one would be unlikely to score patient 1 as CRC positive and patients 2 and 3 as CRC negative in light of patient 1's CO3 level falling between those of patient 2 and 3.

However, using the panel analysis as disclosed herein, one comes to a result that is qualitatively different from the result expected by examination of an individual panel biomarker in isolation. This data as presented in Example 22, below, highlights the fact that the panels herein are not simply quantitatively better but are also in some cases qualitatively different from their individual biomarker constituents.

Accordingly, biomarker panels disclosed herein are understood to perform better than a random collection of candidate markers as taught by the literature. Biomarker panels disclosed herein are also understood to perform better statistically, and in some cases qualitatively differently, than do their individual biomarker constituents, such that a health assessment from the biomarker panel as a whole is either more accurate or in some cases provides a result that is qualitatively different from that of one or more individual biomarker constituents.

Panel Constituents

Some biomarker panels comprise some or all of the protein markers recited herein, subsets thereof or listed markers in combination with additional markers or biological parameters. A lead biomarker panel relevant to colorectal cancer assessment comprises at least 4 markers, up to the full list, alone or in combination with additional markers, said list selected from the following: AACT, CATD, CEA, CO3, CO9, MIF, PSGL, SEPR, and also including age as a biomarker. A lead biomarker panel relevant to advanced adenoma assessment comprises markers selected from the following: CATD, CLUS, GDF15 and SAA1. A lead biomarker panel, or a combination of biomarker panels having combined colorectal cancer and advanced adenoma assessment capabilities comprises biomarkers such as AACT, CEA, CO3, CO9, MIF, PSGL, SEPR, CATD, CLUS, GDF15 and SAA1, and age as a non-protein biomarker, or a subset thereof optionally having at least one individual marker excluded or replaced with one or more markers.

Often, it is convenient or efficient to combine a colorectal cancer biomarker panel and an advanced adenoma panel into a single kit or a single biomarker panel. In these cases, one sees a kit comprising eleven biomarkers, or a subset or larger set thereof, including AACT, CATD, CEA, CO3, CO9, MIF, PSGL, SEPR, CLUS, GDF15 and SAA1, of which AACT, CEA, CO3, CO9, MIF, PSGL, and SEPR or a subset or larger group comprising these markers is informative as to colorectal cancer status; CLUS, GDF15 and SAA1 or a subset or larger group comprising these markers is informative as to advanced adenoma status; and CATD, if included, is informative as to both colorectal cancer status and advanced adenoma status.

Alternate colorectal cancer biomarker panels are listed below. Much like the panel discussed above, these panels, or subsets or additions, are used alone or in combination with the abovementioned advanced adenoma panel, optionally using markers such as CATD, CLUS, GDF15 or SAA1 to be indicative of advanced adenoma and colorectal cancer. An exemplary biomarker panel comprises at least 4 markers, up to the full list, alone or in combination with additional markers, said list selected from the following: A1AG1, A1AT, CATD, CEA, CO9, OSTPxAge, SEPR, wherein OSTPxAge refers to OSTP viewed in combination with individual age. An exemplary biomarker panel comprises at least 4 markers, up to the full list, alone or in combination with additional markers, said list selected from the following: A1AG1, A1AT, APOA1, CATD, CEA, CLUS, CO3, CO9, FGB, FIBG, GARS, GELS, MIF, PRDX1, PSGL, SBP1, SEPR. An exemplary biomarker panel comprises at least 4 markers, up to the full list, alone or in combination with additional markers, said list selected from the following: A1AG1, A1AT, CATD, CEA, CO9, GARS, SEPR. An exemplary biomarker panel comprises at least 4 markers, up to the full list, alone or in combination with additional markers, said list selected from the following: A1AG1, A1AT, AACT, CATD, CEA, CO9, CRP, AACT, CO9, CRP, CRP, CRP, CRP, CRP, CRP, GELS, S10A8, S10A8, S10A8, S10A8, S10A9, S10A9, GARS, SAA1, SEPR. An exemplary biomarker panel comprises at least 4 markers, up to the full list, alone or in combination with additional markers, said list selected from the following: CATD, CEA, CO3, CO9, GARS, GELS, SEPR, TFRC. An exemplary biomarker panel comprises at least 4 markers, up to the full list, alone or in combination with additional markers, said list selected from the following: CATD, CEA, AACT, CO9, SEPR. An exemplary biomarker panel comprises at least 4 markers, up to the full list, alone or in combination with additional markers, said list selected from the following: A1AT, C3218600, C387796, C597612, C979276, CATD, CEA, GARS, GELS, SEPR. An exemplary biomarker panel comprises at least 4 markers, up to the full list, alone or in combination with additional markers, said list selected from the following: A1AG1, A1AT, CATD, CEA, CO9, SEPR, CATD/SEPR, CATD/GELS, CO9/SEPR, A1AT/FIBG, wherein a "/" indicates that a biomarker comprises a ratio of one protein or other biomarker level to a second protein or other biomarker level. An exemplary biomarker panel comprises at least 4 markers, up to the full list, alone or in combination with additional markers, said list selected from the following: CATD, CEA, CO3, CO9, S10A8, GELS, SEPR, TFRC. An exemplary biomarker panel comprises at least 4 markers, up to the full list, alone or in combination with additional markers, said list selected from the following: A1AG1, CATD, CEA, CO3, CO9, GELS, SEPR. For biomarker panels disclosed herein, variants having all but 1, 2, 3, or about 90%, 80%, 70%, 60%, or 50% of the biomarkers recited are also contemplated, as are panels that comprise additional biomarkers or control markers.

Biomarkers are measured through a number of approaches consistent with the disclosure herein. In many cases biomarkers are measured through an immunological interaction, such as that which occurs in an ELISA assay through which proteins or protein fragments in a blood sample from an individual are bound to specific antibodies, and the extent of binding is quantified as a measure of protein abundance in the sample. ELISA assays capable of measuring biomarker panels as disclosed herein are contemplated as embodiments of the present disclosure as kits.

Alternately or in combination, biomarkers are measured through mass spectrometric methods such as MS, MS/MS, MALDI-TOF or other mass spectrometric approaches as appropriate. Often, the MS approach quantifies a fragment of a biomarker rather than the full-length protein. However, such approaches are sufficient to determine the protein level of the biomarker to an accuracy sufficient for a colorectal health assessment as disclosed herein.

Some details of panel performance is dependent upon assay approach, such that some panels perform slightly better using an immunological or a mass spectrometric approach. However, it is observed that in many cases panel performance is largely independent of assay method, such that a panel that performs slightly better using an immunological assay is nonetheless informative as to an individual's colorectal health status when assayed using mass spectrometric analysis, or vice versa.

Once an expression level for a biomarker panel is determined, a colorectal health assessment is available for the individual from which the sample is obtained. A number of approaches are available to one of skill in the art to generate or come to a colorectal health assessment from an individual's biomarker panel expression level.

Some assessments rely upon comparison of an individual's biomarker panel level to a reference level, such as a reference biomarker panel level from an individual known or independently verified to be in good colorectal health, or from an individual known or independently verified to be in poor colorectal health, such as is the case for an individual having colorectal cancer or at least one advanced adenoma. Alternately an individual's biomarker panel level is compared to a reference level constructed from a plurality of individuals of common known colorectal health status. In some cases the reference is an average of known panel levels from a plurality of individuals, or alternately is a range defined by the range of panel levels observed in the reference individuals. A range reference panel level is in some cases a weighted range, such that outlier values among the individuals having a common colorectal health status are given lower predictive value than panel levels that are common to a plurality or majority or all of the panel levels.

In more complex assessment approaches, an individual's biomarker panel level is compared to a reference level constructed from a larger number of individuals of common known colorectal health status, such as at least 10, at least 50, at least 100, at least 500, at least 1000 or more individuals. Often, the reference individuals are evenly distributed in health status between positive and negative for a colorectal health status such as positive and negative for colorectal cancer, or positive and negative for advanced adenoma. Assessment comprises in some cases iterative or simultaneous comparison of an individual's biomarker panel level to a plurality of references of known health status.

Alternately or in combination, a plurality of known reference biomarker panel levels are used to train a computational assessment algorithm such as a machine learning model such that a single comparison between an individual's biomarker panel level and a reference provides an outcome that integrates or aggregates information from a large number of individuals of common known colorectal health status, such as at least 10, at least 50, at least 100, at least 500, at least 1000 or more individuals. Generation of such a reference often facilitates much faster assessment of an individual's colorectal health status, or assessment using much less computational power.

A reference is generated from a plurality of reference individual biomarker levels through any of a number of computational approaches known to one of skill in the art. Machine learning models are readily constructed, for example, using any number of statistical programming programing languages such as R, scripting languages such as Python and associated machine learning packages, data mining software such as Weka or Java, Mathematica, Matlab or SAS.

An individual's biomarker panel level is compared to a reference as generated above or otherwise by one of skill in the art, and an output assessment is generated. A number of output assessments are consistent with the disclosure herein. Output assessments comprise a single assessment, often narrowed by a sensitivity, specificity or sensitivity and specificity parameter, indicating a colorectal health status assessment. Alternately or in combination, additional parameters are provided, such as an odds ratio indicative of the relative increase in chance of suffering from a colorectal health issue in light of the individual's biomarker panel level or biomarker panel level assessment.

Results are variously provided to the individual or to a health care professional or other professional. Results are optionally accompanied by a heath recommendation, such as a recommendation to confirm or independently assess a colorectal health status assessment, for example using a stool sample assay or an invasive approach such as a colonoscopy, sigmoidoscopy or other supplemental assay for colorectal health.

A recommendation optionally includes information relevant to a treatment regimen, such as information indicating that a treatment regimen such as a polypectomy, radiotherapy, chemotherapy, antibody therapy, biosimilar treatment or other treatment regimen, such as information indicative of success or efficacy of the regimen. Efficacy of a regimen is assessed in some cases by comparison of an individual's biomarker panel level at a first time point, optionally prior to a treatment and a later second time point, optionally subsequent to a treatment instance. Biomarker panel levels are compared to one another, each to a reference, or otherwise assessed so as to determine whether a treatment regimen demonstrates efficacy such that it should be continued, increased, replaced with an alternate regimen or discontinued because of its success in addressing the colorectal health issue such as colorectal cancer or advanced adenoma. Some assessments rely upon comparison of an individual's biomarker panel level at multiple time points, such as at least one time point prior to a treatment and at least one time point following a treatment. Biomarker panel levels are compared one to another or to at least one reference biomarker panel level or both to one another and to at least one reference biomarker panel level.

Health Assessment Assays

The biomarker panels, methods, compositions, and kits described herein provide assays for at least one of advanced colorectal adenoma and CRC based on detection or measurement of biomarkers in a biological sample obtained from a subject. The biological sample preferably is a blood sample drawn from an artery or vein of an individual. The blood sample can be a whole blood sample, a plasma sample, or a serum sample. The disclosure provided herein detects at least one of advanced colorectal adenoma and CRC from a sample such as a blood sample with a sensitivity and a specificity that renders the outcome of the test reliable enough to be medically actionable. Health assessment methods, systems, kits and panels herein have at least one of a sensitivity of at least 70% and specificity of at least 70%. Such methods can have at least one of a sensitivity of 70% or greater and specificity of at least 70% based on measurement of 15 or fewer biomarkers in the biological sample. In some cases, a method provided herein detects at least one of advanced colorectal adenoma and CRC. Such method can have at least one of a sensitivity at least 70% and specificity at least 70% based on measurement of no more than 4 biomarkers, 5 biomarkers, 6 biomarkers, 7, biomarkers, 8 biomarkers, 9 biomarkers, 10 biomarkers, 11, biomarkers, 12 biomarkers, 13 biomarkers, 14 biomarkers, or 15 biomarkers. Some preferred embodiments allow one to assess colorectal cancer using a biomarker panel of 8 markers. Some preferred embodiments allow one to assess advanced adenoma using a panel of 4 biomarkers. Some biomarker panels allow one to assess both colorectal cancer and advanced adenoma using a combined panel of 11 biomarkers.

In some cases the biomarker panels, methods, compositions, and kits described herein are useful to screen for individuals at elevated risk for CRC or advanced adenoma. In some cases, a positive detection of at least one of an advanced colorectal adenoma and CRC based upon a method described herein is used to identify patients for whom to recommend an additional diagnostic method. For example, in some cases where a method herein yields a positive result, such method is used to alert a caregiver to perform an additional test such as a colonoscopy, a sigmoidoscopy, an independent cancer assay, or a stool cancer assay.

The biomarker panels, methods, compositions, and kits described herein are also useful as a quality control metric for a colonoscopy, sigmoidoscopy, or colon tissue biopsy. For example, a positive detection of at least one of an advanced colorectal adenoma and CRC based upon a method described herein can be used to validate a result of a colonoscopy, sigmoidoscopy, or colon tissue biopsy. For example, in some cases wherein a colonoscopy, sigmoidoscopy, or colon tissue biopsy yielded a negative result, but a method described herein yielded a positive result, such method can be used to alert a caregiver to perform another colonoscopy, sigmoidoscopy, or colon tissue biopsy, or to initiate a treatment regimen such as administration of a pharmaceutical composition.

Some methods provided herein comprise (a) obtaining a biological sample from a subject; (b) measuring a panel of biomarkers in the biological sample of the subject; (c) detecting a presence or absence of at least one of advanced colorectal adenoma and CRC in the subject based upon the measuring; and (d) either (i) treating the at least one of advanced colorectal adenoma CRC and in the subject based upon the detecting, or (ii) recommending to the subject a colonoscopy, sigmoidoscopy, or colorectal tissue biopsy based upon the results of the detecting. For the purposes of one or more methods described herein, "treating" comprises providing a written report to the subject or to a caretaker of the subject which includes a recommendation to initiate a treatment for the CRC. For the purposes of one or more methods described herein, "recommending to the subject a colonoscopy" comprises providing a written report to the subject or to a caretaker of the subject which includes a recommendation that the subject undergo a colonoscopy, sigmoidoscopy, or tissue biopsy to confirm an assessment of the CRC. In some cases, the colonoscopy, sigmoidoscopy, or tissue biopsy can be used to remove the at least one of advanced colorectal adenoma and CRC, thereby treating the at least one of advanced colorectal adenoma and CRC.

Exemplary methods optionally comprise (a) obtaining data comprising a measurement of a biomarker panel in a biological sample obtained from a subject, (b) generating a subject-specific profile of the biomarker panel based upon the measurement data, (c) comparing the subject-specific profile of the biomarker panel to a reference profile of the biomarker panel; and (d) determining a likelihood of at least one of advanced colorectal adenoma and colorectal cancer based upon (c).

Exemplary methods optionally comprise (a) measuring a biomarker panel in a biological sample obtained from the subject; (b) detecting a presence or absence of colorectal cancer and/or advanced colorectal adenoma in the subject based upon the measuring; and (c) treating the colorectal cancer in the subject based upon the detecting.

Exemplary methods optionally comprise (a) obtaining data comprising a measurement of a biomarker panel in a biological sample obtained from a subject, (b) generating a subject-specific profile of the biomarker panel based upon the measurement data, (c) comparing the subject-specific profile of the biomarker panel to a reference profile of the biomarker panel; and (d) determining a likelihood of at least one of advanced colorectal adenoma and colorectal cancer based upon (c). Some methods provided herein comprise (a) measuring a biomarker panel in a biological sample obtained from the subject; (b) detecting a presence or absence of colorectal cancer and/or advanced colorectal adenoma in the subject based upon the measuring; and (c) recommending to the subject at least one of a colonoscopy, sigmoidoscopy, and tissue biopsy in the subject based upon the detecting. Exemplary methods optionally comprise diagnosis of colorectal cancer or monitoring colorectal cancer, so as to establish a prognosis for the subject. The levels of one or a combination of the proteins listed can over time be linked to differential outcomes for cancer patients, possibly depending on the treatment chosen. Exemplary methods optionally comprise monitoring the progression of cancer in a subject by comparing the accumulation levels of one or more biomarkers in a sample from a subject to the accumulation levels of the one or more biomarkers in a sample obtained from the subject at a subsequent point in time, wherein a difference in the expression of said one or more biomarkers diagnoses or aids in the diagnosis of the progression of the cancer in the subject. Some exemplary methods comprise monitoring the effectiveness of a treatment. In some cases, a method for monitoring the effectiveness of a treatment comprises comparing the accumulation levels of one or more biomarkers in a sample from a subject prior to providing at least a portion of a treatment to the accumulation levels of said one or more biomarkers in a sample obtained from the subject after the subject has received at least a portion of the treatment, and wherein a difference in the accumulation levels of said one or more biomarker diagnoses or aids in the diagnosis of the efficacy of the treatment.

Biomarkers

In some cases, biomarker panels described herein comprise at least two biomarkers. The biomarkers can be selected from the group comprising A1AG1, A1AT, AACT, APOA1, CATD, CEA, CLUS, CO3, CO9, CRP, FGB, FIBG, GARS, GELS, HPT, MIF, OSTP, PRDX1, PSGL, S10A8, S10A9, SAA1, SBP1, SEPR, and TFRC, or fragments thereof. Any of the biomarkers described herein can be protein biomarkers. Furthermore, the group of biomarkers in this example can in some cases additionally comprise polypeptides with the characteristics found in Table 1.

Exemplary protein biomarkers and, when available, their human amino acid sequences, are listed in Table 1, below. Protein biomarkers comprise full length molecules of the polypeptide sequences of Table 1, as well as uniquely identifiable fragments of the polypeptide sequences of Table 1. Markers can be but do not need to be full length to be informative. In many cases, so long as a fragment is uniquely identifiable as being derived from or representing a polypeptide of Table 1, it is informative for purposes herein.

In some embodiments a panel of biomarkers may comprise a panel of proteins Disclosed herein are panels of proteins suitable for CRC or AA detection. In some cases, panels of proteins described herein comprise at least two proteins. In some cases, the proteins is selected from the group consisting of AACT, CATD, CEA, CO3, CO9, MIF, PSGL, SEPR, CLUS, GDF15, and SAA1 or fragments thereof. In some cases the panel is a CRC panel, and the proteins tested comprise AACT, CATD, CEA, CO3, CO9, MIF, PSGL, and SEPR. In some cases, the biomarker panel comprises AACT, CATD, CEA, CO3, CO9, MIF, PSGL, and SEPR and the age of the subject. In some cases, the ratio of one or more pairs of protein accumulation levels is used to categorize a patients CRC status. For example, in some cases the categorizing comprises comparing ratios of CATD/SEPR, CATD/CO3, CO9/SEPR., and/or A.1AT/GDF15. In some cases, the subject's age is included for evaluation in addition to the protein accumulation levels. In some cases, the protein panel comprises AACT, CATD, CEA, CO3, CO9, MIF, PSGL, and SEPR, and the sensitivity for CRC detection is at least 50%, at least 55%, at least 60%, at least 65%, at least 70%, at least 75%, at least 80%, at least 85%, at least 90%, at least 95%, at least 96%, at least 97%, at least 98%, at least 99%, or about 100%.

In some cases, the protein panel comprises AACT, CATD, CE.A, CO3, CO9, MIF, PSGL, and SEPR, and the sensitivity for CRC detection is at least 81%. In some cases, the protein panel comprises AACT, LAID, CEA, CO3, CO9, MIF, PSGL, and SEPR, and the specificity for CRC detection is at least 50%, at least 55%, at least 60%, at least 65%, at least 70%, at least 75%, at least 80%, at least 85%, at least 90%, at least 95%, at least 96%, at least 97%, at least 98%, at least 99%, or about 100%. In some cases, the protein panel comprises AACT, CATD, CEA, CO3, CO9, MIF, PSGL, and SEPR, and the specificity for CRC detection is at least 78%. In some cases, the protein panel comprises AACT, CATD, CEA, CO3, CO9, MIF, PSGL, and SEPR, and the sensitivity for CRC detection is at least 81% and the specificity is 78%. Furthermore, in some cases the panel of proteins in these examples additionally comprises polypeptides with the characteristics found in Table 1. In some cases, the biomarker panel comprises AACT, CATD, CEA, CO3, CO9, MIF, PSGL, and SEPR, and the age of the subject, and the sensitivity for CRC detection is at least 50%, at least 55%, at least 60%, at least 65%, at least 70%, at least 75%, at least 80%, at least 85%, at least 90%, at least 95%, at least 96%, at least 97%, at least 98%, at least 99%, or about 100%. In some cases, the biomarker panel comprises AACT, CATD, CEA, CO3, CO9, MIF, PSGL, and SEPR, and the age of the subject, and the sensitivity for CRC detection is at least 81%. In some cases, the biomarker panel comprises AACT, CATD, CEA, CO3, CO9, MIF, PSGL, and SEPR, and the age of the subject, and the specificity for CRC detection is at least 50%, at least 55%, at least 60%, at least 65%, at least 70%, at least 75%, at least 80%, at least 85%, at least 90%, at least 95%, at least 96%, at least 97%, at least 98%, at least 99%, or about 100%. In some cases, the biomarker panel comprises AACT, CATD, CEA, CO3, CO9, MIF, PSGL, and SEPR, and the age of the subject, and the specificity for CR.0 detection is at least 78%. In some cases, the biomarker panel comprises AACT, CATD, CEA, CO3, CO9, MIF, PSGL, and SEPR, and the age of the subject, and the sensitivity for CRC detection is at least 81% and the specificity is 78%. In some cases, the protein panel comprises AACT, CATD, CEA, CO3, CO9, MIF, PSGL, and SEPR, and the positive predictive value for CRC detection is at least 50%, at least 55%, at least 60%, at least 65%, at least 70%, at least 75%, at least 80%, at least 85%, at least 90%, at least 95%, at least 96%, at least 97%, at least 98%, at least 99%, or about 100%. In some cases, the protein panel comprises AACT, CATD, CEA, CO3, CO9, M PSGL, and SEPR, and positive predictive value is 31%. In some cases, the protein panel comprises AACT, CATD, CEA, CO3, CO9, MIF, PSGL, and SEPR, and the age of the subject, and the positive predictive value for CR.0 detection is at least 50%, at least 55%, at least 60%, at least 65%, at least 70%, at least 75%, at least 80%, at least 85%, at least 90%, at least 95%, at least 96%, at least 97%, at least 98%, at least 99%, or about 100%. In some cases, the protein panel comprises AACT, CATD, CEA, CO3, CO9, MIF, PSGL, and SEPR, and the age of the subject, and positive predictive value is 31%. In some cases, the biomarker panel comprises AACT, CATD, CEA, CO3, CO9, MIF, PSGL, and SEPR, and the age of the subject, and the sensitivity for CRC detection is at least 81%, the specificity is 78%, and the positive predictive value is 31%. In some cases, the biomarker panel comprises AACT, LAID, CEA, CO3, CO9, MW, PSGL, and SEPR, and the sensitivity for CRC detection is at least 81%, the specificity is 78%, and the positive predictive value is 31%. Furthermore, in some cases the panel of proteins in these examples additionally comprises polypeptides with the characteristics found in Table 1.

TABLE 1

Biomarkers and corresponding protein sequences

| Protein Name | Symbol | Sequence |
|---|---|---|
| Alpha-1-acid glycoprotein 1 | A1AG1 | MALSWVLTVLSLLPLLEAQIPLCANLVPVPITNATLDQITGKWFY IASAFRNEEYNKSVQEIQATFFYFTPNKTEDTIFLREYQTRQDQCI YNTTYLNVQRENGTISRYVGGQEHFAHLLILRDTKTYMLAFDVN DEKNWGLSVYADKPETTKEQLGEFYEALDCLRIPKSDVVYTDW KKDKCEPLEKQHEKERKQEEGES (SEQ ID NO: 1) |
| Alpha-1 Antitrypsin | A1AT | MPSSVSWGILLLAGLCCLVPVSLAEDPQGDAAQKTDTSHHDQD HPTFNKITPNLAEFAFSLYRQLAHQSNSTNIFFSPVSIATAFAMLS LGTKADTHDEILEGLNFNLTEIPEAQIHEGFQELLRTLNQPDSQLQ LTTGNGLFLSEGLKLVDKFLEDVKKLYHSEAFTVNFGDTEEAKK QINDYVEKGTQGKIVDLVKELDRDTVFALVNYIFFKGKWERPFE VKDTEEEDFHVDQVTTVKVPMMKRLGMFNIQHCKKLSSWVLL MKYLGNATAIFFLPDEGKLQHLENELTHDIITKFLENEDRRSASL HLPKLSITGTYDLKSVLGQLGITKVFSNGADLSGVTEEAPLKLSK AVHKAVLTIDEKGTEAAGAMFLEAIPMSIPPEVKFNKPFVFLMIE QNTKSPLFMGKVVNPTQK (SEQ ID NO: 2) |
| Alpha-1-Anti-chymotrypsin | AACT | MERMLPLLALGLLAAGFCPAVLCHPNSPLDEENLTQENQDRGT HVDLGLASANVDFAFSLYKQLVLKAPDKNVIFSPLSISTALAFLS LGAHNTTLTEILKGLKFNLTETSEAEIHQSFQHLLRTLNQSSDELQ LSMGNAMPFVKEQLSLLDRFTEDAKRLYGSEAFATDFQDSAAAK KLINDYVKNGTRGKITDLIKDLDSQTMMVLVNYIFFKAKWEMPF DPQDTHQSRFYLSKKKWVMVPMMSLHHLTIPYFRDEELSCTVV ELKYTGNASALFILPDQDKMEEVEAMLLPETLKRWRDSLEFREI GELYLPKFSISRDYNLNDILLQLGIEEAFTSKADLSGITGARNLAV SQVVHKAVLDVFEEGTEASAATAVKITLLSALVETRTIVRFNRPF LMIIVPTDTQNIFFMSKVTNPKQA (SEQ ID NO: 3) |
| Apolipoprotein A-I | APOA1 | MKAAVLTLAVLFLTGSQARHFWQQDEPPQSPWDRVKDLATVY VDVLKDSGRDYVSQFEGSALGKQLNLKLLDNWDSVTSTFSKLR EQLGPVTQEFWDNLEKETEGLRQEMSKDLEEVKAKVQPYLDDF |

TABLE 1-continued

Biomarkers and corresponding protein sequences

| Protein Name | Symbol | Sequence |
|---|---|---|
| | | QKKWQEEMELYRQKVEPLRAELQEGARQKLHELQEKLSPLGEE<br>MRDRARAHVDALRTHLAPYSDELRQRLAARLEALKENGGARL<br>AEYHAKATEHLSTLSEKAKPALEDLRQGLLPVLESFKVSFLSALE<br>EYTKKLNTQ<br>(SEQ ID NO: 4) |
| Cathepsin D | CATD | MQPSSLLPLALCLLAAPASALVRIPLHKFTSIRRTMSEVGGSVED<br>LIAKGPVSKYSQAVPAVTEGPIPEVLKNYMDAQYYGEIGIGTPPQ<br>CFTVVFDTGSSNLWVPSIHCKLLDIACWIHHKYNSDKSSTYVKN<br>GTSFDIHYGSGSLSGYLSQDTVSVPCQSASSASALGGVKVERQVF<br>GEATKQPGITFIAAKFDGILGMAYPRISVNNVLPVFDNLMQQKL<br>VDQNIFSFYLSRDPDAQPGGELMLGGTDSKYYKGSLSYLNVTRK<br>AYWQVHLDQVEVASGLTLCKEGCEAIVDTGTSLMVGPVDEVRE<br>LQKAIGAVPLIQGEYMIPCEKVSTLPAITLKLGGKGYKLSPEDYT<br>LKVSQAGKTLCLSGFMGMDIPPPSGPLWILGDVFIGRYYTVFDR<br>DNNRVGFAEAARL<br>(SEQ ID NO: 5) |
| Carcino-<br>embryonic<br>antigen-<br>related cell<br>adhesion<br>molecule 3 | CEA | MGPPSASPHRECIPWQGLLLTASLLNFWNPPTTAKLTIESMPLSV<br>AEGKEVLLLVHNLPQHLFGYSWYKGERVDGNSLIVGYVIGTQQ<br>ATPGAAYSGRETIYTNASLLIQNVTQNDIGFYTLQVIKSDLVNEE<br>ATGQFHVYQENAPGLPVGAVAGIVTGVLVGVALVAALVCFLLL<br>AKTGRTSIQRDLKEQQPQALAPGRGPSHSSAFSMSPLSTAQAPLP<br>NPRTAASIYEELLKHDTNIYCRMDHKAEVAS<br>(SEQ ID NO: 6) |
| Clusterin | CLUS | MMKTLLLFVGLLLTWESGQVLGDQTVSDNELQEMSNQGSKYV<br>NKEIQNAVNGVKQIKTLIEKTNEERKTLLSNLEEAKKKKEDALN<br>ETRESETKLKELPGVCNETMMALWEECKPCLKQTCMKFYARVC<br>RSGSGLVGRQLEEFLNQSSPFYFWMNGDRIDSLLENDRQQTHML<br>DVMQDHFSRASSIIDELFQDRFFTREPQDTYHYLPFSLPHRRPHFF<br>FPKSRIVRSLMPFSPYEPLNFHAMFQPFLEMIHEAQQAMDIHFHS<br>PAFQHPPTEFIREGDDDRTVCREIRHNSTGCLRMKDQCDKCREIL<br>SVDCSTNNPSQAKLRRELDESLQVAERLTRKYNELLKSYQWKM<br>LNTSSLLEQLNEQFNWVSRLANLTQGEDQYYLRVTTVASHTSDS<br>DVPSGVTEVVVKLFDSDPITVTVPVEVSRKNPKFMETVAEKALQ<br>EYRKKHREE<br>(SEQ ID NO: 7) |
| Complement<br>C3 | CO3 | MGPTSGPSLLLLLLTHLPLALGSPMYSIITPNILRLESEETMVLEA<br>HDAQGDVPVTVTVHDFPGKKLVLSSEKTVLTPATNHMGNVTFTI<br>PANREFKSEKGRNKFVTVQATFGTQVVEKVVLVSLQSGYLFIQT<br>DKTIYTPGSTVLYRIFTVNHKLLPVGRTVMVNIENPEGIPVKQDS<br>LSSQNQLGVLPLSWDIPELVNMGQWKIRAYYENSPQQVFSTEFE<br>VKEYVLPSFEVIVEPTEKFYYIYNEKGLEVTITARFLYGKKVEGT<br>AFVIFGIQDGEQRISLPESLKRIPIEDGSGEVVLSRKVLLDGVQNP<br>RAEDLVGKSLYVSATVILHSGSDMVQAERSGIPIVTSPYQIHFTK<br>TPKYFKPGMPFDLMVFVTNPDGSPAYRVPVAVQGEDTVQSLTQ<br>GDGVAKLSINTHPSQKPLSITVRTKKQELSEAEQATRTMQALPYS<br>TVGNSNNYLHLSVLRTELRPGETLNVNFLLRMDRAHEAKIRYYT<br>YLIMNKGRLLKAGRQVREPGQDLVVLPLSITTDFIPSFRLVAYYT<br>LIGASGQREVVADSVWVDVKDSCVGSLVVKSGQSEDRQPVPGQ<br>QMTLKIEGDHGARVVLVAVDKGVFVLNKKNKLTQSKIWDVVE<br>KADIGCTPGSGKDYAGVFSDAGLTFTSSSGQQTAQRAELQCPQP<br>AARRRRSVQLTEKRMDKVGKYPKELRKCCEDGMRENPMRFSC<br>QRRTRFISLGEACKKVFLDCCNYITELRRQHARASHLGLARSNL<br>DEDIIAEENIVSRSEFPESWLWNVEDLKEPPKNGISTKLMNIFLKD<br>SITTWEILAVSMSDKKGICVADPFEVTVMQDFFIDLRLPYSVVRN<br>EQVEIRAVLYNYRQNQELKVRVELLHNPAFCSLATTKRRHQQT<br>VTIPPKSSLSVPYVIVPLKTGLQEVEVKAAVYHHFISDGVRKSLK<br>VVPEGIRMNKTVAVRTLDPERLGREGVQKEDIPPADLSDQVPDT<br>ESETRILLQGTPVAQMTEDAVDAERLKHLIVTPSGCGEQNMIGM<br>TPTVIAVHYLDETEQWEKFGLEKRQGALELIKKGYTQQLAFRQP<br>SSAFAAFVKRAPSTWLTAYVVKVFSLAVNLIAIDSQVLCGAVKW<br>LILEKQKPDGVFQEDAPVIHQEMIGGLRNNNEKDMALTAFVLISL<br>QEAKDICEEQVNSLPGSITKAGDFLEANYMNLQRSYTVAIAGYA<br>LAQMGRLKGPLLNKFLTTAKDKNRWEDPGKQLYNVEATSYAL<br>LALLQLKDFDFVPPVVRWLNEQRYYGGGYGSTQATFMVFQALA<br>QYQKDAPDHQELNLDVSLQLPSRSSKITHRIHWESASLLRSEETK<br>ENEGFTVTAEGKGQGTLSVVTMYHAKAKDQLTCNKFDLKVTIK<br>PAPETEKRPQDAKNTMILEICTRYRGDQDATMSILDISMMTGFAP<br>DTDDLKQLANGVDRYISKYELDKAFSDRNTLIIYLDKVSHSEDD<br>CLAFKVHQYFNVELIQPGAVKVYAYYNLEESCTRFYHPEKEDG<br>KLNKLCRDELCRCAEENCFIQKSDDKVTLEERLDKACEPGVDYV<br>YKTRLVKVQLSNDFDEYIIVIAIEQTIKSGSDEVQVGQQRT-<br>FISPIK |

TABLE 1-continued

Biomarkers and corresponding protein sequences

| Protein Name | Symbol | Sequence |
|---|---|---|
| | | CREALKLEEKKHYLMWGLSSDFWGEKPNLSYIIGKDTWVEHWP EEDECQDEENQKQCQDLGAFTESMVVFGCPN (SEQ ID NO: 8) |
| Complement C9 | CO9 | MSACRSFAVAICILEISILTAQYTTSYDPELTESSGSASHID-CRMSP WSEWSQCDPCLRQMFRSRSIEVFGQFNGKRCTDAVGDRRQCVP TEPCEDAEDDCGNDFQCSTGRCIKMRLRCNGDNDCGDFSDEDD CESEPRPPCRDRVVEESELARTAGYGINILGMDPLSTPFDNEFYN GLCNRDRDGNTLTYYRRPWNVASLIYETKGEKNFRTEHYEEQIE AFKSIIQEKTSNFNAAISLKFTPTETNKAEQCCEETASSISLHG-KGS FRFSYSKNETYQLFLSYSSKKEKMFLHVKGEIHLGRFVMRNRDV VLTTTFVDDIKALPTTYEKGEYFAFLETYGTHYSSSGSLGGLYEL IYVLDKASMKRKGVELKDIKRCLGYHLDVSLAFSEISVGAEFNK DDCVKRGEGRAVNITSENLIDDVVSLIRGGTRKYAFELKEKLLR GTVIDVTDFVNWASSINDAPVLISQKLSPIYNLVPVKMKNAHLK KQNLERAIEDYINEFSVRKCHTCQNGGTVILMDGKCLCACPFKF EGIACEISKQKISEGLPALEFPNEK (SEQ ID NO: 9) |
| C-reactive protein | CRP | MEKLLCFLVLTSLSHAFGQTDMSRKAFVFPKESDTSYVSLKAPL TKPLKAFTVCLHFYTELSSTRGYSIFSYATKRQDNEILIFWSKDIG YSFTVGGSEILFEVPEVTVAPVHICTSWESASGIVEFWVDGKPRV RKSLKKGYTVGAEASIILGQEQDSFGGNFEGSQSLVGDIGNVNM WDFVLSPDEINTIYLGGPFSPNVLNWRALKYEVQGEVFTKPQLW P (SEQ ID NO: 10) |
| Fibrinogen beta chain | FGB | MKRMVSWSFHKLKTMKHLLLLLLCVFLVKSQGVNDNEEGFFSA RGHRPLDKKREEAPSLRPAPPPISGGGYRARPAKAAATQKKVER KAPDAGGCLHADPDLGVLCPTGCQLQEALLQQERPIRNSVDELN NNVEAVSQTSSSSFQYMYLLKDLWQKRQKQVKDNENVVNEYS SELEKHQLYIDETVNSNIPTNLRVLRSILENLRSKIQKLESDVSAQ MEYCRTPCTVSCNIPVVSGKECEEIIRKGGETSEMYLIQPDSSVKP YRVYCDMNTENGGWTVIQNRQDGSVDFGRKWDPYKQGFGNV ATNTDGKNYCGLPGEYWLGNDKISQLTRMGPTELLIEMEDWKG DKVKAHYGGFTVQNEANKYQISVNKYRGTAGNALMDGASQLM GENRTMTIHNGMFFSTYDRDNDGWLTSDPRKQCSKEDGGGWW YNRCHAANPNGRYYWGGQYTWDMAKHGTDDGVVWMNWKG SWYSMRKMSMKIRPFFPQQ (SEQ ID NO: 11) |
| Fibrinogen gamma chain | FIBG | MSWSLHPRNLILYFYALLFLSSTCVAYVATRDNCCILDERFGSYC PTTCGIADFLSTYQTKVDKDLQSLEDILHQVENKTSEVKQLIKAI QLTYNPDESSKPNMIDAATLKSRKMLEEIMKYEASILTHDSSIRY LQEIYNSNNQKIVNLKEKVAQLEAQCQEPCKDTVQIHDITGKDC QDIANKGAKQSGLYFIKPLKANQQFLVYCEIDGSGNGWTVFQKR LDGSVDFKKNWIQYKEGFGHLSPTGTTEFWLGNEKIHLISTQSAI PYALRVELEDWNGRTSTADYAMFKVGPEADKYRLTYAYFAGG DAGDAFDGFDFGDDPSDKFFTSHNGMQFSTWDNDNDKFEGNC AEQDGSGWWMNKCHAGHLNGVYYQGGTYSKASTPNGYDNGII WATWKTRWYSMKKTTMKIIPFNRLTIGEGQQHHLGGAKQVRPE HPAETEYDSLYPEDDL (SEQ ID NO: 12) |
| Glycine-tRNA ligase | GARS | MPSPRPVLLRGARAALLLLLPPRLLARPSLLLRRSLSAASCPPISL PAAASRSSMDGAGAEEVLAPLRLAVRQQGDLVRKLKEDKAPQV DVDKAVAELKARKRVLEAKELALQPKDDIVDRAKMEDTLKRRF FYDQAFAIYGGVSGLYDFGPVGCALKNNIIQTWRQHFIQEEQILE IDCTMLTPEPVLKTSGHVDKFADFMVKDVKNGECFRADHLLKA HLQKLMSDKKCSVEKKSEMESVLAQLDNYGQQELADLFVNYN VKSPITGNDLSPPVSFNLMFKTFIGPGGNMPGYLRPETAQGIFLNF KRLLEFNQGKLPFAAAQIGNSFRNEISPRSGLIRVREFTMAEIEHF VDPSEKDHPKFQNVADLHLYLYSAKAQVSGQSARKMRLGDAV EQGVINNTVLGYFIGRIYLYLTKVGISPDKLRFRQHMENEMAHY ACDCWDAESKTSYGWIEIVGCADRSCYDLSCHARATKVPLVAE KPLKEPKTVNVVQFEPSKGAIGKAYKKDAKLVMEYLAICDECYI TEMEMLLNEKGEFTIETEGKTFQLTKDMINVKRFQKTLYVEEVV PNVIEPSFGLGRIMYTVFEHTFHVREGDEQRTFFSFPAVVAPFKCS VLPLSQNQEFMPFVKELSEALTRHGVSHKVDDSSGSIGRRYART DEIGVAFGVTIDFDTVNKTPHTATLRDRDSMRQIRAEISELPSIVQ DLANGNITWADVEARYPLFEGQETGKKETIEE (SEQ ID NO: 13) |

TABLE 1-continued

Biomarkers and corresponding protein sequences

| Protein Name | Symbol | Sequence |
| --- | --- | --- |
| Gelsolin | GELS | MAPHRPAPALLCALSLALCALSLPVRAATASRGASQAGAPQGR<br>VPEARPNSMVVEHPEFLKAGKEPGLQIWRVEKFDLVPVPTNLYG<br>DFFTGDAYVILKTVQLRNGNLQYDLHYWLGNECSQDESGAAAI<br>FTVQLDDYLNGRAVQHREVQGFESATFLGYFKSGLKYKKGGVA<br>SGFKHVVPNEVVVQRLFQVKGRRVVRATEVPVSWESFNNGDCF<br>ILDLGNNIHQWCGSNSRYERLKATQVSKGIRDNERSGRARVHV<br>SEEGTEPEAMLQVLGPKPALPAGTEDTAKEDAANRKLAKLYKV<br>SNGAGTMSVSLVADENPFAQGALKSEDCFILDHGKDGKIFVWK<br>GKQANTEERKAALKTASDFITKMDYPKQTQVSVLPEGGETPLFK<br>QFFKNWRDPDQTDGLGLSYLSSHIANVERVPFDAATLHTSTAMA<br>AQHGMDDDGTGQKQIWRIEGSNKVPVDPATYGQFYGGDSYIIL<br>YNYRHGGRQGQIIYNWQGAQSTQDEVAASAILTAQLDEELGGT<br>PVQSRVVQGKEPAHLMSLFGGKPMIIYKGGTSREGGQTAPASTR<br>LFQVRANSAGATRAVEVLPKAGALNSNDAFVLKTPSAAYLWVG<br>TGASEAEKTGAQELLRVLRAQPVQVAEGSEPDGFWEALGGKAA<br>YRTSPRLKDKKMDAHPPRLFACSNKIGRFVIEEVPGELMQEDLA<br>TDDVMLLDTWDQVFVWVGKDSQEEEKTEALTSAKRYIETDPAN<br>RDRRTPITVVKQGFEPPSFVGWFLGWDDDYWSVDPLDRAMAEL<br>AA<br>(SEQ ID NO: 14) |
| Haptoglobin | HPT | MSALGAVIALLLWGQLFAVDSGNDVTDIADDGCPKPPEIAHGYV<br>EHSVRYQCKNYYKLRTEGDGVYTLNDKKQWINKAVGDKLPEC<br>EADDGCPKPPEIAHGYVEHSVRYQCKNYYKLRTEGDGVYTLNN<br>EKQWINKAVGDKLPECEAVCGKPKNPANPVQRILGGHLDAKGS<br>FPWQAKMVSHHNLTTGATLINEQWLLTTAKNLFLNHSENATAK<br>DIAPTLTLYVGKKQLVEIEKVVLHPNYSQVDIGLIKLKQKVSVNE<br>RVMPICLPSKDYAEVGRVGYVSGWGRNANFKFTDHLKYVMLP<br>VADQDQCIRHYEGSTVPEKKTPKSPVGVQPILNEHTFCAGMSKY<br>QEDTCYGDAGSAFAVHDLEEDTWYATGILSFDKSCAVAEYGVY<br>VKVTSIQDWVQKTIAEN<br>(SEQ ID NO: 15) |
| Macrophage migration inhibitory factor | MIF | MPMFIVNTNVPRASVPDGFLSELTQQLAQATGKPPQYIAVHVVP<br>DQLMAFGGSSEPCALCSLHSIGKIGGAQNRSYSKLLCGLLAERLR<br>ISPDRVYINYYDMNAANVGWNNSTFA<br>(SEQ ID NO: 16) |
| Osteopontin | OSTP | MRIAVICFCLLGITCAIPVKQADSGSSEEKQLYNKYPDAVATWL<br>NPDPSQKQNLLAPQNAVSSEETNDFKQETLPSKSNESHDHMDD<br>MDDEDDDHVDSQDSIDSNDSDDVDDTDDSHQSDESHHSDESD<br>ELVTDFPTDLPATEVFTPVVPTVDTYDGRGDSVVYGLRSKSKKF<br>RRPDIQYPDATDEDITSHMESEELNGAYKAIPVAQDLNAPSDWD<br>SRGKDSYETSQLDDQSAETHSHKQSRLYKRKANDESNEHSDVID<br>SQELSKVSREFHSHEFHSHEDMLVVDPKSKEEDKHLKFRISHELD<br>SASSEVN<br>(SEQ ID NO: 17) |
| Peroxiredoxin-1 | PRDX1 | MSSGNAKIGHPAPNFKATAVMPDGQFKDISLSDYKGKYVVFFFY<br>PLDFTFVCPTEIIAFSDRAEEFKKLNCQVIGASVDSHFCHLAWVN<br>TPKKQGGLGPMNIPLVSDPKRTIAQDYGVLKADEGISFRGLFIID<br>DKGILRQITVNDLPVGRSVDETLRLVQAFQFTDKHGEVCPAGWK<br>PGSDTIKPDVQKSKEYFSKQK<br>(SEQ ID NO: 18) |
| P-Selectin glycoprotein ligand 1 | PSGL | MPLQLLLLLILLGPGNSLQLWDTWADEAEKALGPLLARDRRQA<br>TEYEYLDYDFLPETEPPEMLRNSTDTTPLTGPGTPESTTVEPAAR<br>RSTGLDAGGAVTELTTELANNIGNLSTDSSAAMEIQTTQPAATEA<br>QTTQPVPTEAQTTPLAATEAQTTRLTATEAQTTPLAATEAQTTPP<br>AATEAQTTQPTGLEAQTTAPAAMEAQTTAPAAMEAQTTPPAAM<br>EAQTTQTTAMEAQTTAPEATEAQTTQPTATEAQTTPLAAMEALS<br>TEPSATEALSMEPTTKRGLFIPFSVSSVTHKGIPMAASNLSVNYPV<br>GAPDHISVKQCLLAILILALVATIFFVCTVVLAVRLSRKGEIMYPV<br>RNYSPTEMVCISSLLPDGGEGPSATANGGLSKAKSPGLTPEPRED<br>REGDDLTLHSFLP<br>(SEQ ID NO: 19) |
| S100A8 | S10A8 | MLTELEKALNSIIDVYHKYSLIKGNFHAVYRDDLKKLLETECPQ<br>YIRKKGADVWFKELDINTDGAVNFQEFLILVIKMGVAAHKKSHE<br>ESHKE<br>(SEQ ID NO: 20) |

TABLE 1-continued

Biomarkers and corresponding protein sequences

| Protein Name | Symbol | Sequence |
| --- | --- | --- |
| S100A9 | S10A9 | MTCKMSQLERNIETIINTFHQYSVKLGHPDTLNQGEFKELVRKD<br>LQNFLKKENKNEKVIEHIMEDLDTNADKQLSFEEFIMLMARLTW<br>ASHEKMHEGDEGPGHHHKPGLGEGTP<br>(SEQ ID NO: 21) |
| Serum amyloid A-1 protein | SAA1 | MKLLTGLVFCSLVLGVSSRSFFSFLGEAFDGARDMWRAYSDMR<br>EANYIGSDKYFHARGNYDAAKRGPGGVWAAEAISDARENIQRF<br>FGHGAEDSLADQAANEWGRSGKDPNHFRPAGLPEKY<br>(SEQ ID NO: 22) |
| Selenium-binding protein 1 | SBP1 | MATKCGNCGPGYSTPLEAMKGPREEIVYLPCIYRNTGTEAPDYL<br>ATVDVDPKSPQYCQVIHRLPMPNLKDELHHSGWNTCSSCFGDST<br>KSRTKLVLPSLISSRIYVVDVGSEPRAPKLHKVIEPKDIHAKCELA<br>FLHTSHCLASGEVMISSLGDVKGNGKGGFVLLDGETFEVKGTW<br>ERPGGAAPLGYDFWYQPRHNVMISTEWAAPNVLRDGFNPADVE<br>AGLYGSHLYVWDWQRHEIVQTLSLKDGLIPLEIRFLHNPDAAQG<br>FVGCALSSTIQRFYKNEGGTWSVEKVIQVPPKKVKGWLLPEMPG<br>LITDILLLSLDDRFLYFSNWLHGDLRQYDISDPQRPRLTGQLFLGG<br>SIVKGGPVQVLEDEELKSQPEPLVVKGKRVAGGPQMIQLSLDGK<br>RLYITTSLYSAWDKQFYPDLIREGSVMLQVDVDTVKGGLKLNPN<br>FLVDFGKEPLGPALAHELRYPGGDCSSDIWI<br>(SEQ ID NO: 23) |
| Seprase | SEPR | MKTWVKIVFGVATSAVLALLVMCIVLRPSRVHNSEENTMRALT<br>LKDILNGTFSYKTFFPNWISGQEYLHQSADNNIVLYNIETGQSYTI<br>LSNRTMKSVNASNYGLSPDRQFVYLESDYSKLWRYSYTATYYI<br>YDLSNGEFVRGNELPRPIQYLCWSPVGSKLAYVYQNNIYLKQRP<br>GDPPFQITFNGRENKIFNGIPDWVYEEEMLATKYALWWSPNGKF<br>LAYAEFNDTDIPVIAYSYYGDEQYPRTINIPYPKAGAKNPVVRIFI<br>IDTTYPAYVGPQEVPVPAMIASSDYYFSWLTWVTDERVCLQWL<br>KRVQNVSVLSICDFREDWQTWDCPKTQEHIEESRTGWAGGFFVS<br>TPVFSYDAISYYKIFSDKDGYKIHYIKDTVENAIQITSGKWEAIN<br>IFRVTQDSLFYSSNEFEEYPGRRNIYRISIGSYPPSKKCVTCHL-<br>RKE<br>RCQYYTASFSDYAKYYALVCYGPGIPISTLHDGRTDQEIKILEEN<br>KELENALKNIQLPKEEIKKLEVDEITLWYKMILPPQFDRSKKYPL<br>LIQVYGGPCSQSVRSVFAVNWISYLASKEGMVIALVDGRGTAFQ<br>GDKLLYAVYRKLGVYEVEDQITAVRKFIEMGFIDEKRIAIWGWS<br>YGGYVSSLALASGTGLFKCGIAVAPVSSWEYYASVYTERFMGLP<br>TKDDNLEHYKNSTVMARAEYFRNVDYLLIHGTADDNVHFQNSA<br>QIAKALVNAQVDFQAMWYSDQNHGLSGLSTNHLYTHMTHFLK<br>QCFSLSD<br>(SEQ ID NO: 24) |
| Transferrin Receptor Protein 1 | TFRC | MMDQARSAFSNLFGGEPLSYTRFSLARQVDGDNSHVEMKLAVD<br>EEENADNNTKANVTKPKRCSGSICYGTIAVIVFFLIGFMIGYLGY<br>CKGVEPKTECERLAGTESPVREEPGEDFPAARRLYWDDLKRKLS<br>EKLDSTDFTGTIKLLNENSYVPREAGSQKDENLALYVENQFREF<br>KLSKVWRDQHFVKIQVKDSAQNSVIIVDKNGRLVYLVENPGGY<br>VAYSKAATVTGKLVHANFGTKKDFEDLYTPVNGSIVIVRAGKIT<br>FAEKVANAESLNAIGVLIYMDQTKFPIVNAELSFFGHAHLGTGDP<br>YTPGFPSFNHTQFPPSRSSGLPNIPVQTISRAAAEKLFGNMEGDCP<br>SDWKTDSTCRMVTSESKNVKLTVSNVLKEIKILNIFGVIKGFVEP<br>DHYVVVGAQRDAWGPGAAKSGVGTALLLKLAQMFSDMVLKD<br>GFQPSRSIIFASWSAGDFGSVGATEWLEGYLSSLHLKAFTYINLD<br>KAVLGTSNFKVSASPLLYTLIEKTMQNVKHPVTGQFLYQDSNW<br>ASKVEKLTLDNAAFPFLAYSGIPAVSFCFCEDTDYPYLGTTMDT<br>YKELIERIPELNKVARAAAEVAGQFVIKLTHDVELNLDYERYNS<br>QLLSFVRDLNQYRADIKEMGLSLQWLYSARGDFFRATSRLTTDF<br>GNAEKTDRFVMKKLNDRVMRVEYHFLSPYVSPKESPFRHVFWG<br>SGSHTLPALLENLKLRKQNNGAFNETLFRNQLALATWTIQGAAN<br>ALSGDVWDIDNEF<br>(SEQ ID NO: 25) |
| Growth/differentiation factor 15 | GDF15 | MPGQELRTVNGSQMLLVLLVLSWLPHGGALSLAEASRASFPGPS<br>ELHSEDSRFRELRKRYEDLLTRLRANQSWEDSNTDLVPAPAVRI<br>LTPEVRLGSGGHLHLRISRAALPEGLPEASRLHRALFRLSPTASRS<br>WDVTRPLRRQLSLARPQAPALHLRLSPPPSQSDQLLAESSSARPQ<br>LELHLRPQAARGRRRARARNGDHCPLGPGRCCRLHTVRASLED<br>LGWADWVLSPREVQVTMCIGACPSQFRAANMHAQIKTSLHRLK<br>PDTVPAPCCVPASYNPMVLIQKTDTGVSLQTYDDLLAKDCHCI<br>(SEQ ID NO: 26) |

Biomarkers contemplated herein also include polypeptides having an amino acid sequence identical to a listed marker of Table 1 over a span of 8 residues, 9, residues, 10 residues, 20 residues, 50 residues, or alternately 5%, 10%, 20%, 30%, 40%, 50%, 60%, 70% 80% 90%, 95% or grater than 95% of the sequence of the biomarker. Variant or alternative forms of the biomarker include for example polypeptides encoded by any splice-variants of transcripts encoding the disclosed biomarkers. In certain cases the modified forms, fragments, or their corresponding RNA or DNA, may exhibit better discriminatory power in diagnosis than the full-length protein.

Biomarkers contemplated herein also include truncated forms or polypeptide fragments of any of the proteins described herein. Truncated forms or polypeptide fragments of a protein can include N-terminally deleted or truncated forms and C-terminally deleted or truncated forms. Truncated forms or fragments of a protein can include fragments arising by any mechanism, such as, without limitation, by alternative translation, exo- and/or endo-proteolysis and/or degradation, for example, by physical, chemical and/or enzymatic proteolysis. Without limitation, a biomarker may comprise a truncated or fragment of a protein, polypeptide or peptide may represent about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of the amino acid sequence of the protein.

Without limitation, a truncated or fragment of a protein may include a sequence of about 5-20 consecutive amino acids, or about 10-50 consecutive amino acids, or about 20-100 consecutive amino acids, or about 30-150 consecutive amino acids, or about 50-500 consecutive amino acid residues of the corresponding full length protein.

In some instances, a fragment is N-terminally and/or C-terminally truncated by between 1 and about 20 amino acids, such as, for example, by between 1 and about 15 amino acids, or by between 1 and about 10 amino acids, or by between 1 and about 5 amino acids, compared to the corresponding mature, full-length protein or its soluble or plasma circulating form.

Any protein biomarker of the present disclosure such as a peptide, polypeptide or protein and fragments thereof may also encompass modified forms of said marker, peptide, polypeptide or protein and fragments such as bearing post-expression modifications including but not limited to, modifications such as phosphorylation, glycosylation, lipidation, methylation, selenocystine modification, cysteinylation, sulphonation, glutathionylation, acetylation, oxidation of methionine to methionine sulphoxide or methionine sulphone, and the like.

In some instances, a fragmented protein is N-terminally and/or C-terminally truncated. Such fragmented protein can comprise one or more, or all transitional ions of the N-terminally (a, b, c-ion) and/or C-terminally (x, y, z-ion) truncated protein or peptide. Exemplary human markers, nucleic acids, proteins or polypeptides as taught herein are as annotated under NCBI Genbank (accessible at the website ncbi.nlm.nih.gov) or Swissprot/Uniprot (accessible at the website uniprot.org) accession numbers. In some instances said sequences are of precursors (for example, preproteins) of the of markers, nucleic acids, proteins or polypeptides as taught herein and may include parts which are processed away from mature molecules. In some instances although only one or more isoforms is disclosed, all isoforms of the sequences are intended.

Antibodies for the detection of the biomarkers listed herein are commercially available. A partial list of sources for reagents useful for the assay of biomarkers herein is presented in Table 2 below.

TABLE 2

Reagent Sources

| Abbrev. | ELISA KitVendor | Assay Reference | Reference Vendor | Plasma Dilution |
|---|---|---|---|---|
| A1AT | Genway Biotech, San Diego, CA | Native protein | MyBiosource San Diego, CA | 1:240,000 |
| A1AG1 | R&D Systems, Minneapolis, MN | Native protein | BioVendor, Asheville, NC | 1:20,000 |
| AACT | Genway Biotech, San Diego, CA | Native protein | MyBiosource, San Diego, CA | 1:10,00 |
| ANXA1 | Cloud Clone, Wuhan, PRC | Recombinant protein | Origene, Rockville, MD | 1:8,000 |
| APOA1 | Cusabio, Wuhan, PRC | Native protein | MyBiosource, San Diego, CA | 1:800 |
| CRP | BioVendor, Asheville, NC | Recombinant protein | R&D Systems, Minneapolis, MN | 1:1,000 |
| CAH1 | Cloud Clone, Wuhan, PRC | Recombinant protein | MyBiosource, San Diego, CA | 1:32 |
| CEA | IBL International, Toronto, ON | Native protein | Origene, Rockville, MD | 1:1 |
| CATD | AbCam, Cambidge, MA | Native protein | Novus Biologicals, Littleton, CA | 1:250 |
| CLUS | BioVendor, Asheville, NC | Native protein | MyBiosource, San Diego, CA. | 1:3,000 |
| CO3 | Abnova, Taipei, Taiwan | Native protein | MyBiosource, San Diego, CA | 1:250 |
| CO9 | AssayPro, St. Charles, MO | Native protein | MyBiosource, San Diego, CA | 1:20,000 |
| DPP4 | Cloud Clone, Wuhan, PRC | Native protein | BioVendor, Asheville, NC | 1:2,000 |
| FGB | Cloud Clone, Wuhan, PRC | Recombinant protein | Antibodies Online, Atlanta, GA | 1:8,000 |
| FIBG | Cloud Clone, Wuhan, PRC | Native protein | MyBiosource, San Diego, CA | 1:8,000 |
| GELS | Cloud Clone, Wuhan, PRC | Recombinant protein | Origene, Rockville, MD | 1:100 |
| GARS | Cloud Clone, Wuhan, PRC | Recombinant protein | Novus Biologicals, Littleton, CA | 1:40 |
| GDF15 | R&D Systems, Minneapolis, MN | Native protein | Abcam, Cambridge, MA | 1:8 |
| HPT | AssayPro, St. Charles, MO | Recombinant protein | Origene, Rockville, MD | 1:2,000 |
| MIF | R&D Systems, Minneapolis, MN | Recombinant protein | MyBiosource, San Diego, CA | 1:10 |
| OSTP | R&D Systems, Minneapolis, MN | Recombinant protein | Origene, Rockville, MD | 1:20 |
| PSGL | IBLAmerica, Minneapolis, MN | Recombinant protein | Life Technologies, Camarillo, CA | 1:30 |
| PRDX1 | Cloud Clone, Wuhan, PRC | Recombinant protein | MyBiosource, San Diego, CA | 1:100 |
| SBP1 | Cloud Clone, Wuhan, PRC | Recombinant protein | Origene, Rockville, MD | 1:16 |
| SEPR | R&D Systems, Minneapolis, MN | Recombinant protein | Origene, Rockville, MD | 1:40 |
| SAA1 | Life Technologies, Camarillo, CA | Recombinant protein | Origene, Rockville, MD | 1:240 |
| TIMP1 | R&D Systems, Minneapolis, MN | Recombinant protein | Life Technologies, Camarillo, CA | 1:100 |

TABLE 2-continued

Reagent Sources

| Abbrev. | ELISA KitVendor | Assay Reference | Reference Vendor | Plasma Dilution |
|---|---|---|---|---|
| TFRC | Cloud Clone, Wuhan, PRC | Native protein | MyBiosource, San Diego, CA | 1:250 |
| TFF3 | R&D Systems, Minneapolis, MN | Recombinant protein | R&D Systems, Minneapolis, MN | 1:50 |
| PKM2 | ScheBo, Gissen, GER | Recombinant protein | Origene, Rockville, MD | 1:100 |

For a given biomarker panel recited herein, variant biomarker panels differing in one or more than one constituent are also contemplated. Thus, turning to a lead CRC panel AACT, CATD, CEA, CO3, CO9, MIF, PSGL, and SEPR as an example, a number of related panels are disclosed. For this and other panels disclosed herein, variants are contemplated comprising at least 8, at least 7, at least 6, at least 5, at least 4, at least 3, or at least 2 of the biomarker constituents of a recited biomarker panel. Thus, turning to a lead biomarker panel AACT, CATD, CEA, CO3, CO9, MIF, PSGL, and SEPR, one sees the variant panels as listed in Table 3. Age is optionally included as a non-protein feature for any of the panel variants listed herein

TABLE 3

CRC Panel Embodiments

| No. | Protein Features | Panel | Nonprotein feature |
|---|---|---|---|
| 1 | 8 | AACT, CATD, CEA, CO3, CO9, MIF, PSGL, SEPR | +/− Age |
| 2 | 7 | AACT, CATD, CEA, CO3, CO9, MIF, PSGL | +/− Age |
| 3 | 7 | AACT, CATD, CEA, CO3, CO9, MIF, SEPR | +/− Age |
| 4 | 7 | AACT, CATD, CEA, CO3, CO9, PSGL, SEPR | +/− Age |
| 5 | 7 | AACT, CATD, CEA, CO3, MIF, PSGL, SEPR | +/− Age |
| 6 | 7 | AACT, CATD, CEA, CO9, MIF, PSGL, SEPR | +/− Age |
| 7 | 7 | AACT, CATD, CO3, CO9, MIF, PSGL, SEPR | +/− Age |
| 8 | 7 | AACT, CEA, CO3, CO9, MIF, PSGL, SEPR | +/− Age |
| 9 | 7 | CATD, CEA, CO3, CO9, MIF, PSGL, SEPR | +/− Age |
| 10 | 6 | AACT, CATD, CEA, CO3, CO9, MIF | +/− Age |
| 11 | 6 | AACT, CATD, CEA, CO3, CO9, PSGL | +/− Age |
| 12 | 6 | AACT, CATD, CEA, CO3, CO9, SEPR | +/− Age |
| 13 | 6 | AACT, CATD, CEA, CO3, MIF, PSGL | +/− Age |
| 14 | 6 | AACT, CATD, CEA, CO3, MIF, SEPR | +/− Age |
| 15 | 6 | AACT, CATD, CEA, CO3, PSGL, SEPR | +/− Age |
| 16 | 6 | AACT, CATD, CEA, CO9, MIF, PSGL | +/− Age |
| 17 | 6 | AACT, CATD, CEA, CO9, MIF, SEPR | +/− Age |
| 18 | 6 | AACT, CATD, CEA, CO9, PSGL, SEPR | +/− Age |
| 19 | 6 | AACT, CATD, CEA, MIF, PSGL, SEPR | +/− Age |
| 20 | 6 | AACT, CATD, CO3, CO9, MIF, PSGL | +/− Age |
| 21 | 6 | AACT, CATD, CO3, CO9, MIF, SEPR | +/− Age |
| 22 | 6 | AACT, CATD, CO3, CO9, PSGL, SEPR | +/− Age |
| 23 | 6 | AACT, CATD, CO3, MIF, PSGL, SEPR | +/− Age |
| 24 | 6 | AACT, CATD, CO9, MIF, PSGL, SEPR | +/− Age |
| 25 | 6 | AACT, CEA, CO3, CO9, MIF, PSGL | +/− Age |
| 26 | 6 | AACT, CEA, CO3, CO9, MIF, SEPR | +/− Age |
| 27 | 6 | AACT, CEA, CO3, CO9, PSGL, SEPR | +/− Age |
| 28 | 6 | AACT, CEA, CO3, MIF, PSGL, SEPR | +/− Age |
| 29 | 6 | AACT, CEA, CO9, MIF, PSGL, SEPR | +/− Age |
| 30 | 6 | AACT, CO3, CO9, MIF, PSGL, SEPR | +/− Age |
| 31 | 6 | CATD, CEA, CO3, CO9, MIF, PSGL | +/− Age |
| 32 | 6 | CATD, CEA, CO3, CO9, MIF, SEPR | +/− Age |
| 33 | 6 | CATD, CEA, CO3, CO9, PSGL, SEPR | +/− Age |
| 34 | 6 | CATD, CEA, CO3, MIF, PSGL, SEPR | +/− Age |
| 35 | 6 | CATD, CEA, CO9, MIF, PSGL, SEPR | +/− Age |
| 36 | 6 | CATD, CO3, CO9, MIF, PSGL, SEPR | +/− Age |
| 37 | 6 | CEA, CO3, CO9, MIF, PSGL, SEPR | +/− Age |
| 38 | 5 | AACT, CATD, CEA, CO3, CO9 | +/− Age |
| 39 | 5 | AACT, CATD, CEA, CO3, MIF | +/− Age |
| 40 | 5 | AACT, CATD, CEA, CO3, PSGL | +/− Age |
| 41 | 5 | AACT, CATD, CEA, CO3, SEPR | +/− Age |
| 42 | 5 | AACT, CATD, CEA, CO9, MIF | +/− Age |
| 43 | 5 | AACT, CATD, CEA, CO9, PSGL | +/− Age |
| 44 | 5 | AACT, CATD, CEA, CO9, SEPR | +/− Age |

TABLE 3-continued

CRC Panel Embodiments

| No. | Protein Features | Panel | Nonprotein feature |
|---|---|---|---|
| 45 | 5 | AACT, CATD, CEA, MIF, PSGL | +/− Age |
| 46 | 5 | AACT, CATD, CEA, MIF, SEPR | +/− Age |
| 47 | 5 | AACT, CATD, CEA, PSGL, SEPR | +/− Age |
| 48 | 5 | AACT, CATD, CO3, CO9, MIF | +/− Age |
| 49 | 5 | AACT, CATD, CO3, CO9, PSGL | +/− Age |
| 50 | 5 | AACT, CATD, CO3, CO9, SEPR | +/− Age |
| 51 | 5 | AACT, CATD, CO3, MIF, PSGL | +/− Age |
| 52 | 5 | AACT, CATD, CO3, MIF, SEPR | +/− Age |
| 53 | 5 | AACT, CATD, CO3, PSGL, SEPR | +/− Age |
| 54 | 5 | AACT, CATD, CO9, MIF, PSGL | +/− Age |
| 55 | 5 | AACT, CATD, CO9, MIF, SEPR | +/− Age |
| 56 | 5 | AACT, CATD, CO9, PSGL, SEPR | +/− Age |
| 57 | 5 | AACT, CATD, MIF, PSGL, SEPR | +/− Age |
| 58 | 5 | AACT, CEA, CO3, CO9, MIF | +/− Age |
| 59 | 5 | AACT, CEA, CO3, CO9, PSGL | +/− Age |
| 60 | 5 | AACT, CEA, CO3, CO9, SEPR | +/− Age |
| 61 | 5 | AACT, CEA, CO3, MIF, PSGL | +/− Age |
| 62 | 5 | AACT, CEA, CO3, MIF, SEPR | +/− Age |
| 63 | 5 | AACT, CEA, CO3, PSGL, SEPR | +/− Age |
| 64 | 5 | AACT, CEA, CO9, MIF, PSGL | +/− Age |
| 65 | 5 | AACT, CEA, CO9, MIF, SEPR | +/− Age |
| 66 | 5 | AACT, CEA, CO9, PSGL, SEPR | +/− Age |
| 67 | 5 | AACT, CEA, MIF, PSGL, SEPR | +/− Age |
| 68 | 5 | AACT, CO3, CO9, MIF, PSGL | +/− Age |
| 69 | 5 | AACT, CO3, CO9, MIF, SEPR | +/− Age |
| 70 | 5 | AACT, CO3, CO9, PSGL, SEPR | +/− Age |
| 71 | 5 | AACT, CO3, MIF, PSGL, SEPR | +/− Age |
| 72 | 5 | AACT, CO9, MIF, PSGL, SEPR | +/− Age |
| 73 | 5 | CATD, CEA, CO3, CO9, MIF | +/− Age |
| 74 | 5 | CATD, CEA, CO3, CO9, PSGL | +/− Age |
| 75 | 5 | CATD, CEA, CO3, CO9, SEPR | +/− Age |
| 76 | 5 | CATD, CEA, CO3, MIF, PSGL | +/− Age |
| 77 | 5 | CATD, CEA, CO3, MIF, SEPR | +/− Age |
| 78 | 5 | CATD, CEA, CO3, PSGL, SEPR | +/− Age |
| 79 | 5 | CATD, CEA, CO9, MIF, PSGL | +/− Age |
| 80 | 5 | CATD, CEA, CO9, MIF, SEPR | +/− Age |
| 81 | 5 | CATD, CEA, CO9, PSGL, SEPR | +/− Age |
| 82 | 5 | CATD, CEA, MIF, PSGL, SEPR | +/− Age |
| 83 | 5 | CATD, CO3, CO9, MIF, PSGL | +/− Age |
| 84 | 5 | CATD, CO3, CO9, MIF, SEPR | +/− Age |
| 85 | 5 | CATD, CO3, CO9, PSGL, SEPR | +/− Age |
| 86 | 5 | CATD, CO3, MIF, PSGL, SEPR | +/− Age |
| 87 | 5 | CATD, CO9, MIF, PSGL, SEPR | +/− Age |
| 88 | 5 | CEA, CO3, CO9, MIF, PSGL | +/− Age |
| 89 | 5 | CEA, CO3, CO9, MIF, SEPR | +/− Age |
| 90 | 5 | CEA, CO3, CO9, PSGL, SEPR | +/− Age |
| 91 | 5 | CEA, CO3, MIF, PSGL, SEPR | +/− Age |
| 92 | 5 | CEA, CO9, MIF, PSGL, SEPR | +/− Age |
| 93 | 5 | CO3, CO9, MIF, PSGL, SEPR | +/− Age |
| 94 | 4 | AACT, CATD, CEA, CO3 | +/− Age |
| 95 | 4 | AACT, CATD, CEA, CO9 | +/− Age |
| 96 | 4 | AACT, CATD, CEA, MIF | +/− Age |
| 97 | 4 | AACT, CATD, CEA, PSGL | +/− Age |
| 98 | 4 | AACT, CATD, CEA, SEPR | +/− Age |
| 99 | 4 | AACT, CATD, CO3, CO9 | +/− Age |
| 100 | 4 | AACT, CATD, CO3, MIF | +/− Age |
| 101 | 4 | AACT, CATD, CO3, PSGL | +/− Age |
| 102 | 4 | AACT, CATD, CO3, SEPR | +/− Age |
| 103 | 4 | AACT, CATD, CO9, MIF | +/− Age |
| 104 | 4 | AACT, CATD, CO9, PSGL | +/− Age |
| 105 | 4 | AACT, CATD, CO9, SEPR | +/− Age |
| 106 | 4 | AACT, CATD, MIF, PSGL | +/− Age |

TABLE 3-continued

CRC Panel Embodiments

| No. | Protein Features | Panel | Nonprotein feature |
|---|---|---|---|
| 107 | 4 | AACT, CATD, MIF, SEPR | +/− Age |
| 108 | 4 | AACT, CATD, PSGL, SEPR | +/− Age |
| 109 | 4 | AACT, CEA, CO3, CO9 | +/− Age |
| 110 | 4 | AACT, CEA, CO3, MIF | +/− Age |
| 111 | 4 | AACT, CEA, CO3, PSGL | +/− Age |
| 112 | 4 | AACT, CEA, CO3, SEPR | +/− Age |
| 113 | 4 | AACT, CEA, CO9, MIF | +/− Age |
| 114 | 4 | AACT, CEA, CO9, PSGL | +/− Age |
| 115 | 4 | AACT, CEA, CO9, SEPR | +/− Age |
| 116 | 4 | AACT, CEA, MIF, PSGL | +/− Age |
| 117 | 4 | AACT, CEA, MIF, SEPR | +/− Age |
| 118 | 4 | AACT, CEA, PSGL, SEPR | +/− Age |
| 119 | 4 | AACT, CO3, CO9, MIF | +/− Age |
| 120 | 4 | AACT, CO3, CO9, PSGL | +/− Age |
| 121 | 4 | AACT, CO3, CO9, SEPR | +/− Age |
| 122 | 4 | AACT, CO3, MIF, PSGL | +/− Age |
| 123 | 4 | AACT, CO3, MIF, SEPR | +/− Age |
| 124 | 4 | AACT, CO3, PSGL, SEPR | +/− Age |
| 125 | 4 | AACT, CO9, MIF, PSGL | +/− Age |
| 126 | 4 | AACT, CO9, MIF, SEPR | +/− Age |
| 127 | 4 | AACT, CO9, PSGL, SEPR | +/− Age |
| 128 | 4 | AACT, MIF, PSGL, SEPR | +/− Age |
| 129 | 4 | CATD, CEA, CO3, CO9 | +/− Age |
| 130 | 4 | CATD, CEA, CO3, MIF | +/− Age |
| 131 | 4 | CATD, CEA, CO3, PSGL | +/− Age |
| 132 | 4 | CATD, CEA, CO3, SEPR | +/− Age |
| 133 | 4 | CATD, CEA, CO9, MIF | +/− Age |
| 134 | 4 | CATD, CEA, CO9, PSGL | +/− Age |
| 135 | 4 | CATD, CEA, CO9, SEPR | +/− Age |
| 136 | 4 | CATD, CEA, MIF, PSGL | +/− Age |
| 137 | 4 | CATD, CEA, MIF, SEPR | +/− Age |
| 138 | 4 | CATD, CEA, PSGL, SEPR | +/− Age |
| 139 | 4 | CATD, CO3, CO9, MIF | +/− Age |
| 140 | 4 | CATD, CO3, CO9, PSGL | +/− Age |
| 141 | 4 | CATD, CO3, CO9, SEPR | +/− Age |
| 142 | 4 | CATD, CO3, MIF, PSGL | +/− Age |
| 143 | 4 | CATD, CO3, MIF, SEPR | +/− Age |
| 144 | 4 | CATD, CO3, PSGL, SEPR | +/− Age |
| 145 | 4 | CATD, CO9, MIF, PSGL | +/− Age |
| 146 | 4 | CATD, CO9, MIF, SEPR | +/− Age |
| 147 | 4 | CATD, CO9, PSGL, SEPR | +/− Age |
| 148 | 4 | CATD, MIF, PSGL, SEPR | +/− Age |
| 149 | 4 | CEA, CO3, CO9, MIF | +/− Age |
| 150 | 4 | CEA, CO3, CO9, PSGL | +/− Age |
| 151 | 4 | CEA, CO3, CO9, SEPR | +/− Age |
| 152 | 4 | CEA, CO3, MIF, PSGL | +/− Age |
| 153 | 4 | CEA, CO3, MIF, SEPR | +/− Age |
| 154 | 4 | CEA, CO3, PSGL, SEPR | +/− Age |
| 155 | 4 | CEA, CO9, MIF, PSGL | +/− Age |
| 156 | 4 | CEA, CO9, MIF, SEPR | +/− Age |
| 157 | 4 | CEA, CO9, PSGL, SEPR | +/− Age |
| 158 | 4 | CEA, MIF, PSGL, SEPR | +/− Age |
| 159 | 4 | CO3, CO9, MIF, PSGL | +/− Age |
| 160 | 4 | CO3, CO9, MIF, SEPR | +/− Age |
| 161 | 4 | CO3, CO9, PSGL, SEPR | +/− Age |
| 162 | 4 | CO3, MIF, PSGL, SEPR | +/− Age |
| 163 | 4 | CO9, MIF, PSGL, SEPR | +/− Age |
| 164 | 3 | AACT, CATD, CEA | +/− Age |
| 165 | 3 | AACT, CATD, CO3 | +/− Age |
| 166 | 3 | AACT, CATD, CO9 | +/− Age |
| 167 | 3 | AACT, CATD, MIF | +/− Age |
| 168 | 3 | AACT, CATD, PSGL | +/− Age |
| 169 | 3 | AACT, CATD, SEPR | +/− Age |
| 170 | 3 | AACT, CEA, CO3 | +/− Age |
| 171 | 3 | AACT, CEA, CO9 | +/− Age |
| 172 | 3 | AACT, CEA, MIF | +/− Age |
| 173 | 3 | AACT, CEA, PSGL | +/− Age |
| 174 | 3 | AACT, CEA, SEPR | +/− Age |
| 175 | 3 | AACT, CO3, CO9 | +/− Age |
| 176 | 3 | AACT, CO3, MIF | +/− Age |
| 177 | 3 | AACT, CO3, PSGL | +/− Age |
| 178 | 3 | AACT, CO3, SEPR | +/− Age |
| 179 | 3 | AACT, CO9, MIF | +/− Age |
| 180 | 3 | AACT, CO9, PSGL | +/− Age |
| 181 | 3 | AACT, CO9, SEPR | +/− Age |
| 182 | 3 | AACT, MIF, PSGL | +/− Age |
| 183 | 3 | AACT, MIF, SEPR | +/− Age |
| 184 | 3 | AACT, PSGL, SEPR | +/− Age |
| 185 | 3 | CATD, CEA, CO3 | +/− Age |
| 186 | 3 | CATD, CEA, CO9 | +/− Age |
| 187 | 3 | CATD, CEA, MIF | +/− Age |
| 188 | 3 | CATD, CEA, PSGL | +/− Age |
| 189 | 3 | CATD, CEA, SEPR | +/− Age |
| 190 | 3 | CATD, CO3, CO9 | +/− Age |
| 191 | 3 | CATD, CO3, MIF | +/− Age |
| 192 | 3 | CATD, CO3, PSGL | +/− Age |
| 193 | 3 | CATD, CO3, SEPR | +/− Age |
| 194 | 3 | CATD, CO9, MIF | +/− Age |
| 195 | 3 | CATD, CO9, PSGL | +/− Age |
| 196 | 3 | CATD, CO9, SEPR | +/− Age |
| 197 | 3 | CATD, MIF, PSGL | +/− Age |
| 198 | 3 | CATD, MIF, SEPR | +/− Age |
| 199 | 3 | CATD, PSGL, SEPR | +/− Age |
| 200 | 3 | CEA, CO3, CO9 | +/− Age |
| 201 | 3 | CEA, CO3, MIF | +/− Age |
| 202 | 3 | CEA, CO3, PSGL | +/− Age |
| 203 | 3 | CEA, CO3, SEPR | +/− Age |
| 204 | 3 | CEA, CO9, MIF | +/− Age |
| 205 | 3 | CEA, CO9, PSGL | +/− Age |
| 206 | 3 | CEA, CO9, SEPR | +/− Age |
| 207 | 3 | CEA, MIF, PSGL | +/− Age |
| 208 | 3 | CEA, MIF, SEPR | +/− Age |
| 209 | 3 | CEA, PSGL, SEPR | +/− Age |
| 210 | 3 | CO3, CO9, MIF | +/− Age |
| 211 | 3 | CO3, CO9, PSGL | +/− Age |
| 212 | 3 | CO3, CO9, SEPR | +/− Age |
| 213 | 3 | CO3, MIF, PSGL | +/− Age |
| 214 | 3 | CO3, MIF, SEPR | +/− Age |
| 215 | 3 | CO3, PSGL, SEPR | +/− Age |
| 216 | 3 | CO9, MIF, PSGL | +/− Age |
| 217 | 3 | CO9, MIF, SEPR | +/− Age |
| 218 | 3 | CO9, PSGL, SEPR | +/− Age |
| 219 | 3 | MIF, PSGL, SEPR | +/− Age |
| 220 | 2 | AACT, CATD | +/− Age |
| 221 | 2 | AACT, CEA | +/− Age |
| 222 | 2 | AACT, CO3 | +/− Age |
| 223 | 2 | AACT, CO9 | +/− Age |
| 224 | 2 | AACT, MIF | +/− Age |
| 225 | 2 | AACT, PSGL | +/− Age |
| 226 | 2 | AACT, SEPR | +/− Age |
| 227 | 2 | CATD, CEA | +/− Age |
| 228 | 2 | CATD, CO3 | +/− Age |
| 229 | 2 | CATD, CO9 | +/− Age |
| 230 | 2 | CATD, MIF | +/− Age |
| 231 | 2 | CATD, PSGL | +/− Age |
| 232 | 2 | CATD, SEPR | +/− Age |
| 233 | 2 | CEA, CO3 | +/− Age |
| 234 | 2 | CEA, CO9 | +/− Age |
| 235 | 2 | CEA, MIF | +/− Age |
| 236 | 2 | CEA, PSGL | +/− Age |
| 237 | 2 | CEA, SEPR | +/− Age |
| 238 | 2 | CO3, CO9 | +/− Age |
| 239 | 2 | CO3, MIF | +/− Age |
| 240 | 2 | CO3, PSGL | +/− Age |
| 241 | 2 | CO3, SEPR | +/− Age |
| 242 | 2 | CO9, MIF | +/− Age |
| 243 | 2 | CO9, PSGL | +/− Age |
| 244 | 2 | CO9, SEPR | +/− Age |
| 245 | 2 | MIF, PSGL | +/− Age |
| 246 | 2 | MIF, SEPR | +/− Age |
| 247 | 2 | PSGL, SEPR | +/− Age |

In some embodiments a biomarker comprises 8 or more proteins, wherein 8 or more of the proteins comprise: AACT, CATD, CEA, CO3, CO9, MIF, PSGL, and SEPR. In some embodiments a biomarker panel comprises 7 or more proteins, wherein 7 of the proteins comprises AACT, CATD, CEA, CO3, CO9, MIF, and PSGL. In some embodiments a biomarker panel comprises 7 or more proteins, wherein 7 of the proteins comprises AACT, CATD, CEA, CO3, CO9, MIF, and SEPR. In some embodiments a biomarker panel comprises 7 or more proteins, wherein 7 of the proteins comprises AACT, CATD, CEA, CO3, CO9, PSGL, and SEPR. In some embodiments a biomarker panel comprises 7 or more proteins, wherein 7 of the proteins comprises AACT, CATD, CEA, CO3, MIF, PSGL, and SEPR. In some embodiments a biomarker panel comprises 7 or more proteins, wherein 7 of the proteins comprises AACT, CATD, CEA, CO9, MIF, PSGL, and SEPR. In some embodiments a biomarker panel comprises 7 or more proteins, wherein 7 of the proteins comprises AACT, CATD, CO3, CO9, MIF, PSGL, and SEPR. In some embodiments a biomarker panel comprises 7 or more proteins, wherein 7 of the proteins comprises AACT, CEA, CO3, CO9, MIF, PSGL, and SEPR. In some embodiments a biomarker panel comprises 7 or more proteins, wherein 7 of the proteins comprises CATD, CEA, CO3, CO9, MIF, PSGL, and SEPR.

In some embodiments a biomarker panel comprises 6 or more proteins, wherein 6 of the proteins comprises AACT, CATD, CEA, CO3, CO9, and MIF. In some embodiments a biomarker panel comprises 6 or more proteins, wherein 6 of the proteins comprises AACT, CATD, CEA, CO3, CO9, and PSGL. In some embodiments a biomarker panel comprises 6 or more proteins, wherein 6 of the proteins comprises AACT, CATD, CEA, CO3, CO9, and SEPR. In some embodiments a biomarker panel comprises 6 or more proteins, wherein 6 of the proteins comprises AACT, CATD, CEA, CO3, MIF, and PSGL. In some embodiments a biomarker panel comprises 6 or more proteins, wherein 6 of the proteins comprises AACT, CATD, CEA, CO3, MIF, and SEPR. In some embodiments a biomarker panel comprises 6 or more proteins, wherein 6 of the proteins comprises AACT, CATD, CEA, CO3, PSGL, and SEPR. In some embodiments a biomarker panel comprises 6 or more proteins, wherein 6 of the proteins comprises AACT, CATD, CEA, CO9, MIF, and PSGL. In some embodiments a biomarker panel comprises 6 or more proteins, wherein 6 of the proteins comprises AACT, CATD, CEA, CO9, MIF, and SEPR. In some embodiments a biomarker panel comprises 6 or more proteins, wherein 6 of the proteins comprises AACT, CATD, CEA, CO9, PSGL, and SEPR. In some embodiments a biomarker panel comprises 6 or more proteins, wherein 6 of the proteins comprises AACT, CATD, CEA, MIF, PSGL, and SEPR. In some embodiments a biomarker panel comprises 6 or more proteins, wherein 6 of the proteins comprises AACT, CATD, CO3, CO9, MIF, and PSGL. In some embodiments a biomarker panel comprises 6 or more proteins, wherein 6 of the proteins comprises AACT, CATD, CO3, CO9, MIF, and SEPR. In some embodiments a biomarker panel comprises 6 or more proteins, wherein 6 of the proteins comprises AACT, CATD, CO3, MIF, PSGL, and SEPR. In some embodiments a biomarker panel comprises 6 or more proteins, wherein 6 of the proteins comprises AACT, CATD, CO9, MIF, and PSGL, and SEPR. In some embodiments a biomarker panel comprises 6 or more proteins, wherein 6 of the proteins comprises AACT, CEA, CO3, CO9, MIF, and PSGL. In some embodiments a biomarker panel comprises 6 or more proteins, wherein 6 of the proteins comprises AACT, CEA, CO3, CO9, MIF, and SEPR. In some embodiments a biomarker panel comprises 6 or more proteins, wherein 6 of the proteins comprises AACT, CEA, CO3, CO9, PSGL, and SEPR. In some embodiments a biomarker panel comprises 6 or more proteins, wherein 6 of the proteins comprises AACT, CEA, CO3, MIF, PSGL, and SEPR. In some embodiments a biomarker panel comprises 6 or more proteins, wherein 6 of the proteins comprises AACT, CEA, CO9, MIF, PSGL, and SEPR. In some embodiments a biomarker panel comprises 6 or more proteins, wherein 6 of the proteins comprises AACT, CO3, CO9, MIF, PSGL, and SEPR. In some embodiments a biomarker panel comprises 6 or more proteins, wherein 6 of the proteins comprises CATD, CEA, CO3, CO9, MIF, and PSGL. In some embodiments a biomarker panel comprises 6 or more proteins, wherein 6 of the proteins comprises CATD, CEA, CO3, CO9, MIF, and SEPR. In some embodiments a biomarker panel comprises 6 or more proteins, wherein 6 of the proteins comprises CATD, CEA, CO3, CO9, PSGL, and SEPR. In some embodiments a biomarker panel comprises 6 or more proteins, wherein 6 of the proteins comprises CATD, CEA, CO3, MIF, PSGL, and SEPR. In some embodiments a biomarker panel comprises 6 or more proteins, wherein 6 of the proteins comprises CATD, CEA, CO9, MIF, PSGL, and SEPR. In some embodiments a biomarker panel comprises 6 or more proteins, wherein 6 of the proteins comprises CATD, CO3, CO9, MIF, PSGL, and SEPR. In some embodiments a biomarker panel comprises 6 or more proteins, wherein 6 of the proteins comprises CEA, CO3, CO9, MIF, PSGL, and SEPR.

In some embodiments a biomarker panel comprises 5 or more proteins, wherein 5 of the proteins comprises AACT, CATD, CEA, CO3, and CO9. In some embodiments a biomarker panel comprises 5 or more proteins, wherein 5 of the proteins comprises AACT, CATD, CEA, CO3, and MIF. In some embodiments a biomarker panel comprises 5 or more proteins, wherein 5 of the proteins comprises AACT, CATD, CEA, CO3, and PSGL. In some embodiments a biomarker panel comprises 5 or more proteins, wherein 5 of the proteins comprises AACT, CATD, CEA, CO3, and SEPR. In some embodiments a biomarker panel comprises 5 or more proteins, wherein 5 of the proteins comprises AACT, CATD, CEA, CO9, and MIF. In some embodiments a biomarker panel comprises 5 or more proteins, wherein 5 of the proteins comprises AACT, CATD, CEA, CO9, and PSGL. In some embodiments a biomarker panel comprises 5 or more proteins, wherein 5 of the proteins comprises AACT, CATD, CEA, CO9, and SEPR. In some embodiments a biomarker panel comprises 5 or more proteins, wherein 5 of the proteins comprises AACT, CATD, CEA, MIF, and PSGL. In some embodiments a biomarker panel comprises 5 or more proteins, wherein 5 of the proteins comprises AACT, CATD, CEA, MIF, and SEPR. In some embodiments a biomarker panel comprises 5 or more proteins, wherein 5 of the proteins comprises AACT, CATD, CEA, PSGL, and SEPR. In some embodiments a biomarker panel comprises 5 or more proteins, wherein 5 of the proteins comprises AACT, CATD, CO3, CO9, and MIF. In some embodiments a biomarker panel comprises 5 or more proteins, wherein 5 of the proteins comprises AACT, CATD, CO3, CO9, and PSGL. In some embodiments a biomarker panel comprises 5 or more proteins, wherein 5 of the proteins comprises AACT, CATD, CO3, CO9, and SEPR. In some embodiments a biomarker panel comprises 5 or more proteins, wherein 5 of the proteins comprises AACT, CATD, CO3, MIF, and PSGL. In some embodiments a biomarker panel comprises 5 or more proteins, wherein 5 of the proteins comprises AACT, CATD, CO3, MIF, and SEPR. In some embodiments a biomarker panel comprises 5 or more proteins, wherein 5 of the proteins comprises AACT, CATD, CO3, PSGL, and SEPR. In some embodiments a biomarker panel comprises 5 or more proteins, wherein 5 of the proteins comprises AACT, CATD, CO9, MIF, and PSGL. In some embodiments a biomarker panel comprises 5 or more proteins, wherein 5 of the proteins comprises AACT, CATD, CO9, MIF, and SEPR. In some embodiments a biomarker panel comprises 5 or more proteins, wherein 5 of the proteins comprises AACT, CATD, CO9, PSGL, and SEPR. In some embodiments a biomarker panel comprises 5 or more proteins, wherein 5 of the proteins comprises AACT, CATD, MIF, PSGL, and SEPR. In some embodiments a biomarker panel comprises 5 or more proteins, wherein 5 of the proteins comprises AACT, CEA, CO3, CO9, and MIF. In some embodiments a biomarker panel comprises 5 or more proteins, wherein 5 of the proteins comprises AACT, CEA, CO3, CO9, and PSGL. In some embodiments a biomarker panel comprises 5 or more proteins, wherein 5 of the proteins comprises AACT, CEA, CO3, CO9, and SEPR. In some embodiments a biomarker panel comprises 5 or more proteins, wherein 5 of the proteins comprises AACT, CEA, CO3, MIF, and PSGL. In some embodiments a biomarker panel comprises 5 or more proteins, wherein 5 of the proteins comprises AACT, CEA, CO3, MIF, and SEPR. In some embodiments a biomarker panel comprises 5 or more proteins, wherein 5 of the proteins comprises AACT, CEA, CO3, PSGL, and SEPR. In some embodiments a biomarker panel comprises 5 or more proteins, wherein 5 of the proteins comprises AACT, CEA, CO9, MIF, and PSGL. In some embodiments a biomarker panel comprises 5 or more proteins, wherein 5 of the proteins comprises AACT, CEA, CO9, MIF, and SEPR. In some embodiments a biomarker panel comprises 5 or more proteins, wherein 5 of the proteins comprises AACT, CEA, CO9, PSGL, and SEPR. In some embodiments a biomarker panel comprises 5 or more proteins, wherein 5 of the proteins comprises AACT, CEA, MIF, PSGL, and SEPR. In some embodiments a biomarker panel comprises 5 or more proteins, wherein 5 of the proteins comprises AACT, CO3, CO9, MIF, and PSGL. In some embodiments a biomarker panel comprises 5 or more proteins, wherein 5 of the proteins comprises AACT, CO3, CO9, MIF, and SEPR. In some embodiments a biomarker panel comprises 5 or more proteins, wherein 5 of the proteins comprises AACT, CO3, CO9, PSGL, and SEPR. In some embodiments a biomarker panel comprises 5 or more proteins, wherein 5 of the proteins comprises AACT, CO3, MIF, PSGL, and SEPR. In some embodiments a biomarker panel comprises 5 or more proteins, wherein 5 of the proteins comprises AACT, CO9, MIF, PSGL, and SEPR. In some embodiments a biomarker panel comprises 5 or more proteins, wherein 5 of the proteins comprises CATD, CEA, CO3, CO9, and MIF. In some embodiments a biomarker panel comprises 5 or more proteins, wherein 5 of the proteins comprises CATD, CEA, CO3, CO9, and PSGL. In some embodiments a biomarker panel comprises 5 or more proteins, wherein 5 of the proteins comprises CATD, CEA, CO3, CO9, and SEPR. In some embodiments a biomarker panel comprises 5 or more proteins, wherein 5 of the proteins comprises CATD, CEA, CO3, MIF, and PSGL. In some embodiments a biomarker panel comprises 5 or more proteins, wherein 5 of the proteins comprises CATD, CEA, CO3, MIF, and SEPR. In some embodiments a biomarker panel comprises 5 or more proteins, wherein 5 of the proteins comprises CATD, CEA, CO3, PSGL, and SEPR. In some embodiments a biomarker panel comprises 5 or more proteins, wherein 5 of the proteins comprises CATD, CEA, CO9, MIF, and PSGL. In some embodiments a biomarker panel comprises 5 or more proteins, wherein 5 of the proteins comprises CATD, CEA, CO9, MIF, and SEPR. In some embodiments a biomarker panel comprises 5 or more proteins, wherein 5 of the proteins comprises CATD, CEA, CO9, PSGL, and SEPR. In some embodiments a biomarker panel comprises 5 or more proteins, wherein 5 of the proteins comprises CATD, CEA, MIF, PSGL, and SEPR. In some embodiments a biomarker panel comprises 5 or more proteins, wherein 5 of the proteins comprises CATD, CO3, CO9, MIF, and PSGL. In some embodiments a biomarker panel comprises 5 or more proteins, wherein 5 of the proteins comprises CATD, CO3, CO9, MIF, and SEPR. In some embodiments a biomarker panel comprises 5 or more proteins, wherein 5 of the proteins comprises CATD, CO3, CO9, PSGL, and SEPR. In some embodiments a biomarker panel comprises 5 or more proteins, wherein 5 of the proteins comprises CATD, CO3, MIF, PSGL, and SEPR. In some embodiments a biomarker panel comprises 5 or more proteins, wherein 5 of the proteins comprises CATD, CO9, MIF, PSGL, and SEPR. In some embodiments a biomarker panel comprises 5 or more proteins, wherein 5 of the proteins comprises CEA, CO3, CO9, MIF, and PSGL. In some embodiments a biomarker panel comprises 5 or more proteins, wherein 5 of the proteins comprises CEA, CO3, CO9, MIF, and SEPR. In some embodiments a biomarker panel comprises 5 or more proteins, wherein 5 of the proteins comprises CEA, CO3, CO9, PSGL, and SEPR. In some embodiments a biomarker panel comprises 5 or more proteins, wherein 5 of the proteins comprises CEA, CO3, MIF, PSGL, and SEPR. In some embodiments a biomarker panel comprises 5 or more proteins, wherein 5 of the proteins comprises CEA, CO9, MIF, PSGL, and SEPR. In some embodiments a biomarker panel comprises 5 or more proteins, wherein 5 of the proteins comprises CO3, CO9, MIF, PSGL, and SEPR.

In some embodiments a biomarker panel comprises 4 or more proteins, wherein 4 of the proteins comprises: AACT, CATD, CEA, CO3; AACT, CATD, CEA, CO9; AACT, CATD, CEA, MIF; AACT, CATD, CEA, PSGL; AACT, CATD, CEA, SEPR; AACT, CATD, CO3, CO9; AACT, CATD, CO3, MIF; AACT, CATD, CO3, PSGL; AACT, CATD, CO3, SEPR; AACT, CATD, CO9, MIF; AACT, CATD, CO9, PSGL; AACT, CATD, CO9, SEPR; AACT, CATD, MIF, PSGL; AACT, CATD, MIF, SEPR; AACT, CATD, PSGL, SEPR; AACT, CEA, CO3, CO9; AACT, CEA, CO3, MIF; AACT, CEA, CO3, PSGL; AACT, CEA, CO3, SEPR; AACT, CEA, CO9, MIF; AACT, CEA, CO9, PSGL; AACT, CEA, CO9, SEPR; AACT, CEA, MIF, PSGL; AACT, CEA, MIF, SEPR; AACT, CEA, PSGL, SEPR; AACT, CO3, CO9, MIF; AACT, CO3, CO9, PSGL; AACT, CO3, CO9, SEPR; AACT, CO3, MIF, PSGL; AACT, CO3, MIF, SEPR; AACT, CO3, PSGL, SEPR; AACT, CO9, MIF, PSGL; AACT, CO9, MIF, SEPR; AACT, CO9, PSGL, SEPR; AACT, MIF, PSGL, SEPR; CATD, CEA, CO3, CO9; CATD, CEA, CO3, MIF; CATD, CEA, CO3, PSGL; CATD, CEA, CO3, SEPR; CATD, CEA, CO9, MIF; CATD, CEA, CO9, PSGL; CATD, CEA, CO9, SEPR; CATD, CEA, MIF, PSGL; CATD, CEA, MIF, SEPR; CATD, CEA, PSGL, SEPR; CATD, CO3, CO9, MIF; CATD, CO3, CO9, PSGL; CATD, CO3, CO9, SEPR; CATD, CO3, MIF, PSGL; CATD, CO3, MIF, SEPR; CATD, CO3, PSGL, SEPR; CATD, CO9, MIF, PSGL; CATD, CO9, MIF, SEPR; CATD, CO9, PSGL, SEPR; CATD, MIF, PSGL, SEPR; CEA, CO3, CO9, MIF; CEA, CO3, CO9, PSGL; CEA, CO3, CO9, SEPR; CEA, CO3, MIF, PSGL; CEA, CO3, MIF, SEPR; CEA, CO3, PSGL, SEPR; CEA, CO9, MIF, PSGL; CEA, CO9, MIF, SEPR; CEA, CO9, PSGL, SEPR; CEA, MIF, PSGL, SEPR;

CO3, CO9, MIF, PSGL; CO3, CO9, MIF, SEPR; CO3, CO9, PSGL, SEPR; CO3, MIF, PSGL, SEPR; CO9, MIF, PSGL, SEPR.

In some embodiments a bio-marker panel comprises 3 or more proteins, wherein 3 of the proteins comprises: AACT, CATD, CEA; AACT, CATD, CO3; AACT, CATD, CO9; AACT, CATD, MIF; AACT, CATD, PSGL; AACT, CATD, SEPR; AACT, CEA, CO3; AACT, CEA, CO9; AACT, CEA, MIF; AACT, CEA, PSGL; AACT, CEA, SEPR; AACT, CO3, CO9; AACT, CO3, MIF; AACT, CO3, PSGL; AACT, CO3, SEPR; AACT, CO9, MIF; AACT, CO9, PSGL; AACT, CO9, SEPR; AACT, MIF, PSGL; AACT, MIF, SEPR; AACT, PSGL, SEPR; CATD, CEA, CO3; CATD, CEA, CO9; CATD, CEA, MIF; CATD, CEA, PSGL; CATD, CEA, SEPR; CATD, CO3, CO9; CATD, CO3, MIF; CATD, CO3, PSGL; CATD, CO3, SEPR; CATD, CO9, MIF; CATD, CO9, PSGL; CATD, CO9, SEPR; CATD, MIF, PSGL; CATD, MIF, SEPR; CATD, PSGL, SEPR; CEA, CO3, CO9; CEA, CO3, MIF; CEA, CO3, PSGL; CEA, CO3, SEPR; CEA, CO9, MIF; CEA, CO9, PSGL; CEA, CO9, SEPR; CEA, MIF, PSGL; CEA, MIF, SEPR; CEA, PSGL, SEPR; CO3, CO9, MIF; CO3, CO9, PSGL; CO3, CO9, SEPR; CO3, MIF, PSGL; CO3, MIF, SEPR; CO3, PSGL, SEPR; CO9, MIF, PSGL; CO9, MIF, SEPR; CO9, PSGL, SEPR; MIF, PSGL, SEPR.

In some embodiments a bio-marker panel comprises 2 or more proteins, wherein 2 of the proteins comprises: AACT, CATD; AACT, CEA; AACT, CO3; AACT, CO9; AACT, MIF; AACT, PSGL; AACT, SEPR; CATD, CEA; CATD, CO3; CATD, CO9; CATD, MIF; CATD, PSGL; CATD, SEPR; CEA, CO3; CEA, CO9; CEA, MIF; CEA, PSGL; CEA, SEPR; CO3, CO9; CO3, MIF; CO3, PSGL; CO3, SEPR; CO9, MIF; CO9, PSGL; CO9, SEPR; MIF, PSGL; MIF, SEPR; PSGL, SEPR.

The biomarker panels of Table 3 correspond to a number of embodiments of the lead panel, as recited below. Similar variants of other lead panels in the disclosure are contemplated and apparent to one of skill in the art such that they do not warrant redundant recitation.

In some embodiments, a diagnostic method provided herein comprises measuring in the biological sample a biomarker panel comprising at least 7, at least 6, at least 5, at least 4, at least 3, or at least 2 of: A1AG1, A1AT, CATD, CEA, CO9, OSTP, and SEPR. In some embodiments, a diagnostic method provided herein comprises measuring in the biological sample a biomarker panel comprising at least 17, at least 16, at least 15, at least 14, at least 13, at least 12, at least 11, at least 10, at least 9, at least 8, at least 7, at least 6, at least 5, at least 4, at least 3, or at least 2 of: A1AG1, A1AT, APOA1, CATD, CEA, CLUS, CO3, CO9, FGB, FIBG, GARS, GELS, MIF, PRDX1, PSGL, SBP1, and SEPR. In some embodiments, a diagnostic method provided herein comprises measuring in the biological sample a biomarker panel consisting at least 7, at least 6, at least 5, at least 4, at least 3, or at least 2 of: A1AG1, A1AT, CATD, CEA, CO9, GARS, and SEPR. In some embodiments, a diagnostic method provided herein comprises measuring in the biological sample a biomarker panel comprising at least 13, at least 12, at least 11, at least 10, at least 9, at least 8, at least 7, at least 6, at least 5, at least 4, at least 3, or at least 2 of: A1AG1, A1AT, AACT, CATD, CEA, CO9, CRP, GARS, GELS, S10A8, S10A9, SAA1, and SEPR. In some embodiments, a diagnostic method provided herein comprises measuring in the biological sample a biomarker panel comprising at least 8, at least 7, at least 6, at least 5, at least 4, at least 3, or at least 2 of: CATD, CEA, CO3, CO9, GARS, GELS, SEPR, and TFRC. In some embodiments, a diagnostic method provided herein comprises measuring in the biological sample a biomarker panel comprising at least 5, at least 4, at least 3, or at least 2 of: CATD, CEA, AACT, CO9, and SEPR. In some embodiments, a diagnostic method provided herein comprises measuring in the biological sample a biomarker panel comprising at least 6, at least 5, at least 4, at least 3, or at least 2 of: A1AT, CATD, CEA, GARS, GELS, and SEPR. In some embodiments, a diagnostic method provided herein comprises measuring in the biological sample a biomarker panel comprising at least 18, of at least 17, at least 16, at least 15, at least 14, at least 13, at least 12, at least 11, at least 10, at least 9, at least 8, at least 7, at least 6, at least 5, at least 4, at least 3, or at least 2 of: A1AG1, A1AT, APOA1, CATD, CEA, CLUS, CO3, CO9, FGB, FIBG, GARS, GELS, HPT, MIF, PRDX1, PSGL, SBP1, and SEPR. In some embodiments, a diagnostic method provided herein comprises measuring in the biological sample a biomarker panel comprising at least 8, at least 7, at least 6, at least 5, at least 4, at least 3, or at least 2 of: A1AG1, A1AT, CATD, CEA, CO9, FIBG, GELS, and SEPR. In some embodiments, a diagnostic method provided herein comprises measuring in the biological sample a biomarker panel comprising at least 3, or at least 2 of: CATD, CEA, and SEPR. In some embodiments, a diagnostic method provided herein comprises measuring in the biological sample a biomarker panel consisting at least 8, at least 7, at least 6, at least 5, at least 4, at least 3, or at least 2 of: CATD, CEA, CO3, CO9, MIF, PSGL, SEPR, and TFRC. In some embodiments, a diagnostic method provided herein comprises measuring in the biological sample a biomarker panel consisting at least 7, at least 6, at least 5, at least 4, at least 3, or at least 2 of: A1AG1, CATD, CEA, CO3, CO9, GELS, and SEPR. Furthermore, the group of biomarkers in this example can in some cases additionally comprise polypeptides with the characteristics found in Table 1.

In some embodiments, a biomarker panel comprises at least 3 or at least 2 of CATD, CLAUS, GDF15, and SAA1. In some embodiments a panel comprising CATD, CLAUS, GDF15, and SAA1 is designated for advanced adenoma detection. In some embodiments, a diagnostic method provided herein comprises measuring in the biological sample a biomarker panel comprising A1AG1, A1AT, APOA1, CATD, CEA, CLUS, CO3, CO9, FGB, FIBG, GARS, GELS, MIF, PRDX1, PSGL, SBP1, and SEPR.

Biomarker Panel Assessment

Some methods described herein comprise comparing the amount of each of the at least two biomarkers in the biological sample to a reference amount of each of the at least two biomarkers. Some methods herein comprise comparing the profile of the biomarker panel in a subject to a reference profile of the biomarker panel. The reference amount is in some cases an amount of the biomarker in a control subject. The reference profile of the biomarker panel is in some cases a biomarker profile of a control subject. The control subject is in some cases a subject having a known diagnosis. For example, the control subject can be a negative control subject. The negative control subject can be a subject that does not have advanced colorectal adenoma. The negative control subject can be a subject that does not have CRC. The negative control subject can be a subject that does not have a colon polyp. For other example, the control subject can be a positive control subject. The positive control subject can be a subject having a confirmed diagnosis of advanced colorectal adenoma. The positive control subject can be a subject having a confirmed diagnosis of CRC. The positive control subject can be a subject having a confirmed diagnosis of any stage of CRC (for example, Stage 0, Stage I, Stage II, Stage IIA, Stage IIB, Stage IIC, Stage III, Stage IIIA, Stage IIIB, Stage IIIC, Stage IV, Stage IVA, or Stage IVB). The reference amount can be a predetermined level of the biomarker, wherein the predetermined level is set based upon a measured amount of the biomarker in a control subject.

Some reference biomarker panel levels comprises average values for a number of individuals having a common condition status, such as 10 individuals free of CRC or AA, or 10 individuals of a known stage of CRC or a known AA status. Alternately, in some cases references comprise a set of protein accumulation levels, and age in some embodiments, that correspond to a set of individuals of known CRC or AA status. In these cases, levels are not averaged; rather, a patient's levels are compared to each set of accumulation levels of each standard or reference individual in the set, and a determination is made if the patient's accumulation levels do not differ significantly from those of at least one reference set. In some cases the reference set comprises individuals of known cancer-free status, while in some cases the reference set comprises individuals of known CRC or AA stage status, such as Stage 0, Stage I, Stage II, Stage 11A, Stage IIB, Stage TIC, Stage III, Stage 111A, Stage IIIB, Stage IIIC, Stage IV, Stage IVA, or Stage IVB. In some cases a patient is categorized as having a condition if the patient's panel accumulation levels match or do not differ significantly from those of a reference. In some cases a patient is categorized as not having a condition if a patient's panel accumulation levels differ significantly from those of a reference.

In some cases, comparing comprises determining a difference between an amount of the biomarker in the biological sample obtained from the subject and the reference amount of the biomarker. The method comprises, in some cases, detecting a presence or absence of at least one of advanced colorectal adenoma and CRC based upon a deviation (for example, measured difference) of the amount of at least one of the measured biomarkers in the biological sample obtained from the subject as compared to a reference amount of the at least one measured biomarkers. In some cases, the method comprises detecting a presence of at least one of advanced colorectal adenoma and CRC if the deviation of the amount of the at least one measured biomarker from the biological sample obtained from the subject as compared to a positive reference value (for example, an amount of the measured biomarker from a positive control subject) is low. In other cases, the method comprises detecting a presence of at least one of advanced colorectal adenoma and CRC if the deviation of the amount of the at least one measured biomarker from the biological sample obtained from the subject as compared to a negative reference value (for example, measured from a negative control subject) is high. In some cases, the method comprises detecting an absence of at least one of advanced colorectal adenoma and CRC if the deviation of the amount of the at least one measured biomarker from the biological sample obtained from the subject as compared to a positive reference value (for example, measured from a positive control subject) is high. In some examples, the method comprises detecting an absence of at least one of advanced colorectal adenoma and CRC if the deviation of the amount of the at least one measured biomarker from the biological sample obtained from the subject as compared to a negative reference value (for example, measured from a negative control subject) is low. In some cases, detection of a presence or absence of at least one of advanced colorectal adenoma and CRC can be based upon a clinical outcome score produced by an algorithm described herein. In some cases, the method comprises detection of a presence or absence of colorectal cancer based upon a classifier that divides a feature space into feature values that are predictive of the presence of colorectal cancer and feature values that are predictive of the absence of colorectal cancer. In some cases, the method comprises classifying a subject's colorectal cancer status as "undetermined" (e.g., "no call") in order to reduce false positives and/or false negatives. In some cases, patients with an undetermined colorectal cancer status are retested at a later point. The algorithm can be used for assessing the deviation between an amount of a measured biomarker in the biological sample obtained from the subject and a reference amount of the biomarker.

In some cases, a classifier is used to determine the colorectal cancer status of a subject. For example, given N measurements as inputs into the classifier (e.g., the biomarkers comprising proteins and the age of the subject), the subject can be represented as a point in an N-dimensional space wherein each axis is a measurement. In some cases, the classifier defines an N−1)-dimensional shape that divides the N-dimensional space into two or more categories. In some cases, the two categories are a subject with cancer and a subject without cancer. In some cases there are three categories. In some cases the categories are a subject with cancer, a subject without cancer, and a no-cal 1 region where the cancer status of the subject cannot be reliably determined. In some cases, the classifier allows 'shifting' cutoffs for particular proteins. For example, consider a classifier defined by the boundary $y=1/x$, where x and y are both greater than zero, and each of the two axes is the accumulation level of a protein indicative of cancer status. In such a case, all the subjects whose protein accumulation levels fall beneath the boundary (e.g., [0, 0], [2, 0.3], etc . . . ) are classified as not having the condition, whereas any subject whose protein accumulation levels lie above the boundary are classified as having the condition. If the x-axis protein has a value of 1, then in this example the y-axis protein must be more than one to result in a cancer diagnosis. However, if the x-axis protein has a value of 10, then the y-axis protein need only have a value more than 0.1 to result in a cancer diagnosis. This example can be extrapolated to an N-dimensional shape using an (N−1)-dimensional shape as the classifier.

The intrinsic performance of a particular classification model depends on the distributions and separation of model scores for the two classes. With the rare exception of perfect class separation, most classification models make mistakes because of class overlap across the range of classifier scores. For example, such an overlap may occur near the middle of the score range where the probability of being in one class or the other is close to 50%.

Within such an overlap region, it is sometimes advantageous to add a third class to the final set of classification calls. The third class optionally indicates the uncertainty of a call in this score region. This is implemented, for example, by defining an indeterminate region of classification scores. Samples with scores in this region are given an "indeterminate" or "no call" test result. Samples with scores above or below this region would be given standard positive or negative test results depending on their positions relative to the test cutoff. In some cases, the "no call" rate, or the frequency with which samples fall into the "no call" region, is about 1%, about 2%, about 3%, about 4%, about 5%, about 10%, about 15%, or about 20%. In particular, the "no call" rate can be about 10%. The benefit of adding an indeterminate region to a classification model is that classification performance can improve for samples outside of the indeterminate region, i.e. mistakes are less likely for the remaining positive and negative tests. However, if the indeterminate range is too large, there may be too many indeterminate results, and the value of the test may be put into question.

Classifier Construction

Reference classifiers are readily constructed by one of skill in the art using any number of available technologies. Reference classifiers are, for example, generated by assaying panel levels for a plurality of samples, such as blood sample, obtained from individuals of known colorectal health status. As many as 1000 samples or more, comprising samples obtained from individuals known or later confirmed to have colorectal cancer or known or later confirmed not to have colorectal cancer, as assayed as to their biomarker panel levels. Age, a non-protein biomarker constituent of some panels, is also recorded for each individual at the time of sample collection.

In some cases, the biomarker panel levels for each sample are used individually as a reference panel level for comparison so as to classify an individual's biomarker panel level as indicative of a healthy colorectal health status or a colorectal health issue warranting further investigation. A panel level to be classified is compared to the positive and the negative biomarker panel levels, and the outcome as judged by, for example, the number samples of each category from which the testing individual's panel level does not differ significantly.

Alternately, a classifier is assembled from the collection of biomarker panel levels. Classifier assembly is well known to those of skill in the art. Machine learning models, in particular, are useful in assembling a classifier from a set of panel levels obtained from samples of known colorectal health status. Machine learning models are readily constructed, for example, using any number of statistical programming programing languages such as R, scripting languages such as Python and associated machine learning packages, data mining software such as Weka or Java, Mathematica, Matlab or SAS.

Implementation of Classifiers in Colorectal Health Assessment

In practicing any of the methods described herein, comparing optionally comprises determining a difference between a biomarker profile of a subject to a reference biomarker profile. The method can, for example, comprise detecting a presence or absence of at least one of advanced colorectal adenoma and CRC based upon a deviation (for example, measured difference) of the biomarker profile of the subject as compared to a reference biomarker profile. For example, some methods comprise detecting a presence of at least one of advanced colorectal adenoma and CRC if the deviation of the biomarker profile of the subject as compared to a positive reference biomarker profile (for example, a biomarker profile based upon measurements of panel biomarkers from a positive control subject) is low. As an additional example, some methods comprise detecting a presence of at least one of advanced colorectal adenoma and CRC if the deviation of the biomarker profile of the subject as compared to a negative reference biomarker profile (for example, a biomarker profile based upon measurements of panel biomarkers from a negative control subject) is high. In some cases, the method comprises detecting an absence of at least one of advanced colorectal adenoma and CRC if the deviation of the biomarker profile of the subject as compared to a positive reference biomarker profile is high. In some examples, the method comprises detecting an absence of at least one of advanced colorectal adenoma and CRC if the deviation of the biomarker profile of the subject as compared to a negative reference biomarker profile is low. In some cases, detection of a presence or absence of at least one of advanced colorectal adenoma and CRC can be based upon a clinical outcome score produced by an algorithm described herein. The algorithm can be used for assessing the deviation between the biomarker profile of the subject to a reference biomarker profile.

Some methods comprise detecting a presence or absence of an advanced colorectal adenoma in the subject in some cases. The advanced colorectal adenoma can be a colorectal advanced colorectal adenoma. The methods described herein are be used to detect a presence or absence of an advanced colorectal adenoma of any size, such as an advanced adenoma having a dimension that is greater than 1 cm. The methods described herein are used to detect a presence or absence of an advanced colorectal adenoma of villous, serrated, sessile or non-pedunculated character.

In some cases, a diagnostic method provided herein comprises measuring a biomarker panel comprising at least five biomarkers in the biological sample, wherein the at least three biomarkers comprise AACT, CATD, CEA, CO3, CO9, MIF, PSGL, and SEPR. In some cases, the method comprises providing a positive diagnosis of advanced colorectal adenoma if a deviation in the panel level of a panel comprising AACT, CATD, CEA, CO3, CO9, MIF, PSGL, and SEPR in the biological sample obtained from the subject as compared to a positive reference value is low. In some cases, the method comprises providing a positive diagnosis of advanced colorectal adenoma if a deviation in the panel level of a panel comprising AACT, CATD, CEA, CO3, CO9, MIF, PSGL, and SEPR in the biological sample obtained from the subject as compared to a negative reference value is high. In some cases, the method comprises providing a positive diagnosis of advanced colorectal adenoma if a deviation in the panel level of a panel comprising AACT, CATD, CEA, CO3, CO9, MIF, PSGL, and SEPR in the biological sample obtained from the subject as compared to a positive reference value is high. In some cases, the method comprises providing a positive diagnosis of advanced colorectal adenoma if a deviation in the panel level of a panel comprising AACT, CATD, CEA, CO3, CO9, MIF, PSGL, and SEPR in the biological sample obtained from the subject as compared to a negative reference value is low.

Methods, compositions, kits and systems disclosed herein detect advanced colorectal adenoma with a sensitivity greater than 70%, greater than 75%, greater than 80%, greater than 85%, greater than 90%, greater than 95%, greater than 96%, greater than 97%, greater than 98%, greater than 99%, or about 100%. Such diagnostic method detects advanced colorectal adenoma with a sensitivity that is between about 50%-100%, between about 60%-100%, between about 70%-100%, between about 80%-100%, or between about 90-100%. Such diagnostic methods detect advanced colorectal adenoma with a sensitivity of at least 70%, of at least 75%, of at least 80%, of at least 85%, of at least 90%, of at least 95%, of at least 96%, of at least 97%, of at least 98%, of at least 99%, or about 100%. Such diagnostic methods detect advanced colorectal adenoma with a specificity that is between about 50%-100%, between about 60%-100%, between about 70%-100%, between about 80%-100%, or between about 90-100%. In particular cases, such diagnostic method detects advanced colorectal adenoma with a sensitivity and a specificity that is 50% or greater, 60% or greater, 70% or greater, 75% or greater, 80% or greater, 85% or greater, 90% or greater. In particular cases, such diagnostic detects advanced colorectal adenoma with a sensitivity and a specificity that is between about 50%-100%, between about 60%-100%, between about 70%-100%, between about 80%-100%, or between about 90-100%.

In some cases, a panel comprises a ratio of a level of a first biomarker to a level of a second biomarker. Accordingly, in some cases, a diagnostic method provided herein comprises determining a ratio of a level of the first biomarker to a level of the second biomarker in the biological sample obtained from the subject. In some cases, the method comprises providing a positive diagnosis of CRC if a deviation in the ratio of the first biomarker to the second biomarker in the biological sample obtained from the subject as compared to a positive reference value is low. In some cases, the method comprises providing a positive diagnosis of CRC if a deviation in the ratio of the first biomarker to the second biomarker in the biological sample obtained from the subject as compared to a negative reference value is high. In some cases, the method comprises providing a positive diagnosis of if a deviation in the ratio of the first biomarker to the second biomarker in the biological sample obtained from the subject as compared to a positive reference value is high. In some cases, the method comprises providing a positive diagnosis of CRC if a deviation in the ratio of the first biomarker to the second biomarker in the biological sample obtained from the subject as compared to a negative reference value is low.

Diagnostic methods described herein for detection of CRC in a subject detects CRC with a sensitivity greater than 75%, greater than 80%, greater than 85%, greater than 90%, greater than 95%, greater than 96%, greater than 97%, greater than 98%, greater than 99%, or about 100%. Such diagnostic methods detect CRC with a sensitivity that is between about 70%-100%, between about 80%-100%, or between about 90%-100%. Such diagnostic methods detect CRC with a specificity greater than 70%, greater than 75%, greater than 80%, greater than 85%, greater than 90%, greater than 95%, greater than 96%, greater than 97%, greater than 98%, greater than 99%, or about 100%. Such diagnostic methods detect CRC with a specificity that is between about 50%-100%, between about 60%-100%, between about 70%-100%, between about 80%-100%, or between about 90%-100%. In particular embodiments, such diagnostic methods detect CRC with a sensitivity and a specificity that is 50% or greater, 60% or greater, 70% or greater, 75% or greater, 80% or greater, 85% or greater, 90% or greater. In particular embodiments, such diagnostic methods detect CRC with a sensitivity and a specificity that is between about 50%-100%, between about 60%-100%, between about 70%-100%, between about 80%-100%, or between about 90%-100%.

The overall performance of a classifier is assessed in some cases via the AUC of the ROC as reported herein. An ROC considers the performance of the classifier at all possible model score cutoff points. However, when a classification decision needs to be made (e.g., is this patient sick or healthy?), a cutoff point is used to define the two groups. Classification scores at or above the cutoff point are assessed as positive (or sick) while points below are assessed as negative (or healthy) in various embodiments.

For some classification models disclosed herein, a classification score cutoff point is established by selecting the point of maximum accuracy on the validation ROC. The point of maximum accuracy on an ROC is the cutoff point or points for which the total number of correct classification calls is maximized. Here, the positive and negative classification calls are weighted equally. In cases where multiple maximum accuracy points are present on a given ROC, the point with the associated maximum sensitivity is selected in some cases.

Algorithm-Based Methods

Methods, compositions, kits, and systems described herein utilize an algorithm-based diagnostic assay for predicting a presence or absence of at least one of: advanced colorectal adenoma and CRC in a subject. Expression level of one or more protein biomarker, and optionally one or more subject characteristics, such as, for example, age, weight, gender, medical history, risk factors, or family history are used alone or arranged into functional subsets to calculate a quantitative score that is used to predict the likelihood of a presence or absence of at least one of advanced colorectal adenoma and CRC. Although lead embodiments herein focus upon biomarker panels that are predominantly protein or polypeptide panels, the measurements of any of the biomarker panels may comprise protein and non-protein components such as RNA, DNA, organic metabolites, or inorganic molecules or metabolites (e.g. iron, magnesium, selenium, calcium, or others).

The algorithm-based assay and associated information provided by the practice of any of the methods described herein can facilitate optimal treatment decision-making in subjects. For example, such a clinical tool can enable a physician or caretaker to identify patients who have a low likelihood of having an advanced colorectal adenoma or carcinoma and therefore would not need treatment, or increased monitoring for advanced colorectal adenoma or CRC, or who have a high likelihood of having an advanced colorectal adenoma or CRC and therefore would need treatment or increased monitoring of said advanced colorectal adenoma or CRC.

A quantitative score is determined by the application of a specific algorithm in some cases. The algorithm used to calculate the quantitative score in the methods disclosed herein may group the expression level values of a biomarker or groups of biomarkers. The formation of a particular group of biomarkers, in addition, can facilitate the mathematical weighting of the contribution of various expression levels of biomarker or biomarker subsets (for example classifier) to the quantitative score. Described herein are exemplary algorithms for calculating the quantitative scores.

Exemplary biomarkers and, when applicable their human amino acid sequences, are listed in Tables 1 and 3. Biomarkers may comprise full length molecules of the polypeptide sequences of Table 3, as well as uniquely identifiable fragments of the polypeptide sequences of Table 1. Markers can be but do not need to be full length to be informative. In many cases, so long as a fragment is uniquely identifiable as being derived from or representing a polypeptide of Table 3, it is informative for purposes herein.

Exemplary Subjects

Biological samples are collected from a number of eligible subjects, such as subjects who want to determine their likelihood of having at least one of advanced colorectal adenoma and CRC. The subject is in some cases healthy and asymptomatic. The subject's age is not constrained. For example, the subject is between the ages of 0 to about 30 years, about 20 to about 50 years, or about 40 or older. In various cases, the subject is healthy, asymptomatic and between the ages of 0-30 years, 20-50 years, or 40 or older. The subject is at least 30 years of age, at least 40 years of age, or at least 50 years of age. The subject is less than 50 years of age, less than 40 years of age, or less than 30 years of age. In various examples, the subject is healthy and asymptomatic. In various examples, the subject has no family history of at least one of: CRC, adenoma, and polyps. In various examples, the subject has not had a colonoscopy, sigmoidoscopy, or colon tissue biopsy. In various examples, the subject is healthy and asymptomatic and has not received a colonoscopy, sigmoidoscopy, or colon tissue biopsy. In some cases, the subject has not received a colonoscopy, sigmoidoscopy, or colon tissue biopsy and has one or more of: a symptom of CRC, a family history of CRC, and a risk factor for CRC. In some cases, a biological sample can be obtained from a subject during routine examination, or to establish baseline levels of the biomarkers. In some cases, a subject has no symptoms for colorectal carcinoma, has no family history for colorectal carcinoma, has no recognized risk factors for colorectal carcinoma.

In some cases, a subject presents at least one of: a symptom for colorectal carcinoma, a family history for colorectal carcinoma, and a recognized risk factor for colorectal carcinoma. In some cases, a subject is identified through screening assays (for example, fecal occult blood testing or sigmoidoscopy) or rectal digital exam or rigid or flexible colonoscopy or CT scan or other x-ray techniques as being at high risk for or having CRC. For example, one or more methods described herein are applied to a subject undergoing treatment for CRC, to determine the effectiveness of the therapy or treatment they are receiving.

Exemplary Biological Samples

Biological samples in some exemplary embodiments are circulating blood samples or are samples obtained from the vein or artery of an individual. Samples are optionally processed, so as to isolate plasma, circulating free proteins, or a whole protein fraction from the blood sample. Samples are often treated to facilitate storage or to allow shipment at room temperature, although in preferred embodiments samples are shipped frozen, for example with or on dry ice, to preserve the samples for analysis at a processing center separate from a phlebotomist's office.

As a representative sample collection protocol, blood samples for serum, EDTA plasma, citrate plasma and buffy-coats are collected with light tournique from an antecubital vein using endotoxin-, deoxyribonuclease (DNAse-) and ribonuclease (RNAse-) free collection and handling equipment, collection tubes and storage vials from Becton-Dickinson, Franklin Lakes, N.J., USA and Almeco A/S, Esbjerg, Denmark. The blood samples are centrifuged at 3,000×G for 10 mins at 21° C. and serum and plasma are immediately separated from the red cell and buffy-coat layers. Contamination by white cells and platelets is reduced by leaving 0.5 cm of untouched serum or plasma above the buffy-coat, which is separately transferred for freezing. All separated samples are marked with unique barcodes for storage identification, which is performed using the FreezerWorks®, Seattle, Wash., USA tracking system. Separated samples are frozen at −80° C. under continuous electronic surveillance. The entire procedure is completed within 2 hours of initial sample draw.

Additional biological samples include one or more of, but are not limited to: urine, stool, tears, whole blood, serum, plasma, blood constituent, bone marrow, tissue, cells, organs, saliva, cheek swab, lymph fluid, cerebrospinal fluid, lesion exudates and other fluids produced by the body. The biological sample is in some cases a solid biological sample, for example, a tissue biopsy. The biopsy can be fixed, paraffin embedded, or fresh. In many embodiments herein, a preferred sample is a blood sample drawn from a vein or artery of an individual, or a processed product thereof.

Biological samples are optionally processed using any approach known in the art or otherwise described herein to facilitate measurement of one or more biomarkers as described herein. Sample preparation operations comprise, for example, extraction and/or isolation of intracellular material from a cell or tissue such as the extraction of nucleic acids, protein, or other macromolecules. Sample preparation which can be used with the methods of disclosure include but are not limited to, centrifugation, affinity chromatography, magnetic separation, immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, radioisotope assay, protein synthesis assay, histological assay, culture assay, and combinations thereof.

Sample preparation optionally includes dilution by an appropriate solvent and amount to ensure the appropriate range of concentration level is detected by a given assay.

Accessing the nucleic acids and macromolecules from the intercellular space of the sample is performed by either physical, chemical methods, or a combination of both. In some applications of the methods, following the isolation of the crude extract, it will often be desirable to separate the nucleic acids, proteins, cell membrane particles, and the like. In some applications of the methods it will be desirable to keep the nucleic acids with its proteins, and cell membrane particles.

In some applications of the methods provided herein, nucleic acids and proteins are extracted from a biological sample prior to analysis using methods of the disclosure. Extraction is accomplished, for example through use of detergent lysates, sonication, or vortexing using glass beads.

In some applications, molecules can be isolated using any technique suitable in the art including, but not limited to, techniques using gradient centrifugation (for example, cesium chloride gradients, sucrose gradients, glucose gradients, or other gradients), centrifugation protocols, boiling, purification kits, and the use of liquid extraction with agent extraction methods such as methods using Trizol or DNAzol.

In some cases, the sample is partially prepared at a separate location prior to being sent for analysis. For example, a phlebotomist drawsn a blood sample at a clinic or hospital. The sample can be partially processed, for example, by placing in anticoagulant-treated tubes and centrifuging to produce plasma. The partially processed sample, such as the plasma, is then shipped (e.g., mailed on ice or in preservative at room temperature) to a separate facility where any of the methods disclosed herein can be performed to determine a biomarker panel level and/or CRC or advanced adenoma health status.

Samples are prepared according to standard biological sample preparation depending on the desired detection method. For example, for mass spectrometry detection, biological samples obtained from a patient may be centrifuged, filtered, processed by immunoaffinity column, separated into fractions, partially digested, and combinations thereof. Various fractions may be resuspended in appropriate carrier such as buffer or other type of loading solution for detection and analysis, including LCMS loading buffer.

Biomarker Assessment

The present disclosure provides for methods for measuring one or more biomarker panels in biological samples. Any suitable method can be used to detect one or more of the biomarkers of any of the panels described herein.

In some cases, only values falling within specific ranges are reported. For example, in some cases, assayed protein concentrations below a given cutoff indicate a failed assay. Exemplary acceptable ranges for particular biomarkers are disclosed in Table 4.

TABLE 4

Exemplary acceptable ranges for biomarkers of interest.

| Protein | Low | High | Units |
|---|---|---|---|
| AACT | 62.5 | 4000 | µg/ml |
| CATD | 62.5 | 1000 | ng/ml |
| CEA | 3 | 120 | ng/ml |
| CLUS | 30 | 480 | µg/ml |
| CO3 | 117.25 | 7500 | µg/ml |
| CO9 | 4.68 | 300 | µg/ml |
| GDF15 | 187.2 | 12000 | pg/ml |
| MIF | 3.13 | 100 | ng/ml |
| PSGL | 93.75 | 1500 | U/ml |
| SAA1 | 18 | 144 | µg/ml |
| SEPR | 10 | 160 | ng/ml |

Useful analyte capture agents used in practice of methods described herein include but are not limited to antibodies, such as crude serum containing antibodies, purified antibodies, monoclonal antibodies, polyclonal antibodies, synthetic antibodies, antibody fragments (for example, Fab fragments); antibody interacting agents, such as protein A, carbohydrate binding proteins, and other interactants; protein interactants (for example avidin and its derivatives); peptides; and small chemical entities, such as enzyme substrates, cofactors, metal ions/chelates, aptamers, and haptens. Antibodies may be modified or chemically treated to optimize binding to targets or solid surfaces (for example biochips and columns).

Biomarkers are measured in some cases in a biological sample using an immunoassay. Some immunoassays use antibodies that specifically or informatively bind to or recognize an antigen (for example site on a protein or peptide, biomarker target). Some immunoassays include the steps of contacting the biological sample using the antibody and allowing the antibody to form a complex of with the antigen in the sample, washing the sample and detecting the antibody-antigen complex with a detection reagent. Antibodies that recognize the biomarkers may be commercially available. An antibody that recognizes the biomarkers can be generated by known methods of antibody production.

Immunoassays include indirect assays, wherein, for example, a second, labeled antibody can be used to detect bound marker-specific antibody. Exemplary detectable labels include magnetic beads (for example, DYNA-BEADS™), fluorescent dyes, radiolabels, enzymes (for example, horseradish peroxidase, alkaline phosphatase and others commonly used), and calorimetric labels such as colloidal gold or colored glass or plastic beads. The biomarker in the sample can be measured using a competition or inhibition assay wherein, for example, a monoclonal antibody which binds to a distinct epitope of the marker is incubated simultaneously with the mixture.

The conditions to detect an antigen using an immunoassay are dependent on the particular antibody used. Also, the incubation time can depend upon the assay format, marker, volume of solution, concentrations and the like. Immunoassays can be carried out at room temperature, although they can be conducted over a range of temperatures, such as from about 0 degrees to about 40 degrees Celsius depending on the antibody used.

There are various types of immunoassay known in the art that as a starting basis can be used to tailor the assay for the detection of the biomarkers of the present disclosure. Useful assays can include, for example, an enzyme immune assay (EIA) such as enzyme-linked immunosorbent assay (ELISA). For example, if an antigen can be bound to a solid support or surface, it can be detected by reacting it with a specific antibody and the antibody can be quantitated by reacting it with either a secondary antibody or by incorporating a label directly into the primary antibody. Alternatively, an antibody can be bound to a solid surface and the antigen added. A second antibody that recognizes a distinct epitope on the antigen can then be added and detected. Such assay can be referred to as a 'sandwich assay' and can be used to avoid problems of high background or non-specific reactions. These types of assays can be sensitive and reproducible enough to measure low concentrations of antigens in a biological sample.

Immunoassays are used to determine presence or absence of a marker in a sample as well as the quantity of a marker in a sample. Methods for measuring the amount of, or presence of, antibody-marker complex include but are not limited to, fluorescence, luminescence, chemiluminescence, absorbance, reflectance, transmittance, birefringence or refractive index (for example, surface plasmon resonance, ellipsometry, a resonant mirror method, a grating coupler waveguide method or interferometry). Such reagents can be used with optical detection methods, such as various forms of microscopy, imaging methods and non-imaging methods. Electrochemical methods can include voltammetry and amperometry methods. Radio frequency methods can include multipolar resonance spectroscopy.

Measurement of biomarkers optionally involves use of an antibody. Antibodies that specifically bind to any of the biomarkers described herein can be prepared using standard methods known in the art. For example polyclonal antibodies can be produced by injecting an antigen into a mammal, such as a mouse, rat, rabbit, goat, sheep, or horse for large quantities of antibody. Blood isolated from these animals can contain polyclonal antibodies—multiple antibodies that bind to the same antigen. Alternatively, polyclonal antibodies can be produced by injecting the antigen into chickens for generation of polyclonal antibodies in egg yolk. In addition, antibodies can be made to specifically recognize modified forms for the biomarkers such as a phosphorylated form of the biomarker, for example, they can recognize a tyrosine or a serine after phosphorylation, but not in the absence of phosphate. In this way antibodies can be used to determine the phosphorylation state of a particular biomarker.

Antibodies are obtained commercially or produced using well-established methods. To obtain antibodies specific for a single epitope of an antigen, antibody-secreting lymphocytes are isolated from the animal and immortalized by fusing them with a cancer cell line. The fused cells are referred to as hybridomas, and can continually grow and secrete antibody in culture. Single hybridoma cells are isolated by dilution cloning to generate cell clones that all produce the same antibody; these antibodies can be referred to as monoclonal antibodies.

Polyclonal and monoclonal antibodies can be purified in several ways. For example, one can isolate an antibody using antigen-affinity chromatography which can be couple to bacterial proteins such as Protein A, Protein G, Protein L or the recombinant fusion protein, Protein A/G followed by detection of via UV light at 280 nm absorbance of the eluate fractions to determine which fractions contain the antibody. Protein A/G can bind to all subclasses of human IgG, making it useful for purifying polyclonal or monoclonal IgG antibodies whose subclasses have not been determined. In addition, Protein A/G can bind to IgA, IgE, IgM and (in some cases to a lesser extent) IgD. Protein A/G can bind to all subclasses of mouse IgG but in some cases does not bind mouse IgA, IgM or serum albumin. This feature can allow Protein A/G to be used for purification and detection of mouse monoclonal IgG antibodies, without interference from IgA, IgM and serum albumin.

Antibodies are derived from different classes or isotypes of molecules such as, for example, IgA, IgA IgD, IgE, IgM and IgG. The IgA can be designed for secretion in the bodily fluids while others, like the IgM are designed to be expressed on the cell surface. The antibody can be an IgG antibody. In some cases, IgG comprises two subunits including two "heavy" chains and two "light" chains. These can be assembled in a symmetrical structure and each IgG can have two identical antigen recognition domains. The antigen recognition domain can be a combination of amino acids from both the heavy and light chains. The molecule can be roughly shaped like a "Y" and the arms/tips of the molecule comprise the antigen-recognizing regions or Fab (fragment, antigen binding) region, while the stem of Fc (Fragment, crystallizable) region is not necessarily involved in recognition and can be fairly constant. The constant region can be identical in all antibodies of the same isotype, but can differ in antibodies of different isotypes.

It is also possible to use an antibody to detect a protein after fractionation by western blotting. Western blotting is used in some cases for the detection and/or measurement of protein or polypeptide biomarkers.

Some detection methods can employ flow cytometry. Flow cytometry can be a laser based, biophysical technology that can be used for biomarker detection, quantification (cell counting) and cell isolation. This technology can be used in the diagnosis of health disorders, especially blood cancers. In general, flow cytometry can comprise suspending single cells in a stream of fluid. A beam of light (usually laser light) of a single wavelength can be directed onto the stream of liquid, and the scatter light caused by a passing cell can be detected by an electronic detection apparatus. A flow cytometry methodology useful in one or more methods described herein can include Fluorescence-activated cell sorting (FACS). FACS can use florescent-labeled antibodies to detect antigens on cell of interest. This additional feature of antibody labeling use in FACS can enable simultaneous multiparametric analysis and quantification based upon the specific light scattering and fluorescent characteristics of each cell florescent-labeled cell and it provides physical separation of the population of cells of interest as well as traditional flow cytometry does.

A wide range of fluorophores can be used as labels in flow cytometry. Fluorophores can be typically attached to an antibody that recognizes a target feature on or in the cell. Examples of suitable fluorescent labels include, but are not limited to: fluorescein (FITC), 5,6-carboxymethyl fluorescein, Texas red, nitrobenz-2-oxa-1,3-diazol-4-yl (NBD), and the cyanine dyes Cy3, Cy3.5, Cy5, Cy5.5 and Cy7. Other Fluorescent labels such as Alexa Fluor® dyes, DNA content dye such as DAPI, and Hoechst dyes are well known in the art and can be easily obtained from a variety of commercial sources. Each fluorophore can have a characteristic peak excitation and emission wavelength, and the emission spectra often overlap. The absorption and emission maxima, respectively, for these fluors can be: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm). The fluorescent labels can be obtained from a variety of commercial sources. Quantum dots can be used in place of traditional fluorophores. Other methods that can be used for detecting include isotope labeled antibodies, such as lanthanide isotopes.

Immunoassays optionally comprise immunohistochemistry. Immunohistochemistry is used to detect expression of the claimed biomarkers in a tissue sample. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody can be used in conjunction with a labeled secondary antibody, comprising antisera, polyclonal antisera or a monoclonal antibody specific for the primary antibody. Immunohistochemistry protocols are well known in the art and protocols and antibodies are commercially available. Alternatively, one raises an antibody to the biomarkers or modified versions of the biomarker or binding partners as disclosure herein that would be useful for determining the expression levels of the proteins in a tissue sample.

Some measurement of biomarkers comprises use of a biochip. Biochips can be used to screen a large number of macromolecules. Biochips can be designed with immobilized nucleic acid molecules, full-length proteins, antibodies, affibodies (small molecules engineered to mimic monoclonal antibodies), aptamers (nucleic acid-based ligands) or chemical compounds. A chip could be designed to detect multiple macromolecule types on one chip. For example, a chip could be designed to detect nucleic acid molecules, proteins and metabolites on one chip. The biochip can be used to and designed to simultaneously analyze a panel biomarker in a single sample, producing a subjects profile for these biomarkers. The use of the biochip allows for the multiple analyses to be performed reducing the overall processing time and the amount of sample required.

Protein microarray can be a particular type of biochip which can be used with the present disclosure. In some cases, the chip comprises a support surface such as a glass slide, nitrocellulose membrane, bead, or microtitre plate, to which an array of capture proteins can be bound in an arrayed format onto a solid surface. Protein array detection methods can give a high signal and a low background. Detection probe molecules, typically labeled with a fluorescent dye, can be added to the array. Any reaction between the probe and the immobilized protein can result in emission of a detectable signal. Such protein microarrays can be rapid, automated, and offer high sensitivity of protein biomarker read-outs for diagnostic tests. However, it would be immediately appreciated to those skilled in the art that there are a variety of detection methods that can be used with this technology. Exemplary microarrays include analytical microarrays (also known as capture arrays), functional protein microarrays (also known as target protein arrays) and reverse phase protein microarray (RPA).

Analytical protein microarrays can be constructed using a library of antibodies, aptamers or affibodies. The array can be probed with a complex protein solution such as a blood, serum or a cell lysate that function by capturing protein molecules they specifically bind to. Analysis of the resulting binding reactions using various detection systems can provide information about expression levels of particular proteins in the sample as well as measurements of binding affinities and specificities. This type of protein microarray can be especially useful in comparing protein expression in different samples. Functional protein microarrays can be constructed by immobilizing large numbers of purified full-length functional proteins or protein domains and can be used to identify protein-protein, protein-DNA, protein-RNA, protein-phospholipid, and protein-small molecule interactions, to assay enzymatic activity and to detect antibodies and demonstrate their specificity. These protein microarray biochips can be used to study the biochemical activities of the entire proteome in a sample.

One or more biomarkers can be measured using reverse phase protein microarray (RPA). Reverse phase protein microarray can be constructed from tissue and cell lysates that can be arrayed onto the microarray and probed with antibodies against the target protein of interest. These antibodies can be detected with chemiluminescent, fluorescent or colorimetric assays. In addition to the protein in the lysate, reference control peptides can be printed on the slides to allow for protein quantification. RPAs allow for the determination of the presence of altered proteins or other agents that may be the result of disease and present in a diseased cell.

One or more biomarkers can be measured using mass spectroscopy (alternatively referred to as mass spectrometry). Mass spectrometry (MS) can refer to an analytical technique that measures the mass-to-charge ratio of charged particles. It can be primarily used for determining the elemental composition of a sample or molecule, and for elucidating the chemical structures of molecules, such as peptides and other chemical compounds. MS works by ionizing chemical compounds to generate charged molecules or molecule fragments and measuring their mass-to-charge ratios MS instruments typically consist of three modules (1) an ion source, which can convert gas phase sample molecules into ions (or, in the case of electrospray ionization, move ions that exist in solution into the gas phase) (2) a mass analyzer, which sorts the ions by their masses by applying electromagnetic fields and (3) detector, which measures the value of an indicator quantity and thus provides data for calculating the abundances of each ion present.

Suitable mass spectrometry methods to be used with the present disclosure include but are not limited to, one or more of electrospray ionization mass spectrometry (ESI-MS), ESI-MS/MS, ESI-MS/(MS)$_n$, matrix-assisted laser desorption ionization time-of-flight mass spectrometry (MALDI-TOF-MS), surface-enhanced laser desorption/ionization time-of-flight mass spectrometry (SELDI-TOF-MS), tandem liquid chromatography-mass spectrometry (LC-MS/MS) mass spectrometry, desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS), atmospheric pressure photoionization mass spectrometry (APPI-MS), APPI-MS/MS, and APPI-(MS)$_n$, quadrupole mass spectrometry, Fourier transform mass spectrometry (FTMS), and ion trap mass spectrometry, where n can be an integer greater than zero.

LC-MS can be commonly used to resolve the components of a complex mixture. LC-MS method generally involves protease digestion and denaturation (usually involving a protease, such as trypsin and a denaturant such as, urea to denature tertiary structure and iodoacetamide to cap cysteine residues) followed by LC-MS with peptide mass fingerprinting or LC-MS/MS (tandem MS) to derive sequence of individual peptides. LC-MS/MS can be used for proteomic analysis of complex samples where peptide masses may overlap even with a high-resolution mass spectrometer. Samples of complex biological fluids like human serum may be first separated on an SDS-PAGE gel or HPLC-SCX and then run in LC-MS/MS allowing for the identification of over 1000 proteins.

While multiple mass spectrometric approaches are compatible with the methods of the disclosure as provided herein, in some applications it is desired to quantify proteins in biological samples from a selected subset of proteins of interest. One such MS technique that is compatible with the present disclosure is Multiple Reaction Monitoring Mass Spectrometry (MRM-MS), or alternatively referred to as Selected Reaction Monitoring Mass Spectrometry (SRM-MS).

The MRM-MS technique involves a triple quadrupole (QQQ) mass spectrometer to select a positively charged ion from the peptide of interest, fragment the positively charged ion and then measure the abundance of a selected positively charged fragment ion. This measurement is commonly referred to as a transition and/or transition ion. By way of illustrative example only, a peptide fragment comprising the amino acid sequence IAELLSPGSVDPLTR (SEQ ID NO: 27) can comprise one or more of the following exemplary transition ion biomarkers provided in Table 5, below.

TABLE 5

Exemplary transition ions for the peptidesequence IAELLSPGSVDPLTR

| Transition Ion | Amino Acid Sequence |
|---|---|
| b1 | I |
| b2 | IA |
| b3 | IAE |
| b4 | IAEL (SEQ ID NO: 28) |
| b5 | IAELL (SEQ ID NO: 29) |
| b6 | IAELLS (SEQ ID NO: 30) |
| b7 | IAELLSP (SEQ ID NO: 31) |
| b8 | IAELLSPG (SEQ ID NO: 32) |
| b9 | IAELLSPGS (SEQ ID NO: 33) |
| b10 | IAELLSPGSV (SEQ ID NO: 34) |
| b11 | IAELLSPGSVD (SEQ ID NO: 35) |
| b12 | IAELLSPGSVDP (SEQ ID NO: 36) |
| b13 | IAELLSPGSVDPL (SEQ ID NO: 37) |
| b14 | IAELLSPGSVDPLT (SEQ ID NO: 38) |
| y14 | AELLSPGSVDPLTR (SEQ ID NO: 39) |
| y13 | ELLSPGSVDPLTR (SEQ ID NO: 40) |
| y12 | LLSPGSVDPLTR (SEQ ID NO: 41) |
| y11 | LSPGSVDPLTR (SEQ ID NO: 42) |
| y10 | SPGSVDPLTR (SEQ ID NO: 43) |
| y9 | PGSVDPLTR (SEQ ID NO: 44) |
| y8 | GSVDPLTR (SEQ ID NO: 45) |
| y7 | SVDPLTR (SEQ ID NO: 46) |
| y6 | VDPLTR (SEQ ID NO: 47) |

TABLE 5-continued

Exemplary transition ions for the peptidesequence IAELLSPGSVDPLTR

| Transition Ion | Amino Acid Sequence |
|---|---|
| y5 | DPLTR (SEQ ID NO: 48) |
| y4 | PLTR (SEQ ID NO: 49) |
| y3 | LTR |
| y2 | TR |
| y1 | R |

In some applications the MRM-MS is coupled with High-Pressure Liquid Chromatography (HPLC) and more recently Ultra High-Pressure Liquid Chromatography (UHPLC). In other applications MRM-MS can be coupled with UHPLC with a QQQ mass spectrometer to make the desired LC-MS transition measurements for all of the peptides and proteins of interest.

In some applications the utilization of a quadrupole time-of-flight (qTOF) mass spectrometer, time-of-flight time-of-flight (TOF-TOF) mass spectrometer, Orbitrap mass spectrometer, quadrupole Orbitrap mass spectrometer or any Quadrupolar Ion Trap mass spectrometer can be used to select for a positively charged ion from one or more peptides of interest. The fragmented, positively charged ions can then be measured to determine the abundance of a positively charged ion for the quantitation of the peptide or protein of interest.

In some applications the utilization of a time-of-flight (TOF), quadrupole time-of-flight (qTOF) mass spectrometer, time-of-flight time-of-flight (TOF-TOF) mass spectrometer, Orbitrap mass spectrometer or quadrupole Orbitrap mass spectrometer is used to measure the mass and abundance of a positively charged peptide ion from the protein of interest without fragmentation for quantitation. In this application, the accuracy of the analyte mass measurement can be used as selection criteria of the assay. An isotopically labeled internal standard of a known composition and concentration can be used as part of the mass spectrometric quantitation methodology.

In some applications, time-of-flight (TOF), quadrupole time-of-flight (qTOF) mass spectrometer, time-of-flight time-of-flight (TOF-TOF) mass spectrometer, Orbitrap mass spectrometer or quadrupole Orbitrap mass spectrometer is used to measure the mass and abundance of a protein of interest for quantitation. In this application, the accuracy of the analyte mass measurement can be used as selection criteria of the assay. Optionally this application can use proteolytic digestion of the protein prior to analysis by mass spectrometry. An isotopically labeled internal standard of a known composition and concentration can be used as part of the mass spectrometric quantitation methodology.

In some applications, various ionization techniques can be coupled to the mass spectrometers provide herein to generate the desired information. Non-limiting exemplary ionization techniques that are used with the present disclosure include but are not limited to Matrix Assisted Laser Desorption Ionization (MALDI), Desorption Electrospray Ionization (DESI), Direct Assisted Real Time (DART), Surface Assisted Laser Desorption Ionization (SALDI), or Electrospray Ionization (ESI).

In some applications, HPLC and UHPLC can be coupled to a mass spectrometer a number of other peptide and protein separation techniques can be performed prior to mass spectrometric analysis. Some exemplary separation techniques which can be used for separation of the desired analyte (for example, peptide or protein) from the matrix background include but are not limited to Reverse Phase Liquid Chromatography (RP-LC) of proteins or peptides, offline Liquid Chromatography (LC) prior to MALDI, 1 dimensional gel separation, 2-dimensional gel separation, Strong Cation Exchange (SCX) chromatography, Strong Anion Exchange (SAX) chromatography, Weak Cation Exchange (WCX), and Weak Anion Exchange (WAX). One or more of the above techniques can be used prior to mass spectrometric analysis.

One or more biomarkers can be measured using a microarray. Differential gene expression can also be identified, or confirmed using the microarray technique. Thus, the expression profile biomarkers can be measured in either fresh or fixed tissue, using microarray technology. In this method, polynucleotide sequences of interest (including cDNAs and oligonucleotides) can be plated, or arrayed, on a microchip substrate. The arrayed sequences can be then hybridized with specific DNA probes from cells or tissues of interest. The source of mRNA can be total RNA isolated from a biological sample, and corresponding normal tissues or cell lines may be used to determine differential expression.

One or more biomarkers can be measured by sequencing. Differential gene expression can also be identified, or confirmed using the sequencing technique. Thus, the expression profile biomarkers can be measured in either fresh or fixed sample, using sequencing technology. In this method, polynucleotide sequences of interest (including cDNAs and oligonucleotides) can used as templates to synthesize sequencing libraries. The libraries can be sequenced, and the reads mapped to an appropriate reference. The source of mRNA can be total RNA isolated from a biological sample, and corresponding normal tissues or cell lines may be used to determine differential expression. Exemplary sequencing techniques can include, for example emulsion PCR (pyrosequencing from Roche 454, semiconductor sequencing from Ion Torrent, SOLiD sequencing by ligation from Life Technologies, sequencing by synthesis from Intelligent Biosystems), bridge amplification on a flow cell (e.g. Solexa/Illumina), isothermal amplification by Wildfire technology (Life Technologies) or rolonies/nanoballs generated by rolling circle amplification (Complete Genomics, Intelligent Biosystems, Polonator). Sequencing technologies like Heliscope (Helicos), SMRT technology (Pacific Biosciences) or nanopore sequencing (Oxford Nanopore) allow direct sequencing of single molecules without prior clonal amplification may be suitable sequencing platforms. Sequencing may be performed with or without target enrichment. In some cases, polynucleotides from a sample are amplified by any suitable means prior to and/or during sequencing.

PCR amplified inserts of cDNA clones can be applied to a substrate in a dense array. Preferably at least 10,000 nucleotide sequences can be applied to the substrate. The microarrayed genes, immobilized on the microchip at 10,000 elements each, can be suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the microarray chip can be scanned by a device such as, confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA can be hybridized pair-wise to the array. The relative abundance of the transcripts from the two sources corresponding to each specified gene can be thus determined simultaneously. Microarray analysis can be performed by commercially available equipment, following manufacturer's protocols.

One or more biomarkers can be measured using qRT-PCR, which can be used to compare mRNA levels in different sample populations, in normal and tumor tissues, with or without drug treatment, to characterize patterns of gene expression, to discriminate between closely related mRNAs, and to analyze RNA structure. The first step in gene expression profiling by RT-PCR can be extracting RNA from a biological sample followed by the reverse transcription of the RNA template into cDNA and amplification by a PCR reaction. The reverse transcription reaction step can be generally primed using specific primers, random hexamers, or oligo-dT primers, depending on the goal of expression profiling. Reverse transcriptases can be avilo myeloblastosis virus reverse transcriptase (AMV-RT) and/or Moloney murine leukemia virus reverse transcriptase (MLV-RT).

Although the PCR step can use a variety of thermostable DNA-dependent DNA polymerases, it typically employs the Taq DNA polymerase, which can have a 5'-3' nuclease activity but lacks a 3'-5' proofreading endonuclease activity. Thus, TaqMan™ PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers can be used to generate an amplicon typical of a PCR reaction. A third oligonucleotide, or probe, can be designed to detect nucleotide sequence located between the two PCR primers. The probe can be non-extendible by Taq DNA polymerase enzyme, and can be labeled with a reporter fluorescent dye and a quencher fluorescent dye. Any laser-induced emission from the reporter dye can be quenched by the quenching dye when the two dyes are located close together as they are on the probe. During the amplification reaction, the Taq DNA polymerase enzyme can cleave the probe in a template-dependent manner. The resultant probe fragments can disassociate in solution, and signal from the released reporter dye can be freed from the quenching effect of the second fluorophore. One molecule of reporter dye can be liberated for each new molecule synthesized, and detection of the unquenched reporter dye can provide basis for quantitative interpretation of the data.

TaqMan™ RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system comprises a thermocycler, laser, charge-coupled device (CCD), camera and computer. The system includes software for running the instrument and for analyzing the data. 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant can be the threshold cycle (Ct).

To minimize errors and the effect of sample-to-sample variation, RT-PCR can be performed using an internal standard. An internal standard can be expressed at a constant level among different tissues, and can be unaffected by the experimental treatment. RNAs most frequently used to normalize patterns of gene expression are mRNAs for the housekeeping genes glyceraldehyde-3-phosphate-dehydrogenase (GAPDH) and Beta-Actin.

A more recent variation of the RT-PCR technique can include the real time quantitative PCR, which can measure PCR product accumulation through a dual-labeled fluorogenic probe (i.e., TaqMan™ probe). Real time PCR can be compatible both with quantitative competitive PCR, where internal competitor for each target sequence can be used for normalization, and with quantitative comparative PCR using a normalization gene contained within the sample, or a housekeeping gene for RT-PCR. For further details see, for example Held et al., Genome Research 6:986-994 (1996).

Normalization of Data

Measurement data used in the methods, systems, kits and compositions disclosed herein are optionally normalized. Normalization refers to a process to correct for example, differences in the amount of genes or protein levels assayed and variability in the quality of the template used, to remove unwanted sources of systematic variation measurements involved in the processing and detection of genes or protein expression. Other sources of systematic variation are attributable to laboratory processing conditions.

In some instances, normalization methods are used for the normalization of laboratory processing conditions. Non-limiting examples of normalization of laboratory processing that may be used with methods of the disclosure include but are not limited to: accounting for systematic differences between the instruments, reagents, and equipment used during the data generation process, and/or the date and time or lapse of time in the data collection.

Assays can provide for normalization by incorporating the expression of certain normalizing standard genes or proteins, which do not significantly differ in expression levels under the relevant conditions, that is to say they are known to have a stabilized and consistent expression level in that particular sample type. Suitable normalization genes and proteins that can be used with the present disclosure include housekeeping genes. (See, for example, E. Eisenberg, et al., Trends in Genetics 19(7):362-365 (2003). In some applications, the normalizing biomarkers (genes and proteins), also referred to as reference genes, known not to exhibit meaningfully different expression levels in subjects with advanced colorectal adenoma or CRC as compared to control subjects without advanced colorectal adenoma or CRC. In some applications, it may be useful to add a stable isotope labeled standards which can be used and represent an entity with known properties for use in data normalization. In other applications, a standard, fixed sample can be measured with each analytical batch to account for instrument and day-to-day measurement variability.

Clinical Outcome Score

Machine learning algorithms for sub-selecting discriminating biomarkers and optionally subject characteristics, and for building classification models, are used in some methods and systems herein to determine clinical outcome scores. These algorithms include, but are not limited to, elastic networks, random forests, support vector machines, and logistic regression. These algorithms can aid in selection of important biomarker features and transform the underlying measurements into a score or probability relating to, for example, clinical outcome, disease risk, disease likelihood, presence or absence of disease, treatment response, and/or classification of disease status.

A clinical outcome score is determined by comparing a level of at least two biomarkers in the biological sample obtained from the subject to a reference level of the at least two biomarkers. Alternately or in combination, a clinical outcome score is determined by comparing a subject-specific profile of a biomarker panel to a reference profile of the biomarker panel. In some cases, a reference level or reference profile represents a known diagnosis. For example, a reference level or reference profile represents a positive diagnosis of advanced colorectal adenoma. A reference level or reference profile can represent a positive diagnosis of CRC. As another example, a reference level or reference profile represents a negative diagnosis of advanced colorectal adenoma. Similarly, a reference level or reference profile can represent a negative diagnosis of CRC In some cases, an increase in a score indicates an increased likelihood of one or more of: a poor clinical outcome, good clinical outcome, high risk of disease, low risk of disease, complete response, partial response, stable disease, non-response, and recommended treatments for disease management. In some cases, a decrease in the quantitative score indicates an increased likelihood of one or more of: a poor clinical outcome, good clinical outcome, high risk of disease, low risk of disease, complete response, partial response, stable disease, non-response, and recommended treatments for disease management.

A similar biomarker profile from a patient to a reference profile often indicates an increased likelihood of one or more of: a poor clinical outcome, good clinical outcome, high risk of disease, low risk of disease, complete response, partial response, stable disease, non-response, and recommended treatments for disease management. In some applications, a dissimilar biomarker profile from a patient to a reference profile indicates one or more of: an increased likelihood of a poor clinical outcome, good clinical outcome, high risk of disease, low risk of disease, complete response, partial response, stable disease, non-response, and recommended treatments for disease management.

An increase in one or more biomarker threshold values often indicates an increased likelihood of one or more of: a poor clinical outcome, good clinical outcome, high risk of disease, low risk of disease, complete response, partial response, stable disease, non-response, and recommended treatments for disease management. In some applications, a decrease in one or more biomarker threshold values indicates an increased likelihood of one or more of: a poor clinical outcome, good clinical outcome, high risk of disease, low risk of disease, complete response, partial response, stable disease, non-response, and recommended treatments for disease management.

An increase in at least one of a quantitative score, one or more biomarker thresholds, a similar biomarker profile values indicates an increased likelihood of one or more of: a poor clinical outcome, good clinical outcome, high risk of disease, low risk of disease, complete response, partial response, stable disease, non-response, and recommended treatments for disease management. Similarly, a decrease in at least one of a quantitative score, one or more biomarker thresholds, a similar biomarker profile values or combinations thereof indicates an increased likelihood of one or more of: a poor clinical outcome, good clinical outcome, high risk of disease, low risk of disease, complete response, partial response, stable disease, non-response, and recommended treatments for disease management.

A clinical outcome score is optionally updated based on additional information derived during treatment. Such updates often comprise the addition of other biomarkers. Such biomarkers include additional proteins, metabolite accumulation levels, physical characteristics of the subject (e.g., age, race, weight, demographic history), medical history of the subject (e.g., family history of advanced colorectal adenoma, prior quantitative score of the protein panels). Such updates can comprise an adjustment of the test sensitivity. Such updates can comprise an adjustment of the test sensitivity. Such updates can comprise an adjustment of the test thresholds. Such updates can comprise an adjustment of the predicted clinical outcomes.

For example, in some cases a patient at risk of advanced colorectal adenoma is tested using a panel as disclosed herein. The patient may be categorized as having or being likely to have, advanced colorectal adenoma. In some cases, the thresholds of a protein panel disclosed herein will be updated based on additional biomarkers, such as age of the patient. For example, a patient over the age of 60 is more likely than a patient under 60 to have advanced colorectal adenoma. Therefore, the positive predictive value of the protein panel can be higher in the population over 60 than the population under 60. In some cases, the threshold for proteins in the protein panel can be altered based on an additional biomarker (e.g., age) to reflect this, such as by lowering the threshold in a population over 60 compared to a population under 60. A patient's personal threshold may be updated based on previous test results. For example, a patient may have an indeterminate or positive clinical outcome score. Such a patient may have additional tests recommended. Such a patient may have a colonoscopy recommended. Such additional tests and colonoscopies can come back negative, and the persistence of an indeterminate or positive clinical outcome score can lead to the patient's thresholds being updated to reflect their persistent indeterminate or positive clinical outcome score.

In some cases, the specificity and sensitivity of the test is adjusted based on an additional biomarker. For example, the protein panels disclosed herein may have different sensitivities or specificities in populations of individuals with a given genetic or racial background. In some cases, based on an additional biomarker, the clinical outcome score may be adjusted to reflect a changing sensitivity or specificity of the test.

Treatment and Diagnostic Regimens

Provided herein are treatment and diagnostic regimens for implementing any of the methods described herein for detecting a presence or absence of advanced colorectal adenoma and treatment of the same.

Provided herein are methods for detecting a presence or absence of colorectal cancer. Methods disclosed herein can comprise performing a test for colorectal cancer, performing a colonoscopy, during which detected colorectal cancers are surgically excised or otherwise removed, and performing the test for colorectal cancer a second time at a later date. The second test can be positive and a second colonoscopy can be performed. In some cases, the second colonoscopy can include searching for and monitoring sessile colorectal cancers. In some cases, the second colonoscopy can include searching for and surgically removing sessile colorectal cancers. In some cases the second test for colorectal cancer can be positive and an additional treatment regimen can be recommended. In some cases, the second test for colorectal cancer can be negative and no additional testing can be recommended. In some cases, the second test for advanced colorectal adenoma can be negative and more frequent testing can be recommended for a given period of time.

In some cases, a positive clinical outcome score can lead to the recommendation of a drug therapeutic regimen. For example, a positive clinical outcome score can result in the recommendation that a Wnt pathway inhibitor be administered to the subject. After the Wnt pathway inhibitor is administered, a second test for advanced colorectal adenoma can be administered to the subject. A negative or less severe clinical outcome score can indicate that the treatment is effective. A second positive or more severe clinical outcome score can indicate that the treatment is not effective.

Computer Systems

Provided herein are computer systems for implementing any of the methods described herein for detecting a presence or absence of at least one of advanced colorectal adenoma and CRC. Also provided herein are computer systems for detecting a presence or absence of CRC. Computer systems disclosed herein comprises a memory unit. The memory unit can be configured to receive data comprising measurement of a biomarker panel from a biological sample of a subject. The biomarker panel can be any biomarker panel described herein. For example, the biomarker panel can comprise at least two biomarkers selected from the group comprising AACT, CATD, CEA, CO3, CO9, MIF, PSGL, and SEPR, and in some cases includes age as an additional biomarker. Optionally, the biomarker panel includes CATD, CLUS, GDF15, and SAA1, and in some cases includes age as an additional biomarker.

Computer systems disclosed herein comprise computer executable code for performing at least one of: generating a subject-specific profile of a biomarker panel described herein based upon the measurement data, comparing the subject-specific profile of the biomarker panel to a reference profile of the biomarker panel, and determining a likelihood of advanced colorectal adenoma in the subject. Computer systems disclosed herein comprises computer executable code for performing at least one of: generating a subject-specific profile of a biomarker panel described herein based upon the measurement data, comparing the subject-specific profile of the biomarker panel to a reference profile of the biomarker panel, and determining a likelihood of CRC in the subject.

Additionally, provided herein are computer systems for implementing any of the methods described herein for detecting a presence or absence of at least one of advanced colorectal adenoma and CRC. For example, provided herein are computer systems for detecting a presence or absence of advanced colorectal adenoma. Also provided herein are computer systems for detecting a presence or absence of CRC. Computer systems disclosed herein comprises a memory unit. The memory unit can be configured to receive data comprising measurement of a biomarker panel from a biological sample of a subject. The biomarker panel can be any biomarker panel described herein. For example, the biomarker panel can comprise at least two biomarkers selected from the group comprising AACT, CATD, CEA, CO3, CO9, MIF, PSGL, SEPR, CATD, CLUS, GDF15, and SAA1.

Computer systems disclosed herein optionally comprise computer executable code for performing at least one of: generating a subject-specific profile of a biomarker panel described herein based upon the measurement data, comparing the subject-specific profile of the biomarker panel to a reference profile of the biomarker panel, and determining a likelihood of advanced colorectal adenoma in the subject. Computer systems disclosed herein optionally comprise computer executable code for performing at least one of: generating a subject-specific profile of a biomarker panel described herein based upon the measurement data, comparing the subject-specific profile of the biomarker panel to a reference profile of the biomarker panel, and determining a likelihood of CRC in the subject.

Computer systems described herein optionally comprise computer-executable code for performing any of the algorithms described herein. The computer system can further comprise computer-executable code for providing a report communicating the presence or absence of the at least one of advanced colorectal adenoma and CRC, for recommending a colonoscopy, sigmoidoscopy, or colorectal tissue biopsy, and/or for recommending a treatment. In some embodiments, the computer system executes instructions contained in a computer-readable medium.

In some embodiments, the processor is associated with one or more controllers, calculation units, and/or other units of a computer system, or implanted in firmware. In some embodiments, one or more steps of the method are implemented in hardware. In some embodiments, one or more steps of the method are implemented in software. Software routines may be stored in any computer readable memory unit such as flash memory, RAM, ROM, magnetic disk, laser disk, or other storage medium as described herein or known in the art. Software may be communicated to a computing device by any known communication method including, for example, over a communication channel such as a telephone line, the internet, a wireless connection, or by a transportable medium, such as a computer readable disk, flash drive, etc. The one or more steps of the methods described herein may be implemented as various operations, tools, blocks, modules and techniques which, in turn, may be implemented in firmware, hardware, software, or any combination of firmware, hardware, and software. When implemented in hardware, some or all of the blocks, operations, techniques, etc. may be implemented in, for example, an application specific integrated circuit (ASIC), custom integrated circuit (IC), field programmable logic array (FPGA), or programmable logic array (PLA).

FIG. 19 depicts an exemplary computer system 1900 adapted to implement a method described herein. The system 1900 includes a central computer server 1901 that is programmed to implement exemplary methods described herein. The server 1901 includes a central processing unit (CPU, also "processor") 1905 which can be a single core processor, a multi core processor, or plurality of processors for parallel processing. The server 1901 also includes memory 1910 (for example random access memory, read-only memory, flash memory); electronic storage unit 1915 (for example hard disk); communications interface 1920 (for example network adaptor) for communicating with one or more other systems; and peripheral devices 1925 which may include cache, other memory, data storage, and/or electronic display adaptors. The memory 1910, storage unit 1915, interface 1920, and peripheral devices 1925 are in communication with the processor 1905 through a communications bus (solid lines), such as a motherboard. The storage unit 1915 can be a data storage unit for storing data. The server 1901 is operatively coupled to a computer network ("network") 1930 with the aid of the communications interface 1920. The network 1930 can be the Internet, an intranet and/or an extranet, an intranet and/or extranet that is in communication with the Internet, a telecommunication or data network. The network 1930 in some cases, with the aid of the server 1901, can implement a peer-to-peer network, which may enable devices coupled to the server 1901 to behave as a client or a server.

The storage unit 1915 can store files, such as subject reports, and/or communications with the caregiver, sequencing data, data about individuals, or any aspect of data associated with the invention.

The server can communicate with one or more remote computer systems through the network 1930. The one or more remote computer systems may be, for example, personal computers, laptops, tablets, telephones, Smart phones, or personal digital assistants.

In some situations the system 1900 includes a single server 1901. In other situations, the system includes multiple servers in communication with one another through an intranet, extranet and/or the Internet.

The server 1901 can be adapted to store measurement data, patient information from the subject, such as, for example, polymorphisms, mutations, medical history, family history, demographic data and/or other information of potential relevance. Such information can be stored on the storage unit 1915 or the server 1901 and such data can be transmitted through a network.

Methods as described herein are in some cases implemented by way of machine (or computer processor) executable code (or software) stored on an electronic storage location of the server 1901, such as, for example, on the memory 1910, or electronic storage unit 1915. During use, the code can be executed by the processor 1905. In some cases, the code can be retrieved from the storage unit 1915 and stored on the memory 1910 for ready access by the processor 1905. In some situations, the electronic storage unit 115 can be precluded, and machine-executable instructions are stored on memory 1910. Alternatively, the code can be executed on a second computer system 1940.

Aspects of the systems and methods provided herein, such as the server 1901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (for example, read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" can refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

The results of detection of a presence or absence of at least one of an advanced colorectal adenoma and CRC, generating a subject report, and/or communicating the report to a caregiver can be presented to a user with the aid of a user interface, such as a graphical user interface.

A computer system may be used to implement one or more steps of a method described herein, including, for example, sample collection, sample processing, measurement of an amount of one or more proteins described herein to produce measurement data, determination of a ratio of a protein to another protein to produce measurement data, comparing measurement data to a reference amount, generating a subject-specific profile of a biomarker panel, comparing the subject-specific profile to a reference profile, receiving medical history, receiving medical records, receiving and storing measurement data obtained by one or more methods described herein, analyzing said measurement data to determine a presence or absence of at least one of an advanced colorectal adenoma and CRC (for example, by performing an algorithm described herein), generating a report, and reporting results to a receiver.

A client-server and/or relational database architecture can be used in any of the methods described herein. In general, a client-server architecture is a network architecture in which each computer or process on the network is either a client or a server. Server computers can be powerful computers dedicated to managing disk drives (file servers), printers (print servers), or network traffic (network servers). Client computers can include PCs (personal computers) or workstations on which users run applications, as well as example output devices as disclosed herein. Client computers can rely on server computers for resources, such as files, devices, and even processing power. The server computer handles all of the database functionality. The client computer can have software that handles front-end data management and receive data input from users.

After performing a calculation, a processor can provide the output, such as from a calculation, back to, for example, the input device or storage unit, to another storage unit of the same or different computer system, or to an output device. Output from the processor can be displayed by a data display, for example, a display screen (for example, a monitor or a screen on a digital device), a print-out, a data signal (for example, a packet), a graphical user interface (for example, a webpage), an alarm (for example, a flashing light or a sound), or a combination of any of the above. In an embodiment, an output is transmitted over a network (for example, a wireless network) to an output device. The output device can be used by a user to receive the output from the data-processing computer system. After an output has been received by a user, the user can determine a course of action, or can carry out a course of action, such as a medical treatment when the user is medical personnel. In some embodiments, an output device is the same device as the input device. Example output devices include, but are not limited to, a telephone, a wireless telephone, a mobile phone, a PDA, a flash memory drive, a light source, a sound generator, a fax machine, a computer, a computer monitor, a printer, an iPod, and a webpage. The user station may be in communication with a printer or a display monitor to output the information processed by the server. Such displays, output devices, and user stations can be used to provide an alert to the subject or to a caregiver thereof.

Data relating to the present disclosure can be transmitted over a network or connections for reception and/or review by a receiver. The receiver can be but is not limited to the subject to whom the report pertains; or to a caregiver thereof, for example, a health care provider, manager, other healthcare professional, or other caretaker; a person or entity that performed and/or ordered the genotyping analysis; a genetic counselor. The receiver can also be a local or remote system for storing such reports (for example servers or other systems of a "cloud computing" architecture). In one embodiment, a computer-readable medium includes a medium suitable for transmission of a result of an analysis of a biological sample.

Kits

The present disclosure also provides kits. In some cases, a kit described herein comprises one or more compositions, reagents, and/or device components for measuring and/or detecting one or more biomarkers described herein. A kit as described herein can further comprise instructions for practicing any of the methods provided herein. The kits can further comprise reagents to enable the detection of biomarker by various assays types such as ELISA assay, immunoassay, protein chip or microarray, mass spectrometry, immunohistochemistry, flow cytometry, or high content cell screening. Kits can also comprise a computer readable medium comprising computer executable code for implementing a method described herein.

In some embodiments, a kit provided herein comprises antibodies to the biomarkers described elsewhere in the disclosure. A kit may comprise at least two antibodies that are each reactive against a biomarkers selected from the group consisting of CATD, CLUS, GDF15, SAA1, AACT, CATD, CEA, CO3, CO9, MIF, PSGL, and SEPR. In some cases, a kit provided herein comprises antibodies to AACT, CATD, CEA, CO3, CO9, MIF, PSGL, and SEPR. In other cases, a kit provided herein comprises antibodies to CATD, CLUS, GDF15, and SAA1.

In some embodiments, kits described herein include a packaging material. As used herein, the term "packaging material" can refer to a physical structure housing the components of the kit. The packaging material can maintain sterility of the kit components, and can be made of material commonly used for such purposes (for example, paper, corrugated fiber, glass, plastic, foil, ampules, etc.). Kits can also include a buffering agent, a preservative, or a protein/nucleic acid stabilizing agent. Kits can include components for obtaining a biological sample from a patient. Non-limiting examples of such components can be gloves, hypodermic needles or syringes, tubing, tubes or vessels to hold the biological sample, sterilization components (e.g. isopropyl alcohol wipes or sterile gauze), and/or cooling material (e.g., freezer pack, dry ice, or ice).

In some cases, kits disclosed herein are used in accordance of any of the disclosed methods.

Panel Development

Study Design and Patient Sample Collection 300 total samples were selected for analysis, taken from the Endoscopy II study performed at the Hvidovre Hospital in Denmark. In this study, 45-mL blood samples were collected from enrolled participants across seven different centers prior to performing a colonoscopy. Blood samples were stored at −80° C. with constant monitoring. Co-morbidities were recorded by ICD codes, and pathology, disease, and death reports were retained on file. Participants entered the study based upon observed symptoms, such as pain, bleeding, and anemia, which suggested further medical follow-up. Participants had no prior history of malignancy. Participants had no previous bowel neoplasia. Participants were not members of FAP or HNPCC families. Participants had not had a major operation in the preceding three months. Participants had not undergone a prior bowel endoscopy.

TABLE 5

Characteristics of patients enrolled in study

| Group | Count |
|---|---|
| CRC | 512 |
| Colon/Rectal | 320/192 |
| Other primary malignancies | 177 |
| Adenoma | 699 |
| High/Low risk | 198/501 |
| Colonic/Rectal | 498/201 |
| Benign bowel lesions | 1,176 |
| Negative findings, with co-morbidity | 1,014 |
| Negative findings, without co-morbidity | 1,113 |
| Total | 4,698 |

Enrolled patients received colonoscopies to diagnosis any problems associated with the colon and rectum, and the results were used to confirm the presence or absence of colorectal cancers and/or polyps. For the biomarker discovery study performed here, the 302 blood plasma samples selected for analysis comprised 150 control samples that had no comorbidities and no adverse findings from colonoscopy, and 150 disease samples that had confirmed colorectal cancer or advanced adenoma lesions in advanced stage. For this study, advanced colorectal adenomas were defined as having at least one of the following: any adenoma >=1 cm, sessile serrated polyps >=1 cm, adenomas with high grade dysplasia, or adenomas with villous histological features. The control and disease samples were matched in pairs for age, gender, and enrollment site (see FIGS. 17A-17B). The 300 samples were further divided into discovery and validation sets, each with 75 control samples and 75 disease samples. To more rigorously test the generalization performance of the investigated biomarker panels in the validation set, the discovery and validation sets consisted of patent samples from non-overlapping sites. A summary table of the samples and their characteristic is provided in Table 7.

TABLE 7

Discovery and training sets for developing protein biomarker panels for CRC diagnosis.

|  | Discovery (n = 150) | | Validation (n = 150) | |
|---|---|---|---|---|
|  | Control | CRC | Control | CRC |
| Total | 75 | 75 | 75 | 75 |
| By Site |  |  |  |  |
| 31 | 23 | 23 |  |  |
| 32 |  |  | 7 | 7 |
| 33 | 30 | 30 |  |  |
| 34 |  |  | 5 | 5 |
| 35 |  |  | 36 | 36 |
| 36 | 22 | 22 |  |  |
| 37 |  |  | 27 | 27 |
| Male | 35 | 35 | 40 | 40 |
| Female | 40 | 40 | 35 | 35 |
| Mean Age | 63.8 | 64.5 | 64.8 | 65.6 |
| CRC Stage |  |  |  |  |
| I |  | 17 |  | 17 |
| II |  | 30 |  | 21 |
| III |  | 16 |  | 18 |
| IV |  | 12 |  | 19 |
| CRC Lesion |  |  |  |  |
| Location |  |  |  |  |
| Colon |  | 43 |  | 47 |
| Rectum |  | 32 |  | 28 |
| No comorbidity- no finding | 75 |  | 75 |  |

Data Preparation

A total of 300 samples were analyzed using ELISA for 30 different proteins, resulting in a concentration measurement (e.g. accumulation level) for each of the 30 proteins across the 302 samples. 300 total samples were analyzed using ELISA, targeted proteomics (TP) and SAT platforms quantifying protein levels for 226 total proteins (ELISA: 30, SAT: 9, TP: 187). An additional mode of data collection was used, comprising unlabeled liquid chromatography/mass spectrometry (LCMS) measurements. For the LCMS data collection, the protein identity of the measured signals is not known a priori so the resulting measurements are treated as anonymous marker values, simply referred to with arbitrary ID numbers and their m/z and LC time locations. Data from these four assay platforms were analyzed both individually and in combination with one another to find the top performing biomarker panels within the discovery set. Unlabeled LCMS features present in the marker panel included C3218600, having an m/z of 1465.78, an LC time of 14.3 minutes and a charge state 1; C387796, having an m/z 1051.55, an LC of 3.1 minutes, and a charge state 1; C597612, having an m/z of 845.44 and an LC of 2.8 minutes and a charge state of 1; C979276, having m/z 752.91, 20.6 minutes and a charge state of 2.

After data collection, the concentration values were prepared in a variety of ways. For some analyses, the concentration measurements were log 2 transformed, while for others, the concentration values were left untransformed. Analyses were also performed on measurements that were both standardized (zero mean, unit variance) and un-standardized (i.e. original measurements). For some analyses, age interaction terms were added to the standard marker concentration values. Here, the product of all age and marker pairs were calculated and added into the total set of markers for analysis. In other analyses, the ratios of marker pairs were calculated and used as new marker values for classification builds.

Classification Analysis

The goal of the classification analysis was to determine the top performing marker panels and classification models that distinguish between samples with and without colorectal cancer. Classifier models and the associated classification performance were assessed using a 10 by 10-fold cross validation procedure. The 10 by 10-fold cross validation was performed using the discovery set only, and incorporated feature selection and classification model assembly. In the cross validation procedure, feature selection was first applied to reduce the number of features used, followed by development of the classifier model and subsequent classification performance evaluation. For each of the 10-fold cross validations, the data were segregated into 10 splits each containing 90% of the samples as a training set and the remaining 10% of the samples as a testing set. In this process, each sample was evaluated one time in a test set. The feature selection and model assembly was performed using the training set only, and these models were then applied to the testing set to evaluate classifier performance, typically via the area under the curve (AUC) from the receiver operating characteristic (ROC) plot. Here, the mean or median AUC value obtained from each of the 10 10-fold cross validation procedures was used to assess the overall marker panel and classification model performance.

To investigate the performance of different sized marker panels, a variety of feature selection and reduction methods were used including Elastic Network feature selection, Random Forest feature importance ranking, t-test p-value ranking, hierarchical clustering, and exhaustive combination search. With the exception of exhaustive combination search, the feature selection methods were embedded within the individual folds of the cross validation procedure to incorporate the variability of marker selection into the final performance assessment for a given classifier model build. For the exhaustive combination search, all n-choose-r combinations of features were evaluated, where a particular combination was selected prior to model building and used across all the cross validation folds. For both computational feasibility reasons and to limit the possibility for over-fitting, n and r were chosen to have relatively small values, with n typically <=30 total markers, and r typically between 2 and 10.

Within the 10 by 10-fold cross validation folds and after the feature selection step, a classifier model was built using one of several classification algorithms including, as examples, the support vector machine (SVM) algorithm, the Random Forest algorithm, Elastic Network (ENet) regression models with and without boosting, k-nearest neighbors (kNN), and combinations of these models applied in an ensemble. The classification models were built using established classification modeling packages implemented in the R statistical programming language. In the case of the ensemble models, individual classification models were built using two or more of the described algorithms, and the resulting classification scores were combined in a linear combination to obtain a final classification score. Another classification model approach was also used for some analyses, referred to here as Status of Univariates (SUn). In the SUn approach, all samples are initially evaluated using a standard multivariate model as described above. Next, univariate classification performance from single markers is used to potentially adjust the multivariate prediction score. If a particular sample's value for a given single marker is particularly high or low (i.e. in a score region of 100% positive or negative predictive value as assessed in the training set), the sample's probability score is changed to 0 or 1 accordingly. Overall, this approach enables augmentation of the complex multivariate models with simple high confidence classification calls based on individual markers.

After construction of the classifier model on the training set, it was directly applied without modification to the testing set resulting in classification scores for the held-out test set samples. After the completion of a complete 10-fold cross validation iteration, the test set classification scores from all the samples were merged into a single dataset or set of values, and the associated receiver operating characteristic (ROC) curve was generated. From this ROC, the area under the curve (AUC) was computed, with one AUC value for each of the 10 iterations of 10-fold cross validation. The mean and median AUC's across the 10 iterations was then used to assess the performance of the particular classifier assembly process, representing an estimate of the anticipated hold-out set validation performance utilizing only the discovery data.

To investigate the performance of different sized marker panels, a variety of feature selection and reduction methods were used including Elastic Network feature selection, Random Forest feature importance ranking, t-test p-value ranking, hierarchical clustering, and exhaustive combination search. With the exception of exhaustive combination search, the feature selection methods were embedded within the individual folds of the cross validation procedure to incorporate the variability of marker selection into the final performance assessment for a given classifier model build. For the exhaustive combination search, all n-choose-r combinations of features were evaluated, where a particular combination was selected prior to model building and used across all the cross validation folds. For both computational feasibility reasons and to limit the possibility for over-fitting, n and r were chosen to have relatively small values, with n typically <=30 total markers, and r typically between 2 and 10.

Within the 10 by 10-fold cross validation folds and after the feature selection step, a classifier model was built using one of several classification algorithms including, as examples, the support vector machine (SVM) algorithm, the Random Forest algorithm, Elastic Network (ENet) regression models with and without boosting, and k-nearest neighbors (kNN). The classification models were built using established classification modeling packages implemented in the R statistical programming language.

After construction of the classifier model on the training set, it was directly applied without modification to the testing set resulting in classification scores for the held-out test set samples. After the completion of a complete 10-fold cross validation iteration, the test set classification scores from all the samples were merged into a single set of values and the associated receiver operating characteristic (ROC) curve was generated. From this ROC, the area under the curve (AUC) was computed, with one AUC value for each of the 10 iterations of 10-fold cross validation. The mean and median AUC's across the 10 iterations was then used to assess the performance of the particular classifier assembly process, representing an estimate of the anticipated hold-out set validation performance utilizing only the discovery data.

Classification Model Results

Utilizing the 10 by 10-fold cross validation procedure described above, a large number of classifier assembly methods were evaluated. Of these methods, 10 were selected for validation that provided the highest classification performance across a range of different feature selection and classification model methods. To validate a particular classifier model, a final model was built using all of the discovery data and the same feature selection and classifier model methods used in the associated 10 by 10-fold cross validation procedure. Each final model consisted of a set of markers and a classification model with associated model parameters. This model was locked prior to validation and directly applied to the validation set with no addition tuning. A final ROC was generated from the validation set classification scores, and the final validation performance was measured via the AUC with 95% confidence intervals on the ROC/AUC calculated from a bootstrap sampling procedure.

Table 7 provides a summary of the 10 classification models that were validated. Across the models, the discovery set AUC's range between 0.81 and 0.86, and the validation AUC's range between 0.75 and 0.82. In all models except model 10, the discovery AUC's were within the 95% confidence intervals of the validation AUC indicating good validation was achieved with the selected models.

The associated discovery and validation ROC curves are shown in FIGS. 7A-18. Table 8 gives a summary of the 10 classification models that were validated. Across the models, the discovery set AUC's range between 0.81 and 0.86, and the validation AUC's range between 0.75 and 0.82. In all models except model 10, the discovery AUC's were within the 95% confidence intervals of the validation AUC indicating good validation was achieved with the selected models.

TABLE 8

Summary of 13 high performing models for CRC assessment.

| Model | Input Data | Feature Selection | Classifier | No. of Features | Proteins | Discovery AUC | Validation Validation AUC (95% CI) |
|---|---|---|---|---|---|---|---|
| 1 | ELISA-28 + Age Interactions | Random Forest | Random Forest | 7 | A1AG1, A1AT, CATD, CEA, CO9, OSTPxAge, SEPR | 0.84 | 0.80 (0.73-0.86) |
| 2 | ELISA-28 | GLMNet | SVM | 17 | A1AG1, A1AT, APOA1, CATD, CEA, CLUS, CO3, CO9, FGB, FIBG, GARS, GELS, MIF, PRDX1, PSGL, SBP1, SEPR | 0.83 | 0.81 (0.74-0.88) |

TABLE 8-continued

Summary of 13 high performing models for CRC assessment.

| Model | Input Data | Feature Selection | Classifier | No. of Features | Proteins | Discovery AUC | Validation Validation AUC (95% CI) |
|---|---|---|---|---|---|---|---|
| 3 | ELISA-28 + TP | GLMNet | GLMNet | 7 | A1AG1, A1AT, CATD, CEA, CO9, GARS, SEPR | 0.82 | 0.82 (0.75-0.88) |
| 4 | ELISA-28 + TP | GLMNet | GLMBoost | 25 | A1AG1, A1AT, AACT, CATD, CEA, CO9, CRP, AACT, CO9, CRP, CRP, CRP, CRP, CRP, CRP, GELS, S10A8, S10A8, S10A8, S10A8, S10A9, S10A9, GARS, SAA1, SEPR | 0.81 | 0.81 (0.74-0.88) |
| 5 | ELISA-28 | Brute Force | SVM | 8 | CATD, CEA, CO3, CO9, GARS, GELS, SEPR, TFRC | 0.86 | 0.82 (0.75-0.88) |
| 6 | ELISA-28 + TP (Trace Classification Filtered) | Brute Force | SVM | 5 | CATD, CEA, AACT, CO9, SEPR | 0.86 | 0.80 (0.72-0.86) |
| 7 | ELISA-28 + Unlabeled LCMS | GLMNet + Top by p-Value | SVM | 10 | A1AT, C3218600, C387796, C597612, C979276, CATD, CEA, GARS, GELS, SEPR | 0.83 | 0.81 (0.74-0.88) |
| 8 | ELISA-28 | GLMNet | SVM + SUn | 18 | A1AG1, A1AT, APOA1, CATD, CEA, CLUS, CO3, CO9, FGB, FIBG, GARS, GELS, HPT, MIF, PRDX1, PSGL, SBP1, SEPR | 0.84 | 0.78 (0.71-0.85) |
| 9 | ELISA-28 (Individual Features and Pair Ratios) | Random Forest | 2 SVM Models | 11 | A1AG1, A1AT, CATD, CEA, CO9, SEPR, CATD/SEPR, CATD/GELS, CO9/SEPR, A1AT/FIBG | 0.85 | 0.80 (0.73-0.87) |
| 10 | ELISA-28 + TP (Trace Classification filtered) + SAT-29 | H-Clustering + GLMNet | GLMNet | 41 | H-Clustered Agglomerated Features | 0.85 | 0.75 (0.67-0.82) |
| 11 | ELISA-28 + TP (model 5 with GARS feature swap) | Brute Force, GARS Swap by Correlation | SVM | 8 | CATD, CEA, CO3, CO9, S10A8, GELS, SEPR, TFRC | 0.85 | 0.815 (0.75-0.88) |
| 12 | ELISA-28 | Brute Force, Protein Subset 1 | SVM | 8 | AACT, CATD, CEA, CO3, CO9, MIF, PSGL, SEPR | 0.85 | 0.815 (0.75-0.88) |
| 13 | ELISA-28 | Brute Force, Protein Subset 2 | SVM | 7 | A1AG, CATD, CEA, CO3, CO9, GELS, SEPR | 0.86 | 0.80 (0.73-0.87) |

Figure 7A:
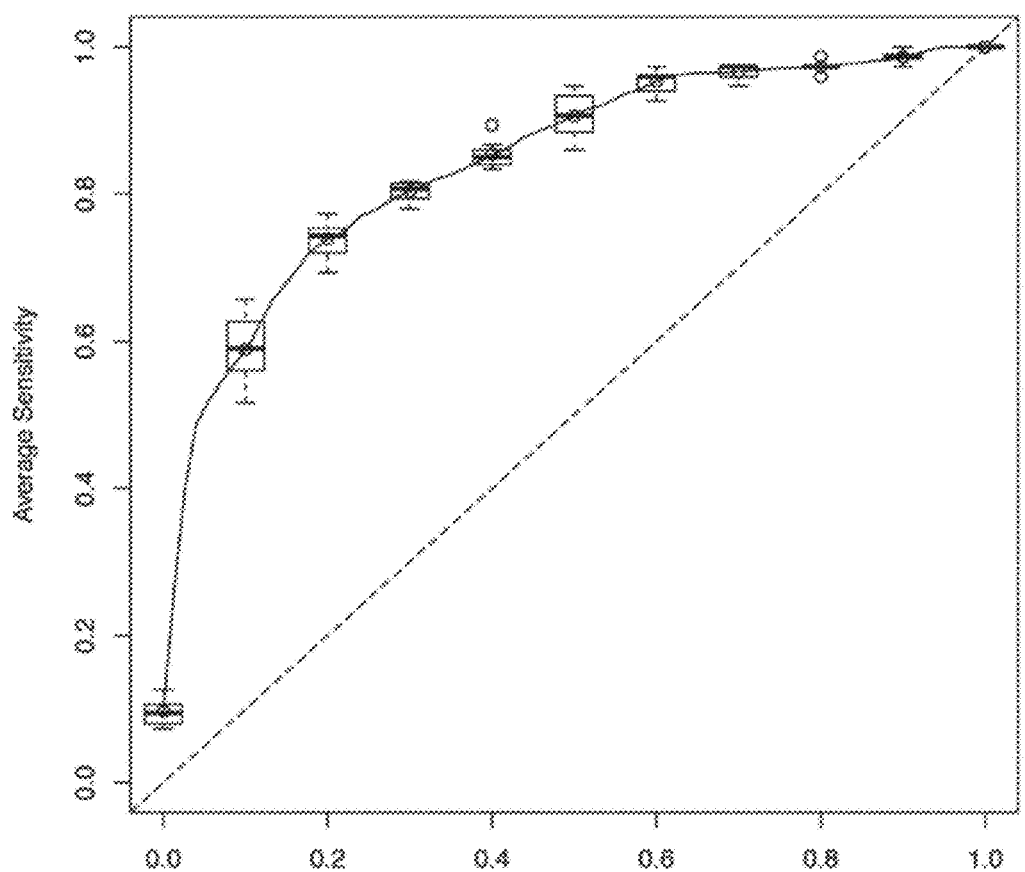
FIG. 7A illustrates a Discovery ROC AUC plot for CRC Model 1.

Model 1, as referenced in Table 8, included seven proteins which were A1AG1, A1AT, CATD, CEA, CO9, OSTP, and SEPR. ROC curves resulting from the discovery set and the validation set for Model 1 are depicted in FIGS. 7A and 7B, respectively. The resulting discovery set AUC was 0.84 and the validation set AUC was 0.80. At a validation ROC specificity of 90%, the sensitivity is >50%, at a specificity of 75%, the sensitivity is >60%, and at a specificity of 50%, the sensitivity is >80%.

Model 2, as referenced in Table 8, included seven proteins which were A1AG1, A1AT, APOA1, CATD, CEA, CLUS, CO3, CO9, FGB, FIBG, GARS, GELS, MIF, PRDX1, PSGL, SBP1, and SEPR. ROC curves resulting from the discovery set and the validation set for Model 2 are depicted in FIGS. 8A and 8B, respectively. The resulting discovery set AUC was 0.83 and the validation set AUC was 0.81. At a validation ROC specificity of 90%, the sensitivity is about 50%, at a specificity of 75%, the sensitivity is >60%, and at a specificity of 50%, the sensitivity is >80%.

Model 3, as referenced in Table 8, included seven proteins which were A1AG1, A1AT, CATD, CEA, CO9, GARS, and SEPR. ROC curves resulting from the discovery set and the validation set for Model 3 are depicted in FIGS. 9A and 9B, respectively. The resulting discovery set AUC was 0.82 and the validation set AUC was 0.82. At a validation ROC specificity of 90%, the sensitivity is >50%, at a specificity of 75%, the sensitivity is >70%, and at a specificity of 50%, the sensitivity is about 80%.

Model 4, as referenced in Table 8, included seven proteins which were A1AG1, A1AT, AACT, CATD, CEA, CO9, CRP, GARS, GELS, 510A8, 510A9, SAA1, and SEPR. ROC curves resulting from the discovery set and the validation set for Model 4 are depicted in FIGS. 10A and 10B, respectively. The resulting discovery set AUC was 0.81 and the validation set AUC was 0.81. At a validation ROC specificity of 90%, the sensitivity is about 60%, at a specificity of 75%, the sensitivity is >70%, and at a specificity of 50%, the sensitivity is >80%.

Model 5, as referenced in Table 8, included seven proteins which were CATD, CEA, CO3, CO9, GARS, GELS, SEPR, and TFRC. ROC curves resulting from the discovery set and the validation set for Model 5 are depicted in FIGS. 11A and 11B, respectively. The resulting discovery set AUC was 0.86 and the validation set AUC was 0.82. At a validation ROC specificity of 90%, the sensitivity is about 50%, at a specificity of 75%, the sensitivity is >70%, and at a specificity of 50%, the sensitivity is about 90%.

Model 6, as referenced in Table 8, included seven proteins which were CATD, CEA, AACT, CO9, and SEPR. ROC curves resulting from the discovery set and the validation set for Model 6 are depicted in FIGS. 12A and 12B, respectively. The resulting discovery set AUC was 0.86 and the validation set AUC was 0.80. At a validation ROC specificity of 90%, the sensitivity is >40%, at a specificity of 75%, the sensitivity is >60%, and at a specificity of 50%, the sensitivity is >80%.

Model 7, as referenced in Table 8, included seven proteins which were A1AT, CATD, CEA, GARS, GELS, and SEPR. ROC curves resulting from the discovery set and the validation set for Model 7 are depicted in FIGS. 13A and 13B, respectively. The resulting discovery set AUC was 0.83 and the validation set AUC was 0.81. At a validation ROC specificity of 90%, the sensitivity is >50%, at a specificity of 75%, the sensitivity is >60%, and at a specificity of 50%, the sensitivity is >80%.

Model 8, as referenced in Table 8, included seven proteins which were A1AG1, A1AT, APOA1, CATD, CEA, CLUS, CO3, CO9, FGB, FIBG, GARS, GELS, HPT, MIF, PRDX1, PSGL, SBP1, and SEPR. ROC curves resulting from the discovery set and the validation set for Model 8 are depicted in FIGS. 14A and 14B, respectively. The resulting discovery set AUC was 0.84 and the validation set AUC was 0.78. At a validation ROC specificity of 90%, the sensitivity is >30%, at a specificity of 75%, the sensitivity is >60%, and at a specificity of 50%, the sensitivity is >80%.

Model 9, as referenced in Table 8, included seven proteins which were A1AG1, A1AT, CATD, CEA, CO9, FIBG, GELS, and SEPR. ROC curves resulting from the discovery set and the validation set for Model 9 are depicted in FIGS. 15A and 15B, respectively. The resulting discovery set AUC was 0.85 and the validation set AUC was 0.80. At a validation ROC specificity of 90%, the sensitivity is >50%, at a specificity of 75%, the sensitivity is >60%, and at a specificity of 50%, the sensitivity is about 80%.

Model 11, as referenced in Table 8, included seven proteins which were CATD, CEA, CO3, CO9, 510A8, GELS, SEPR, TFRC. The resulting discovery set AUC was 0.85 and the validation set AUC was 0.82.

Model 12, as referenced in Table 8, included seven proteins which were AACT, CATD, CEA, CO3, CO9, MIF, PSGL, SEPR. The resulting discovery set AUC was 0.85 and the validation set AUC was 0.82.

Model 13, as referenced in Table 8, included seven proteins which were A1AG, CATD, CEA, CO3, CO9, GELS, SEPR. The resulting discovery set AUC was 0.86 and the validation set AUC was 0.80.

Models 4 and 6 incorporated data from the targeted proteomics platform, and therefore included measurements from transition ions from specific peptides from the underlying protein measurements. The transitions used in these models are given in Table 9.

TABLE 9

Transition ions from specific peptides

| Model Number | Protein | Peptide | SEQ ID NO: | Transition |
|---|---|---|---|---|
| 4 | AACT | ADLSGITGAR | 50 | b3 |
| 4 | CO9 | TEHYEEQIEAFK | 51 | y2 |
| 4 | CRP | ESDTSYVSLK | 52 | y3 |
| 4 | CRP | ESDTSYVSLK | 52 | y5 |
| 4 | CRP | GYSIFSYATK | 53 | y7 |
| 4 | CRP | GYSIFSYATK | 53 | y8 |
| 4 | CRP | KAFVFPK | 54 | y5 |
| 4 | CRP | KAFVFPK | 54 | y6 |
| 4 | GELS | AGALNSNDAFVLK | 55 | b4 |
| 4 | S10A8 | ALNSIIDVYHK | 56 | y6 |
| 4 | S10A8 | ALNSIIDVYHK | 56 | y7 |
| 4 | S10A8 | GADVWFK | 57 | b3 |
| 4 | S10A8 | GADVWFK | 57 | y5 |
| 4 | S10A9 | DLQNFLK | 58 | y5 |
| 4 | S10A9 | LGHPDTLNQGEFK | 59 | y10 |

TABLE 9-continued

Transition ions from specific peptides

| Model Number | Protein | Peptide | SEQ ID NO: | Transition |
|---|---|---|---|---|
| 6 | AACT | GKITDLIK | 60 | y5 |
| 6 | CO9 | TEHYEEQIEAFK | 51 | y2 |

Of the ten models, model 5 is of particular note because of the high discovery AUC of 0.86 and associated high validation AUC of 0.82. This model comprises 8 individual proteins all from a single assay platform (ELISA), facilitating the measurement of this marker panel for clinical applications.

Model 3 is also of interest because of the high validation AUC of 0.82, though the discovery AUC was slightly lower, also at 0.82. Though targeted proteomics markers were included as input to this model, only ELISA markers were selected in the final model. This panel is also slightly smaller, comprising 5 proteins.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Incorporation of Indeterminate Classification Calls (NoC Method)

The intrinsic performance of a particular classification model depends on the distributions and separation of model scores for the two classes. With the rare exception of perfect class separation, most classification models make mistakes because of class overlap across the range of classifier scores. For example, such an overlap may occur near the middle of the score range where the probability of being in one class or the other is close to 50%.

Within such an overlap region, it may be advantageous to add a third class to the final set of classification calls; the third class would indicate the uncertainty of a call in this score region. This could be implemented, for example, by defining an indeterminate region of classification scores. Samples with scores in this region would be given an "indeterminate" or "no call" test result. Samples with scores above or below this region would be given standard positive or negative test results depending on their positions relative to the test cutoff. The benefit of adding an indeterminate region to a classification model is that classification performance can improve for samples outside of the indeterminate region, i.e. mistakes are less likely for the remaining positive and negative tests. However, if the indeterminate range is too large, there may be too many indeterminate results, and the value of the test may be put into question.

In another analysis, referred to here as NoC ("No Call"), the effect of using an indeterminate region with the classification models was investigated. In this analysis, the percentage of samples targeted to receive a "no call" result was set to 10%. To determine the optimal score range for the indeterminate region (NoC region) with 10% of the samples, the specificity was maximized at a sensitivity of >=90% as follows: All possible contiguous sets of 10% of samples were determined across the classifier scores range. For each set, the associated set of 10% of samples were marked as no calls. These samples were removed from the analysis set and the ROC curve was generated from the remaining 90% of the samples. The maximum specificity at >=90% sensitivity was then determined and used as the evaluation score for the NoC region in question. After all NoC regions were evaluated in this manner, the region with the highest specificity score was selected as the optimal NoC region. The score range defining this NOC region was taken from the upper and lower classification scores of the associated 10% no call samples.

To predict how the NoC procedure would affect classification performance in the hold-out validation set, the analysis was performed within the 10 by 10-fold cross validation assessment of model 5 described above. Like all previous model builds, only the discovery set was used in this assessment. The resulting median AUC determined from this 10 by 10-fold validation procedure was 0.87, slightly higher than the original discovery AUC of 0.86 without the application of NoC, suggesting the NoC procedure could be beneficial to employ in practice.

A final NoC region was determined by using the same NoC procedure described above on all of the discovery samples. This yielded a NoC region encompassing scores between 0.298 and 0.396. This NoC region was applied directly to the validation set with 20 samples (13.3%) falling within the region (10 disease, 10 control). The ROC determined from the remaining validation samples yielded an AUC of 0.85 (95% CI's: 0.78-0.91), an improvement of 0.03 over the validation ROC without application of NoC. The results from the NoC analysis are given in Table 10 and the discovery and validation ROC data in FIGS. 17A-17B.

TABLE 10

Summary of Model 5 with subset of samples categorized as indeterminate

| Model | NoC Score Region | # of Samples in NoC Region Discovery | Discovery AUC w/o NoC | Discovery AUC w/ NoC | # of Samples in NoC Region Validation | Validation AUC w/o NoC | Validation AUC w/ NoC |
|---|---|---|---|---|---|---|---|
| 5 | 0.298-0.396 | 15 | 0.86 | 0.87 | 20 | 0.82 | 0.85 |

Comparing the ROC curves with and without NOC applied, NoC improved performance most in the region around 80%-60% specificity. With NOC, a clear improvement in sensitivity is apparent. In particular, the point at 85% sensitivity and 78% specificity is of interest because of the good overall performance for both sensitivity and specificity.

Selection of Classifier Cutoff Points

The overall performance of a classifier can be assessed via the AUC of the ROC as reported above. An ROC considers the performance of the classifier at all possible model score cutoff points. However, when a classification decision needs to be made (i.e. is this patient sick or healthy?), a cutoff point must be used to define the two groups. Classification scores at or above the cutoff point are assessed as positive (or sick) while points below are assessed as negative (or healthy).

For the 10 classification models and the single model with NoC applied, summarized above, classification score cutoff points were established by selecting the point of maximum accuracy on the validation ROC's. The point of maximum accuracy on an ROC is the cutoff point or points for which the total number of correct classification calls is maximized. Here, the positive and negative classification calls were weighted equally. In cases where multiple maximum accuracy points were present on a given ROC, the point with the associated maximum sensitivity was selected.

The results for the cutoff point selection process are summarized in Table 11 and FIG. 13. The cutoff scores selected are representative of the type of score output by the associated model. For some models, the resulting classification score represents a probability and the scores span 0-1. For other models, e.g. Model 10, the classification score is simply a score, with larger scores more likely to represent CRC patients. In these cases, the cutoff score can be greater than 1.

TABLE 11

Cutoff points for classification of a subject for colorectal cancer biomarker panels

| Model # | Sensitivity | Specificity | Accuracy | Cutoff |
|---|---|---|---|---|
| 1 | 0.63 | 0.87 | 0.75 | 0.60 |
| 2 | 0.68 | 0.83 | 0.75 | 0.56 |
| 3 | 0.72 | 0.84 | 0.78 | 0.54 |
| 4 | 0.69 | 0.85 | 0.77 | 0.51 |
| 5 | 0.73 | 0.81 | 0.77 | 0.62 |
| 5 w/NoC | 0.85 | 0.78 | 0.82 | 0.62 |
| 6 | 0.80 | 0.65 | 0.73 | 0.41 |
| 7 | 0.61 | 0.88 | 0.75 | 0.66 |
| 8 | 0.77 | 0.69 | 0.73 | 0.44 |
| 9 | 0.65 | 0.83 | 0.74 | 1.07 |
| 10 | 0.65 | 0.76 | 0.71 | 8.69 |

Advanced Adenoma Panel Combination

Advanced colorectal adenoma and CRC are assayed in parallel in some cases as described herein. For example a panel for colorectal cancer and a panel for advanced adenoma, having a single biomarker overlap at CATD, are measured in combination. In these embodiments a panel for diagnosing advance adenoma may be derived using the methods previously disclosed. One panel for assessing a risk for advanced adenoma, and variants as disclosed herein was derived using the steps of classification analysis from previous studies including the classification analysis on samples taken from the Endoscopy II study.

For advanced adenoma biomarker discovery with the Endoscopy II study, 302 samples selected for analysis comprised 151 control samples that had no comorbidities and no adverse findings from colonoscopy, and 151 disease samples that had confirmed colon or rectal adenoma lesions in advanced stage. For this study, advanced colorectal adenomas were defined as having at least one of the following: any adenoma >=1 cm, sessile serrated polyps >=1 cm, adenomas with high grade dysplasia, or adenomas with villous histological features. The control and disease samples were matched in pairs for age, gender, and enrollment site. The 302 samples were further divided into discovery and validation sets, with 75 control and 75 advanced colorectal adenoma samples in the discovery set, and 76 control and 76 advanced colorectal adenomas samples in the validation set. To more rigorously test the generalization performance of the investigated biomarker panels in the validation set, the discovery and validation sets consisted of patient samples from non-overlapping sites. A summary table of the samples and their characteristics is provided in Table 12.

TABLE 12

Summary of the study design and patient samples

| | Discovery (n = 150) | | Validation (n = 151) | |
|---|---|---|---|---|
| | Control | AA | Control | AA |
| Total | 75 | 75 | 76 | 76 |
| By Site | | | | |
| 31 | 15 | 15 | | |
| 32 | | | 9 | 9 |
| 33 | 28 | 28 | | |
| 34 | | | 14 | 14 |
| 35 | | | 24 | 24 |
| 36 | 32 | 32 | | |
| 37 | | | 29 | 29 |
| Gender | | | | |
| Male | 38 | 38 | 38 | 38 |
| Female | 37 | 37 | 38 | 38 |
| Mean Age | 62.7 | 63.1 | 62.5 | 62.9 |
| Diagnosis | | | | |
| Adenoma colon | | 53 | | 52 |
| Adenoma rectum | | 22 | | 24 |
| No comorbidity/ no finding | 75 | | 76 | |

For data preparation, the 302 total samples were analyzed using ELISA assays for 30 different proteins, resulting in a concentration measurement (e.g. accumulation level) for each of the 30 proteins across the 302 samples. After data collection, the concentration values were prepared in a variety of ways. For some analyses, the concentration measurements were log 2 transformed, while for others, the concentration values were left untransformed. Analyses were also performed on measurements that were both standardized (zero mean, unit variance) and un-standardized (i.e. original measurements).

Classification analysis was also performed. The goal of the classification analysis was to determine the top performing marker panels and classification models that distinguish between samples with and without advanced adenomas. Classifier models and the associated classification performance were assessed using a 10 by 10-fold cross validation procedure. The 10 by 10-fold cross validation was performed using the discovery set only, and incorporated feature selection and classification model assembly. In the cross validation procedure, feature selection was first applied to reduce the number of features used, followed by development of the classifier model and subsequent classification performance evaluation. For each of the 10-fold cross validations, the data were segregated into 10 splits each containing 90% of the samples as a training set and the remaining 10% of the samples as a testing set. In this process, each sample was evaluated one time in a test set. The feature selection and model assembly was performed using the training set only, and these models were then applied to the testing set to evaluate classifier performance, typically via the area under the curve (AUC) from the receiver operating characteristic (ROC) plot. Here, the mean or median AUC value obtained from each of the 10 10-fold cross validation procedures was used to assess the overall marker panel and classification model performance.

To investigate the performance of different sized marker panels, a variety of feature selection and reduction methods were used including Elastic Network feature selection, Random Forest feature importance ranking, t-test p-value ranking, hierarchical clustering, and exhaustive combination search. With the exception of exhaustive combination search, the feature selection methods were embedded within the individual folds of the cross validation procedure to incorporate the variability of marker selection into the final performance assessment for a given classifier model build. For the exhaustive combination search, all n-choose-r combinations of features were evaluated, where a particular combination was selected prior to model building and used across all the cross validation folds. For both computational feasibility reasons and to limit the possibility for over-fitting, n and r were chosen to have relatively small values, with n typically <=30 total markers, and r typically between 2 and 10.

Within the 10 by 10-fold cross validation folds and after the feature selection step, a classifier model was built using one of several classification algorithms including, as examples, the support vector machine (SVM) algorithm, the Random Forest algorithm, Elastic Network (ENet) regression models with and without boosting, and k-nearest neighbors (kNN). The classification models were built using established classification modeling packages implemented in the R statistical programming language.

After construction of the classifier model on the training set, it was directly applied without modification to the testing set resulting in classification scores for the held-out test set samples. After the completion of a complete 10-fold cross validation iteration, the test set classification scores from all the samples were merged into a single set of values and the associated receiver operating characteristic (ROC) curve was generated. From this ROC, the area under the curve (AUC) was computed, with one AUC value for each of the 10 iterations of 10-fold cross validation. The mean and median AUC's across the 10 iterations was then used to assess the performance of the particular classifier assembly process, representing an estimate of the anticipated hold-out set validation performance utilizing only the discovery data.

The classification model results were analyzed. Utilizing the 10 by 10-fold cross validation procedure described above, a large number of classifier assembly methods were evaluated. Of these methods, one was selected for validation that provided the highest classification performance across a range of different feature selection and classification model methods. To validate this classifier model, a final model was built using all of the discovery data and the same feature selection and classifier model methods used in the associated 10 by 10-fold cross validation procedure. The final model consisted of a set of markers and a classification model with associated model parameters. This model was locked prior to validation and directly applied to the validation set with no addition tuning A final ROC was generated from the validation set classification scores, and the final validation performance was measured via the AUC with 95% confidence intervals on the ROC/AUC calculated from a bootstrap sampling procedure.

In sum, the AA model demonstrated the following parameters. The model consisted of 4 protein measurements from CATD, CLUS, GDF15 and SAA1. The median discovery AUC was 0.77 and AUC performance in the validation set was 0.65. Despite the AUC drop from discovery to validation, the 95% confidence intervals on the ROC were 0.56 to 0.74 indicating that the model provides classification discrimination significantly above random performance. The input data was ELISA-30 input and the classifier used was KNN.

The overall performance of a classifier is assessed in some cases via the AUC of the ROC as reported herein. An ROC considers the performance of the classifier at all possible model score cutoff points. However, when a classification decision needs to be made (e.g., is this patient sick or healthy?), a cutoff point is used to define the two groups. Classification scores at or above the cutoff point are assessed as positive (or sick) while points below are assessed as negative (or healthy) in various embodiments.

For some classification models disclosed herein, a classification score cutoff point is established by selecting the point of maximum accuracy on the validation ROC. The point of maximum accuracy on an ROC is the cutoff point or points for which the total number of correct classification calls is maximized. Here, the positive and negative classification calls are weighted equally. In cases where multiple maximum accuracy points are present on a given ROC, the point with the associated maximum sensitivity is selected in some cases. For some AA panels herein, the following parameters were observed: sensitivity of 0.83, specificity of 0.45, accuracy of 0.64 and a cutoff of 0.25. For some AA panels herein, the following parameters were observed: sensitivity of 0.80 and specificity of 0.50.

ADDITIONAL REFERENCE TO FIGURES

The disclosure herein is delineated throughout the specification and claims appended herewith, supported by the figures. Referring to the figures in more detail, one observes the following.

FIG. 1 depicts a workflow pipeline for the development of a lead CRC biomarker panel. In box 1, at top, 28 best proteins are identified using a targeted-mass spectrometry platform from 187 candidates compiled from literature. In box 2, a CRC test panel of 8 proteins is identified via machine-learning in an unbiased, case-control study using ELISA. In box 3, age as a biomarker is added to model as a parameter using a CRC vs. no comorbidities-no findings, case-control subset. In box 4, indeterminate call boundaries are added to the model using an intent-to-test patient subset. In box 5, at bottom, the 8 protein plus age classifier is validated using an intent-to-test patient subset.

FIG. 2 depicts a CRC panel AUC. The X axis indicates Specificity, at intervals of 20%, from 100% to 0%. The Y axis indicates Sensitivity, at intervals of 20%, from 0% to 100%. The slope along the diagonal indicates a 50% sensitivity and 50% Specificity. Shaded areas indicate the 95% confidence interval for the graph. The dark curve indicates performance for the nine-member CRC panel comprising the proteins AACT, CO3, CO9, MIF, PSGL, CATD, CEA and SEPR, and the non-protein biomarker of age. The AUC position corresponding to 81% sensitivity and 78% specificity is indicated. The performance is assessed using a 20% targeted indeterminate rate in discovery and a 15% validated indeterminate rate.

Our study indicated that there was no significant difference in early verses late CRC performance. For CRC Stage I-II, there were 15 true values verses 5 false values with a sensitivity of 0.75. For CRC Stage there were 15 true values verses 2 false values with a sensitivity of 0.88. The average for both CRC Stage I-II results and CRC Stage III-IV results was 15 true values and 7 false values with a sensitivity of 0.81. The Fisher's Test p-value for this CRC stage assay was 0.415, and the Chi-Square Test p-value was 0.546. No preferential class of samples was excluded in the indeterminate call group. Our study results indicated that for the no call group (NoC), the CRC class had 5 true verses 37 false. The Non-CRC class had 51 true verses 280 false. The average of the CRC class and nonCRC class NoC groups was 56 true verses 317 false. For the NoC group, the Fisher's Test p-value for this assay was 0.652, and the Chi-Square Test p-value was 0.712.

FIG. 3 depicts an AA panel AUC. The X axis indicates 1-Specificity, at intervals of 0.2, from 0.0 to 1.0. The Y axis indicates Sensitivity, at intervals of 0.2, from 0.0 to 1.0. The slope at x=y indicates a 50% sensitivity and 50% (1-Specificity). Shaded areas indicate the 95% confidence interval for the graph. The dark curve indicates performance for the four-member panel, while the light grey lines indicate performance of constituents.

Figure 4:
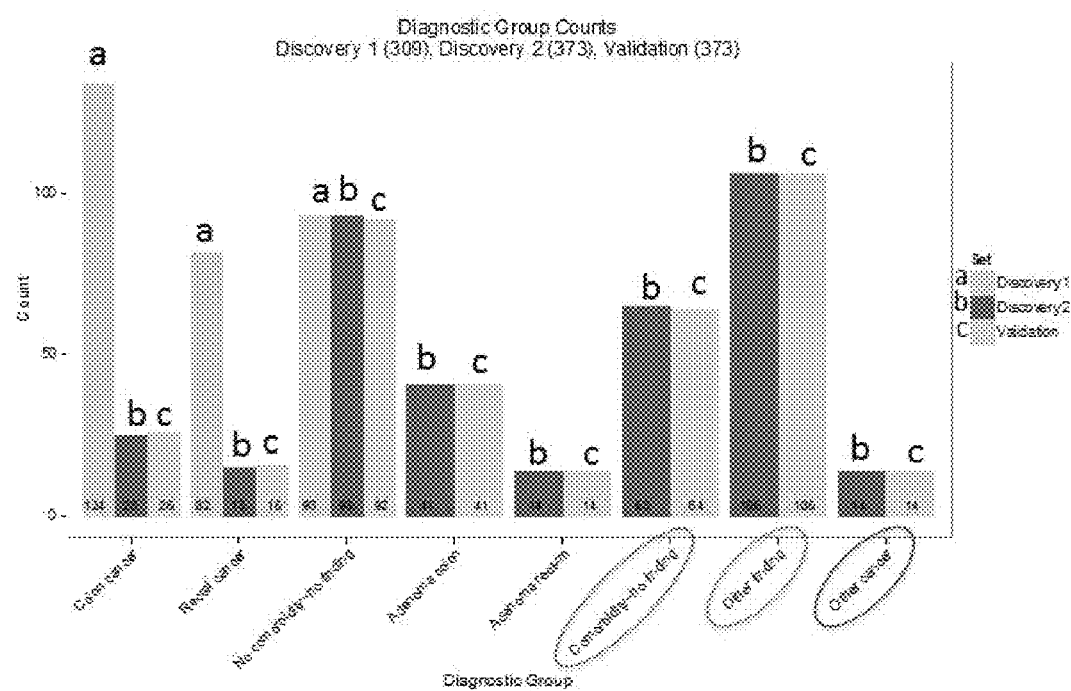
FIG. 4 presents validation data for a lead CRC panel.

FIG. 4 presents validation data for the CRC panel of FIG. 2. The CRC panel is developed on a 'Discovery 1' sample collection, labeled 'a'. The CRC panel is then re-derived and validated on a second sample set, divided into 'Discovery 2,' labeled 'b,' and a 'Validation' population, labeled 'c.' As seen in FIG. 4, counts for columns b and c do not differ significantly for any given category. This indicates that the CRC panel, as generated in the Discovery 1 set and recovered in the Discovery 2 set, for a given category, was reliably validated. The close correlation between the discovery 2 and Validation results is an indication of the repeatability of the test. Columns are labeled, left to right, as follows: Colon cancer, Rectal Cancer, No comorbidity—No finding, Adenoma—colon, Adenoma-rectum, Comorbidity—no finding, Other indication, and Other cancer.

FIG. 4 demonstrates that the CRC panel tested distinguishes not only between CRC and healthy samples generally, but between CRC and non-CRC samples, even those having other types of cancers. Accordingly, FIG. 4 demonstrates that CRC panels disclosed herein distinguish CRC from non-CRC as indicated in circulating blood samples, even in samples from individuals suffering from other cancers.

FIG. 5 depicts Protein levels for CRC and healthy control samples for protein markers relevant to the panels herein. For each protein, the left or upper boxplot range indicates the control sample population protein level, and the right or lower boxplot indicates the CRC positive sample population protein level. Log 2 (concentration) ranges from 2-20 across the top of the image. Proteins discussed herein are listed across the left side of the image. The proteins in order are A1AG1, A1AT, AACT, ANAX1, APOA1, CAH1, CATD, CEA, CLUS, CO3, CO9, CRP, DPP4, FGB, FIBG, GARS, GDF15, GELS, HPT, MIF, OSTP, PKM, PRDX1, PSGL, SAA1, SBP1, SEPR, TFF3, TFRC, and TIMP1. FIG. 5 demonstrates that individual markers often do not vary substantially between CRC and healthy control samples, emphasizing the synergistic improvement of the biomarker panels as presented herein over their individual biomarker constituents.

FIG. 6 depicts Protein levels for AA and healthy control samples for protein markers relevant to the panels herein. For each protein, the left or upper boxplot range indicates the control sample population protein level, and the right or lower boxplot indicates the CRC positive sample population protein level. Log 2 (concentration) ranges from 2-20 across the top of the image. Proteins discussed herein are listed across the left side of the image. The proteins in order are A1AG1, A1AT, AACT, ANAX1, APOA1, CAH1, CATD, CEA, CLUS, CO3, CO9, CRP, DPP4, FGB, FIBG, GARS, GDF15, GELS, HPT, MIF, OSTP, PKM, PRDX1, PSGL, SAA1, SBP1, SEPR, TFF3, TFRC, and TIMP1. FIG. 5 demonstrates that individual markers often do not vary substantially between AA and healthy control samples, emphasizing the synergistic improvement of the biomarker panels as presented herein over their individual biomarker constituents.

FIGS. 7A-16B present Discovery and Validation AUC plots for Panel Models 1-10 as presented herein. For each figure, the X axis indicates Specificity, at intervals of 20%, from 0% to 100%, or alternately 1-Specificity, at intervals of 0.2, from 0.0 to 1.0. The Y axis indicates Sensitivity, at intervals of 20%, from 0% to 100%. The slope along the diagonal indicates a 50% sensitivity and 50% Specificity. The box-plot indicated the 95% confidence interval for the graph.

Model 1 included A1AG1, A1AT, CATD, CEA, CO9, OSTP, and SEPR. ROC curves resulting from the discovery set and the validation set for Model 1 are depicted in FIGS. 7A and 7B, respectively. The resulting discovery set AUC was 0.84 and the validation set AUC was 0.80. At a validation ROC specificity of 90%, the sensitivity is >50%, at a specificity of 75%, the sensitivity is >60%, and at a specificity of 50%, the sensitivity is >80%. Model 2 included A1AG1, A1AT, APOA1, CATD, CEA, CLUS, CO3, CO9, FGB, FIBG, GARS, GELS, MIF, PRDX1, PSGL, SBP1, and SEPR. ROC curves resulting from the discovery set and the validation set for Model 2 are depicted in FIGS. 8A and 8B, respectively. The resulting discovery set AUC was 0.83 and the validation set AUC was 0.81. At a validation ROC specificity of 90%, the sensitivity is about 50%, at a specificity of 75%, the sensitivity is >60%, and at a specificity of 50%, the sensitivity is >80%. Model 3 included A1AG1, A1AT, CATD, CEA, CO9, GARS, and SEPR. ROC curves resulting from the discovery set and the validation set for Model 3 are depicted in FIGS. 9A and 9B, respectively. The resulting discovery set AUC was 0.82 and the validation set AUC was 0.82. At a validation ROC specificity of 90%, the sensitivity is >50%, at a specificity of 75%, the sensitivity is >70%, and at a specificity of 50%, the sensitivity is about 80%. Model 4 included A1AG1, A1AT, AACT, CATD, CEA, CO9, CRP, GARS, GELS, 510A8, 510A9, SAM, and SEPR. ROC curves resulting from the discovery set and the validation set for Model 4 are depicted in FIGS. 10A and 10B, respectively. The resulting discovery set AUC was 0.81 and the validation set AUC was 0.81. At a validation ROC specificity of 90%, the sensitivity is about 60%, at a specificity of 75%, the sensitivity is >70%, and at a specificity of 50%, the sensitivity is >80%. Model 5 included CATD, CEA, CO3, CO9, GARS, GELS, SEPR, and TFRC. ROC curves resulting from the discovery set and the validation set for Model 5 are depicted in FIGS. 11A and 11B, respectively. The resulting discovery set AUC was 0.86 and the validation set AUC was 0.82. At a validation ROC specificity of 90%, the sensitivity is about 50%, at a specificity of 75%, the sensitivity is >70%, and at a specificity of 50%, the sensitivity is about 90%. Model 6 included seven proteins which were CATD, CEA, AACT, CO9, and SEPR. ROC curves resulting from the discovery set and the validation set for Model 6 are depicted in FIGS. 12A and 12B, respectively. The resulting discovery set AUC was 0.86 and the validation set AUC was 0.80. At a validation ROC specificity of 90%, the sensitivity is >40%, at a specificity of 75%, the sensitivity is >60%, and at a specificity of 50%, the sensitivity is >80%. Model 7, as referenced in Table 5 included seven proteins which were A1AT, CATD, CEA, GARS, GELS, and SEPR. ROC curves resulting from the discovery set and the validation set for Model 7 are depicted in FIGS. 13A and 13B, respectively. The resulting discovery set AUC was 0.83 and the validation set AUC was 0.81. At a validation ROC specificity of 90%, the sensitivity is >50%, at a specificity of 75%, the sensitivity is >60%, and at a specificity of 50%, the sensitivity is >80%. Model 8, as referenced in Table 5, included A1AG1, A1AT, APOA1, CATD, CEA, CLUS, CO3, CO9, FGB, FIBG, GARS, GELS, HPT, MIF, PRDX1, PSGL, SBP1, and SEPR. ROC curves resulting from the discovery set and the validation set for Model 8 are depicted in FIGS. 14A and 14B, respectively. The resulting discovery set AUC was 0.84 and the validation set AUC was 0.78. At a validation ROC specificity of 90%, the sensitivity is >30%, at a specificity of 75%, the sensitivity is >60%, and at a specificity of 50%, the sensitivity is >80%. Model 9 included A1AG1, A1AT, CATD, CEA, CO9, FIBG, GELS, and SEPR. ROC curves resulting from the discovery set and the validation set for Model 9 are depicted in FIGS. 15A and 15B, respectively. The resulting discovery set AUC was 0.85 and the validation set AUC was 0.80. At a validation ROC specificity of 90%, the sensitivity is >50%, at a specificity of 75%, the sensitivity is >60%, and at a specificity of 50%, the sensitivity is about 80%. Model 10 curves resulting from the discovery set and the validation set for Model 10 are depicted in FIGS. 16A and 16B, respectively. The resulting discovery set AUC was 0.85 and the validation set AUC was 0.75.

FIGS. 17A-17B depict an alternate analysis of Model 5 using 'NOC' analysis. The X axis indicates Specificity, at intervals of 20%, from 100% to 0%. The Y axis indicates Sensitivity, at intervals of 20%, from 0% to 100%. The slope along the diagonal indicates a 50% sensitivity and 50% Specificity. The box-plot indicated the 95% confidence interval for the graph.

In this analysis, referred to here as NoC ("No Call"), the effect of using an indeterminate region with the classification models was investigated. In this analysis, the percentage of samples targeted to receive a "no call" result was set to 10%. To determine the optimal score range for the indeterminate region (NoC region) with 10% of the samples, the specificity was maximized at a sensitivity of >=90% as follows: All possible contiguous sets of 10% of samples were determined across the classifier scores range. For each set, the associated set of 10% of samples were marked as no calls. These samples were removed from the analysis set and the ROCcurve was generated from the remaining 90% of the samples. The maximum specificity at >=90% sensitivity was then determined and used as the evaluation score for the NoC region in question. After all NoC regions were evaluated in this manner, the region with the highest specificity score was selected as the optimal NoC region. The score range defining this NOC region was taken from the upper and lower classification scores of the associated 10% no call samples. To predict how the NoC procedure would affect classification performance in the hold-out validation set, the analysis was performed within the 10 by 10-fold cross validation assessment of model 5 described above. Like all previous model builds, only the discovery set was used in this assessment. The resulting median AUC determined from this 10 by 10-fold validation procedure was 0.87, slightly higher than the original discovery AUC of 0.86 without the application of NoC, suggesting the NoC procedure could be beneficial to employ in practice.

A final NoC region was determined by using the same NoC procedure described above on all of the discovery samples. This yielded a NoC region encompassing scores between 0.298 and 0.396. This NoC region was applied directly to the validation set with 20 samples (13.3%) falling within the region (10 disease, 10 control). The ROC determined from the remaining validation samples yielded an AUC of 0.85 (95% CI's: 0.78-0.91), an improvement of 0.03 over the validation ROC without application of NoC.

Comparing the ROC curves with and without NOC applied, NoC improved performance most in the region around 80%-60% specificity. With NOC, a clear improvement in sensitivity is apparent. In particular, the point at 85% sensitivity and 78% specificity is of interest because of the good overall performance for both sensitivity and specificity.

FIG. 17B depicts further NOC analysis results. The X axis indicates 1-Specificity, at intervals of 0.2, from 0.0 to 1.0. The Y axis indicates Sensitivity, at intervals of 0.2, from 0.0 to 1.0. The slope at x=y indicates a 50% sensitivity and 50% (1-Specificity). Shaded areas indicate the 95% confidence interval for the graph. The dark curve indicates performance for the four-member panel, while the light grey lines indicate performance of constituents.

FIG. 18 depicts Sensitivity and Specificity for Models 1-10 at the point of their AUCs corresponding to Maximum Accuracy. Sensitivity, on the Y axis, ranges from 0-1 in intervals of 0.25. The X axis depicts 1-Specificity, ranging from 0 to 1 in intervals of 0.25. Models 1-10 are labeled a-k, respectively.

FIG. 19 depicts a Computer System consistent with the methods, systems, kits and compositions disclosed herein.

FIG. 20 depicts AUC values for randomly generated panels from a biomarker set enriched to be predictive of CRC. The mean and median AUC values are well below those of the CRC panels disclosed herein.

NUMBERED EMBODIMENTS

The disclosure is further understood through review of the numbered embodiments recited herein. 1. An ex vivo method of assessing a colorectal cancer risk status in a blood sample of an individual, comprising the steps of obtaining a circulating blood sample from the individual; obtaining a biomarker panel level for a biomarker panel comprising a list of proteins in the sample comprising AACT, CO3, CO9, MIF, and PSGL to comprise panel information from said individual; comparing said panel information from said individual to a reference panel information set corresponding to a known colorectal cancer status; and categorizing said individual as having said colorectal cancer risk status if said individual's reference panel information does not differ significantly from said reference panel information set. 2. The method of embodiment 1, wherein obtaining a circulating blood sample comprises drawing blood from a vein or artery of the individual. 3. The method of any one of embodiments 1-2, wherein the panel information comprises age information for the individual. 4. The method of any one of embodiments 1-3, wherein the list of proteins comprises AACT, CO3, CO9, MIF, PSGL, CATD, CEA and SEPR. 5. The method of any one of embodiments 1-4, wherein the list of proteins comprises no more than 15 proteins. 6. The method of any one of embodiments 1-5, wherein the list of proteins comprises no more than 8 proteins. 7. The method of any one of embodiments 1-6, wherein the list of proteins comprises AACT, CO3, CO9, MIF, PSGL, CATD, CEA and SEPR. 8. The method of any one of embodiments 1-7, wherein the categorizing has a sensitivity of at least 81% and a specificity of at least 78%. 9. The method of any one of embodiments 1-8, comprising transmitting a report of results of said categorizing a health practitioner. 10. The method of any one of embodiments 1-9, wherein the report indicates a sensitivity of at least 81%. 11. The method of any one of embodiments 1-9, wherein the report indicates a specificity of at least 78%. 12. The method of any one of embodiments 1-9, wherein the report recommends that a colonoscopy be performed. 13. The method of any one of embodiments 1-12, comprising performing a colonoscopy on the individual. 14. The method of any one of embodiments 1-9, wherein the report recommends an independent surgical intervention. 15. The method of any one of embodiments 1-14, comprising performing an independent surgical intervention on the individual. 16. The method of any one of embodiments 1-9, wherein the report recommends undergoing an independent cancer assay. 17. The method of any one of embodiments 1-16, comprising performing an independent cancer assay on the individual. 18. The method of any one of embodiments 1-9, wherein the report recommends undergoing a stool cancer assay. 19. The method of any one of embodiments 1-18, comprising performing a stool cancer assay. 20. The method of any one of embodiments 1-9, wherein the report recommends administering an anticancer composition. 21. The method of any one of embodiments 1-18, comprising administering an anticancer composition. 22. The method of any one of embodiments 1-9, wherein the report recommends continued monitoring. 23. The method of any one of embodiments 1-22, wherein at least one biomarker level of said individual's panel information differs significantly from a corresponding value from said reference panel, and wherein said individual's panel level as a whole does not differ significantly from said reference panel level. 24. The method of any one of embodiments 1-23, wherein no parameter of said individual's reference panel information in isolation is indicative of said colorectal cancer status in said individual at a sensitivity of greater than 65% or a specificity of greater than 65%. 25. The method of any one of embodiments 1-24, wherein the obtaining protein levels comprises contacting a fraction of the circulating blood sample to a set of antibodies, wherein the set of antibodies comprises antibodies specific to AACT, CO3, CO9, MIF, and PSGL. 26. The method of any one of embodiments 1-25, wherein the obtaining protein levels comprises subjecting a fraction of the circulating blood sample to a mass spectrometric analysis. 27. The method of any one of embodiments 1-26, wherein at least one of said comparing and said categorizing is performed on a computer configured to analyze reference panel information. 28. The method of any one of embodiments 1-27, wherein said reference panel information set corresponding to a known colorectal cancer status comprises a product of a machine learning model. 29. The method of any one of embodiments 1-28, wherein the machine learning model is trained using at least 100 biomarker panels corresponding to known colorectal health status. 30. An ex vivo method of monitoring efficacy of a colorectal cancer treatment in an individual, comprising the steps of obtaining a first sample comprising circulating blood from the individual at a first time point; obtaining a second sample comprising circulating blood from the same individual receiving a colorectal cancer treatment at a second time point; obtaining a first panel level comprising protein levels for a list of proteins in the first sample and a second panel level comprising protein levels for a list of proteins in the second sample, said list comprising AACT, CO3, CO9, MIF, and PSGL to comprise panel information for said first sample and said second sample; wherein a change in protein levels indicates efficacy of the colorectal cancer treatment. 31. The method of embodiment 30, wherein obtaining the first sample comprises drawing blood from a vein or artery of the individual. 32. The method of any one of embodiments 30-31, wherein the colorectal cancer treatment comprises administration of a pharmaceutical composition. 33. The method of any one of embodiments 30-32, wherein the colorectal cancer treatment comprises administration of a chemotherapeutic agent. 34. The method of any one of embodiments 30-33, wherein the colorectal cancer treatment comprises a colonoscopy. 35. The method of any one of embodiments 30-34, wherein the colorectal cancer treatment comprises a polypectomy. 36. The method of any one of embodiments 30-35, wherein the colorectal cancer treatment comprises radiotherapy. 37. The method of any one of embodiments 30-36, comprising comparing said first sample panel level and said second panel level to at least one panel level of a healthy reference, wherein the second sample panel level being more similar to the panel level of the healthy reference indicates efficacy of the colorectal cancer treatment. 38. The method of any one of embodiments 30-37, comprising said first sample panel level and said second panel level to at least one panel level of a healthy reference, wherein the first sample panel level being more similar to the panel level of the colorectal cancer reference indicates efficacy of the colorectal cancer treatment. 39. The method of any one of embodiments 30-38, wherein the list of proteins comprises AACT, CO3, CO9, MIF, PSGL, CATD, CEA and SEPR. 40. The method of any one of embodiments 30-39, wherein the list of proteins comprises no more than 15 proteins. 41. The method of any one of embodiments 30-40, wherein the list of proteins comprises no more than 8 proteins. 42. The method of any one of embodiments 30-41, wherein the list of proteins comprises AACT, CO3, CO9, MIF, PSGL, CATD, CEA and SEPR. 43. The method of any one of embodiments 30 to 42, comprising changing the colorectal cancer treatment if no efficacy is indicated. 44. The method of any one of embodiments 30 to 42, comprising repeating the colorectal cancer treatment if no efficacy is indicated. 45. The method of any one of embodiments 30 to 42, comprising continuing the colorectal cancer treatment if no efficacy is indicated. 46. The method of any one of embodiments 30 to 42, comprising discontinuing the colorectal cancer treatment if efficacy is indicated. 47. A panel of proteins indicative of an individual's colorectal cancer status, comprising at least 5 proteins selected from the list consisting of AACT, CO3, CO9, MIF, PSGL, CATD, CEA and SEPR, wherein measurement of the panel at a level that does not differ significantly from a reference panel from circulating blood of an individual is indicative of the individual's colorectal cancer status corresponding to a reference panel colorectal cancer status at a sensitivity of at least 81% and a specificity of at least 78%; and wherein no constituent protein level of said panel is indicative of the individual's colorectal cancer status at a sensitivity of greater than 65% and a specificity of greater than 65%. 48. The panel of embodiment 47, comprising at least 6 proteins selected from the list consisting of AACT, CO3, CO9, MIF, PSGL, CATD, CEA and SEPR. 49. The panel of any one of embodiments 47-48, comprising no more than 12 proteins, of which at least 4 proteins selected from the list consisting of AACT, CO3, CO9, MIF, PSGL, CATD, CEA and SEPR. 50. The panel of any one of embodiments 47-49, comprising no more than 12 proteins, wherein the panel of proteins comprises AACT, CO3, CO9, MIF, PSGL, CATD, CEA and SEPR. 51. The panel of any one of embodiments 47-50, consisting of AACT, CO3, CO9, MIF, PSGL, CATD, CEA and SEPR. 52. The panel of proteins according to any one of embodiments 47-51, for use in a method of assessing a colorectal cancer status according to any one of embodiments 1-29, or for use in a method of monitoring efficacy of a colorectal cancer treatment according to any one of embodiments 30-46. 53. A kit comprising an antibody panel, said antibody panel comprising antibodies that identify at least 5 proteins selected from the list consisting of AACT, CO3, CO9, MIF, PSGL, CATD, CEA and SEPR. 54. The kit of embodiment 53, comprising an antibody that binds to a control protein. 55. The kit of any one of embodiments 53-54, wherein said antibody panel comprises no more than 15 antibodies. 56. The kit of any one of embodiments 53-55, wherein said antibody panel comprises no more than 12 antibodies. 57. The kit of any one of embodiments 53-56, wherein said antibody panel comprises antibodies that identify all of AACT, CO3, CO9, MIF, PSGL, CATD, CEA and SEPR. 58. The kit of any one of embodiments 53-57, comprising instructions functionally related to use of the kit to assess a patient colorectal cancer status. 59. The kit comprising an antibody panel according to any one of embodiments 47-52, for use in a method of assessing a colorectal cancer status according to any one of embodiments 1-29, or for use in a method of monitoring efficacy of a colorectal cancer treatment according to any one of embodiments 30-46. 60. A computer system configured to assess a colorectal cancer risk in an individual, said computer system comprising A memory unit for receiving data comprising measurement of a panel of proteins comprising at least 5 proteins selected from the list consisting of AACT, CO3, CO9, MIF, PSGL, CATD, CEA and SEPR from a biological sample comprising circulating blood Computer-executable instructions for assessing a colorectal cancer risk associated with said measurement of said panel of proteins An output unit for delivering a report assessing said colorectal cancer risk associated with said measurement of said panel of proteins. 61. The computer system of embodiment 60, wherein said panel comprises at least 6 proteins selected from the list consisting of AACT, CO3, CO9, MIF, PSGL, CATD, CEA and SEPR. 62. The computer system of any one of embodiments 60-61, wherein said panel comprises no more than 12 proteins, of which at least 5 proteins selected from the list consisting of AACT, CO3, CO9, MIF, PSGL, CATD, CEA and SEPR. 63. The computer system of any one of embodiments 60-62, wherein said panel comprises no more than 12 proteins, wherein the panel of proteins comprises AACT, CO3, CO9, MIF, PSGL, CATD, CEA and SEPR. 64. The computer system of any one of embodiments 60-63, wherein said panel consists of AACT, CO3, CO9, MIF, PSGL, CATD, CEA and SEPR. 65. The computer system of any one of embodiments 60-64, wherein the memory unit is configured for receiving data comprising measurement of a second panel of proteins. 66. The computer system of any one of embodiments 60-65, wherein said data comprising measurement of a panel of proteins comprises ELISA data. 67. The computer system of any one of embodiments 60-66, wherein said data comprising measurement of a panel of proteins comprises mass spectrometry data. 68. The computer system of any one of embodiments 60-67, wherein assessing a colorectal cancer risk comprises comparing said data to a reference panel associated with a known colorectal cancer status. 69. The computer system of any one of embodiments 60-68, wherein said individual is assigned said known colorectal cancer status when said data does not differ significantly from said reference panel. 70. The computer system of any one of embodiments 60-68, wherein said reference panel indicates presence of colorectal cancer. 71. The computer system of any one of embodiments 60-68, wherein said reference panel indicates absence of colorectal cancer. 72. The computer system of any one of embodiments 60-71, wherein assessing a colorectal cancer risk is performed on a computer configured to analyze reference panel information. 73. The computer system of any one of embodiments 60-72, wherein said memory unit comprises at least one reference panel information set corresponding to a known colorectal cancer status. 74. The computer system of any one of embodiments 60-73, wherein the at least one reference panel information set comprises a machine learning model. 75. The computer system of any one of embodiments 60-74, wherein the machine learning model is trained using at least 100 biomarker panels corresponding to known colorectal health status. 76. The computer system of any one of embodiments 60-75, wherein said report indicates a sensitivity of at least 81% and a specificity of at least 78%. 77. The computer system of any one of embodiments 60-76, wherein said report indicates a sensitivity of at least 81%. 78. The computer system of any one of embodiments 60-77, wherein said report indicates a specificity of at least 78%. 79. The computer system of any one of embodiments 60-78, wherein said report recommends that a colonoscopy be performed. 80. The computer system of any one of embodiments 60-79, wherein said report recommends an independent surgical intervention. 81. The computer system of any one of embodiments 60-80, wherein said report recommends undergoing an independent cancer assay. 82. The computer system of any one of embodiments 60-81, wherein said report recommends undergoing a stool cancer assay. 83. The computer system of any one of embodiments 60-82, wherein said report recommends administering an anticancer composition. 84. The computer system of any one of embodiments 60-83, wherein said report recommends continued monitoring. 85. The computer system of any one of embodiments 60-84, wherein at least one parameter of said individual's reference panel information differs significantly from a corresponding value from said reference panel information set, and wherein said individual's reference panel information does not differ significantly from said reference panel information set. 86. The computer system of any one of embodiments 60-85, wherein no single protein of said panel indicates the individual's colorectal cancer status at a specificity of greater than 65% or a sensitivity of greater than 65%. 87. The computer system of any one of embodiments 60-86, wherein the memory unit is configured to receive age information from said individual. 88. The computer system of any one of embodiments 60-87, wherein the computer-executable instructions factor in age of the individual when assessing said colorectal cancer risk associated with said measurement of said panel of proteins. 89. An ex vivo method of assessing an advanced adenoma risk status in a blood sample of an individual, comprising the steps of obtaining a circulating blood sample from the individual; obtaining protein levels for a list of proteins relevant to advanced adenoma in the sample comprising at least three of CATD, CLUS, GDF15 and SAA1 to comprise biomarker panel information from said individual; comparing said panel information from said individual to a reference panel information set corresponding to a known advanced adenoma status; and categorizing said individual as having said advanced adenoma risk status if said individual's reference panel information does not differ significantly from said reference panel information set. 90. The method of any one of embodiments 89, wherein obtaining a circulating blood sample comprises drawing blood from a vein or artery of the individual 91. The method of any one of embodiments 89-90, wherein the panel information comprises age information for the individual. 92. The method of any one of embodiments 89-91, wherein the list of proteins comprises no more than 15 proteins. 93. The method of any one of embodiments 89-92, wherein the list of proteins comprises no more than 5 proteins. 94. The method of any one of embodiments 89-93, wherein the list of proteins comprises CATD, CLUS, GDF15 and SAA1. 95. The method of any one of embodiments 89-94, wherein the categorizing has a sensitivity of at least 50% and a specificity of at least 80%. 96. The method of any one of embodiments 89-95, comprising transmitting a report of results of said categorizing to a healthcare professional. 97. The method of any one of embodiments 89-96, wherein the report indicates a sensitivity of at least 50%. 98. The method of any one of embodiments 89-96, wherein the report indicates a specificity of at least 80%. 99. The method of any one of embodiments 89-96, wherein the report recommends that a colonoscopy be performed. 100. The method of any one of embodiments 89-99, wherein the individual undergoes a colonoscopy. 101. The method of any one of embodiments 89-96, wherein the report recommends an independent surgical intervention. 102. The method of any one of embodiments 89-101, wherein the individual undergoes an independent surgical intervention. 103. The method of any one of embodiments 89-96, wherein the report recommends undergoing an independent cancer assay. 104. The method of any one of embodiments 89-103, wherein the individual undergoes an independent cancer assay. 105. The method of any one of embodiments 89-96, wherein the report recommends undergoing a stool cancer assay. 106. The method of any one of embodiments 89-105, wherein the individual undergoes a stool cancer assay. 107. The method of any one of embodiments 89-96, wherein the report recommends administering an anticancer composition. 108. The method of any one of embodiments 89-107, wherein an anticancer composition is administered to the individual. 109. The method of any one of embodiments 89-96, wherein the report recommends continued monitoring. 110. The method of any one of embodiments 89-109, wherein at least one parameter of said individual's reference panel differs significantly from a corresponding value from said reference panel set, and wherein said individual's reference panel information as a whole does not differ significantly from said reference panel information set. 111. The method of any one of embodiments 89-110, wherein no parameter of said individual's reference panel information in isolation is indicative of said advanced adenoma status in said individual at a sensitivity of greater than 65% or a specificity of greater than 65%. 112. The method of any one of embodiments 89-111, wherein the obtaining protein levels comprises contacting a fraction of the circulating blood sample to a set of antibodies, wherein the set of antibodies comprises antibodies specific to CATD, CLUS, GDF15 and SAA1. 113. The method of any one of embodiments 89-112, wherein the obtaining protein levels comprises subjecting a fraction of the circulating blood sample to a mass spectrometric analysis. 114. The method of any one of embodiments 89-113, wherein the obtaining protein levels comprises contacting the sample to protein binding DNA aptamers. 115. The method of any one of embodiments 89-114, wherein the obtaining protein levels comprises contacting the sample to an antibody array. 116. The method of any one of embodiments 89-115, wherein at least one of said comparing and said categorizing is performed on a computer configured to analyze reference panel information. 117. The method of any one of embodiments 89-116, wherein said reference panel information set corresponding to a known advanced adenoma status comprises is a product of a machine learning model. 118. The method of any one of embodiments 89-117, wherein the machine learning model is trained using at least 100 biomarker panels corresponding to known colorectal health status. 119. An ex vivo method of monitoring efficacy of an advanced adenoma treatment in an individual, comprising the steps of obtaining a first sample comprising circulating blood from the individual at a first time point; obtaining a second sample comprising circulating blood from the same individual receiving an advanced adenoma treatment at a second time point; obtaining a first panel level protein levels for a list of proteins relevant to advanced adenoma assessment in the first sample and a second panel level protein levels for a list of proteins relevant to advanced adenoma assessment in the second sample, said list comprising CATD, CLUS, GDF15 and SAA1 to comprise panel information for said first sample and said second sample; wherein a change in protein levels indicates efficacy of the advanced adenoma treatment. 120. The method of embodiment 119, wherein obtaining the first sample comprises drawing blood from a vein or artery of the individual. 121. The method of any one of embodiments 119-120, wherein the advanced adenoma treatment comprises administration of a pharmaceutical composition. 122. The method of any one of embodiments 119-121, wherein the advanced adenoma treatment comprises administration of a chemotherapeutic agent. 123. The method of any one of embodiments 119-122, wherein the advanced adenoma treatment comprises a colonoscopy. 124. The method of any one of embodiments 119-123, wherein the advanced adenoma treatment comprises a polypectomy. 125. The method of any one of embodiments 119-124, wherein the advanced adenoma treatment comprises radiotherapy. 126. The method of any one of embodiments 119-125, comprising comparing said first sample protein levels and said second panel protein levels to protein levels of a healthy reference, wherein the second sample levels being more similar to the protein levels of the healthy reference indicates efficacy of the advanced adenoma treatment. 127. The method of any one of embodiments 119-126, comprising comparing said first sample protein levels and said second panel protein levels to protein levels of an advanced adenoma reference, wherein the first sample levels being more similar to the protein levels of the advanced adenoma reference indicates efficacy of the advanced adenoma treatment. 128. The method of any one of embodiments 119-127, wherein the list of proteins relevant to advanced adenoma assessment comprises CATD, CLUS, GDF15 and SAA1. 129. The method of any one of embodiments 119-128, wherein the list of proteins relevant to advanced adenoma assessment comprises no more than 12 proteins. 130. The method of any one of embodiments 119-129, wherein the list of proteins relevant to advanced adenoma assessment comprises no more than 8 proteins. 131. The method of any one of embodiments 119-130, wherein the list of proteins relevant to advanced adenoma assessment consists of CATD, CLUS, GDF15 and SAA1. 132. The method of any one of embodiments 119 to 131, comprising changing the advanced adenoma treatment if no efficacy is indicated. 133. The method of any one of embodiments 119 to 131, comprising repeating the advanced adenoma treatment if no efficacy is indicated. 134. The method of any one of embodiments 119 to 131, comprising continuing the advanced adenoma treatment if no efficacy is indicated. 135. The method of any one of embodiments 119 to 131, comprising discontinuing the advanced adenoma treatment if efficacy is indicated. 136. A panel of proteins indicative of an individual's advanced adenoma status, comprising at least 3 proteins relevant to advanced adenoma assessment selected from the list consisting of CATD, CLUS, GDF15 and SAA1, wherein measurement of the panel at a level that does not differ significantly from a reference panel from circulating blood of an individual is indicative of the individual's advanced adenoma status corresponding to a reference panel advanced adenoma status at a sensitivity of at least 50% and a specificity of at least 80%; and wherein no constituent protein level of said panel is indicative of the individual's advanced adenoma status at a sensitivity of greater than 65% and a specificity of greater than 65%. 137. The panel of embodiment 136, comprising proteins relevant to advanced adenoma assessment CATD, CLUS, GDF15 and SAA1. 138. The panel of proteins according to any one of embodiments 136-137, for use in a method of assessing an advanced adenoma status according to any one of embodiments 89-119, or for use in a method of monitoring efficacy of an advanced adenoma treatment according to any one of embodiments 120-136. 139. A kit comprising an antibody panel, said antibody panel comprising antibodies that identify at least 3 proteins relevant to advanced adenoma assessment selected from the list consisting of CATD, CLUS, GDF15 and SAA1. 140. The kit of any one of embodiments 139, comprising an antibody that binds to a control protein. 141. The kit of any one of embodiments 139-140, wherein said antibody panel comprises no more than 15 antibodies. 142. The kit of any one of embodiments 139-141, wherein said antibody panel comprises no more than 12 antibodies. 143. The kit of any one of embodiments 139-142, wherein said antibody panel comprises antibodies that identify all of CATD, CLUS, GDF15 and SAA1. 144. The kit of any one of embodiments 139-143, comprising instructions functionally related to use of the kit to assess a patient advanced adenoma status. 145. The kit comprising an antibody panel according to any one of embodiments 136-138, for use in a method of assessing an advanced adenoma status according to any one of embodiments 89-119, or for use in a method of monitoring efficacy of an advanced adenoma treatment according to any one of embodiments 120-136. 146. A computer system configured to assess an advanced adenoma risk in an individual, said computer system comprising A memory unit for receiving data comprising measurement of a panel of proteins comprising at least 3 proteins indicative of an individual's advanced adenoma status selected from the list consisting of CATD, CLUS, GDF15 and SAA1 from a biological sample comprising circulating blood Computer-executable instructions for assessing an advanced adenoma risk associated with said measurement of said panel of proteins An output unit for delivering a report assessing said advanced adenoma risk associated with said measurement of said panel of proteins. 147. The computer system of embodiment 146, wherein said panel comprises CATD, CLUS, GDF15 and SAA1. 148. The computer system of any one of embodiments 146-147, wherein said panel comprises no more than 12 proteins. 149. The computer system of any one of embodiments 146-148, wherein the memory unit is configured for receiving data comprising measurement of a second panel of proteins. 150. The computer system of any one of embodiments 146-149, wherein said data comprising measurement of a panel of proteins comprises ELISA data. 151. The computer system of any one of embodiments 146-150, wherein said data comprising measurement of a panel of proteins comprises mass spectrometry data. 152. The computer system of any one of embodiments 146-151, wherein assessing an advanced adenoma risk comprises comparing said data to a reference panel associated with a known advanced adenoma status. 153. The computer system of any one of embodiments 146-152, wherein said individual is assigned said known advanced adenoma status when said data does not differ significantly from said reference panel. 154. The computer system of any one of embodiments 146-152, wherein said reference panel indicates presence of colorectal cancer. 155. The computer system of any one of embodiments 146-152, wherein said reference panel indicates absence of colorectal cancer. 156. The computer system of any one of embodiments 146-155, wherein assessing an advanced adenoma risk is performed on a computer configured to analyze reference panel information. 157. The method of any one of embodiments 146-156, wherein said memory unit comprises at least one reference panel information set corresponding to a known advanced adenoma status. 158. The method of any one of embodiments 146-157, wherein the at least one reference panel information set comprises a machine learning model. 159. The method of any one of embodiments 146-158, wherein the machine learning model is trained using at least 100 biomarker panels corresponding to known colorectal health status. 160. The computer system of any one of embodiments 146-159, wherein said report indicates a sensitivity of at least 50% and a specificity of at least 80%. 161. The computer system of any one of embodiments 146-160, wherein said report indicates a sensitivity of at least 50%. 162. The computer system of any one of embodiments 146-161, wherein said report indicates a specificity of at least 80%. 163. The computer system of any one of embodiments 146-162, wherein said report recommends that a colonoscopy be performed. 164. The computer system of any one of embodiments 146-163, wherein said report recommends an independent surgical intervention. 165. The computer system of any one of embodiments 146-164, wherein said report recommends undergoing an independent cancer assay. 166. The computer system of any one of embodiments 146-165, wherein said report recommends undergoing a stool cancer assay. 167. The computer system of any one of embodiments 146-166, wherein said report recommends administering an anticancer composition. 168. The computer system of any one of embodiments 146-167, wherein said report recommends continued monitoring. 169. The computer system of any one of embodiments 146-168, wherein at least one parameter of said individual's reference panel information differs significantly from a corresponding value from said reference panel information set, and wherein said individual's reference panel information does not differ significantly from said reference panel information set. 170. The computer system of any one of embodiments 146-169, wherein no single protein of said panel indicates the individual's advanced adenoma status at a specificity of greater than 65% or a sensitivity of greater than 65%. 171. The computer system of any one of embodiments 146-170, wherein the memory unit is configured to receive age information from said individual. 172. The computer system of any one of embodiments 146-171, wherein the computer-executable instructions factor in age of the individual when assessing said advanced adenoma risk associated with said measurement of said panel of proteins. 173. An ex vivo method of assessing a colorectal health risk status in a blood sample of an individual, comprising the steps of obtaining a circulating blood sample from the individual; obtaining a biomarker panel level for a biomarker panel comprising a list of proteins in the sample comprising AACT, CO3, CO9, MIF, PSGL, SEPR, CEA, CATD, CLUS, GDF15 and SAA1, and obtaining an age for the individual, wherein AACT, CO3, CO9, MIF, PSGL, SEPR, CEA, CATD, and age comprise colorectal cancer panel information from said individual; and wherein CATD, CLUS, GDF15 and SAA1 comprise advanced adenoma panel information from said individual; comparing said colorectal cancer panel information from said individual to a reference colorectal cancer panel information set corresponding to a known colorectal cancer status; comparing said advanced adenoma panel information from said individual to a reference advanced adenoma panel information set corresponding to a known advanced adenoma status; and categorizing said individual as having a colorectal health risk if either of said colorectal cancer panel or said advanced adenoma panel does not differ significantly from a reference panel positive for a colorectal health risk. 174. The method of any one of embodiments 173, wherein obtaining a circulating blood sample comprises drawing blood from a vein or artery of the individual. 175. The method of any one of embodiments 173-174, wherein the list of proteins comprises no more than 20 proteins. 176. The method of any one of embodiments 173-175, wherein the list of proteins comprises no more than 11 proteins. 177. The method of any one of embodiments 173-176, wherein the categorizing has a sensitivity of at least 8% and a specificity of at least 50%. 178. The method of any one of embodiments 173-177, comprising transmitting a report of results of said categorizing to a health practitioner. 179. The method of any one of embodiments 173-178, wherein the report recommends that a colonoscopy be performed. 180. The method of any one of embodiments 173-179, wherein the individual undergoes a colonoscopy. 181. The method of any one of embodiments 173-178, wherein the report recommends an independent surgical intervention. 182. The method of any one of embodiments 173-181, wherein the individual undergoes an independent surgical intervention. 183. The method of any one of embodiments 178-82, wherein the report recommends undergoing an independent cancer assay. 184. The method of any one of embodiments 173-183, wherein the individual undergoes an independent cancer assay. 185. The method of any one of embodiments 173-178, wherein the report recommends undergoing a stool cancer assay. 186. The method of any one of embodiments 173-185, wherein the individual undergoes a stool cancer assay. 187. The method of any one of embodiments 173-178, wherein the report recommends administering an anticancer composition. 188. The method of any one of embodiments 173-187, wherein the individual is administered an anticancer composition. 189. The method of any one of embodiments 173-178, wherein the report recommends continued monitoring. 190. The method of any one of embodiments 173-178, wherein at least one biomarker level of said individual's panel information differs significantly from a corresponding value from at least one of said reference panels, and wherein said individual's panel level as a whole does not differ significantly from said reference panel level. 191. The method of any one of embodiments 178-190, wherein no parameter of said individual's reference panel information in isolation is indicative of said colorectal cancer status in said individual at a sensitivity of greater than 65% or a specificity of greater than 65%. 192. The method of any one of embodiments 173-178, wherein the obtaining protein levels comprises contacting a fraction of the circulating blood sample to a set of antibodies, wherein the set of antibodies comprises antibodies specific to AACT, CO3, CO9, MIF, PSGL, SEPR, CEA, CATD, CLUS, GDF15 and SAA1. 193. The method of any one of embodiments 173-178, wherein the obtaining protein levels comprises subjecting a fraction of the circulating blood sample to a mass spectrometric analysis. 194. The method of any one of embodiments 173-178, wherein the obtaining protein levels comprises contacting the sample to protein binding DNA aptamers. 195. The method of any one of embodiments 173-178, wherein the obtaining protein levels comprises contacting the sample to an antibody array. 196. The method of any one of embodiments 173-178, wherein the obtaining protein levels comprises subjecting a fraction of the circulating blood sample to a mass spectrometric analysis. 197. The method of any one of embodiments 173-178, wherein at least one of said comparing and said categorizing is performed on a computer configured to analyze reference panel information. 198. The method of any one of embodiments 173-178, wherein said reference panel information set corresponding to a known colorectal cancer status comprises a product of a machine learning model. 199. The method of any one of embodiments 173-198, wherein the machine learning model is trained using at least 100 biomarker panels corresponding to known colorectal health status. 200. The embodiment of any one of 1-199, wherein the panel comprises more biomarkers than those listed, but wherein a significant colorectal health assessment arises from the listed biomarkers, alone or in combination with age. 201. An embodiment of any one of 1-200, wherein the panel distinguishes CRC samples from samples derived from a CRC-negative individual that is positive for at least one non-CRC cancer.

REFERENCE ART AND DEFINITIONS

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention can employ, unless otherwise indicated, conventional techniques of immunology, biochemistry, chemistry, molecular biology, microbiology, cell biology, genomics and recombinant DNA, which are within the skill of the art. See, for example, Sambrook, Fritsch and Maniatis, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), CULTURE OF ANIMAL CELLS: A MANUAL OF BASIC TECHNIQUE AND SPECIALIZED APPLICATIONS, 6th Edition (R. I. Freshney, ed. (2010), and Lange, et. al., Molecular Systems Biology Vol. 4: Article 222 (2008), which are hereby incorporated by reference.

DEFINITIONS

As used in the specification and claims, the singular forms "a", "an" and "the" include plural references unless the context clearly dictates otherwise. For example, the term "a sample" includes a plurality of samples, including mixtures thereof.

The terms "determining", "measuring", "evaluating", "assessing," "assaying," and "analyzing" are often used interchangeably herein to refer to forms of measurement, and include determining if an element is present or not (for example, detection). These terms can include quantitative, qualitative or quantitative and qualitative determinations. Assessing is alternatively relative or absolute. "Detecting the presence of" includes determining the amount of something present, as well as determining whether it is present or absent.

The terms "panel", "biomarker panel", "protein panel", "classifier model", and "model" are used interchangeably herein to refer to a set of biomarkers, wherein the set of biomarkers comprises at least two biomarkers. Exemplary biomarkers are proteins or polypeptide fragments of proteins that are uniquely or confidently mapped to particular proteins. However, additional biomarkers are also contemplated, for example age or gender of the individual providing a sample. The biomarker panel is often predictive and/or informative of a subject's health status, disease, or condition.

The "level" of a biomarker panel refers to the absolute and relative levels of the panel's constituent markers and the relative pattern of the panel's constituent biomarkers.

The terms "colorectal cancer" and "CRC" are used interchangeably herein. The term "colorectal cancer status", "CRC status" can refer to the status of the disease in subject. Examples of types of CRC statuses include, but are not limited to, the subject's risk of cancer, including colorectal carcinoma, the presence or absence of disease (for example, polyp or adenocarcinoma), the stage of disease in a patient (for example, carcinoma), and the effectiveness of treatment of disease.

The term "mass spectrometer" can refer to a gas phase ion spectrometer that measures a parameter that can be translated into mass-to-charge (m/z) ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" can refer to the use of a mass spectrometer to detect gas phase ions.

The term "tandem mass spectrometer" can refer to any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that can be capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector-magnetic sector mass spectrometers, and combinations thereof.

The term "biochip" can refer to a solid substrate having a generally planar surface to which an adsorbent is attached. In some cases, a surface of the biochip comprises a plurality of addressable locations, each of which location may have the adsorbent bound there. Biochips can be adapted to engage a probe interface, and therefore, function as probes. Protein biochips are adapted for the capture of polypeptides and can be comprise surfaces having chromatographic or biospecific adsorbents attached thereto at addressable locations. Microarray chips are generally used for DNA and RNA gene expression detection.

The term "biomarker" and "marker" are used interchangeably herein, and can refer to a polypeptide, gene, nucleic acid (for example, DNA and/or RNA) which is differentially present in a sample taken from a subject having a disease for which a diagnosis is desired (for example, CRC) as compared to a comparable sample taken from control subject that does not have the disease (for example, a person with a negative diagnosis or undetectable CRC, normal or healthy subject, or, for example, from the same individual at a different time point). Common biomarkers herein include proteins, or protein fragments that are uniquely or confidently mapped to a particular protein, transition ion of an amino acid sequence, or one or more modifications of a protein such as phosphorylation, glycosylation or other post-translational or co-translational modification. In addition, a protein biomarker can be a binding partner of a protein, protein fragment, or transition ion of an amino acid sequence.

The terms "polypeptide," "peptide" and "protein" are often used interchangeably herein in reference to a polymer of amino acid residues. A protein, generally, refers to a full-length polypeptide as translated from a coding open reading frame, or as processed to its mature form, while a polypeptide or peptide informally refers to a degradation fragment or a processing fragment of a protein that nonetheless uniquely or identifiably maps to a particular protein. A polypeptide can be a single linear polymer chain of amino acids bonded together by peptide bonds between the carboxyl and amino groups of adjacent amino acid residues. Polypeptides can be modified, for example, by the addition of carbohydrate, phosphorylation, etc. Proteins can comprise one or more polypeptides.

An "immunoassay" is an assay that uses an antibody to specifically bind an antigen (for example, a marker). The immunoassay can be characterized by the use of specific binding properties of a particular antibody to isolate, target, and/or quantify the antigen.

The term "antibody" can refer to a polypeptide ligand substantially encoded by an immunoglobulin gene or immunoglobulin genes, or fragments thereof, which specifically binds and recognizes an epitope. Antibodies exist, for example, as intact immunoglobulins or as a number of well-characterized fragments produced by digestion with various peptidases. This includes, for example, Fab" and F(ab)"2 fragments. As used herein, the term "antibody" also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody can refer to that portion of an immunoglobulin heavy chain that comprises one or more heavy chain constant region domains, but does not include the heavy chain variable region.

The term "tumor" can refer to a solid or fluid-filled lesion or structure that may be formed by cancerous or non-cancerous cells, such as cells exhibiting aberrant cell growth or division. The terms "mass" and "nodule" are often used synonymously with "tumor". Tumors include malignant tumors or benign tumors. An example of a malignant tumor can be a carcinoma which is known to comprise transformed cells.

The term "binding partners" can refer to pairs of molecules, typically pairs of biomolecules that exhibit specific binding. Protein—protein interactions can occur between two or more proteins, when bound together they often to carry out their biological function. Interactions between proteins are important for the majority of biological functions. For example, signals from the exterior of a cell are mediated via ligand receptor proteins to the inside of that cell by protein—protein interactions of the signaling molecules. For example, molecular binding partners include, without limitation, receptor and ligand, antibody and antigen, biotin and avidin, and others.

The term "control reference" can refer to a known or determined amount of a biomarker associated with a known condition that can be used to compare to an amount of the biomarker associated with an unknown condition. A control reference can also refer to a steady-state molecule which can be used to calibrate or normalize values of a non-steady state molecule. A control reference value can be a calculated value from a combination of factors or a combination of a range of factors, such as a combination of biomarker concentrations or a combination of ranges of concentrations.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. The disease can be cancer. The cancer can be CRC (CRC). In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An "ex vivo" assay is not performed on a subject. Rather, it is performed upon a sample separate from a subject. An example of an 'ex vivo' assay performed on a sample is an 'in vitro' assay.

The term "in vitro" is used to describe an event that takes places contained in a container for holding laboratory reagent such that it is separated from the living biological source organism from which the material is obtained. In vitro assays can encompass cell-based assays in which cells alive or dead are employed. In vitro assays can also encompass a cell-free assay in which no intact cells are employed.

The term specificity, or true negative rate, can refer to a test's ability to exclude a condition correctly. For example, in a diagnostic test, the specificity of a test is the proportion of patients known not to have the disease, who will test negative for it. In some cases, this is calculated by determining the proportion of true negatives (i.e. patients who test negative who do not have the disease) to the total number of healthy individuals in the population (i.e., the sum of patients who test negative and do not have the disease and patients who test positive and do not have the disease).

The term sensitivity, or true positive rate, can refer to a test's ability to identify a condition correctly. For example, in a diagnostic test, the sensitivity of a test is the proportion of patients known to have the disease, who will test positive for it. In some cases, this is calculated by determining the proportion of true positives (i.e. patients who test positive who have the disease) to the total number of individuals in the population with the condition (i.e., the sum of patients who test positive and have the condition and patients who test negative and have the condition).

The quantitative relationship between sensitivity and specificity can change as different diagnostic cut-offs are chosen. This variation can be represented using ROC curves. The x-axis of a ROC curve shows the false-positive rate of an assay, which can be calculated as (1−specificity). The y-axis of a ROC curve reports the sensitivity for an assay. This allows one to easily determine a sensitivity of an assay for a given specificity, and vice versa.

As used herein, the term 'about' a number refers to that number plus or minus 10% of that number. The term 'about' a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

Examples

Example 1

A patient at risk of colorectal cancer is tested using a panel as disclosed herein. A blood sample is taken from the patient and protein accumulation levels are measured for a panel comprising AACT, CATD, CEA, CO3, CO9, MIF, PSGL, and SEPR. The patient's age is also factored in to the assessment, with age (in units of time) treated as a biomarker of the panel much like the other markers. The patient's panel results are compared to panel results of known status, and the patient is categorized with an 81% sensitivity, a 78% specificity, and a 31% positive predictive value as having colon cancer.

A colonoscopy is recommended and evidence of colorectal cancer is detected in the individual.

Example 2

The patient of Example 1 is prescribed a treatment regimen comprising a surgical intervention. A blood sample is taken from the patient prior to surgical intervention and protein accumulation levels are measured for a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer.

A blood sample is taken from the patient subsequent to surgical intervention and protein accumulation levels are measured for a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as no longer having colon cancer.

Example 3

The patient of Example 1 is prescribed a treatment regimen comprising a chemotherapeutic intervention comprising 5-FU administration. A blood sample is taken from the patient prior to chemotherapeutic intervention and protein accumulation levels are measured for a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized an 81% sensitivity, a 78% specificity, and a 31% positive predictive value as having colon cancer.

A blood sample is taken from the patient at weekly intervals during chemotherapy treatment and protein accumulation levels are measured for a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status. The patient's panel results over time indicate that the cancer has responded to the chemotherapy treatment and that the colorectal cancer is no longer detectable by completion of the treatment regimen.

Example 4

The patient of Example 1 is prescribed a treatment regimen comprising a chemotherapeutic intervention comprising oral capecitabine administration. A blood sample is taken from the patient prior to chemotherapeutic intervention and protein accumulation levels are measured for a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer.

A blood sample is taken from the patient at weekly intervals during chemotherapy treatment and protein accumulation levels are measured for a panel comprising AACT, CATD, CEA, CO3, CO9, MIF, PSGL, and SEPR. The patient's panel results are compared to panel results of known status. The patient's panel results over time indicate that the cancer has responded to the chemotherapy treatment and that the colorectal cancer is no longer detectable by completion of the treatment regimen.

Example 5

The patient of Example 1 is prescribed a treatment regimen comprising a chemotherapeutic intervention comprising oral oxaliplatin administration. A blood sample is taken from the patient prior to chemotherapeutic intervention and protein accumulation levels are measured for a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer.

A blood sample is taken from the patient at weekly intervals during chemotherapy treatment and protein accumulation levels are measured for a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status. The patient's panel results over time indicate that the cancer has responded to the chemotherapy treatment and that the colorectal cancer is no longer detectable by completion of the treatment regimen.

Example 6

The patient of Example 1 is prescribed a treatment regimen comprising a chemotherapeutic intervention comprising oral oxaliplatin administration in combination with bevacizumab. A blood sample is taken from the patient prior to chemotherapeutic intervention and protein accumulation levels are measured for a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer.

A blood sample is taken from the patient at weekly intervals during chemotherapy treatment and protein accumulation levels are measured for a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status. The patient's panel results over time indicate that the cancer has responded to the chemotherapy treatment and that the colorectal cancer is no longer detectable by completion of the treatment regimen.

Example 7

A patient at risk of colorectal cancer is tested using a panel as disclosed herein. A blood sample is taken from the patient and protein accumulation levels are measured using reagents in an ELISA kit to detect members of a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer. A colonoscopy is recommended and evidence of colorectal cancer is detected in the individual.

Example 8

A patient at risk of colorectal cancer is tested using a panel as disclosed herein. A blood sample is taken from the patient and protein accumulation levels are measured using mass spectrometry to detect members of a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer. A colonoscopy is recommended and evidence of colorectal cancer is detected in the individual.

Example 9

1000 patients at risk of colorectal cancer are tested using a panel as disclosed herein. A blood sample is taken from the patient and protein accumulation levels are measured to detect members of a panel comprising AACT, CATD, CEA, CO3, CO9, MIF, PSGL, and SEPR. The patient's age is also factored in to the assessment, with age treated as an 'accumulation level' of time rather than protein. The patients' panel results are compared to panel results of known status, and the patients are categorized with an 81% sensitivity, a 78% specificity, and a 31% positive predictive value into a colon cancer category. A colonoscopy is recommended for patients categorized as positive. Of the patients categorized as having colon cancer, 80% are independently confirmed to have colon cancer. Of the patients categorized as not having colon cancer, 20% are later found to have colon cancer through an independent follow up test, confirmed via a colonoscopy.

Example 10

A patient at risk of colorectal cancer is tested using a panel as disclosed herein. A blood sample is taken from the patient and protein accumulation levels are measured for a panel comprising CATD, CLUS, GDF15, and SAA1. The patient's panel results are compared to panel results of known status, and the patient is categorized with a 50% sensitivity and an 80% specificity as having advanced colorectal adenoma. A colonoscopy is recommended and evidence of advanced colorectal adenoma is detected in the individual.

Example 11

A patient at risk of colorectal cancer is tested using a panel as disclosed herein. A blood sample is taken from the patient and protein accumulation levels are measured for a panel comprising CATD, CLUS, GDF15, and SAA1. The patient's panel results are compared to panel results of known status, and the patient is categorized with a 45% sensitivity and an 80% specificity as having advanced colorectal adenoma. Further monitoring is recommended and the health professional obtains subsequent blood or stool tests for colorectal cancer and/or advanced adenoma.

Example 12

A patient at risk of colorectal cancer is tested using a panel as disclosed herein. A blood sample is taken from the patient and protein accumulation levels are measured using reagents in an ELISA kit to detect members of a panel comprising CATD, CLUS, GDF15, and SAA1. The patient's panel results are compared to panel results of known status, and the patient is categorized with a 45% sensitivity and an 80% specificity as having advanced colorectal adenoma. A colonoscopy is recommended and evidence of advanced colorectal adenoma is detected in the individual.

Example 13

A patient at risk of colorectal cancer is tested using a panel as disclosed herein. A blood sample is taken from the patient and protein accumulation levels are measured using mass spectrometry to detect members of a panel comprising CATD, CLUS, GDF15, and SAA1. The patient's panel results are compared to panel results of known status, and the patient is categorized with a 45% sensitivity and an 80% specificity as having advanced colorectal adenoma. A colonoscopy is recommended and evidence of colorectal cancer is detected in the individual.

Example 14

A patient at risk of colorectal cancer is tested using a panel as disclosed herein. A blood sample is taken from the patient. The blood sample is mailed to a facility, where protein accumulation levels are measured using mass spectrometry to detect members of a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer. A colonoscopy is recommended and evidence of colorectal cancer is detected in the individual.

Example 15

A patient at risk of colorectal cancer is tested using a panel as disclosed herein. A blood sample is taken from the patient. The blood sample is mailed to a facility, where protein accumulation levels are measured using ELISA to detect members of a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer. A colonoscopy is recommended and evidence of colorectal cancer is detected in the individual.

Example 16

A patient at risk of colorectal cancer is tested using a panel as disclosed herein. A blood sample is taken from the patient. The blood sample is mailed to a facility, where plasma is prepared and protein accumulation levels are measured using ELISA to detect members of a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer. A colonoscopy is recommended and evidence of colorectal cancer is detected in the individual.

Example 17

A patient at risk of colorectal cancer is tested using a panel as disclosed herein. A blood sample is taken from the patient.

The blood sample is mailed to a facility, where plasma is prepared and protein accumulation levels are measured using mass spectrometry to detect members of a panel comprising AACT, CATD, CEA, CO3, CO9, MIF, PSGL, and SEPR. The patient's age is also factored in to the assessment, with age treated as an 'accumulation level' of time rather than protein. The patient's panel results are compared to panel results of known status, and the patient is categorized with an 81% sensitivity, a 78% specificity, and a 31% positive predictive value as having colon cancer. A colonoscopy is recommended and evidence of colorectal cancer is detected in the individual.

Example 18

Potential protein biomarkers were tested in an intent-to-test study design that included factors that would be present in an above-average-risk population (e.g., co-morbidities, other GI pathologies, age). 1,045 samples were evaluated by ELISA. Age was added as a model parameter in a case-control discovery partition of 309 patients (see FIG. 1). Indeterminate call boundaries were added in an intent-to-test discovery partition of 373 patients. The final protein biomarker panel comprising AACT, CATD, CEA, CO3, CO9, MIF, PSGL, and SEPR, and the age of the subject, was validated in 373 patients to have an 81% sensitivity and a 78% specificity with a 15% indeterminate call rate. No statistical difference was detected between early and late CRC performance.

Example 19

For a CRC protein marker panel discovery and validation study, 137 CRC patient plasma samples and 137 age- and gender-matched controls from three different commercial sample biobanks were acquired to conduct a study with case-control design. Samples were selected across the relevant age range for CRC screening guidelines, 50-75, across the stages of CRC, I-IV, and across the site of cancer, colon versus rectum. The patients were divided into a discovery partition of 138 paired samples and a validation partition of 136 paired samples. A 187 protein targeted MS assay was used to collect data from all 274 patients selected for this validation study, and the 138 paired patient samples in the discovery partition were used, to determine the abundance levels for the proteins to be evaluated in a variety of feature selection and classifier assembly workflows.

Based on the analysis, 12 models were built and selected for validation 30 of the original 187 proteins. These 12 models had AUCs that ranged from about 0.77 to 0.83. Classifier models were then selected and their protein components and algorithms locked to evaluate them using the data collected from the held-out validation partition. The samples were blinded to the laboratory and analysis staff. All 12 models validated successfully and their AUC's were not significantly different than predicted from the discovery partition. One classifier with 13 component proteins had a validation AUC of 0.91 and a test performance of 87% sensitivity and 81% specificity at the point of maximum accuracy. This classifier's performance on early CRC was 90% sensitivity (46 out of 51 stage I/II cancers correctly classified).

To confirm clinical validity, selected proteins were evaluated in a new cohort of samples and with another detection technology, ELISA. This approach helps ensure the results achieved in the first study were not the result of technological or study design bias. For a second validation sample set, patient plasma samples were obtained from a Danish study, Endoscopy II, performed by Dr. Hans Nielsen of Hvidovre Hospital/University of Copenhagen. This study collected samples from 4, 698 patients who were referred for diagnostic colonoscopy based on at least one symptom of bowel neoplasia. Plasma was collected prior to colonoscopy and processed to plasma and stored using validated standard operating procedures. Using this cohort of patient samples, 150 CRC plasma samples and 150 age- and gender-matched controls were selected for a second discovery and validation study. The samples collected ranged from patient ages 50 to 75, across all four CRC stages, and across the colon and rectum. The controls were designed from the subset of patients who had no comorbidities and no findings on colonoscopy in order to most closely mimic anticipated intent-to-test population: patients with above-average risk but no prior clear indications for colonoscopy. Commercially available ELISA reagents were used for 28 of the 30 proteins that comprised the 12 classifiers from the first study.

Using the 300-patient plasma samples selected from the Endoscopy II study and the 28 ELISAs for proteins previously validated, protein abundance data was collected target. Based on new ELISA data for the 28 proteins in the 150 sample discovery partition, a machine learning approach was used in ten rounds of 10-fold cross validation to build 5 models for evaluation. The models ranged in size from 7 to 18 proteins and produced a range of discovery performance from 0.83 to 0.86, based on Receiver Operating Characteristic, or ROC, area under the curve, or AUC. An ideal test, with 100% sensitivity and 100% specificity would begin in the lower left corner, go straight to the upper left corner, then to the upper right corner, and the AUC would be 1.00. On the other hand, a test without predictive value would be a straight diagonal line from the lower left corner to the upper right corner, with an AUC of 0.50. Once models were selected and their components and algorithm were locked, the data from the validation partition were used to evaluate the models.

CRC marker proteins were further validated for their ability to comprise panels that have significant detection performance for advanced adenoma, the precursor lesion to CRC. In the natural history of CRC development it is generally accepted that all CRC's come from advanced adenomas but not all advanced adenomas become CRCs. Nevertheless, several studies have demonstrated that the removal of advanced adenomas during screening colonoscopy significantly reduces the incidence of subsequent colorectal cancer.

Using the Danish Endoscopy II study, a new 302 patient, age- and gender-matched, site-stratified, subset of samples was selected using the definition for advanced adenoma commonly used in other recent, external studies. Using the same ELISAs for the 28 proteins as in the prior CRC validation study, data were collected from each of the 302 samples, divided into a 150-sample discovery partition and a 152-sample validation partition. Using the same methods for classifier assembly in cross-validation and final validation as described above, an advanced adenoma classifier was identified that comprises 4 of the 28 proteins and has 45% sensitivity and 80% specificity (ROC AUC 0.65)

Example 20

A total of 6 biomarkers were selected at random from a panel comprising: AACT, CATD, CEA, CO3, CO9, MIF, PSGL, and SEPR. A total of 6 biomarkers were also selected at random from the mass spec analyzed validation study comprising 187 proteins. The panel comprising 6 proteins selected from a biomarker panel comprising AACT, CATD, CEA, CO3, CO9, MIF, PSGL, and SEPR was validated in 373 patients and performed 95% better than the 6 biomarkers selected at random from the mass spec analyzed validation study comprising 187 proteins.

Example 21—Panel Comparison

Panels disclosed herein were compared to randomly determined panels derived from enriched biomarker lists to assess their performance relative to background chance.

As discussed above and as demonstrated in FIG. 1, panels disclosed herein were derived by generating a 187 member list of markers identified in the literature as being of potential relevance to cancer detection. Biomarkers in this list were then assayed in a sample set derived from individuals of known colorectal health status, and 28 biomarkers that correlated strongly with sample colorectal health status were identified. These 28 markers were assayed through an ELISA based approach on a second set of samples derived from a second set of individuals of known colorectal health status, and the panels disclosed herein were produced.

Thus, the MS-identified 28 marker set was already substantially enriched over the initial 187 member set identifiable to one of skill in the art. Nonetheless, an investigation was made into the performance of the panels disclosed herein relative to the MS-enriched biomarker dataset.

Panels of various sizes were generated from the 28-member MS enriched set, and these panels were assessed as to their predictive value on a marker-quantified sample set derived from individuals of known colorectal health status. Random panels were generated using Random Forest models and using SVM models. AUC values were determined for each random panel. AUC distribution curves for panels of a given size were generated.

The AUC distribution curves are presented in FIG. 20. The three top graphs represent panels generated through SVM, while the three bottom graphs depict panels generated through Random Forest modeling. For each plot, the panel size is listed at top with grey back shading. The Y axis indicates number of panels, while the X axis indicates AUC value for the panel columns indicated. The dashed line indicates the AUC value which 95% of the randomly generated panels from the MS-enriched dataset fall below.

The results are summarized in Tables 13 and 14.

TABLE 13

SVM MS-Enriched Panel Characteristics

| Panel Size | Number of Combos | Min AUC | Max AUC | Mean AUC | Stdev AUC | Median AUC | 95% AUC |
|---|---|---|---|---|---|---|---|
| 2 | 378 | 0.380 | 0.711 | 0.544 | 0.074 | 0.545 | 0.667 |
| 3 | 3276 | 0.389 | 0.806 | 0.594 | 0.079 | 0.600 | 0.714 |
| 4 | 10000 | 0.387 | 0.822 | 0.637 | 0.076 | 0.644 | 0.745 |
| 5 | 10000 | 0.401 | 0.834 | 0.669 | 0.068 | 0.676 | 0.769 |
| 6 | 10000 | 0.406 | 0.837 | 0.694 | 0.061 | 0.701 | 0.782 |
| 7 | 10000 | 0.416 | 0.843 | 0.711 | 0.055 | 0.716 | 0.792 |
| 8 | 10000 | 0.416 | 0.851 | 0.725 | 0.049 | 0.730 | 0.797 |
| 9 | 10000 | 0.409 | 0.848 | 0.734 | 0.045 | 0.737 | 0.800 |
| 10 | 10000 | 0.427 | 0.848 | 0.743 | 0.041 | 0.746 | 0.863 |

TABLE 14

Random forest-Enriched Panel Characteristics

| Panel Size | Number of Combos | Min AUC | Max AUC | Mean AUC | Stdev AUC | Median AUC | 95% AUC |
|---|---|---|---|---|---|---|---|
| 2 | 378 | 0.410 | 0.799 | 0.610 | 0.083 | 0.616 | 0.746 |
| 3 | 3276 | 0.391 | 0.832 | 0.844 | 0.077 | 0.654 | 0.755 |
| 4 | 10000 | 0.388 | 0.840 | 0.668 | 0.070 | 0.678 | 0.765 |
| 5 | 10000 | 0.395 | 0.835 | 0.685 | 0.062 | 0.693 | 0.774 |
| 6 | 10000 | 0.397 | 0.834 | 0.697 | 0.059 | 0.703 | 0.781 |
| 7 | 10000 | 0.439 | 0.836 | 0.708 | 0.054 | 0.713 | 0.789 |
| 8 | 10000 | 0.443 | 0.839 | 0.718 | 0.049 | 0.722 | 0.791 |
| 9 | 10000 | 0.448 | 0.835 | 0.723 | 0.046 | 0.725 | 0.794 |
| 10 | 10000 | 0.483 | 0.833 | 0.730 | 0.043 | 0.732 | 0.796 |

As indicated in the graphs and models, panels of 8-10 members demonstrate mean and median AUC values of about 0.71-0.73. 95% of the curves display an AUC of 0.80 or less.

Referring to FIG. 2, one sees that a lead 9 member panel disclosed herein for the assessment of colorectal health has a validated AUC value of 0.83. This value is greater than the 95% threshold AUC of comparable 9 and even 10 member panels, and is comparable to the maximum AUC values observed for the entire datasets.

Referring also to Table 8, one sees that comparable AUC values, far superior to those of the randomly generated panels, are obtained for Models 1-13. Model 12, it is observed, differs from the panel of FIG. 2 in that age is excluded as a biomarker.

This analysis makes clear that panels herein outperform randomly generated panels, even randomly derived panels selected from biomarkers that are already experimentally enriched to the 28 best targeted-MS identified markers from a 187 member set identified in the art. That is, even upon 6x enrichment of markers above a set taught in the art, panels herein outperform essentially 100% of the randomly generated panels derived therefrom.

Example 22—CRC and AA Test Implementation

Throughout this example, patients 1, 2, and 3 are representative of patient data generated through the methods, kits, systems and compositions herein but in the interest of patient confidentiality, none of patients 1, 2 and 3 represent any patient's actual data.

An exemplary first patient, second patient and third patient each provide a blood sample for analysis. The samples are shipped to a processing center and ELISA reagents are used to determine CRC and AA panel levels using reagents to determine levels of AACT, CEA, CO3, CO9, MIF, PSGL, SEPR, CATD, CLUS, GDF15, SAA1. Patient age is also provided.

Biomarkers are measured and the results presented in Table 15.

TABLE 15

CRC/AA Test Input Measurements

| Panel | CRC | | | | | | | | CRC/AA | AA | | |
|---|---|---|---|---|---|---|---|---|---|---|---|---|
| Patient | AACT | CEA | CO9 | SEPR | CO3 | MIF | PSGL | Age | CATD | CLUS | GDF15 | SAA1 |
| 1 | 246600 | 19 | 161800 | 105500 | 820 | 8 | 500 | 46 | 37100 | 5440 | 119 | 4537 |
| 2 | 171300 | 7 | 20800 | 108100 | 270 | 90 | 290 | 68 | 6190 | 8450 | 179 | 2290 |
| 3 | 215000 | 7 | 54100 | 16600 | 490 | 85 | 500 | 79 | 45100 | 5310 | 24 | 4178 |

The biomarker panel levels for each of the three patients are assigned Model Scores according to a Machine Learning Model assembled from panel levels of samples from reference individuals of known colorectal health status as depicted in FIG. 1. From the Machine Learning Model, a cutoff score of 2.9 is calculated as the lower limit for a positive CRC score. Scores below this cutoff are called negative for colorectal cancer. An 'indeterminate range' is identified among the negative scores, such that patient scores falling within the intermediate range are marked for further analysis. The indeterminate range spans scores of 1.24-2.46. Scores above the intermediate range but below the positive cutoff are in some cases additionally scrutinized. Through a similar approach, a cutoff score of 0.25 is calculated as the lower limit for a positive AA score.

Patient panel levels are assessed and a score assigned to each panel for CRC and AA. Depending on the score, a follow up assay is recommended and a diagnosis is generated according to this follow-up assay. The results are presented in Table 16.

TABLE 16

CRC/AA Test Output Scores and Measurements

| Patient | CRC Score | CRC Call | CRC Diagnosis | AA Score | AA Call | AA Diagnosis |
|---|---|---|---|---|---|---|
| 1 | 1.7 | Indeterminate | Adenoma | 1.0 | Positive | Adv. Adenoma |
| 2 | 0.7 | Negative | No findings | 0.3 | Negative | No findings |
| 3 | 5.9 | Positive | Colon Cancer | 0.9 | Positive | No findings |

Patient 1 is assigned a CRC model score of 1.7. The score is below the 2.9 cutoff score for a positive call, but is scored as indeterminate. Patient 1 is assigned an AA score of 1.0, and is called positive for advanced adenoma. A report is generated and provided to the patient.

The patient undergoes a colonoscopy. No colorectal cancer is detected, but a noncancerous adenoma is detected. The adenoma is removed and the patient is later confirmed to be colon cancer and adenoma free by a follow-up test. The patient is observed for 5 years and no symptoms or change in colorectal cancer status is observed, indicating that the test correctly identified the patient's status as negative for colon cancer.

Patient 2 is assigned a CRC model score of 0.72 and is called negative for colorectal cancer. Patient 2 is assigned an AA model score of 0.29 and is called negative for advanced adenoma. A report is generated and provided to the patient.

The patient follows up with a stool sample test and the results are similarly negative. The patient is observed for 5 years and no symptoms or change in colorectal health status is observed, indicating that the test correctly predicted no colorectal cancer and no advanced adenoma in the individual.

Patient 3 is assigned a CRC model score of 5.9 and is called positive for colorectal cancer. Patient 3 is assigned an AA score of 0.9 and is called positive for AA. A report is generated and provided to the patient.

The patient undergoes a colonoscopy. Early stage colorectal cancer is detected, but no adenoma is detected.

The patient undergoes colon cancer treatment and symptoms are alleviated. A second blood sample is taken from the patient following treatment and a CRC score below 2.9 is assigned. A colonoscopy confirms that the colorectal cancer is no longer present in the individual.

This example demonstrates various features of the panels herein. The CRC and AA panels are used in combination and share common markers. The panels are derived from blood and are shipped to be tested elsewhere. A report is generated and provided to the patient. The results are independently corroborated using an invasive approach such as a colonoscopy or noninvasive approach such as a stool test. The test results are largely corroborated by independent assays.

Example 23—CRC and AA Score Analysis

The data in Table 15 allows further analysis of the CRC and AA panel performances.

For instance, an examination of Table 15 is illustrative of relevant aspects of panel performance relative to the predictive value of its individual markers.

One sees that for some markers, the individual marker level corresponds with the overall panel result. For example, SEPR levels for patient 1 and patient 2 are similar at about 10,000, while patient 3 scores substantially lower at 1,600. This grouping is consistent with the overall scoring of patient 1 and patient 2 as negative or indeterminate for CRC, while patient 3 scored positive.

However, in the majority of the cases, individual marker levels do not predict the outcome that one finds upon analyzing the panel level as a whole. For biomarkers AACT, CO9, and CO3, patient 3 levels are intermediate between those of patient 1 and patient 2. For biomarkers CEAMIF and PSGL, patient 3 levels roughly match those of either patient 1 or patient 2.

Thus, looking at these biomarkers individually, one does not find an indication that patient 3 rather than patient 1 or patient 2 is likely positive for CRC.

These measurements indicate that the CRC panel as a whole possesses a predictive value that surpasses that of its constituent biomarker members. Furthermore, the CRC biomarker panel as a whole provides a predictive value that in some cases, contradicts the prediction of its individual members. Accordingly, the CRC biomarker panel as a whole provides a predictive value that is better than its components and that is more than a simple collection of its individual marker results.

Example 24—Clinical Utility of Noninvasive, Accurate Colorectal Health Assay

A recalcitrant patient demonstrated symptoms of CRC but refused a colonoscopy. The patient's primary care physician ordered a SimpliPro colorectal health assessment test. The results indicated that the patient was at a high risk for CRC and for AA. The patient consulted with family and was convinced to schedule a colonoscopy. The colonoscopy revealed polyps and an early stage cancerous mass, all of which were removed during the procedure. A follow-up colorectal health assessment indicated that the patient is cancer free. The patient's early stage cancerous mass would likely have progressed to advanced disease with a high probability of death without the colonoscopy and concurrent polypectomy.

This Example demonstrates the benefit to the public of offering a noninvasive colorectal health assay that is both sensitive and specific, and is easily complied with. In combination with Example 25, below, this example demonstrates that the reluctance to undergo a colonoscopy is common, and that it can have severe health consequences if it results in an early stage cancer not being detected when it is relatively easily treated.

Example 25—Clinical Utility of Noninvasive, Accurate Colorectal Health Assay

A recalcitrant patient demonstrated symptoms of CRC but delayed a colonoscopy for over 6 months. The patient's primary care physician ordered a SimpliPro colorectal health assessment test. The results indicated that the patient was at a high risk for CRC and for AA. The patient scheduled a colonoscopy. During the procedure, a 6 cm malignant mass was identified and removed. A follow-up colorectal health assessment indicated that the patient is cancer free. The patient's early stage cancerous mass would likely have progressed to advanced disease with a high probability of death without the colonoscopy and concurrent polypectomy.

This Example demonstrates the benefit to the public of offering a noninvasive colorectal health assay that is both sensitive and specific, and is easily complied with. In combination with Example 24, above, this example demonstrates that the reluctance to undergo a colonoscopy is common, and that it can have severe health consequences if it results in an early stage cancer not being detected when it is relatively easily treated.

While preferred embodiments of the disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method comprising:
   obtaining a circulating blood sample from an individual; and
   detecting protein levels for each member of a list of proteins in the sample, said list comprising AACT, CO3, CO9, MIF, and PSGL.

2. The method of claim 1, further comprising;
   diagnosing said individual as having a colorectal cancer risk status when said protein levels from said individual do not differ significantly from a reference panel information set corresponding to a known colorectal cancer risk status; and
   performing a polypectomy on said individual.

3. The method of claim 1, further comprising obtaining age information for the individual.

4. The method of claim 1, wherein the list of proteins further comprises CATD, CEA and SEPR.

5. The method of claim 1, further comprising transmitting a report of results of said detecting to a health practitioner.

6. The method of claim 5, wherein the report recommends that a colonoscopy be performed.

7. The method of claim 1, wherein the detecting protein levels comprises contacting a fraction of the circulating blood sample to a set of antibodies comprising antibodies specific to AACT, CO3, CO9, MIF, and PSGL.

8. A method of monitoring efficacy of a colorectal cancer treatment regimen in an individual, comprising the steps of
obtaining a first sample comprising circulating blood from the individual at a first time point;
administering the treatment regimen to the individual;
obtaining a second sample comprising circulating blood from the individual at a second time point;
determining protein levels for each member of a list of proteins comprising AACT, CO3, CO9, MIF, and PSGL in said first sample and determining protein levels for each member of the list of proteins comprising AACT, CO3, CO9, MIF, and PSGL in said second sample.

9. The method of claim 8, wherein obtaining the first sample comprises drawing blood from a vein or artery of the individual.

10. The method of claim 8, wherein the treatment regimen comprises a polypectomy.

11. The method of claim 8, wherein the list of proteins further comprises CATD, CEA and SEPR.

12. The method of claim 8, further comprising changing the treatment regimen when protein levels for the first sample are the same as the protein levels for the second sample.

13. The method of claim 8, further comprising repeating the treatment regimen when protein levels for the first sample are the same as the protein levels for the second sample.

14. The method of claim 8, further comprising discontinuing the treatment regimen when protein levels of the second sample return to levels corresponding to a healthy individual.

15. A method comprising:
obtaining a circulating blood sample from an individual;
determining protein levels for each member of a list of proteins in the sample, said list comprising AACT, CO3, CO9, MIF, PSGL, SEPR, CEA, CATD, CLUS, GDF15 and SAA1.

16. The method of claim 15, wherein the list of proteins comprises no more than 20 proteins.

17. The method of claim 15, further comprising transmitting a report of results of said determining to a health practitioner.

18. The method of claim 17, wherein the report recommends that a colonoscopy be performed.

19. The method of claim 15, further comprising performing a polypectomy on the individual.

20. The method of claim 15, further comprising performing a stool cancer assay on a stool sample from the individual.

21. The method of claim 15, wherein the determining protein levels comprises contacting a fraction of the circulating blood sample to a set of antibodies comprising antibodies specific to AACT, CO3, CO9, MIF, PSGL, SEPR, CEA, CATD, CLUS, GDF15 and SAA1.

* * * * *